US007960349B2

(12) United States Patent
Ewing et al.

(10) Patent No.: US 7,960,349 B2
(45) Date of Patent: *Jun. 14, 2011

(54) N-TERMINALLY MODIFIED GLP-1 RECEPTOR MODULATORS

(75) Inventors: William R. Ewing, Yardley, PA (US); Claudio Mapelli, Plainsboro, NJ (US); Douglas James Riexinger, Flemington, NJ (US); Ving G. Lee, Hamilton, NJ (US); Richard B. Sulsky, West Trenton, NJ (US); Yeheng Zhu, Stockton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 921 days.

This patent is subject to a terminal disclaimer.

(21) Appl. No.: 11/753,616

(22) Filed: May 25, 2007

(65) Prior Publication Data

US 2008/0045461 A1 Feb. 21, 2008

Related U.S. Application Data

(60) Provisional application No. 60/809,134, filed on May 26, 2006.

(51) Int. Cl.
*A61K 38/08* (2006.01)
*A61K 38/00* (2006.01)

(52) U.S. Cl. .......................... 514/21.8; 514/1.1; 530/330

(58) Field of Classification Search .................. None
See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,647,576 A | 3/1987 | Hoefle et al. | |
| 4,681,893 A | 7/1987 | Roth | |
| 4,686,237 A | 8/1987 | Anderson | |
| 4,759,923 A | 7/1988 | Buntin et al. | |
| 4,871,721 A | 10/1989 | Biller | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,354,772 A | 10/1994 | Kathawala | |
| 5,385,929 A | 1/1995 | Bjorge et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |
| 5,594,016 A | 1/1997 | Ueno et al. | |
| 5,595,872 A | 1/1997 | Wetterau, II et al. | |
| 5,612,359 A | 3/1997 | Murugesan | |
| 5,614,492 A | 3/1997 | Habener | |
| 5,686,104 A | 11/1997 | Mills et al. | |
| 5,691,322 A | 11/1997 | Robl | |
| 5,712,279 A | 1/1998 | Biller et al. | |
| 5,712,396 A | 1/1998 | Magnin et al. | |
| 5,739,135 A | 4/1998 | Biller et al. | |
| 5,753,675 A | 5/1998 | Wattanasin | |
| 5,760,246 A | 6/1998 | Biller et al. | |
| 5,770,615 A | 6/1998 | Cheng et al. | |
| 5,776,983 A | 7/1998 | Washburn et al. | |
| 5,827,875 A | 10/1998 | Dickson, Jr. et al. | |
| 5,885,983 A | 3/1999 | Biller et al. | |
| 5,962,440 A | 10/1999 | Sulsky | |
| 5,998,375 A | 12/1999 | Thøgersen et al. | |
| 6,043,265 A | 3/2000 | Murugesan et al. | |
| 6,548,667 B2 | 4/2003 | Park et al. | |
| 6,579,889 B2 | 6/2003 | De Laszlo et al. | |
| 6,737,417 B2 | 5/2004 | Jo et al. | |
| 7,145,040 B2 | 12/2006 | Mathur et al. | |
| 7,238,670 B2 | 7/2007 | Natarajan et al. | |

(Continued)

FOREIGN PATENT DOCUMENTS

EP        0 142 146        5/1985

(Continued)

OTHER PUBLICATIONS

Ashworth, D.M. et al., "2-Cyanopyrrolidides as Potent, Stable Inhibitors of Dipeptidyl Peptidase IV", Bioorganic & Medicinal Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinal Chemistry Letters, vol. 6, No. 22, pp. 2745-2748 (1996).

Atherton, E. et al., Chapter 1: "The Fluorenylmethoxycarbonyl Amino Protecting Group", The Peptides: Analysis, Synthesis, Biology, vol. 9: Special Methods in Peptide Synthesis, Part C, Academic Press, Inc., publ., Udenfriend, S. et al., eds., pp. 1-38 (1987).

Barany, G. et al., Chapter 1: "Solid-Phase Peptide Synthesis", The Peptides: Analysis, Synthesis, Biology, vol. 2: Special Methods in Peptide Synthesis, Part A, Academic Press, Inc., publ., Gross, E. et al., eds., pp. 1-284 (1979).

(Continued)

*Primary Examiner* — Andrew D Kosar
*Assistant Examiner* — Satyanarayana R Gudibande
(74) *Attorney, Agent, or Firm* — Briana C. Bergen; Eve Frank

(57) ABSTRACT

The subject matter described herein provides novel human glucagon-like peptide-1 (GLP-1) receptor modulators that have biological activity similar or superior to native GLP-1 peptide and thus are useful for the treatment or prevention of diseases or disorders associated with GLP activity. The described compounds include chemically modified peptides that may stimulate insulin secretion in type II diabetics, but also produce other beneficial insulinotropic responses. These synthetic peptide GLP-1 receptor modulators exhibit increased stability to proteolytic cleavage making them ideal therapeutic candidates for oral or parenteral administration. The disclosed and claimed peptides show desirable pharmacokinetic properties and desirable potency in efficacy models of diabetes.

18 Claims, 9 Drawing Sheets

U.S. PATENT DOCUMENTS

| | | | |
|---|---|---|---|
| 7,238,671 | B2 | 7/2007 | Natarajan et al. |
| 7,417,028 | B2* | 8/2008 | Ewing et al. ............... 514/17 |
| 7,534,763 | B2* | 5/2009 | Qian et al. ............... 514/2 |
| 2006/0287242 | A1 | 12/2006 | Ewing et al. |
| 2007/0021346 | A1 | 1/2007 | Ewing et al. |

FOREIGN PATENT DOCUMENTS

| | | |
|---|---|---|
| EP | 0 221 025 | 5/1987 |
| FR | 2 596 393 | 10/1987 |
| GB | 2 205 837 | 12/1988 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/34332 | 6/2000 |
| WO | WO 03/033671 A | 4/2003 |
| WO | WO 2004/094461 | 11/2004 |
| WO | WO 2004/096179 | 11/2004 |
| WO | WO 2006/014287 | 2/2006 |
| WO | WO 2006/127948 | 11/2006 |
| WO | WO 2007 017892 | 2/2007 |
| WO | WO 2007/139589 | 12/2007 |

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).
Biller, S.A. et al., "Squalene Synthase Inhibitors", Current Pharmaceutical Design, vol. 2, No. 1, pp. 1-40 (1996).
Burgess, K. et al., "Solid Phase Syntheses of Oligoureas", J. Am. Chem. Soc., vol. 119, No. 7, pp. 1556-1564 (1997).
Byrne, M.M. et al., "Inhibitory effects of hyperglycaemia on fed jejunal motility: potential role of hyperinsulinaemia", European Journal of Clinical Investigation, vol. 28, pp. 72-78 (1998).
Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).
Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).
Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).
Davern, P. et al., "Chemical and Biological Reactivity of Sulfamidopenicillins", J. Chem. Soc. Perkin Trans. 2, pp. 381-387 (1994).
Fehder, W.P. et al., "Development and Evaluation of a Chromatographic Procedure for Partial Purification of Substance P with Quantitation by an Enzyme Immunoassay", Clinical and Diagnostic Laboratory Immunology, vol. 5, No. 3, pp. 303-307 (1998).
Fehrentz, J.-A. et al., "An Efficient Synthesis of Optically Active α-(t-Butoxycarbonylamino)-aldehydes from α-Amino Acids", Synthesis, pp. 676-678 (1983).
Fingl, E. et al., Section I: "Introduction", Chapter I: "General Principles", The Pharmacological Basics of Therapeutics, 5$^{th}$ Ed., Macmillan Publishing Co., Inc., publ., Goodman, L.S. et al., eds., pp. 1-46 (1975).
Flint, A. et al., "Glucagon-like Peptide 1 Promotes Satiety and Suppresses Energy Intake in Humans", J. Clin. Invest., vol. 101, No. 3, pp. 515-520 (1998).

Gennaro, A.R., ed., Remington's Pharmaceutical Sciences, 18$^{th}$ Ed., Mack Publishing Company, publ., pp. xv-xvi (table of contents) (1990).
Gennaro, A.R., ed., Remington: Practice of the Science and Pharmacy, 19$^{th}$ Ed., Mack Publishing Company, publ., pp. xv-xvi (table of contents) (1995).
Gennaro, A.R., ed., Remington: Practice of the Science and Pharmacy, vol. II, 19$^{th}$ Ed., Mack Publishing Company, publ., pp. vii-viii (table of contents) (1995).
Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).
Gluschankof, P. et al., "Enzymes processing somatostatin precursors: An Arg-Lys esteropeptidase from the rat brain cortex converting somatostatin-28 into somatostatin-14", Proc. Natl. Acad. Sci. USA, vol. 81, pp. 6662-6666 (1984).
Gutzwiller, J.-P. et al., "Glucagon-like peptide-1: a potent regulator of food intake in humans", Gut, vol. 44, pp. 81-86 (1999).
Hara, S., "Ileal Na$^+$/bile acid cotransporter inhibitors", Drugs of the Future, vol. 24, No. 4, pp. 425-430 (1999).
Hoist, J.J., "Glucagon-like Peptide-1, A Gastrointestinal Hormone with a Pharmaceutical Potential", Current Medicinal Chemistry, vol. 6, No. 11, pp. 1005-1017 (1999).
Ito, Y. et al., "Difference in cholesterol-binding and cytolytic activities between listeriolysin O and seeligeriolysin O: a possible role of alanine residue in tryptophan-rich undecapeptide", FEMS Microbiology Letters, vol. 203, pp. 185-189 (2001).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).
King, D.S. et al., "A cleavage method which minimizes side reactions following Fmoc solid phase peptide synthesis", Int. J. Peptide Protein Res., vol. 36, pp. 255-266 (1990).
Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).
McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).
Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).
Näslund, E. et al., "Energy intake and appetite are suppressed by glucagon-like peptide-1 (GLP-1) in obese men", International Journal of Obesity, vol. 23, pp. 304-311 (1999).
Nicolosi, R.J. et al., "The ACAT inhibitor, CI-1011 is effective in the prevention and regression of aortic fatty streak area in hamsters", Atherosclerosis, vol. 137, pp. 77-85 (1998).
Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).
Rosenblum, S.B. et al., "Discovery of 1-(4-Fluorophenyl)-(3R)[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).
Salisbury, B.G. et al., "Hypocholesterolemic activity of a novel inhibitor of cholesterol absorption, SCH 48461", Atherosclerosis, vol. 115, pp. 45-63 (1995).
Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Stewart, J.M. et al., Solid Phase Peptide Synthesis, $2^{nd}$ Ed., Pierce Chemical Company, publ., pp. vii-xi (table of contents), 92 (1984).

Stoffers, D.A. et al., "Insulinotropic Glucagon-Like Peptide 1 Agonists Stimulate Expression of Homeodomain Protein IDX-1 and Increase Islet Size in Mouse Pancreas", Diabetes, vol. 49, pp. 741-748 (2000).

Stout, D.M. et al., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT). 7. Development of a Series of Substituted N-Phenyl-N'-[(1-phenylcyclopentyl)-methyl]ureas with Enhanced Hypocholestrolemic Activity", Chemtracts—Organic Chemistry, vol. 8, pp. 359-362 (1995).

Wettergren, A. et al., "Truncated GLP-1 (Proglucagon 78-107-Amide) Inhibits Gastric and Pancreatic Functions in Man", Digestive Diseases and Sciences, vol. 38, No. 4, pp. 665-673 (1993).

Yamada, M. et al., "A Potent Dipeptide Inhibitor of Dipeptidyl Peptidase IV", Bioorganic & Medicinal Chemistry Letters, vol. 8, pp. 1537-1540 (1998).

* cited by examiner

N-TERMINALLY MODIFIED GLP-1 RECEPTOR MODULATORS

This application claims priority benefit to U.S. application Ser. No. 60/809,134, filed May 26, 2006, the contents of which are incorporated by reference in their entirety.

FIELD OF THE INVENTION

The subject matter disclosed and claimed herein provides novel human glucagon-like peptide-1 (GLP-1) peptide receptor modulators, agonists or partial agonists, which exhibit similar or superior biological properties of the native peptide, GLP-1, and exhibit increased stability to proteolytic cleavage as compared to GLP-1 native sequences, and thus are useful for the amelioration of the diabetic condition.

BACKGROUND OF THE INVENTION

GLP-1 is an important gut hormone with regulatory function in glucose metabolism and gastrointestinal secretion and metabolism. Human GLP-1 is a 30 amino acid peptide originating from preproglucagon, which is synthesized for example, in the L-cells in the distal ileum and in the brain. Processing of preproglucagon to yield GLP-1 (7-36)amide and GLP-2 occurs mainly in the L-cells. GLP-1 is normally secreted in response to food intake, in particular carbohydrates and lipids stimulate GLP-1 secretion. GLP-1 has been identified as a very potent and efficacious stimulator for insulin release. GLP-1 lowers plasma glucagon concentrations, slows gastric emptying, stimulates insulin biosynthesis and enhances insulin sensitivity (Nauck, 1997, Horm. Metab. Res. 47:1253-1258). GLP-1 also enhances the ability of the beta-cells to sense and respond to glucose in subjects with impaired glucose tolerance (Byrne, Eur. J. Clin. Invest., 28:72-78, 1998). The insulinotropic effect of GLP-1 in humans increases the rate of glucose metabolism partly due to increased insulin levels and partly due to enhanced insulin sensitivity (D'Alessio, Eur. J. Clin. Invest., 28:72-78, 1994). The above stated pharmacological properties of GLP-1 make it a highly desirable therapeutic agent for the treatment of type-II diabetes.

Additionally, recent studies have shown that infusions of slightly supraphysiological amounts of GLP-1 significantly enhance satiety and reduce food intake in normal subjects (Flint, A., Raben, A., Astrup, A. and Holst, J. J., J. Clin. Invest, 101:515-520, 1998; Gutswiller, J. P., Goke, B., Drewe, J., Hildebrand, P., Ketterer, S., Handschin, D., Winterhaider, R., Conen, D and Beglinger, C. Gut 44:81-86, 1999;). The effect on food intake and satiety has also been reported to be preserved in obese subjects (Naslund, E., Barkeling, B., King, N., Gutniak, M., Blundell, J. E., Holst, J. J., Rossner, S., and Hellstrom, P. M., Int. J. Obes. Relat. Metab. Disord., 23:304-311, 1999).

In the above-cited studies a pronounced inhibitory effect of GLP-1 on gastric emptying was also suspected to occur. Gastric emptying results in post-prandial glucose excursions. It has also been shown that in addition to stimulation of insulin secretion, GLP-1 stimulates the expression of the transcription factor, islet-duodenal homeobox-1 (IDX-1), while stimulating beta-cell neogenesis and may thereby be an effective treatment and/or preventive agent for diabetes (Stoffers, D. A., Kieffer, T. J. Hussain, M. A., Drucker, D. J., Bonner-Weir, S., Habener, J. F. and Egan, J. M. Diabetes, 40:741-748, 2000). GLP-1 has also been shown to inhibit gastric acid secretion (Wettergren, A., Schjoldager, B., Mortensen, P. E., Myhre, J., Christiansen, J., Holst, J. J., Dig. Dis. Sci., 38:665-673, 1993), which may provide protection against gastric ulcers.

GLP-1 is an incretin hormone, for example, an intestinal hormone that enhances meal-induced insulin secretion (Holst, J. J., Curr. Med. Chem., 6:1005-1017, 1999). It is a product of the glucagon gene encoding proglucagon. This gene is expressed not only in the A-cells of the pancreas but also in the endocrine L-cells of the intestinal mucosa. Proglucagon is a peptide (protein) containing 160 amino acids. Further processing of proglucagon results in the generation of a) glucagon, b) an N-terminal, presumably inactive fragment, and c) a large C-terminal fragment commonly referred as "the major proglucagon fragment". This fragment is considered to be biologically inactive. Even though this fragment is present in both pancreas and in the L-cells of the gut, it is only in the intestines the breakdown products of the "the major proglucagon fragment" resulting in two highly homologous peptides commonly referred as GLP-1 and GLP-2 are observed. These two peptides have important biological activities. As such, the amino acid sequence of GLP-1, which is present in the L-cells, is identical to the 78-107 portion of proglucagon.

Presently, therapy involving the use of GLP-1-type molecules has presented a significant problem because the serum half-life of such peptides is quite short. For example, GLP-1 (7-37) has a serum half-life of less than 5 min. Thus there exists a critical need for biologically active GLP-1 receptor modulators, agonists or antagonists, that possess extended pharmacodynamic profiles. It is to this and other needs that the disclosed and claimed subject matter is directed.

Disclosed herein are novel peptides that act as GLP-1 receptor modulators, agonists or partial agonists, which exhibit similar or superior biological properties of the native peptide, GLP-1, and thus are useful for the amelioration of the diabetic and related conditions.

SUMMARY OF THE INVENTION

The synthetic isolated peptides described herein are capable of modulating the GLP-1 receptor, desirably as agonists or partial agonists of the GLP-1 receptor. These synthetic peptides exhibit similar in vivo efficacy and superior pharmacokinetic properties relative to GLP-1, including postprandial plasma glucose lowering and concomitant increase in plasma insulin levels, thus making them ideal therapeutic candidates for subcutaneous, pulmonary, nasal, buccal or sustained release formulations.

In a first embodiment of the subject matter described herein, is an isolated polypeptide comprising a sequence of Formula I:

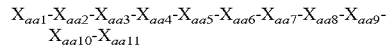

$X_{aa1}$-$X_{aa2}$-$X_{aa3}$-$X_{aa4}$-$X_{aa5}$-$X_{aa6}$-$X_{aa7}$-$X_{aa8}$-$X_{aa9}$-$X_{aa10}$-$X_{aa11}$ wherein, $X_{aa1}$ is a naturally or nonnaturally occurring amino acid comprising an imidazole or thiazole ring, such as histidine or thiazolylalanine; wherein any of the carbon atoms of said amino acid are optionally substituted with hydrogen or with one or more alkyl groups, or with one or more halo groups; wherein the free amino group of said amino acid may be replaced with a hydroxyl or an alkoxy group, or is optionally substituted with hydrogen, alkyl, acyl, benzoyl, alkyloxycarbonyl (e.g., methyloxycarbonyl), aryloxycarbonyl, aralkyloxycarbonyl, heterocyclyloxycarbonyl, heteroarylalkyloxycarbonyl, alkylcarbamoyl, arylcarbamoyl, aralkylcarbamoyl, heterocyclylsulfonyl, alkylsulfonyl, arylsulfonyl, arylalkylsulfonyl, heteroarylalkylsulfonyl or heteroarylsulfonyl;

and wherein the amino group of $X_{aa1}$ is optionally absent, such that $X_{aa1}$ is des-amino acid of histidine or thiazolylalanine in which any of the carbon atoms are optionally substituted with alkyl, halo, or hydroxyl groups;

$X_{aa2}$ is a naturally or nonnaturally occurring amino acid selected from the group consisting of α-amino-isobutryic acid (Aib); (D)-alanine, (L)-alanine, N-methyl-L-Alanine, N-methyl-D-Alanine, (L)-proline, (S)-α-methyl-proline, (L)-azetidine (Azt), (S)-α-methyl-azetidine (α-Me-Azt), (L)-valine, and (R)- or (S)-isovaline, and wherein the carbon atoms of said amino acid are optionally substituted with one or more alkyl groups or halo groups;

$X_{aa3}$ is a naturally or nonnaturally occurring amino acid comprising an amino acid side chain which contains a carboxylic acid, for example aspartic acid or glutamic acid; and wherein any of the carbon atoms of said amino acid are optionally substituted with one or more alkyl groups or halo groups;

$X_{aa4}$ is glycine;

$X_{aa5}$ is a naturally or nonnaturally occurring amino acid selected from the group consisting of (L)-threonine, (L)-allo-threonine, (L)-serine, (L)-norvaline, (L)-norleucine; and wherein any of the carbon atoms of said amino acid are optionally substituted with one or more alkyl groups or halo groups;

$X_{aa6}$ is a naturally or nonnaturally occurring amino acid comprising an alpha carbon which is disubstituted; wherein one of the side chains of said amino acid contains an aromatic or heteroaromatic ring, for example alpha-methyl-phenylalanine, alpha-methyl-2-fluorophenylalanine, and alpha-methyl-2,6-difluorophenylalanine, wherein any of the carbon atoms of said amino acid are optionally substituted with one or more alkyl groups; and wherein any of the carbon atoms of said amino acid are optionally substituted with one or more halo groups;

$X_{aa7}$ is a naturally or nonnaturally occurring amino acid comprising an amino acid side chain which is substituted with a hydroxyl group, for example L-threonine or L-allo-threonine; wherein any of the carbon atoms of said amino acid are optionally substituted with one or more alkyl or halo groups;

$X_{aa8}$ is a naturally or nonnaturally occurring amino acid selected from the group consisting of L-serine, L-histidine and L-asparagine; wherein one or more of the carbon atoms of said amino acid is optionally substituted with one or more alkyl groups or halo groups;

$X_{aa9}$ is a naturally or nonnaturally occurring amino acid comprising an amino acid side chain which contains a carboxylic acid, for example L-aspartic acid or L-glutamic acid; wherein one or more of the carbon atoms of said amino acid is optionally substituted with one or more alkyl or halo groups;

$X_{aa10}$ is a naturally or nonnaturally occurring amino acid of Formula II, III, or IV:

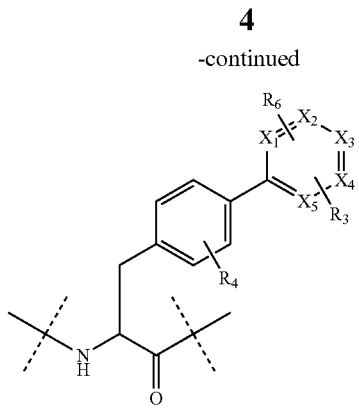

Formula II

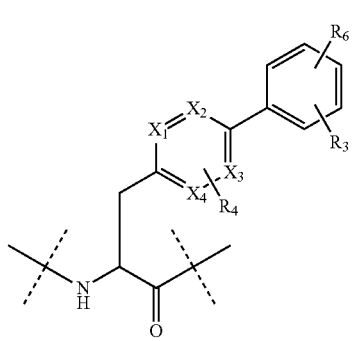

Formula III

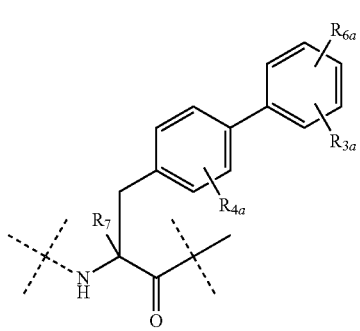

Formula IV wherein $R_3$, $R_4$ and $R_6$ are each selected from the group consisting of hydrogen, methyl, ethyl, alkyl, aryl, heterocyclyl, heteroaryl, halogen, hydroxyl, hydroxyalkyl, cyano, amino, aminoalkyl, carboxyl, carboxyalkyl, methoxy, alkoxy, aryloxy, carboxamides, substituted carboxamides, alkyl esters, aryl esters, alkyl sulfonyl, and aryl sulfonyl;

and wherein $X_1$, $X_2$, $X_3$, $X_4$, and $X_5$ are each C or N, with the proviso that at least one of $X_1$, $X_2$, $X_3$, $X_4$, and $X_5$ is N;

$X_{aa11}$ is a naturally or nonnaturally occurring amino acid of Formula IIa, IIIa, or IVa:

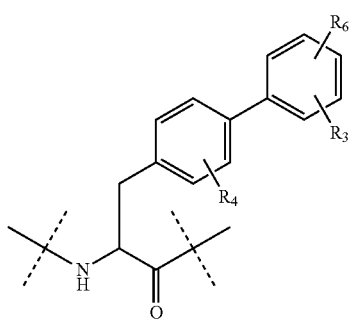

Formula IIa

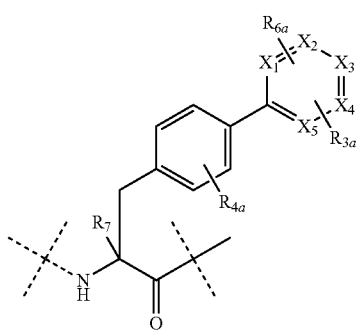

Formula IIIa

-continued

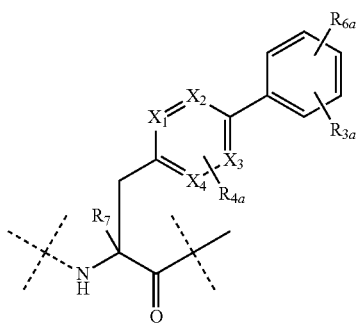

Formula IVa wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein $R_{3a}$, $R_{4a}$ and $R_{6a}$ are each selected from the group consisting of hydrogen, alkyl (e.g., methyl, ethyl), aryl, heterocyclyl, heteroaryl, halogen, hydroxyl, hydroxyalkyl, cyano, amino, aminoalkyl, carboxyl, carboxyalkyl, alkoxy, aryloxy, carboxamides, substituted carboxamides, alkyl esters, aryl esters, alkyl sulfonyl, and aryl sulfonyl;

wherein $R_7$ is selected from the group consisting of hydrogen, methyl, and ethyl; and wherein $X_1$, $X_2$, $X_3$, $X_4$, and $X_5$ are each C or N, with the proviso that at least one of $X_1$, $X_2$, $X_3$, $X_4$, and $X_5$ is N;

wherein $X_{aa11}$ is not an amino acid of Formula IIa when $X_{aa10}$ is an amino acid of Formula II.

The naturally or nonnaturally occurring amino acid of Formula II may further comprise more than one $R_3$, $R_4$ or $R_6$ groups. The naturally or nonnaturally occurring amino acid of Formula III may further comprise more than one $R_3$, $R_4$ or $R_6$ groups. The naturally or nonnaturally occurring amino acid of Formula IV may further comprise more than one $R_3$, $R_4$ or $R_6$ groups. The naturally or nonnaturally occurring amino acid of Formula V may further comprise one or more $R_4$ or $R_5$ groups.

The naturally or nonnaturally occurring amino acid of Formula IIa may further comprise more than one $R_{3a}$, $R_{4a}$ or $R_{6a}$ groups. The naturally or nonnaturally occurring amino acid of Formula IIIa may further comprise more than one $R_{3a}$, $R_{4a}$ or $R_{6a}$ groups. The naturally or nonnaturally occurring amino acid of Formula IVa may further comprise more than one $R_{3a}$, $R_{4a}$ or $R_{6a}$ groups.

$X_{aa10}$ of the first embodiment of Formula I, may also be a compound of Formula VI:

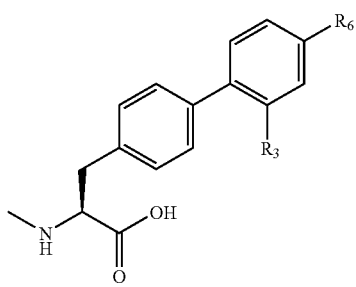

wherein, $R_3$ is selected from the group consisting of alkyl (e.g. methyl, ethyl) and halogen (e.g., fluoro, chloro) and $R_6$ is selected from the group consisting of hydroxyl and methoxy.

$X_{aa11}$ of the first embodiment of Formula I, may also be a compound of Formula VIa:

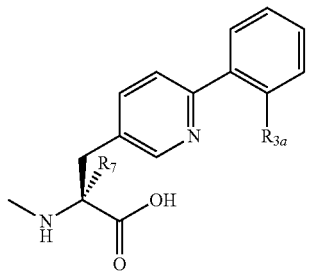

Formula VIa wherein, $R_{3a}$ is selected from the group consisting of methyl, ethyl and fluoro; and wherein $R_7$ is selected from the group consisting of hydrogen and methyl.

$X_{aa11}$ of the first embodiment of Formula I, may also be a compound of Formula VIIa:

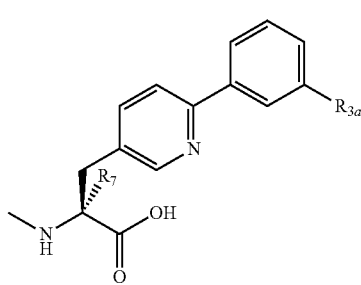

Formula VIIa wherein $R_{3a}$ is methoxy; and wherein $R_7$ is selected from the group consisting of hydrogen and methyl.

In another embodiment, $X_{aa1}$ is selected from the group consisting of L-His, D-His, L-N-Methyl-His, D-N-Methyl-His, L-4-ThiazolylAla, D-4-ThiazolylAla, des-amino-His, des-amino-thiazolylAla, 3-(1H-imidazol-4-yl)-2-methylpropanoyl, (S)-3-(1H-imidazol-4-yl)-2-hydroxypropanoyl (L-β-imidazolelactyl), (S)- or (R)-3-(1H-imidazol-4-yl)-2-methoxypropanoyl (IMeOp), and wherein if a terminal amino group is present, said terminal amino group is optionally substituted with hydrogen, alkyl, dialkyl, acyl, benzoyl, alkyloxycarbonyl (e.g. methyloxycarbonyl), aryloxycarbonyl, aralkyloxycarbonyl, heterocycly-loxycarbonyl, heteroarylalkyloxycarbonyl, alkylcarbamoyl, arylcarbamoyl, aralkylcarbamoyl, heterocyclylsulfonyl, alkylsulfonyl, arylsulfonyl, arylalkylsulfonyl, heteroarylalkylsulfonyl or heteroarylsulfonyl.

$X_{aa2}$ is selected from the group consisting of L-Ala, D-Ala, N-methyl-L-Ala, N-methyl-D-Ala, L-Pro, (S)-α-methyl-L-Pro, (L)-azetidine (Azt), (S)-α-methyl-azetidine (α-Me-Azt) and α-aminoisobutyric (Aib).

$X_{aa3}$ is selected from the group consisting of L-Glu, L-Asp, and L-Gla.

$X_{aa4}$ is Gly.

$X_{aa5}$ is selected from the group consisting of L-Thr, L-Nle, L-Nva, L-Aoc and L-allo-Thr.

$X_{aa6}$ is selected from the group consisting of L-α-Me-Phe, L-α-Et-Phe, L-α-Me-2-fluoroPhe, L-α-Me-3-fluoroPhe, L-α-Me-2,3-di-fluoroPhe, L-(1-Me-2,6-di-fluoroPhe, L-α-Me-Phe(penta-Fluoro), and $X_{aa7}$ is L-Thr or L-allo-threonine.

$X_{aa8}$ is selected from the group consisting of L-Ser, L-His, and L-Asn.

$X_{aa9}$ is L-Asp.

$X_{aa10}$ is a naturally or nonnaturally occurring amino acid of Formula II.

The naturally or nonnaturally occurring amino acid of Formula II is selected from the group consisting of 4-[(4'-methoxy-2'-ethyl)-phenyl]phenylalanine; 4-[(4'-ethoxy-2'-ethyl)phenyl]phenylalanine; 4-[(4'-methoxy-2'-methyl)phenyl]phenylalanine; 4-[(4'-ethoxy-2'-methyl)phenyl]phenylalanine; 4-(2'-ethylphenyl)phenylalanine; 4-(2'-methylphenyl)phenylalanine; 4-[(3',5'-dimethyl)phenyl]phenylalanine, 4-[(3',4'-dimethoxy)phenyl]phenylalanine; 4-[(2'-ethyl-4'-hydroxy)phenyl]phenylalanine;

$X_{aa10}$ is a naturally or nonnaturally occurring amino acid of Formula III.

The naturally or nonnaturally occurring amino acid of Formula III is selected from the group consisting of 4-[2'-(4'-methoxy-6'-ethyl)pyridyl]phenylalanine; 4-[2'-(4'-methoxy-6'-methyl)pyridyl]-4-phenylalanine; 4-[2'-(6'-ethyl)pyridyl]phenylalanine; 4-[2'-(6'-methyl)pyridyl]phenylalanine; 4-[2'-(3',5'-dimethyl)pyridyl]phenylalanine; 4-[2'-(4'-methoxy-6'-ethyl)pyridyl]phenylalanine; 4-[3'-(4'-methoxy-6'-methyl)pyridyl]phenylalanine; 4-[3'-(2'-ethyl)pyridyl]phenylalanine; and 4-[3'(6'-methyl)pyridyl)phenylalanine;

$X_{aa10}$ is a naturally or nonnaturally occurring amino acid of Formula IV.

The naturally or nonnaturally occurring amino acid of Formula IV is selected from the group consisting of 4-[(4'-methoxy-2'-ethyl)phenyl]-3-pyridylalanine; 4-[(4'-methoxy-2'-methyl)phenyl]-3-pyridylalanine; 4-(2'-ethylphenyl)-3-pyridylalanine; 4-(2'-methylphenyl)-3-pyridylalanine; 4-[(3',5'-dimethyl)phenyl]-3-pyridylalanine; and 4-[(2'-ethyl-4'-hydroxy)phenyl]-3-pyridylalanine;

$X_{aa11}$ is a naturally or nonnaturally occurring amino acid of Formula IIa.

The naturally or nonnaturally occurring amino acid of Formula IIa is selected from the group consisting of 4-(2'-methylphenyl)phenylalanine; 4-(2'-fluorophenyl)phenylalanine; and 4-[(3',5'-dimethyl)phenyl]phenylalanine;

$X_{aa11}$ is a naturally or nonnaturally occurring amino acid of Formula IIIa.

The naturally or nonnaturally occurring amino acid of Formula IIIa is selected from the group consisting of 4-[(6'-methyl)-2'-pyridyl]phenylalanine; 4-[(6'-methyl)-3'-pyridyl]phenylalanine; 4-[(6'-ethyl)-2'-pyridyl)]phenylalanine; and 4-[(6'-ethyl)-3'-pyridyl)]phenylalanine;

$X_{aa11}$ is a naturally or nonnaturally occurring amino acid of Formula IVa.

The naturally or nonnaturally occurring amino acid of Formula IVa is selected from the group consisting of 4-(2'-methylphenyl)-3-pyridylalanine; 4-(2'-fluorophenyl)-3-pyridylalanine; 4-[(3',5'-dimethyl)phenyl]-3-pyridylalanine; 4-(4'-trifluoromethylphenyl)-3-pyridylalanine; and 4-(2'-ethylphenyl)-3-pyridylalanine;

and wherein the C-terminal carbonyl carbon of said amino acid is attached to a nitrogen to form a carboxamide ($NH_2$), an alkyl carboxamide ($NHR_1$) or a dialkylcarboxamide ($NR_1R_2$), where each of $R_1$ and $R_2$ is an alkyl or arylalkyl group.

In another aspect, $X_{aa1}$ is an amino acid selected from the group consisting of L-His, D-His, L-N-Methyl-His, D-N-Methyl-His, L-4-ThiazolylAla, D-4-ThiazolylAla, des-amino-His, des-amino-thiazolylAla, 3-(1H-imidazol-4-yl)-2-methylpropanoyl, (S)-3-(1H-imidazol-4-yl)-2-hydroxypropanoyl (L-β-imidazolelactyl), and (S)- or (R)-3-(1H-imidazol-4-yl)-2-methoxypropanoyl (IMeOp);

wherein if a terminal amino group is present, said terminal amino group is optionally substituted with hydrogen, alkyl, acyl, benzoyl, alkyloxycarbonyl (e.g. methyloxycarbonyl), aryloxycarbonyl, aralkyloxycarbonyl, heterocyclyloxycarbonyl, heteroarylalkyloxycarbonyl, alkylcarbamoyl, arylcarbamoyl, aralkylcarbamoyl, heterocyclylsulfonyl, alkylsulfonyl, arylsulfonyl, arylalkylsulfonyl, heteroarylalkylsulfonyl or heteroarylsulfonyl;

$X_{aa2}$ is an amino acid selected from the group consisting of L-Alanine, D-Alanine, N-methyl-L-Alanine, N-methyl-D-Alanine, L-Proline, (S)-α-methyl-Proline, (L)-azetidine (Azt), (S)-α-methyl-azetidine (α-Me-Azt) and α-aminoisobutyric (Aib);

$X_{aa3}$ is an amino acid selected from the group consisting of L-Glu, L-Asp, and L-Gla;

$X_{aa4}$ is Gly;

$X_{aa5}$ is an amino acid selected from the group consisting of L-Thr, L-Nle, L-Nva, L-Aoc and L-allo-Thr;

$X_{aa6}$ is an amino acid selected from the group consisting of L-α-Me-Phe, L-α-Et-Phe, L-α-Me-2-fluoroPhe, L-α-Me-3-fluoroPhe, L-α-Me-2,3-di-fluoroPhe, L-α-Me-2,6-di-fluoroPhe, and L-α-Me-Phe (penta-Fluoro);

$X_{aa7}$ is an amino acid selected from the group consisting of L-Thr and L-allo-threonine;

$X_{aa8}$ is an amino acid selected from the group consisting of L-Ser, L-His, and L-Asn;

$X_{aa9}$ is L-Asp;

$X_{aa10}$ is a naturally or nonnaturally occurring amino acid selected from the group consisting of amino acids of Formulas II, III, IV, and V;

wherein Formula II is an amino acid selected from the group consisting of 4-[(2'-ethyl-4'-hydroxy)phenyl]phenylalanine; 4-[(4'-methoxy-2'-ethyl)phenyl]phenylalanine; 4-[(4'-methoxy-2'-methyl)phenyl]phenylalanine; 4-(2'-ethylphenyl)phenylalanine; 4-(2'-methylphenyl)phenylalanine; 4-[(3',5'-dimethyl)phenyl]phenylalanine, and 4-[(3',4'-dimethoxy)phenyl]phenylalanine;

wherein Formula III is an amino acid selected from the group consisting of 4-[2'-(4'-methoxy-6'-ethyl)pyridyl]phenylalanine; 4-[2'-(4'-methoxy-6'-methyl)pyridyl]-4-phenylalanine; 4-[2'-(6'-ethyl)pyridyl]phenylalanine; 4-[2'-(6'-methyl)pyridyl]phenylalanine; 4-[2'-(3',5'-dimethyl)pyridyl]phenylalanine; 4-[2'-(4'-methoxy-6'-ethyl)pyridyl]phenylalanine; 4-[3'-(4'-methoxy-6'-methyl)pyridyl]phenylalanine; 4-[3'-(2'-ethyl)pyridyl]phenylalanine; and 4-[3'-(6'-methyl)pyridyl)phenylalanine;

wherein Formula IV is an amino acid selected from the group consisting of 4-[(2'-ethyl-4'-hydroxy)phenyl]-3-pyridylalanine, 4-[(4'-methoxy-2'-ethyl)phenyl]-3-pyridylalanine; 4-[(4'-methoxy-2'-methyl)phenyl]-3-pyridylalanine; 4-(2'-ethylphenyl)-3-pyridylalanine; 4-(2'-methylphenyl)-3-pyridylalanine; and 4-[(3',5'-dimethyl)phenyl]-3-pyridylalanine;

and $X_{aa11}$ is a naturally or nonnaturally occurring amino acid selected from the group consisting amino acids of Formulas IIa, IIIa, and IVa;

wherein Formula IIa is an amino acid selected from the group consisting of 4-(2'-methylphenyl)phenylalanine; 4-(2'-fluorophenyl)phenylalanine; and 4-[(3',5'-dimethyl)phenyl]phenylalanine;

wherein Formula IIIa is an amino acid selected from the group consisting of 4-[2'-(6'-methyl)pyridyl]phenylalanine; 4-[2'-(6'-methyl)pyridyl]phenylalanine; 4-[2'-(6'-ethyl)pyridyl]phenylalanine; and 4-[3'-(6'-ethyl)pyridyl]phenylalanine;

wherein Formula IVa is an amino acid selected from the group consisting of 4-(2'-methylphenyl)-3-pyridylalanine; 4-(2'-fluorophenyl)-3-pyridylalanine; 4-[(3',5'-dimethyl phenyl]-3-pyridylalanine; 4-(4'-trifluoromethylphenyl)-3-pyridylalanine; and 4-(2'-ethylphenyl)-3-pyridylalanine;

wherein $X_{aa11}$ is not an amino acid of formula IIa when $X_{aa10}$ is an amino acid of Formula II;

wherein the C-terminal carbonyl carbon is attached to a nitrogen to form a carboxamide ($NH_2$), an alkyl carboxamide ($NHR_1$), or a dialkylcarboxamide ($NR_1R_2$), where each of $R_1$ and $R_2$ is an alkyl or arylalkyl group; and wherein $X_{aa10}$ and $X_{aa11}$ are not both simultaneously an amino acid of Formula Other embodiments include isolated polypeptides comprising any of the following sequences:

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-$NH_2$ |
|---|---|---|---|---|---|---|---|---|---|---|---|
| 1. | H | Aib | E | G | T | L-α-Me-Phe(2-Fluoro) | T | S | D | Bip(2'-Me) | 4-(2'-pyridyl)Phenylalanine-$NH_2$ |
| 2. | H | Aib | E | G | T | L-α-Me-Phe(2-Fluoro) | T | S | D | Bip(3',5'-di-Me) | 4-(2'-pyridyl)Phenylalanine-$NH_2$ |
| 3. | H | Aib | E | G | T | L-α-Me-Phe(2-Fluoro) | T | S | D | Bip(2'-OBu) | 4-(2'-pyridyl)Phenylalanine-$NH_2$ |
| 4. | H | Aib | E | G | T | L-α-Me-Phe(2-Fluoro) | T | S | D | Bip(2'-Me) | 4-(4'-pyridyl)Phenylalanine-$NH_2$ |
| 5. | H | Aib | E | G | T | L-α-Me-Phe(2-Fluoro) | T | S | D | Bip(2'-Cl) | 4-(4'-pyridyl)Phenylalanine-$NH_2$ |
| 6. | H | Aib | E | G | T | L-α-Me-Phe(2-Fluoro) | T | S | D | Bip(2'-methoxy-5'-iso-propyl) | 4-(4'-pyridyl)Phenylalanine-$NH_2$ |
| 7. | H | Aib | E | G | T | L-α-Me-Phe(2-Fluoro) | T | S | D | 4-(2'-Ethylphenyl)-3-pyridylalanine | Bip(2'-Me)—$NH_2$ |
| 8. | H | Aib | E | G | T | L-α-Me-Phe(2-Fluoro) | T | S | D | 4-[(2'-Ethyl-4'-methoxy)phenyl]-3-pyridylalanine | Bip(2'-Me)—$NH_2$ |
| 9. | H | Aib | E | G | T | L-α-Me-Phe(2-Fluoro) | T | S | D | Bip(2'-Et-4'-OMe) | 4-(2'-Methylphenyl)-3-pyridylalanine-$NH_2$ |
| 10. | H | Aib | E | G | T | L-α-Me-Phe(2,6-di-Fluoro) | T | S | D | Bip(2'-Et-4'-OMe) | 4-(2'-Methylphenyl)-3-pyridylalanine-$NH_2$ |
| 11. | Des-$NH_2$-His | Aib | E | G | T | L-α-Me-Phe(2-Fluoro) | T | S | D | Bip(2'-Et-4'-OMe) | 4-(2'-Methylphenyl)-3-pyridylalanine-$NH_2$ |
| 12. | Des-$NH_2$-His | Aib | E | G | T | L-α-Me-Phe(2,6-di-Fluoro) | T | S | D | Bip(2'-Et-4'-OMe) | 4-(2'-Methylphenyl)-3-pyridylalanine-$NH_2$ |
| 13. | H | Aib | E | G | T | L-α-Me-Phe(2-Fluoro) | T | S | D | 4-(2'-ethylphenyl)-3-pyridylalanine | 4-(2'-Methylphenyl)-3-pyridylalanine-$NH_2$ |
| 14. | H | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-$NH_2$ |
| 15. | H | Aib | E | G | T | L-α-Me-Phe(2-Fluoro) | T | S | D | Bip(2'-Et-4'-OMe) | 4-[3-(4-Methyl)pyridyl]phenylalanine-$NH_2$ |
| 16. | H | Aib | E | G | T | L-α-Me-Phe(2,6-di-Fluoro) | T | S | D | Bip(2'-Et-4'-OMe) | 4-[3-(4-Methyl)pyridyl]phenylalanine-$NH_2$ |

-continued

| SEQ ID No. | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| 17. | H | Aib | E | G | T | L-α-Me-Phe(2-Fluoro) | T | S | D | Bip(2'-Et-4'-OMe) | 4-(3-Pyridazyl)phenylalanine-NH2 |
| 18. | H | Aib | E | G | T | L-α-Me-Phe(2,6-di-Fluoro) | T | S | D | Bip(2'-Et-4'-OMe) | 4-(3-Pyridazyl)phenylalanine-NH2 |
| 19. | H | Aib | E | G | T | L-α-Me-Phe(2-Fluoro) | T | S | D | Bip(2'-Et-4'-OMe) | 4-[3-(4-Me,6-OMe)pyridyl]phenylalanine-NH2 |
| 20. | H | Aib | E | G | T | L-α-Me-Phe(2,6-di-Fluoro) | T | S | D | 4-[3-(4'-Methyl)pyridyl]phenylalanine | Bip(2'-Me)—NH2 |
| 21. | H | Aib | E | G | T | L-α-Me-Phe(2-Fluoro) | T | S | D | 4-[(4'-Me-6'-OMe)-3-pyridyl]phenylalanine | Bip(2'-Me)—NH2 |
| 22. | H | Aib | E | G | T | L-α-Me-Phe(2,6-di-Fluoro) | T | S | D | 4-[(4'-Me-6'-OMe)-3-pyridyl]phenylalanine | Bip(2'-Me)—NH2 |
| 23. | H | Aib | E | G | T | L-α-Me-Phe(2,6-di-Fluoro) | T | S | D | Bip(2'-Et-4'-OMe) | 4-[2(1H)Pyridonyl]phenylalanine-NH2 |
| 24. | H | Aib | E | G | T | L-α-Me-Phe(2-Fluoro) | T | S | D | Bip(2'-Et-4'-OMe) | Bip(8-Quinoline)-NH2 |
| 25. | H | Aib | E | G | T | L-α-Me-Phe(2-Fluoro) | T | S | D | Bip(2'-Et-4'-OMe) | Bip(3-Quinoline)-NH2 |
| 26. | H | Aib | E | G | T | L-α-Me-Phe(2-Fluoro) | T | S | D | Bip(2'-Et-4'-OMe) | Bip(6-Quinoline)-NH2 |
| 27. | H | Aib | E | G | T | L-α-Me-Phe(2-Fluoro) | T | S | D | Bip(2'-Et-4'-OMe) | Bip(5-Quinoline)-NH2 |
| 28. | H | Aib | E | G | T | L-α-Me-Phe(2-Fluoro) | T | S | D | Bip(2'-Et-4'-OMe) | 4-(3-(6-OMe)pyridyl)phenylalanine-NH2 |
| 29. | H | Aib | E | G | T | L-α-Me-Phe(2-Fluoro) | T | S | D | Bip(2'-Et-4'-OMe) | 4-(3-(2-Methoxy)pyridyl)phenylalanine-NH2 |
| 30. | H | Aib | E | G | T | L-α-Me-Phe(2-Fluoro) | T | S | D | Bip(2'-Et-4'-OMe) | 4-(3'-pyridyl)phenylalanine-NH2 |
| 31. | Des-NH2-His | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-NH2 |
| 32. | H | Aib | E | G | T | L-α-Me-Phe(2-Fluoro) | T | S | D | 4-(5-Quinoline)phenylalanine | Bip(2'-Me)—NH2 |
| 33. | H | Aib | E | G | T | L-α-Me-Phe(2-Fluoro) | T | S | D | 4-[3-(2'-OMe)pyridyl]phenylalanine | Bip(2'-Me)—NH2 |
| 34. | H | Aib | E | G | T | L-α-Me-Phe(2-Fluoro) | T | S | D | 4-(6-Quinoline)phenylalanine | Bip(2'-Me)—NH2 |
| 35. | H | Aib | E | G | T | L-α-Me-Phe(2-Fluoro) | T | S | D | 4-(4'-pyridyl)phenylalanine | Bip(2'-Me)—NH2 |
| 36. | H | Aib | E | G | T | L-α-Me-Phe(2-Fluoro) | T | S | D | 4-[4'-(3',5'-dimethylisoxazole)]phenylalanine | Bip(2'-Me)—NH2 |
| 37. | H | Aib | E | G | T | L-α-Me-Phe(2-Fluoro) | T | S | D | Bip(2'-Et-4'-OMe) | 4-(2-trifluoromethylphenyl)-3-pyridylalanine-NH2 |
| 38. | H | Aib | E | G | T | L-α-Me-Phe(2-Fluoro) | T | S | D | Bip(2'-Et-4'-OMe) | 4-(2-methyl-5-fluorophenyl)-3-pyridylalanine-NH2 |

-continued

| SEQ ID No. | X_{aa1} | X_{aa2} | X_{aa3} | X_{aa4} | X_{aa5} | X_{aa6} | X_{aa7} | X_{aa8} | X_{aa9} | X_{aa10} | X_{aa11}-NH$_2$ |
|---|---|---|---|---|---|---|---|---|---|---|---|
| 39. | H | Aib | E | G | T | L-α-Me-Phe(2-Fluoro) | T | S | D | Bip(2'-Et-4'-OMe) | 4-(4-methanesulfonylphenyl)-3-pyridylalanine-NH$_2$ |
| 40. | H | Aib | E | G | T | L-α-Me-Phe | T | S | D | Bip(2'-Et-4'-OMe) | 4-(2'-Methylphenyl)-3-pyridylalanine-NH$_2$ |
| 41. | H | Aib | E | G | T | L-α-Me-Phe(2-Fluoro) | T | S | D | Bip(2'-Et) | 4-(2'-Methylphenyl)-3-pyridylalanine-NH$_2$ |
| 42. | H | Aib | E | G | Nle | L-α-Me-Phe(2-Fluoro) | T | S | D | Bip(2'-Et-4'-OMe) | 4-(2'-Methylphenyl)-3-pyridylalanine-NH$_2$ |
| 43. | H | Aib | E | G | T | L-α-Me-Phe(2-Fluoro) | T | S | D | Bip(2'-Et-4'-OMe) | 4-[(2'-Cl, 4'-CF3)-3'-pyridyl]phenylalanine-NH$_2$ |
| 44. | H | Aib | E | G | T | L-α-Me-Phe(2,6-di-Fluoro) | T | S | D | Bip(2'-Et-4'-OMe) | 4-[3'-(2'-CN-6'-Me)pyridyl]phenylalanine-NH$_2$ |
| 45. | H | Aib | E | G | T | L-α-Me-Phe(2,6-di-Fluoro) | T | S | D | Bip(2'-Cl) | 4-(2'-Methylphenyl)-3-pyridylalanine-NH$_2$ |
| 46. | H | Aib | E | G | T | L-α-Me-Phe(2,6-di-Fluoro) | T | S | D | Bip(2',4'-di-OMe) | 4-(2'-Methylphenyl)-3-pyridylalanine-NH$_2$ |
| 47. | H | Aib | E | G | T | L-α-Me-Phe(2,6-di-Fluoro) | T | S | D | 4-(3'-pyridyl)phenylalanine | 4-(2'-Methylphenyl)-3-pyridylalanine-NH$_2$ |
| 48. | H | Aib | E | G | T | L-α-Me-Phe(2,6-di-Fluoro) | T | S | D | 4-(4'-pyridyl)phenylalanine | 4-(2'-Methylphenyl)-3-pyridylalanine-NH$_2$ |
| 49. | H | Aib | E | G | T | L-α-Me-Phe(2,6-di-Fluoro) | T | S | D | Bip(2'-Me-3'-F) | 4-(2'-Methylphenyl)-3-pyridylalanine-NH$_2$ |
| 50. | H | Aib | E | G | T | L-α-Me-Phe(2-Fluoro) | T | S | D | Bip(2'-F) | 4-(2'-Methylphenyl)-3-pyridylalanine-NH$_2$ |
| 51. | H | Aib | E | G | T | L-α-Me-Phe(2,6-di-Fluoro) | T | S | D | 4-[3'-(2'-Cl-6'-CF3)pyridyl]phenylalanine | 4-(2'-Methylphenyl)-3-pyridylalanine-NH$_2$ |
| 52. | H | Aib | E | G | T | L-α-Me-Phe(2,6-di-Fluoro) | T | S | D | 4-(2'-ethylphenyl)-3-pyridylalanine | Bip(2'-Cl)—NH$_2$ |
| 53. | H | Aib | E | G | T | L-α-Me-Phe(2,6-di-Fluoro) | T | S | D | 4-(2'-ethylphenyl)-3-pyridylalanine | Bip(3'-Cl-4'-F)—NH$_2$ |
| 54. | H | Aib | E | G | Nva | L-α-Me-Phe(2-Fluoro) | T | S | D | Bip(2'-Et-4'-OMe) | 4-(2'-Methylphenyl)-3-pyridylalanine-NH$_2$ |
| 55. | H | Aib | E | G | T | L-α-Me-Phe(2,6-di-Fluoro) | T | S | D | 4-(2'-ethylphenyl)-3-pyridylalanine | Bip(3',5'-di-Me)—NH$_2$ |

-continued

| SEQ ID No. | X<sub>aa1</sub> | X<sub>aa2</sub> | X<sub>aa3</sub> | X<sub>aa4</sub> | X<sub>aa5</sub> | X<sub>aa6</sub> | X<sub>aa7</sub> | X<sub>aa8</sub> | X<sub>aa9</sub> | X<sub>aa10</sub> | X<sub>aa11</sub>-NH$_2$ |
|---|---|---|---|---|---|---|---|---|---|---|---|
| 56. | H | Aib | E | G | T | L-α-Me-Phe(2,6-di-Fluoro) | T | S | D | 4-(2'-ethylphenyl)-3-pyridylalanine | 4-(2',3'-pyridazyl)phenylalanine-NH$_2$ |
| 57. | H | Aib | E | G | T | L-α-Me-Phe(2-Fluoro) | T | S | D | Bip(2'-Et-4'-OMe) | 4-(2'-ethylphenyl)-3-pyridylalanine-NH$_2$ |
| 58. | H | Aib | E | G | T | L-α-Me-Phe(2,6-di-Fluoro) | T | S | D | 4-(2'-ethylphenyl)-3-pyridylalanine | 4-[3'-(2'-Cl-6'-CF3)pyridyl]phenylalanine-NH$_2$ |
| 59. | H | Aib | E | G | T | L-α-Me-Phe(2,6-di-Fluoro) | T | S | D | 4-(2'-ethylphenyl)-3-pyridylalanine | 4-[3'-(2'-CN-6'-Me)pyridyl]phenylalanine-NH$_2$ |
| 60. | H | Aib | E | G | T | L-α-Me-Phe(2,6-di-Fluoro) | T | S | D | 4-[3'-(4'-Me)pyridyl]phenylalanine | Bip(2'-Cl)—NH$_2$ |
| 61. | H | Aib | E | G | T | L-α-Me-Phe(2,6-di-Fluoro) | T | S | D | 4-[3'-(4'-Me)pyridyl]phenylalanine | Bip(3'-Cl-4'-F)—NH$_2$ |
| 62. | H | Aib | E | G | T | L-α-Me-Phe(2,6-di-Fluoro) | T | S | D | 4-[3'-(4'-Me)pyridyl]phenylalanine | Bip(3',5'-di-Me)—NH$_2$ |
| 63. | H | Aib | E | G | T | L-α-Me-Phe(2,6-di-Fluoro) | T | S | D | 4-[3'-(4'-Me)pyridyl]phenylalanine | Bip(2'-Me-4'-OMe)—NH$_2$ |
| 64. | H | Aib | E | G | T | L-α-Me-Phe(2,6-di-Fluoro) | T | S | D | 4-[3'-(4'-Me)pyridyl]phenylalanine | Bip(2'-Me-3'-F)—NH$_2$ |
| 65. | H | Aib | E | G | T | L-α-Me-Phe(2,6-di-Fluoro) | T | S | D | 4-[3'-(4'-Me)pyridyl]phenylalanine | Bip(2'-F)—NH$_2$ |
| 66. | H | Aib | E | G | T | L-α-Me-Phe(2,6-di-Fluoro) | T | S | D | 4-[(4'-Me-6'-OMe)-3-pyridyl]phenylalanine | Bip(2'-Cl)—NH$_2$ |
| 67. | H | Aib | E | G | T | L-α-Me-Phe(2,6-di-Fluoro) | T | S | D | 4-[(4'-Me-6'-OMe)-3-pyridyl]phenylalanine | Bip(3',4'-di-OMe)—NH$_2$ |
| 68. | H | Aib | E | G | T | L-α-Me-Phe(2,6-di-Fluoro) | T | S | D | 4-[(4'-Me-6'-OMe)-3-pyridyl]phenylalanine | 4-(2'-pyridyl)phenylalanine-NH$_2$ |
| 69. | H | Aib | E | G | T | L-α-Me-Phe(2,6-di-Fluoro) | T | S | D | 4-[(4'-Me-6'-OMe)-3-pyridyl]phenylalanine | Bip(2'-Me-4'-OMe)—NH$_2$ |
| 70. | H | Aib | E | G | T | L-α-Me-Phe(2,6-di-Fluoro) | T | S | D | 4-[(4'-Me-6'-OMe)-3-pyridyl]phenylalanine | 4-(2'-Methylphenyl)-3-pyridylalanine-NH$_2$ |
| 71. | H | Aib | E | G | T | L-α-Me-Phe(2,6-di-Fluoro) | T | S | D | Bip(2'-Et) | 4-(2'-ethylphenyl)-3-pyridylalanine-NH$_2$ |
| 72. | H | Aib | E | G | T | L-α-Me-Phe(2,6-di-Fluoro) | T | S | D | 4-[3'-(4'-Methyl)pyridyl]phenylalanine | 4-(2'-Methylphenyl)-3-pyridylalanine-NH$_2$ |
| 73. | H | Aib | E | G | T | L-α-Me-Phe(2,6-di-Fluoro) | T | S | D | Bip(2'-Et-4'-OMe) | 4-(4'-pyridyl)-phenylalanine-NH$_2$ |
| 74. | H | Aib | E | G | T | L-α-Me-Phe(2-Fluoro) | T | S | D | Bip(2'-Et-4'-OMe) | 4-(3'-quinoline)phenylalanine-NH$_2$ |
| 75. | H | Aib | E | G | T | L-α-Me-Phe(2-Fluoro) | T | S | D | Bip(2'-Et-4'-OMe) | 4-(3'-(2'-Methoxy)pyridyl)phenylalanine-NH$_2$ |
| 76. | H | Aib | E | G | T | L-α-Me-Phe(2-Fluoro) | T | S | D | Bip(2'-Et-4'-OMe) | 4-phenyl-3-pyridylalanine-NH$_2$ |
| 77. | H | Aib | E | G | T | L-α-Me-Phe(2-Fluoro) | T | S | D | Bip(2'-Et-4'-OMe) | 4-(3',5'-dimethylphenyl)-3-pyridylalanine-NH$_2$ |

-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 78. | H | Aib | E | G | T | L-α-Me-Phe(2-Fluoro) | T | S | D | Bip(2'-Et-4'-OMe) | 4-[(3'-chloro-4'-fluoro)phenyl]-3-pyridylalanine-NH$_2$ |
| 79. | H | Aib | E | G | T | L-α-Me-Phe(2-Fluoro) | T | S | D | Bip(2'-Et-4'-OMe) | 4-[(3',4'-dimethoxy)phenyl]-3-pyridylalanine-NH$_2$ |
| 80. | H | Aib | E | G | T | L-α-Me-Phe(2-Fluoro) | T | S | D | Bip(2'-Et-4'-OMe) | 4-[(2'-ethyl-4'-methoxy)phenyl]-3-pyridylalanine-NH$_2$ |
| 81. | L-β-Imidazole-lactyl | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 82. | H | Aib | E | G | T | L-α-Me-Phe(2-Fluoro) | T | S | D | Bip(2'-Et-4'-OMe) | 2-(5-o-Tolyl)thienylalanine-NH$_2$ |
| 83. | H | Aib | E | G | T | L-α-Me-Phe(2-Fluoro) | T | S | D | Bip(2'-Et-4'-OMe) | 2-[(5-(3'-Methoxy)phenyl]thienylalanine-NH$_2$ |
| 84. | H | Aib | E | G | T | L-α-Me-Phe(2-Fluoro) | T | S | D | Bip(2'-Et-4'-OMe) | 2-[(5-(3',5'-di-Methyl)phenyl]thienylalanine-NH$_2$ |
| 85. | H | Aib | E | G | T | L-α-Me-Phe(2-Fluoro) | T | S | D | Bip(2'-Et-4'-OMe) | 2-[(5-(3'-Cl,5'-F)phenyl]thienylalanine-NH$_2$ |
| 86. | H | Aib | E | G | T | L-α-Me-Phe(2-Fluoro) | T | S | D | Bip(2'-Et-4'-OMe) | 4-(3'-Isopropoxyphenyl)-3-pyridylalanine-NH$_2$ |
| 87. | H | Aib | E | G | T | L-α-Me-Phe(2-Fluoro) | T | S | D | Bip(2'-Et-4'-OMe) | 4-(2'-Methyl, 5'-Fluoro)phenyl)-3-pyridylalanine-NH$_2$ |
| 88. | H | Aib | E | G | T | L-α-Me-Phe(2-Fluoro) | T | S | D | Bip(2'-Et-4'-OMe) | 4-(2'-Isopropoxyphenyl)-3-pyridylalanine-NH$_2$ |
| 89. | H | Aib | E | G | T | L-α-Me-Phe(2-Fluoro) | T | S | D | Bip(2'-Et-4'-OMe) | 3-(4-Br)pyridylalanine-NH$_2$ |
| 90. | H | Aib | E | G | T | L-α-Me-Phe(2-Fluoro) | T | S | D | Bip(2'-Et-4'-OMe) | 4-(4'-Methoxyphenyl)-3-pyridylalanine-NH$_2$ |
| 91. | H | Aib | E | G | T | L-α-Me-Phe(2-Fluoro) | T | S | D | Bip(2'-Et-4'-OMe) | 4-(2'-Methyl, 4'-Fluoro)phenyl)-3-pyridylalanine-NH$_2$ |
| 92. | H | Aib | E | G | T | L-α-Me-Phe(2-Fluoro) | T | S | D | Bip(2'-Et) | 4-(2'-Methylphenyl)-3-pyridylalanine-NH$_2$ |
| 93. | H | Aib | E | G | T | L-α-Me-Phe(2-Fluoro) | T | S | D | Bip(2'-Et-4'-OMe) | 4-(2'-Trifluoromethoxyphenyl)-3-pyridylalanine-NH$_2$ |

-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 94. | H | Aib | E | G | T | L-α-Me-Phe(2-Fluoro) | T | S | D | Bip(2'-Et-4'-OMe) | 4-(4'-Trifluoromethoxyphenyl)-3-pyridylalanine-NH$_2$ |
| 95. | H | Aib | E | G | T | L-α-Me-Phe(2-Fluoro) | T | S | D | Bip(2'-Et-4'-OMe) | 3-pyridylalanine-NH$_2$ |
| 96. | H | Aib | E | G | T | L-α-Me-Phe(2-Fluoro) | T | S | D | Bip(2'-Et-4'-OMe) | 4-(2'-Methyl, 4'-Chloro)phenyl)-3-pyridylalanine-NH$_2$ |
| 97. | H | Aib | E | G | T | L-α-Me-Phe(2-Fluoro) | T | S | D | Bip(2'-Me-4'-OMe) | 4-(2'-Methylphenyl)-3-pyridylalanine-NH$_2$ |
| 98. | H | Aib | E | G | T | L-α-Me-Phe(2-Fluoro) | T | S | D | Bip(2'-Et-4'-OMe) | 4-(3'-Trifluoromethylphenyl)-3-pyridylalanine-NH$_2$ |
| 99. | H | Aib | E | G | T | L-α-Me-Phe(2-Fluoro) | T | S | D | Bip(2'-Et-4'-OMe) | 4-(4'-Fluorophenyl)-3-pyridylalanine-NH$_2$ |
| 100. | H | Aib | E | G | T | L-α-Me-Phe(2-Fluoro) | T | S | D | Bip(2'-Et-4'-OMe) | 4-(2'-Trifluoromethylphenyl)-3-pyridylalanine-NH$_2$ |
| 101. | H | Aib | E | G | T | L-α-Me-Phe(2-Fluoro) | T | S | D | Bip(2'-Et-4'-OMe) | 4-(2'-Chlorophenyl)-3-pyridylalanine-NH$_2$ |
| 102. | H | Aib | E | G | T | L-α-Me-Phe(2-Fluoro) | T | S | D | Bip(2'-Et-4'-OMe) | 4-(3'-Chlorophenyl)-3-pyridylalanine-NH$_2$ |
| 103. | H | Aib | E | G | T | L-α-Me-Phe(2-Fluoro) | T | S | D | Bip(2'-Et-4'-OMe) | 4-(4'-Isopropylphenyl)-3-pyridylalanine-NH$_2$ |
| 104. | H | Aib | E | G | T | L-α-Me-Phe(2-Fluoro) | T | S | D | Bip(2'-Et-4'-OMe) | 4-(3',5'-dimethylisoxazol-4'-yl)-3-pyridylalanine-NH$_2$ |
| 105. | H | Aib | E | G | T | L-α-Me-Phe(2-Fluoro) | T | S | D | Bip(2'-Et-4'-OMe) | 4-[(2'-Methyl-4'-methoxy)phenyl]-3-pyridylalanine-NH$_2$ |
| 106. | H | Aib | E | G | T | L-α-Me-Phe(2-Fluoro) | T | S | D | Bip(2'-Et-4'-OMe) | 4-(4'-Trifluoromethylphenyl)-3-pyridylalanine-NH$_2$ |
| 107. | H | Aib | E | G | T | L-α-Me-Phe(2-Fluoro) | T | S | D | Bip(2'-Et-4'-OMe) | 4-(4'-Chlorophenyl)-3-pyridylalanine-NH$_2$ |
| 108. | H | Aib | E | G | T | L-α-Me-Phe(2-Fluoro) | T | S | D | Bip(2'-Et-4'-OMe) | 4-(4'-Pyridyl)-3-pyridylalanine-NH$_2$ |

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-$NH_2$ |
|---|---|---|---|---|---|---|---|---|---|---|---|
| 109. | H | Aib | E | G | T | L-α-Me-Phe(2-Fluoro) | T | S | D | Bip(2'-Et-4'-OMe) | 4-(3'-Methoxyphenyl)-3-pyridylalanine-NH₂ |
| 110. | H | Aib | E | G | T | L-α-Me-Phe(2-Fluoro) | T | S | D | Bip(2'-Et-4'-OMe) | 4-(6'-Methoxypyridin-3'-yl)-3-pyridylalanine-NH₂ |
| 111. | H | Aib | E | G | T | L-α-Me-Phe(2-Fluoro) | T | S | D | Bip(2'-Et-4'-OMe) | 4-(2'-Isopropylphenyl)-3-pyridylalanine-NH₂ |
| 112. | H | Aib | E | G | T | L-α-Me-Phe(2-Fluoro) | T | S | D | Bip(2'-Et-4'-OMe) | 4-(2'-Methoxyphenyl)-3-pyridylalanine-NH₂ |
| 113. | H | Aib | E | G | T | L-α-Me-Phe(2-Fluoro) | T | S | D | Bip(2'-Et-4'-OMe) | 4-[(3',5'-di-Fluoro-2'-methoxy)phenyl]-3-pyridylalanine-NH₂ |
| 114. | H | Aib | E | G | T | L-α-Me-Phe(2-Fluoro) | T | S | D | Bip(2'-Et-4'-OMe) | 4-(3'-methylphenyl)-3-pyridylalanine-NH₂ |
| 115. | H | Aib | E | G | T | L-α-Me-Phe(2-Fluoro) | T | S | D | Bip(2'-Et-4'-OMe) | 4-(2'-fluorophenyl)-3-pyridylalanine-NH₂ |
| 116. | H | Aib | E | G | T | L-α-Me-Phe(2,6-di-Fluoro) | T | S | D | Bip(2'-Et-4'-OMe) | 4-(2'-fluorophenyl)-3-pyridylalanine-NH₂ |
| 117. | H | Aib | E | G | T | L-α-Me-Phe(2,6-di-Fluoro) | T | S | D | Bip(2'-Et-4'-OMe) | 4-(3'-Methoxyphenyl)-3-pyridylalanine-NH₂ |
| 118. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH₂ |
| 119. | H | N-Me-(D)-Ala | E | G | T | L-α-Me-Phe(2-Fluoro) | T | S | D | Bip(2'-Et-4'-OMe) | 4-(2'-Methylphenyl)-3-pyridylalanine-NH₂ |
| 120. | H | (S)-α-Me-Pro | E | G | T | L-α-Me-Phe(2-Fluoro) | T | H | D | Bip(2'-Et-4'-OMe) | 4-(2'-Methylphenyl)-3-pyridylalanine-NH₂ |
| 121. | H | (S)-α-Me-Pro | E | G | T | L-α-Me-Phe(2-Fluoro) | T | S | D | Bip(2'-Et-4'-OMe) | (S)-4-(2'-Methylphenyl)-α-Me-3-pyridylalanine-NH₂ |
| 122. | H | Aib | E | G | T | L-α-Me-Phe(2-Fluoro) | T | S | D | Bip(2'-Et-4'-OMe) | (S)-4-(2'-Methylphenyl)-α-Me-3-pyridylalanine-NH₂ |
| 123. | H | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH₂ |

-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-$NH_2$ |
|---|---|---|---|---|---|---|---|---|---|---|---|
| 124. | H | (S)-α-Me-Pro | E | G | T | L-α-Me-Phe(2,6-di-Fluoro) | T | H | D | Bip(2'-Et-4'-OMe) | 4-(2'-Methylphenyl)-3-pyridylalanine-$NH_2$ |
| 125. | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-$NH_2$ |
| 126. | H | (S)-α-Me-Pro | E | G | T | L-α-Me-Phe(2,6-di-Fluoro) | T | S | D | Bip(2'-Et-4'-OMe) | 4-(3'-Methoxyphenyl)-3-pyridylalanine-$NH_2$ |
| 127. | H | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-$NH_2$ |
| 128. | H | (S)-α-Me-Pro | E | G | T | L-α-Me-Phe(2,6-di-Fluoro) | T | S | D | Bip(2'-Et-4'-OMe) | 4-(2'-Fluorophenyl)-3-pyridylalanine-$NH_2$ |
| 129. | H | N-Me-(L)-Ala | E | G | T | L-α-Me-Phe(2-Fluoro) | T | S | D | Bip(2'-Et-4'-OMe) | 4-(2'-Methylphenyl)-3-pyridylalanine-$NH_2$ |
| 130. | H | Aib | E | G | T | L-α-Me-Phe(2-Fluoro) | T | S | D | Bip(2'-Et-4'-OMe) | 4-(2'-Methylphenyl)-3,5-pyrimidylalanine-$NH_2$ |
| 131. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-$NH_2$ |
| 132. | H | (S)-α-Me-Pro | E | G | T | L-α-Me-Phe(2-Fluoro) | T | S | D | Bip(2'-Et) | 4-(2'-Ethylphenyl)-3-pyridylalanine-$NH_2$ |
| 133. | Des-$NH_2$-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-$NH_2$ |
| 134. | Des-$NH_2$-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-$NH_2$ |
| 135. | Des-$NH_2$-His | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-$NH_2$ |
| 136. | Des-$NH_2$-His | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-$NH_2$ |
| 137. | (R)-Imp | Aib | E | G | T | L-α-Me-Phe(2-Fluoro) | T | S | D | Bip(2'-Et-4'-OMe) | 4-(2'-Methylphenyl)-3-pyridylalanine-$NH_2$ |
| 138. | (S)-Imp | Aib | E | G | T | L-α-Me-Phe(2-Fluoro) | T | S | D | Bip(2'-Et-4'-OMe) | 4-(2'-Methylphenyl)-3-pyridylalanine-$NH_2$ |

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH$_2$ |
|---|---|---|---|---|---|---|---|---|---|---|---|
| 139. | CH3O—CO-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 140. | CH3O—CO-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 141. | CH3O—CO-His | N-Me-(D)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 142. | CH3O—CO-His | N-Me-(D)-Ala | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 143. | CH3SO2-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 144. | CH3SO2-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 145. | L-Lactyl-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 146. | L-Lactyl-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 147. | H | Aib | E | G | T | L-α-Me-Phe(2-Fluoro) | T | S | D | Bip(2'-Et-4'-OMe) | 4-(3',5'-di-Me)phenyl-3-pyridylalanine-NH$_2$ |
| 148. | H | Aib | E | G | T | L-α-Me-Phe(2-Fluoro) | T | H | D | Bip(2'-Et-4'-OMe) | 4-(2'-Methylphenyl)-3-pyridylalanine-NH$_2$ |
| 149. | H | D-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 150. | H | Aib | H | G | T | L-α-Me-Phe(2-Fluoro) | T | S | D | Bip(2'-Et-4'-OMe) | 4-(2'-Methylphenyl)-3-pyridylalanine-NH$_2$ |
| 151. | L-β-Imidazole-lactyl | (S)-α-Me-Pro | E | G | T | L-α-Me-Phe (2-Fluoro) | T | H | D | Bip(2'-Et-4'-O-Me) | 4-(2'-Methylphenyl)-3-pyridylalanine-NH$_2$ |
| 152. | L-β-Imidazole-lactyl | (S)-α-Me-Pro | E | G | T | L-α-Me-Phe (2-Fluoro) | T | S | D | Bip(2'-Et-4'-O-Me) | 4-(2'-Methylphenyl)-3-pyridylalanine-NH$_2$ |
| 153. | L-β-Imidazole-lactyl | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 154. | L-β-Imidazole-lactyl | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH$_2$ |
|---|---|---|---|---|---|---|---|---|---|---|---|
| 155. | L-β-Imidazole-lactyl | N-Me-D-Ala | E | G | T | L-α-Me-Phe (2-Fluoro) | T | H | D | Bip(2'-Et-4'-O-Me) | 4-(2'-Methylphenyl)-3-pyridylalanine-NH$_2$ |
| 156. | L-β-Imidazole-lactyl | N-Me-D-Ala | E | G | T | L-α-Me-Phe (2-Fluoro) | T | S | D | Bip(2'-Et-4'-O-Me) | 4-(2'-Methylphenyl)-3-pyridylalanine-NH$_2$ |
| 157. | CH$_3$O—CO-His | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 158. | CH$_3$O—CO-His | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 159. | CH$_3$O—CO-His | N-Me-D-Ala | E | G | T | L-α-Me-Phe (2-Fluoro) | T | H | D | Bip(2'-Et-4'-OH) | 4-(2'-Methylphenyl)-3-pyridylalanine-NH$_2$ |
| 160. | CH$_3$O—CO-His | N-Me-D-Ala | E | G | T | L-α-Me-Phe (2-Fluoro) | T | S | D | Bip(2'-Et-4'-OH) | 4-(2'-Methylphenyl)-3-pyridylalanine-NH$_2$ |
| 161. | CH$_3$O—CO-His | Aib | E | G | T | L-α-Me-Phe (2-Fluoro) | T | H | D | Bip(2'-Et-4'-OH) | 4-(2'-Methylphenyl)-3-pyridylalanine-NH$_2$ |
| 162. | CH$_3$O—CO-His | Aib | E | G | T | L-α-Me-Phe (2-Fluoro) | T | S | D | Bip(2'-Et-4'-OH) | 4-(2'-Methylphenyl)-3-pyridylalanine-NH$_2$ |
| 163. | L-β-Imidazole-lactyl | N-Me-D-Ala | E | G | T | L-α-Me-Phe (2-Fluoro) | T | H | D | Bip(2'-Et-4'-OH) | 4-(2'-Methylphenyl)-3-pyridylalanine-NH$_2$ |
| 164. | CH$_3$O—CO-His | (S)-α-Me-Pro | E | G | T | L-α-Me-Phe (2-Fluoro) | T | S | D | Bip(2'-Et-4'-OH-5'-I) | 4-(2'-Methylphenyl)-3-pyridylalanine-NH$_2$ |
| 165. | Des-NH$_2$-His | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 166. | Des-NH$_2$-His | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 167. | (R)-Imp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 168. | (S)-Imp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 169. | (R)-Imp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 170. | (S)-Imp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 171. | (R)-IMe Op | (S)-α-Me-Pro | E | G | T | L-α-Me-Phe (2-Fluoro) | T | H | D | Bip(2'-Et-4'-OMe) | 4-(2'-Methylphenyl)-3-pyridylalanine-NH$_2$ |
| 172. | (S)-IMe Op | (S)-α-Me-Pro | E | G | T | L-α-Me-Phe (2-Fluoro) | T | H | D | Bip(2'-Et-4'-OMe) | 4-(2'-Methylphenyl)-3-pyridylalanine-NH$_2$ |
| 173. | (R)-IMe Op | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |

-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 174. | (S)-1Me Op | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 175. | (R)-1Me Op | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 176. | (S)-1Me Op | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 177. | | | | | | | T | S | D | Bip(2'-Et-4-OH) | 4-(2'-Methylphenyl)-3-pyridylalanine-NH$_2$ |
| 178. | | (S)-α-Me-Pro | | | | | T | S | D | Bip(2'-Et-4'-OH) | 4-(2'-Methylphenyl)-3-pyridylalanine-NH$_2$ |
| 179. | | | | | | | T | H | D | Bip(2'-Et-4'-OH) | 4-(2'-Methylphenyl)-3-pyridylalanine-NH$_2$ |

Other embodiments include isolated polypeptides comprising the following structures:

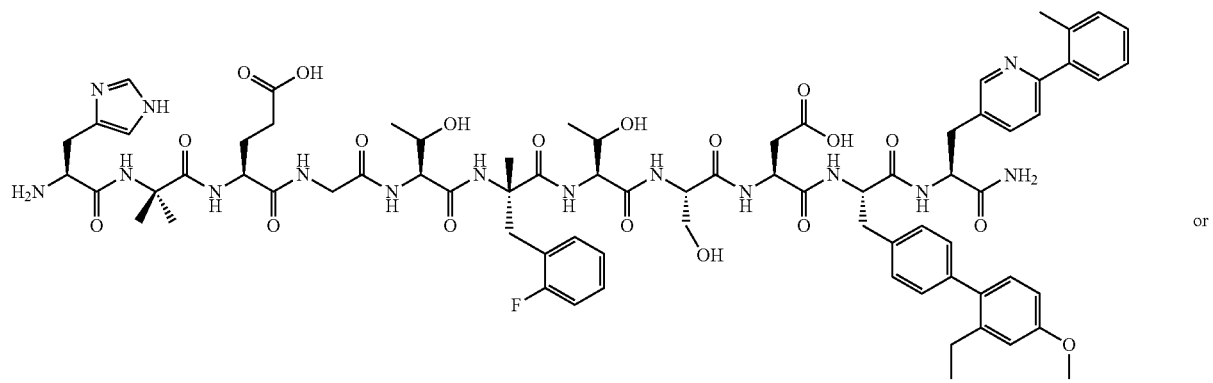

SEQ ID NO: 9 or

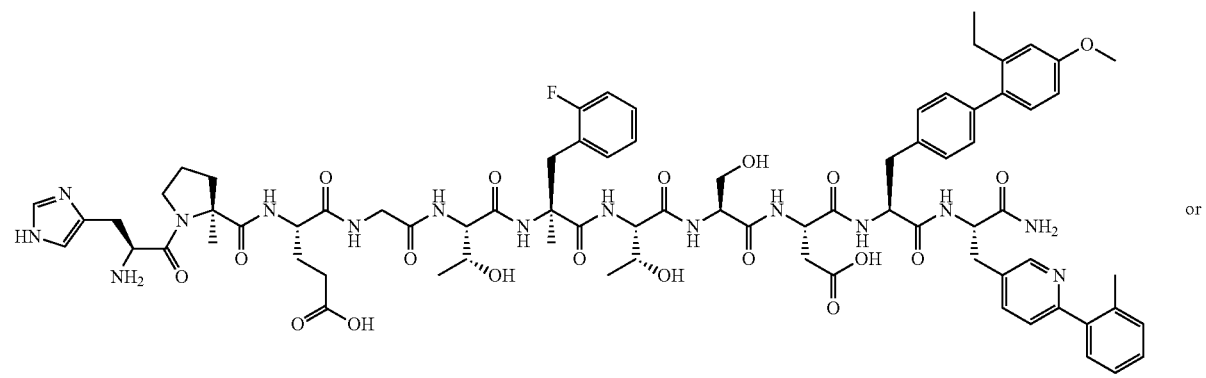

SEQ ID NO: 118 or

SEQ ID NO: 159

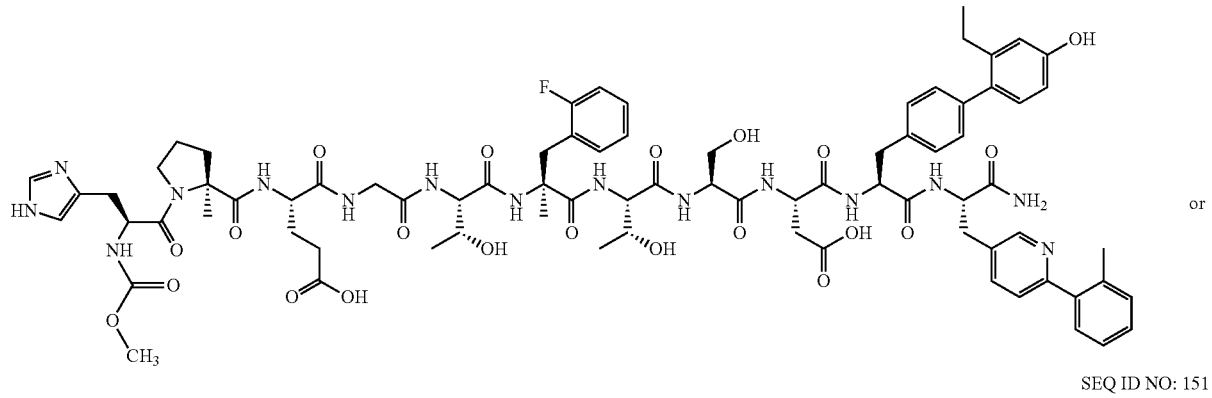

or

SEQ ID NO: 151

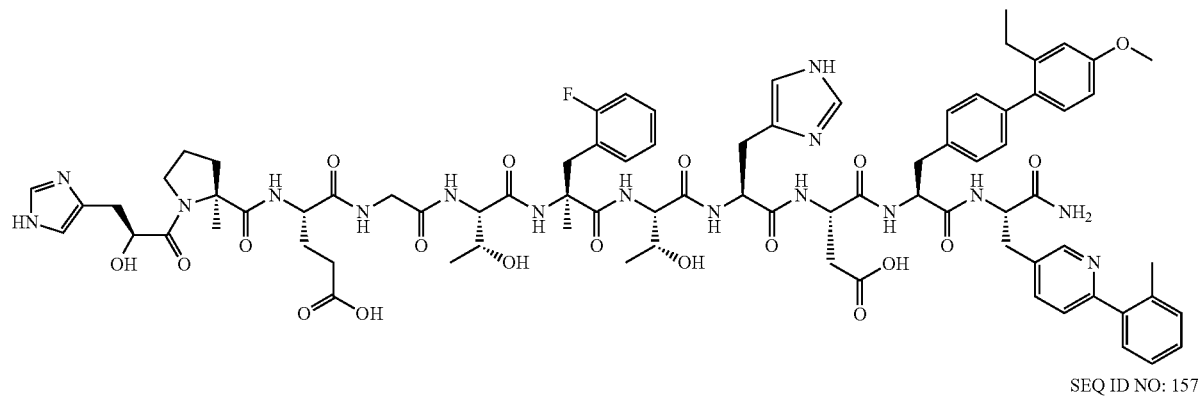

SEQ ID NO: 157

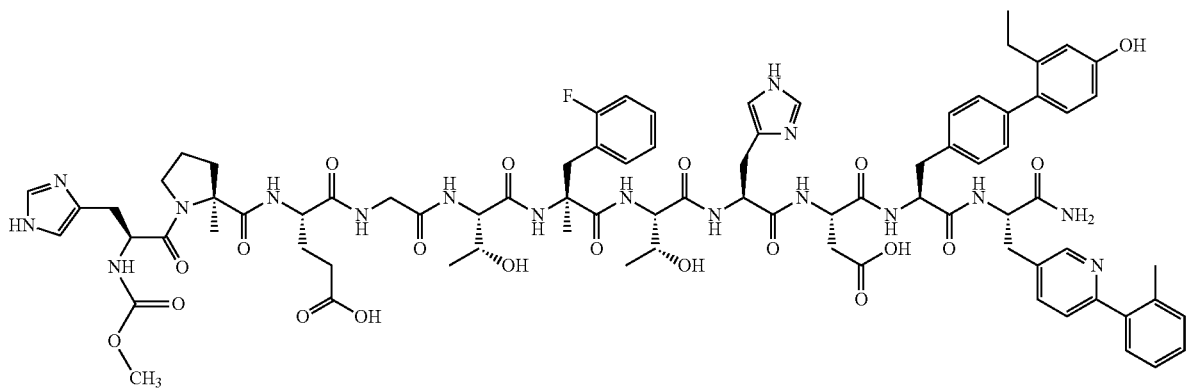

Additional embodiments include a polypeptide comprising the sequence Thr-Ser-Asp-Bip (2-Et-4'-OH)-pyridylalanine (SEQ ID NO: 177) or Thr-Ser-Asp-Bip (2-Et-4'-OH) pyridylalanine (SEQ ID NO: 179) wherein said polypeptide binds and activates a GLP-1 receptor. Such peptides may further comprise: a proline (e.g., alpha methyl proline) at the second residue from the amino terminal residue; a substituted pyridylalanine (e.g., 4-(2'methyl phenyl) 3-pyridyl alanine); and an amino terminal carbamate.

The afore-described sequences of SEQ ID NO: 177 or 179 may be at the seventh, eighth, ninth, and tenth residues of the peptide comprising said sequence, respectively. Such a peptide may further comprise a position two proline (e.g. alpha methyl proline). An exemplary peptide comprising the sequence of SEQ ID NO: 177 is a peptide of SEQ ID NO: 158. An exemplary peptide comprising the sequence of SEQ ID NO: 179 is a peptide of SEQ ID NO: 157.

Another embodiment is a pharmaceutical composition comprising an isolated polypeptide of Formula I, or a peptide comprising at least one of SEQ ID NOs: 1-179.

Another embodiment is directed to a pharmaceutical combination comprising an isolated polypeptide of Formula I or a peptide comprising any of SEQ ID NOs: 1-179, and at least one therapeutic agent selected from the group consisting of an antidiabetic agent, an anti-obesity agent, an anti-hypertensive agent, an anti-atherosclerotic agent and a lipid-lowering agent.

Another embodiment is directed to a pharmaceutical combination of an isolated polypeptide of Formula I or a peptide comprising any of SEQ ID NOs: 1-179, wherein the antidiabetic agent is selected from the group consisting of a biguanide, a sulfonyl urea, a glucosidase inhibitor, a PPAR γ agonist, a PPAR α/γ dual agonist, an aP2 inhibitor, a DPP4 inhibitor, a SGLT-2 inhibitor, an insulin sensitizer, a glucagon-like peptide-1 (GLP-1), a GPR119 modulator, insulin and a meglitinide.

Another embodiment is directed to a pharmaceutical combination of an isolated polypeptide of Formula I or a peptide comprising any of SEQ ID NOs: 1-179, wherein the antidiabetic agent is selected from the group consisting of metformin, glyburide, glimepiride, glipyride, glipizide, chlorpropamide, gliclazide, acarbose, miglitol, pioglitazone, troglitazone, rosiglitazone, muraglitazar, insulin, G1-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, and NVP-DPP-728A.

Another embodiment is directed to a pharmaceutical combination of an isolated polypeptide of Formula I or a peptide comprising any of SEQ ID NOs: 1-179, wherein the anti-obesity agent is selected from the group consisting of a CB-1 antagonist (or inverse agonist), a MCHR-1 antagonist, a DGAT inhibitor, beta 3 adrenergic agonist, a lipase inhibitor, a serotonin (and dopamine) reuptake inhibitor, a thyroid receptor beta compound, and an anorectic agent.

Another embodiment is directed to a pharmaceutical combination of an isolated polypeptide of Formula I or a peptide comprising any of SEQ ID NOs: 1-179, wherein the anti-obesity agent is selected from the group consisting of orlistat, ATL-962, AJ9677, L750355, CP331648, acomplia, MK-0364, SLV-319, sibutramine, topiramate, axokine, dexamphetamine, phentermine, phenylpropanolamine and mazindol.

Another embodiment is directed to a pharmaceutical combination of an isolated polypeptide of Formula I or a peptide comprising any of SEQ ID NOs: 1-179, wherein the lipid lowering agent is selected from the group consisting of an MTP inhibitor, cholesterol ester transfer protein, an HMG CoA reductase inhibitor, a squalene synthetase inhibitor, a fibric acid derivative, an upregulator of LDL receptor activity, a lipoxygenase inhibitor, and an ACAT inhibitor.

Another embodiment is directed to a pharmaceutical combination of an isolated polypeptide of Formula I or a peptide comprising any of SEQ ID NOs: 1-179, wherein the lipid lowering agent is selected from the group consisting of pravastatin, lovastatin, simvastatin, atorvastatin, cerivastatin, fluvastatin, nisvastatin, visastatin, fenofibrate, gemfibrozil, clofibrate, avasimibe, TS-962, MD-700, CP-529414, and LY295427.

Another embodiment is directed to a method for treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, which comprises administering to a mammalian species in need of treatment a therapeutically effective amount of an isolated polypeptide of Formula I or a peptide comprising any of SEQ ID NOs: 1-179.

Another embodiment is directed to a method of such treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, comprising administering, concurrently or sequentially, a therapeutically effective amount of one or more therapeutic agents selected from the group consisting of an antidiabetic agent, an anti-obesity agent, a anti-hypertensive agent, and an anti-atherosclerotic agent and a lipid-lowering agent and an isolated polypeptide of Formula I or a peptide comprising any of SEQ ID NOs: 1-179.

Another embodiment is directed to a method for treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, which comprises administering to a mammalian species in need of treatment a therapeutically effective amount of any of the pharmaceutical combinations above.

An additional aspect of the subject matter described herein is the use of the disclosed peptides as radiolabels for development of ligand binding assays. For example, the peptide of SEQ ID NO:164 may be prepared using the radioactive isotope $^{125}$I and that the resulting radiolabeled peptide may be used to develop a binding assay. Alternatively, and for the same purpose, the peptide of SEQ ID NO:164 may be converted to a radiolabeled form of the peptide of SEQ ID NO:158 by catalytic tritiation using methods known to those skilled in the art.

DETAILED DESCRIPTION OF THE INVENTION

Figure 1:
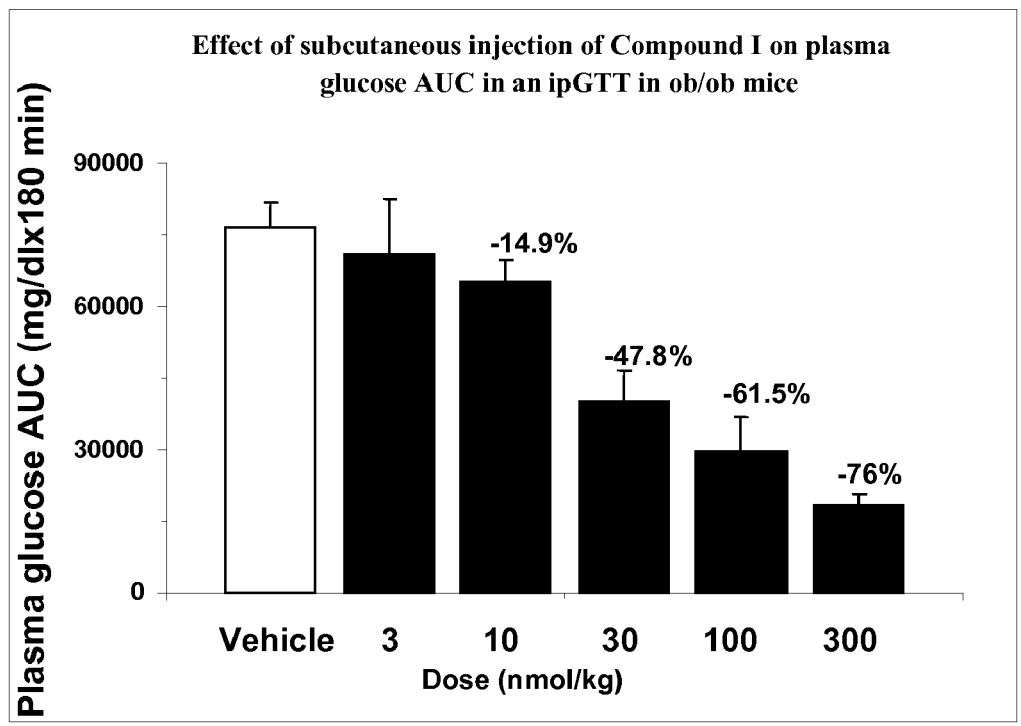
FIG. 1 illustrates the effects of subcutaneous injection of Compound I on plasma glucose in an ipGTT in ob/ob mice.

The synthetic isolated peptides described herein are capable of modulating the GLP-1 receptor, desirably as agonists or partial agonists of the GLP-1 receptor. These synthetic peptide exhibit similar in vivo efficacy and superior pharmacokinetic properties relative to GLP-1, including postprandial plasma glucose lowering and concomitant increase in plasma insulin levels, thus making them ideal therapeutic candidates for subcutaneous, pulmonary, nasal, buccal or sustained release.

The subject matter described and claimed herein includes an isolated polypeptide comprising a sequence of Formula I:

$$X_{aa1}\text{-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}X_{aa10}\text{-}X_{aa11}$$ Formula I wherein, $X_{aa1}$ is naturally or nonnaturally occurring amino acid comprising an imidazole or thiazole ring, such as histidine or thiazolylalanine; wherein any of the carbon atoms of said amino acid are optionally substituted with hydrogen, with one or more alkyl groups, or with one or more halo groups; wherein the free amino group of said amino acid is optionally substituted hydrogen, hydroxyl, alkyl, acyl, benzoyl, alkoxy, alkyloxycarbonyl (e.g. methyloxycarbonyl), aryloxycarbonyl, aralkyloxycarbonyl, heterocyclyloxycarbonyl, heteroarylalkyloxycarbonyl, alkylcarbamoyl, arylcarbamoyl, aralkylcarbamoyl, heterocyclylsulfonyl, alkylsulfonyl, arylsulfonyl, arylalkylsulfonyl, heteroarylalkylsulfonyl or heteroarylsulfonyl;

and wherein the amino group of $X_{aa1}$ is optionally absent, such that $X_{aa1}$ is the des-amino acid of histidine or thiazolylalanine in which any of the carbon atoms are optionally substituted with alkyl, halo, or hydroxyl groups;

$X_{aa2}$ is naturally or nonnaturally occurring amino acid selected from the group consisting of α-amino-isobutryic acid; L-alanine, D-Alanine, N-methyl-L-Alanine, N-methyl-D-Alanine, L-proline, (S)-α-methyl-proline, L-azetidine (Azt), (L)-α-methyl-azetidine (α-Me-Azt), L-valine, and (R)- or (S)-isovaline, and wherein the carbon atoms of said amino acid are optionally substituted with one or more alkyl groups or halo groups;

$X_{aa3}$ is a naturally or nonnaturally occurring amino acid comprising an amino acid side chain which contains a carboxylic acid, for example aspartic acid or glutamic acid; and wherein any of the carbon atoms of said amino acid are optionally substituted with one or more alkyl groups or halo groups;

$X_{aa4}$ is glycine;

$X_{aa5}$ is a naturally or nonnaturally occurring amino acid selected from the group consisting of L-threonine, L-allothreonine, L-serine, L-norvaline, L-norleucine; and wherein any of the carbon atoms of said amino acid are optionally substituted with one or more alkyl groups or halo groups;

$X_{aa6}$ is a naturally or nonnaturally occurring amino acid comprising an alpha carbon which is disubstituted; wherein one of the side chains of said amino acid contains an aromatic or heteroaromatic ring, for example alpha-methyl-phenylalanine, alpha-methyl-2-fluorophenylalanine, alpha-methyl-2,6-difluorophenylalanine, wherein any of the carbon atoms of said amino acid are optionally substituted with one or more alkyl groups; and wherein any of the carbon atoms of said amino acid are optionally substituted with one or more halo groups;

$X_{aa7}$ is a naturally or nonnaturally occurring amino acid comprising an amino acid side chain which is substituted with a hydroxyl group, for example L-threonine or L-allo-threonine; wherein any of the carbon atoms of said amino acid are optionally substituted with one or more alkyl or halo groups;

$X_{aa8}$ is a naturally or nonnaturally occurring amino acid selected from the group consisting of L-serine, L-histidine and L-asparagine; wherein one or more of the carbon atoms of said amino acid is optionally substituted with one or more alkyl groups or halo groups;

$X_{aa9}$ is a naturally or nonnaturally occurring amino acid comprising an amino acid side chain which contains a carboxylic acid, for example L-aspartic acid or L-glutamic acid; wherein one or more of the carbon atoms of said amino acid is optionally substituted with one or more alkyl or halo groups;

$X_{aa10}$ is a naturally or nonnaturally occurring amino acid of Formula II, III, or IV:

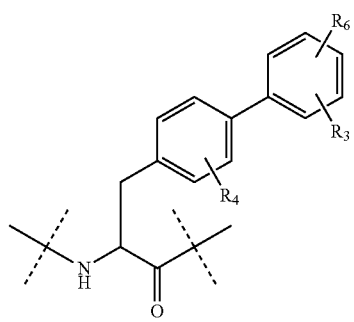

Formula II

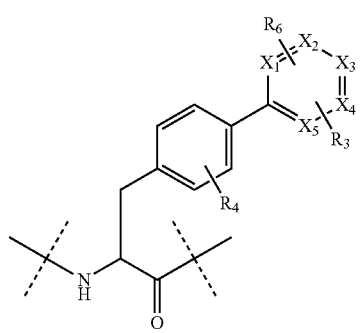

Formula III

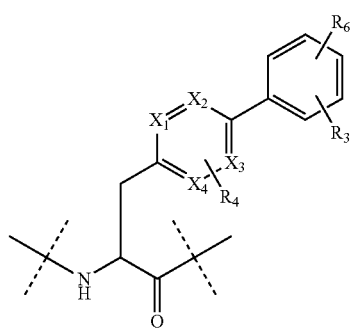

Formula IV wherein $R_3$, $R_4$ and $R_6$ are each selected from the group consisting of hydrogen, alkyl, aryl, heterocyclyl, heteroaryl, halogen, hydroxyl, hydroxyalkyl, cyano, amino, aminoalkyl, alkoxy, aryloxy, carboxyl, carboxyalkyl, carboxamide, substituted carboxamide, alkyl ester, aryl ester, alkyl sulfonyl, and aryl sulfonyl;

and wherein $X_1$, $X_2$, $X_3$, $X_4$, and $X_5$ are each C or N, with the proviso that one of $X_1$, $X_2$, $X_3$, $X_4$, and $X_5$ is N;

$X_{aa11}$ is a naturally or nonnaturally occurring amino acid of Formula IIa, IIIa, or IVa:

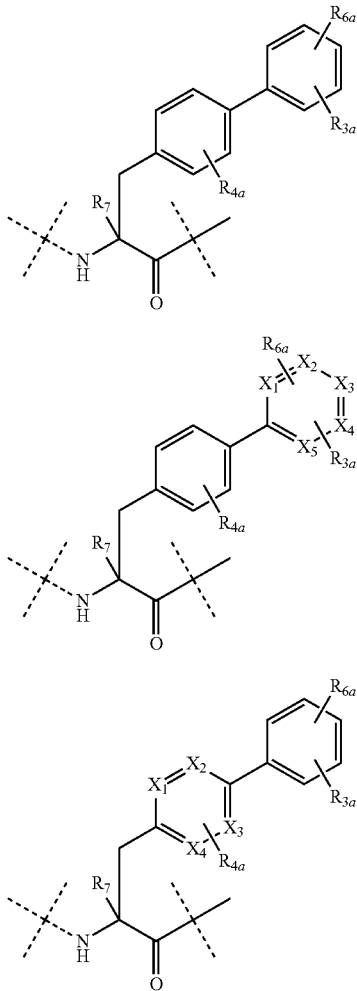

wherein the C-terminus carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein $R_{3a}$, $R_{4a}$ and $R_{6a}$ are each selected from the group consisting of hydrogen, alkyl, aryl, heterocyclyl, heteroaryl, halogen, hydroxyl, hydroxyalkyl, cyano, amino, aminoalkyl, alkoxy, aryloxy, carboxyl, carboxyalkyl, carboxamide, substituted carboxamide, alkyl ester, aryl ester, alkyl sulfonyl, and aryl sulfonyl;

wherein $R_7$ is selected from the group consisting of hydrogen, methyl, and ethyl; and wherein $X_1$, $X_2$, $X_3$, $X_4$, and $X_5$ are each C or N, with the proviso that one of $X_1$, $X_2$, $X_3$, $X_4$, and $X_5$ is N;

wherein $X_{aa11}$ is not an amino acid of formula IIa when $X_{aa10}$ is an amino acid of Formula II.

A preferred embodiment is a polypeptide comprising the sequence Thr-Ser-Asp-Bip (2-Et-4'-OH)-pyridylalanine (SEQ ID NO: 177) or Thr-Ser-Asp-Bip (2-Et-4'-OH) pyridylalanine (SEQ ID NO: 179) wherein said polypeptide binds and activates a GLP-1 receptor. Such peptides may further comprise: a proline (e.g., alpha methyl proline) at the second residue from the amino terminal residue; a substituted pyridylalanine (e.g., 4-(2'methyl phenyl) 3-pyridyl alanine); and an amino terminal carbamate.

Preferred peptides include peptides of SEQ ID NOs: 157 and 158 and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

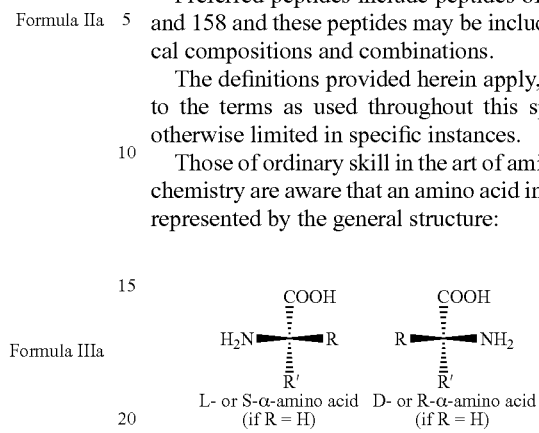

where R and R' are as discussed herein.

Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'" (prime) substituents equal hydrogen, the amino acid is glycine and is not chiral.

Unless otherwise indicated, the term "amino-alcohol" as employed herein alone or as part of another group includes, without limitation, a natural or un-natural amino acid in which the carboxy group is replaced (reduced) to a methyl alcohol such as valinol, glycinol, alaninol, arylalaninol, heteroarylalaninol.

Unless otherwise indicated, the term "alkyl" as employed herein alone or as part of another group includes, without limitation, both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl

carboxamido, amino, alkylamino, dialkylamino, amido, alkylamino, arylamido, heterarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "alkenyl" as employed herein alone or as part of another group includes, without limitation, both straight and branched chain hydrocarbons, containing 2 to 40 carbons with one or more double bonds, preferably 2 to 20 carbons with one to three double bonds, more preferably 2 to 8 carbons with one to two double bonds, in the normal chain, such that any carbon may be optionally substituted as described above for "alkyl".

Unless otherwise indicated, the term "alkynyl" as employed herein alone or as part of another group includes, without limitation, both straight and branched chain hydrocarbons, containing 2 to 40 carbons with one or more triple bonds, preferably 2 to 20 carbons with one to three triple bonds, more preferably 2 to 8 carbons with one to two triple bonds, in the normal chain, such that any carbon may be optionally substituted as described above for "alkyl".

Unless otherwise indicated, the term "cycloalkyl" as employed herein alone or as part of another group includes, without limitation, saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

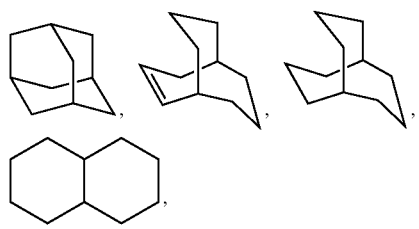

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl

carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers, without limitation, to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, heteroarylalkyloxy, heteroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalykaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers, without limitation, to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy" "arylalkyloxy", or "heteroarylalkyloxy" as employed herein alone or as part of another group includes, without limitation, an alkyl or aryl group as defined above linked through an oxygen atom.

The term "heterocyclo", "heterocycle" "heterocyclyl" or "heterocyclic", as used herein, represents, without limitation, an unsubstituted or substituted stable 4-, 5-, 6-, or 7-membered monocyclic ring system which may be saturated or unsaturated, and which consists of carbon atoms and from one to four heteroatoms selected from nitrogen, sulfur, oxygen and/or a SO or SO$_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers, without limitation, to alkyl groups as defined above having a heterocycloalkyl substituent, wherein said "heterocyclo" and/or alkyl groups may optionally be substituted as defined above.

The term "heteroaryl" as used herein refers, without limitation, to a 5-, 6- or 7-membered aromatic heterocyclic ring which contains one or more heteroatoms selected from nitrogen, sulfur, oxygen and/or a SO or SO$_2$ group. Such rings may be fused to another aryl or heteroaryl ring and include possible N-oxides; Examples of such heteroaryl groups include, but are not limited to, furan, pyrrole, thiophene, pyridine, pyrimidine, pyrazine, pyridazine, isoxazole, oxazole, imidazole and the like. Optionally a heteroaryl group may be substituted with one or more functional groups commonly attached to such chains, such as those described for "alkyl" or "aryl".

The term "heteroarylalkyl" as used herein alone or as part of another group refers, without limitation, to alkyl groups as defined above having a heteroaryl substituent, wherein said heteroaryl and/or alkyl groups may optionally be substituted as defined above.

The term "receptor modulator" refers to a compound that acts at the GLP-1 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g., E. M. Ross and T. P. Kenakin in Goodman and Gilman's The Pharmacological Basis of Therapeutics, 10th edition (2001) McGraw Hill, Chapter 2, pp. 31-43).

One of ordinary skill in the art will readily appreciate the meaning of such terms as provided in the present case and in the art.

The term "diabetes and related diseases or related conditions" refers, without limitation, to Type II diabetes, Type I diabetes, impaired glucose tolerance, obesity, hyperglycemia, Syndrome X, dysmetabolic syndrome, diabetic complications, and hyperinsulinemia.

The term "lipid-modulating" or "lipid lowering" agent as employed herein refers, without limitation, to agents that lower LDL and/or raise HDL and/or lower triglycerides and/or lower total cholesterol and/or other known mechanisms for therapeutically treating lipid disorders.

Administration of a therapeutic agent described herein includes, without limitation, administration of a therapeutically effective amount of the therapeutic agent. The term "therapeutically effective amount" as used herein refers, without limitation, to an amount of a therapeutic agent to treat or prevent a condition treatable by administration of a composition of the GLP-1 receptor modulators described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The peptides disclosed and claimed herein show superior potency, with comparable exposures, in an efficacy model of glucose lowering (ob/ob mouse model) and superior pharmacokinetics (as measured by subcutaneous injection in dogs), as illustrated in the tables and figures provided.

Compound 1

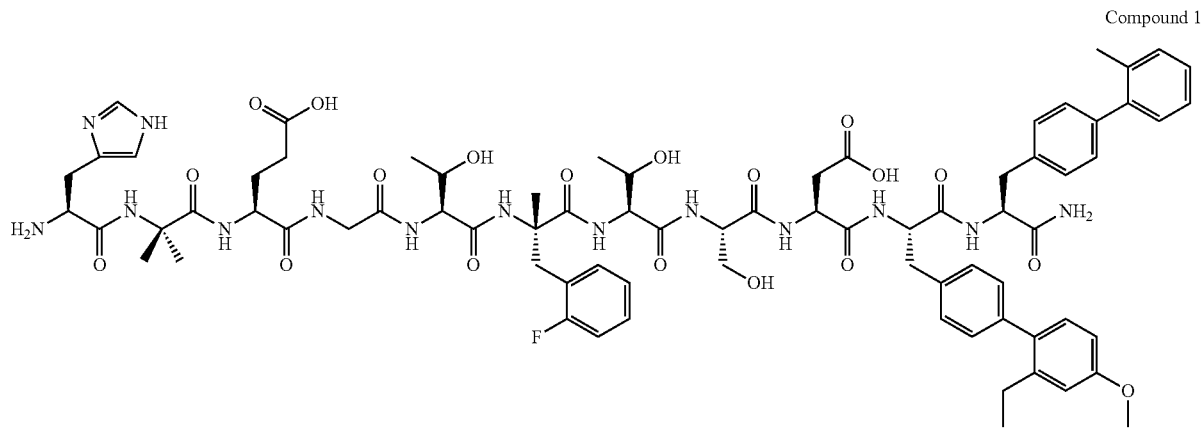

SEQ ID NO: 9

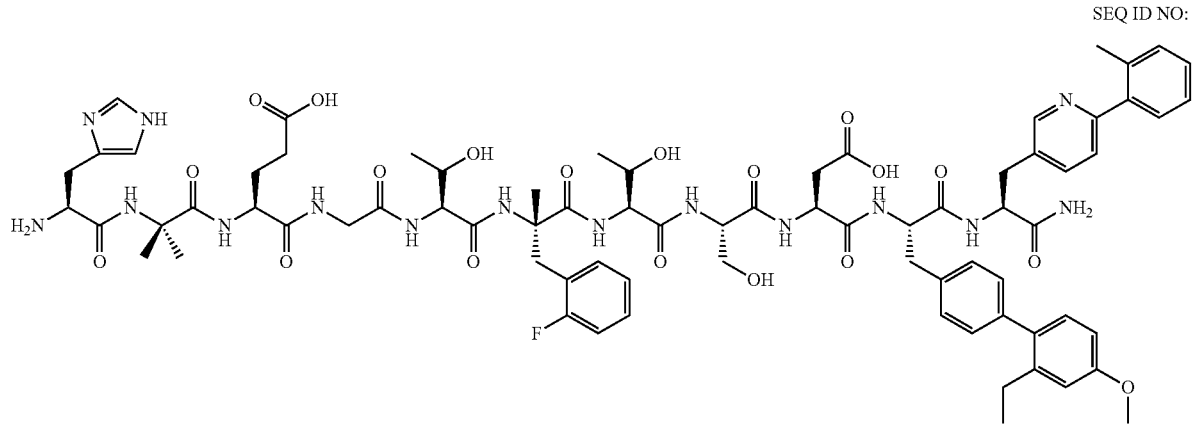

SEQ ID NO: 118
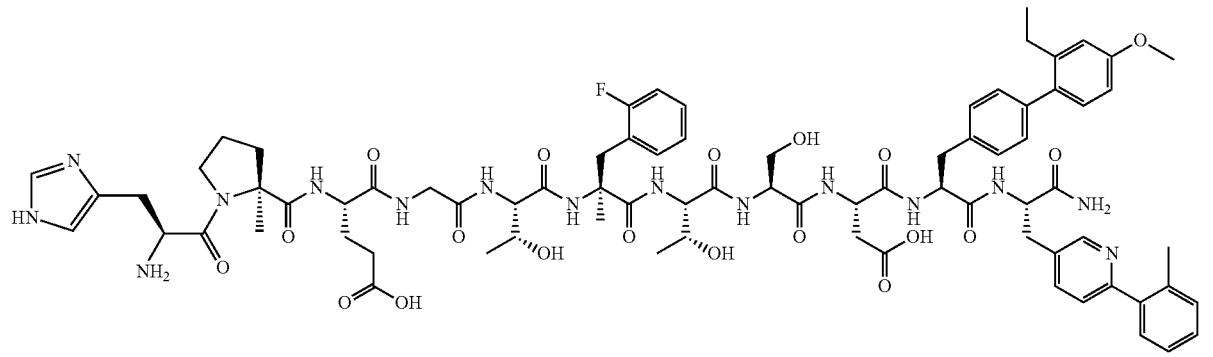
SEQ ID NO: 133
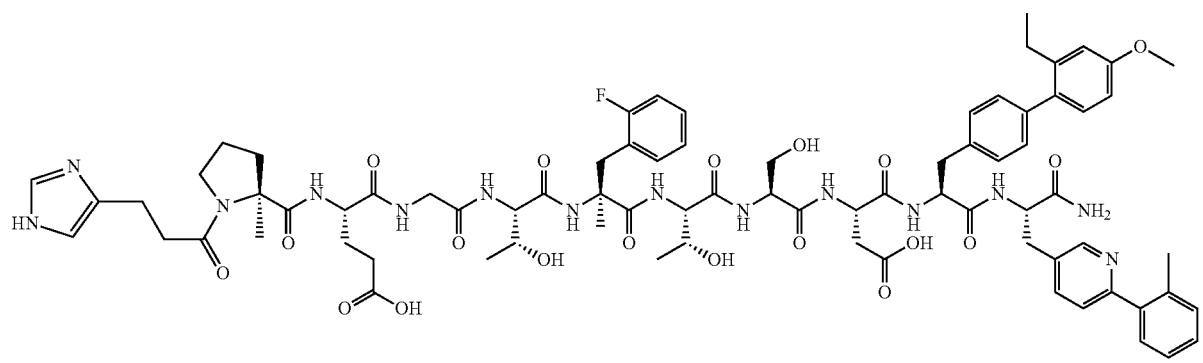
SEQ ID NO: 139
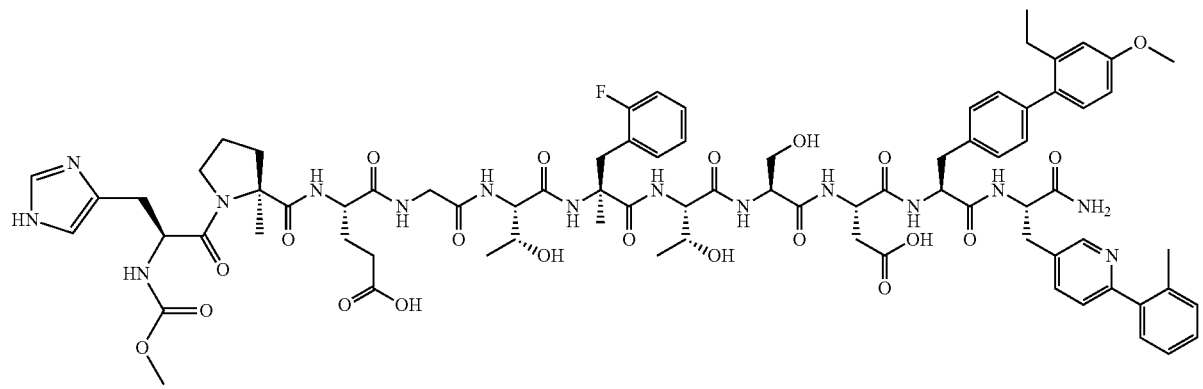
SEQ ID NO: 151
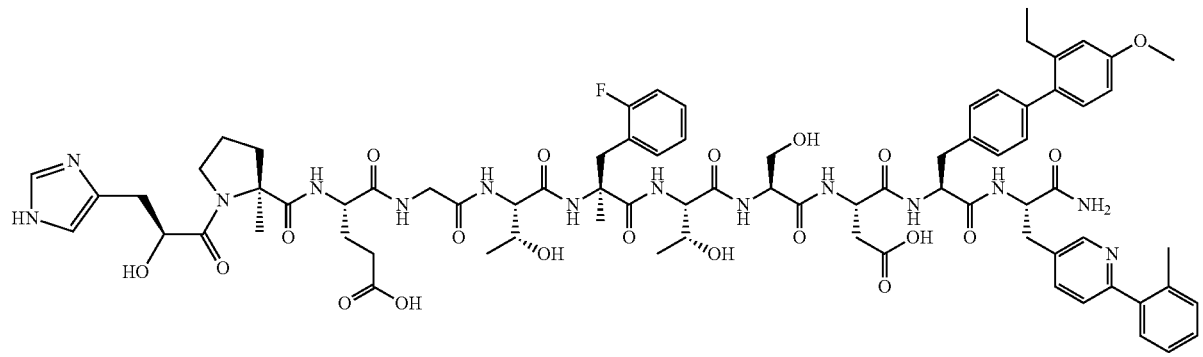

SEQ ID NO: 157

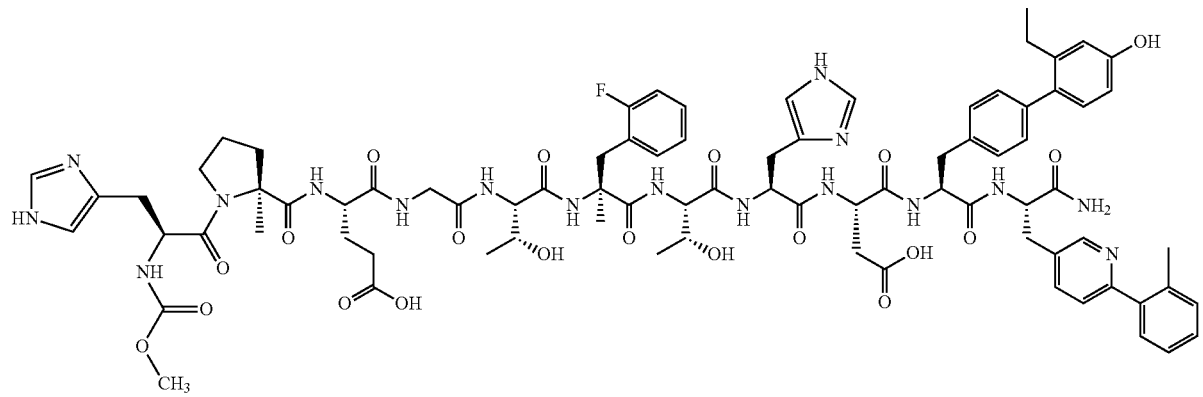

SEQ ID NO: 158

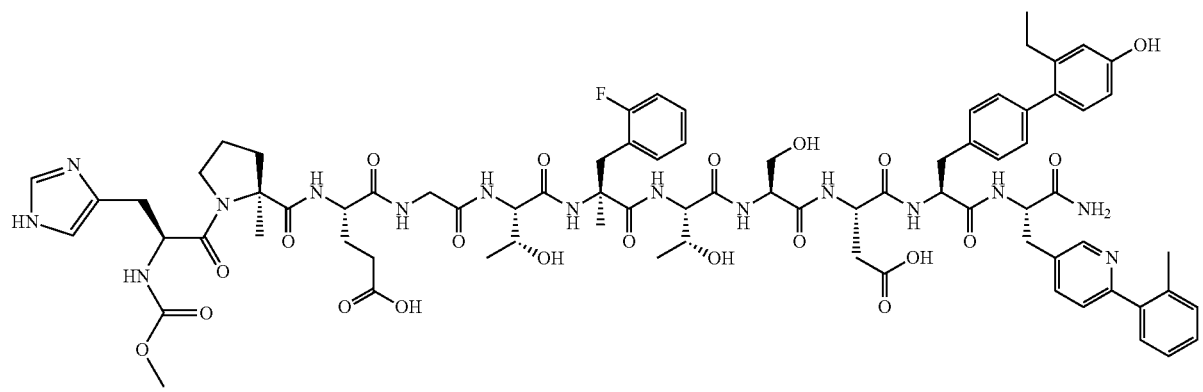

TABLE 1

| Compound/ SEQ ID NO: | Potency in ob/ob mice | Exposure/dose during ipGTT in ob/ob mice (nM * h/nmol/kg) | Exposure in dogs* (sc@67 µg/kg) |
|---|---|---|---|
| Compound I | ED50 = 50 nmoles/kg | 22 | 89 nM * h |
| 9 | ED50 = 5 nmoles/kg | 18 | 452 nM * h |
| 118 | ED50 = 2.5 nmoles/kg | 4.4 | 4020 nM * h |
| 151 | ED50 = 1 nmoles/kg | 16 | 1566 nM * h |
| 158 | ED50 = 2 nmoles/kg | 11 | 1467 nM * h |

*Compound I and the compound of SEQ ID NO: 118 were dosed in propylene glycol/pH 7.4 phosphate buffer (1:1); Compounds of SEQ ID Nos: 9, 151 and 158 were dosed in 0.2 M Tris buffer (pH 8.0).

TABLE 2

| Compound/ SEQ ID NO | Potency in ob/ob mice: % AUC Reduction in Plasma Glucose in an IP Glucose Tolerance Test after SC Injection of Compound* | Exposure in dogs***(sc@67 µg/kg) |
|---|---|---|
| Compound I | −15% (p = 0.247, NS) (10 nmol/kg) | 89 nM * h |
| 9 | −68% (p < 0.0001) (10 nmol/kg) | 1230 nM * h |
| 118 | −70% (p < 0.001) (10 nmol/kg) | 4020 nM * h |
| 130 | −72% (p < 0.0001) (10 nmol/kg) | 541 nM * h |
| 149 | −54%(p < 0.0001) (10 nmol/kg) | 940 nM * h |
| 140 | −73% (p < 0.001) (10 nmol/kg) | 283 nM * h |
| 120 | −68% (p < 0.0001) (10 nmol/kg) | 1116 nM * h |
| 139 | −63% (p < 0.01) (10 nmol/kg) | 1603 nM * h |
| 119 | −61% (p < 0.0001) (5 nmol/kg) | 1257 nM * h |
| 150 | −38% (p < 0.05) (10 nmol/kg) | 979 nM * h |

AUC = area under the curve. AUC values are calculated using the fasting plasma glucose value as the baseline in each individual animal. The percentage change in the AUC is calculated relative to the AUC for the vehicle-treated group in the same study. The p values given are determined by comparison to the vehicle-treated group using analysis of variance (ANOVA) followed by Fisher's post-hoc test,

** NS = non-statistically significant.

***Dosing vehicle: propylene glycol/pH 7.4 phosphate buffer (1:1).

Tables 3a and 3b

Potency and Efficacy for Stimulation of cAMP Synthesis in CHO Cells Expressing Human or Mouse GLP-1 Receptor

TABLE 3a

Human GLP-1 Receptor

| | Mean EC$_{50}$ (nM) | Mean E$_{max}$ (%) | Mean Hill | |
|---|---|---|---|---|
| Compound of SEQ ID NO: 158 | 0.018 ± 0.004 | 100.8 ± 6.7 | 1.5 | n = 10 |
| Compound of SEQ ID NO: 157 | 0.026 | 99.4 | 1.9 | n = 1 |
| Compound of SEQ ID NO: 164 | 0.010 | 97.2 | 1.5 | n = 1 |
| Compound of SEQ ID NO: 173 (or 174)* | 0.018 | 95.6 | 2.6 | n = 1 |
| Compound of SEQ ID NO: 174 (or 173)* | 0.024 | 103.7 | 2.7 | n = 1 |
| Compound of SEQ ID NO: 175 (or 176)* | 0.030 | 105.3 | 2.8 | n = 1 |
| Compound of SEQ ID NO: 176 (or 175)* | 0.030 | 95.8 | 3.1 | n = 1 |
| GLP-1 | 0.010 ± 0.002 | 108.5 ± 5.8 | 1.6 | n = 10 |

TABLE 3b

Mouse GLP-1 Receptor

| | Mean EC$_{50}$ (nM) | Mean E$_{max}$ (%) | Mean Hill | |
|---|---|---|---|---|
| Compound of SEQ ID NO: 158 | 0.191 ± 0.058 | 100.9 ± 7.2 | 1.5 | n = 10 |
| Compound of SEQ ID NO: 157 | 0.046 | 106.4 | 2.9 | n = 1 |
| Compound of SEQ ID NO: 164 | 0.055 | 103.0 | 2.7 | n = 1 |
| Compound of SEQ ID NO: 173 (or 174)* | 0.114 | 99.7 | 1.4 | n = 1 |
| Compound of SEQ ID NO: 174 (or 173)* | 0.273 | 105.0 | 2.1 | n = 1 |
| Compound of SEQ ID NO: 175 (or 176)* | 0.084 | 100.2 | 2.7 | n = 1 |
| Compound of SEQ ID NO: 176 (or 175)* | 0.126 | 104.7 | 1.9 | n = 1 |
| GLP-1 | 0.041 ± 0.015 | 106.4 ± 14.5 | 1.9 | n = 10 |

For Tables 3a and 3b, compounds of SEQ ID NO:173 and SEQ ID NO:174 and Compounds of SEQ ID NO:175 and SEQ ID NO:176 were prepared as mixtures of diastereomers, and separated by HPLC as isomers A and B (Example 31). The absolute configuration of the 3-(1H-imidazol-4-yl)-2-methoxypropanoyl (IMeOp) Xaa$_1$ group was not determined.

The peptides and analogs thereof described herein may be produced by chemical synthesis using various solid-phase techniques such as those described in G. Barany and R. B. Merrifield, "The Peptides: Analysis, Synthesis, Biology"; Volume 2—"Special Methods in Peptide Synthesis, Part A", pp. 3-284, E. Gross and J. Meienhofer, Eds., Academic Press, New York, 1980; and in J. M. Stewart and J. D. Young, "Solid-Phase Peptide Synthesis", 2nd Ed., Pierce Chemical Co., Rockford, Ill., 1984. The desired strategy is based on the Fmoc (9-Fluorenylmethyl methyl-oxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in "The Peptides: Analysis, Synthesis, Biology"; Volume 9-"Special Methods in Peptide Synthesis, Part C", pp. 1-38, S. Undenfriend and J. Meienhofer, Eds., Academic Press, San Diego, 1987.

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) as described herein and, after completion of the peptide sequence assembly, the resulting peptide alcohol is released with LiBH$_4$ in THF (see J. M. Stewart and J. D. Young, supra, p. 92).

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBT or HOAT active esters produced from DIC/HOBT, HBTU/HOBT, BOP, PyBOP, or from DIC/HOAT, HATU/HOAT, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a peptide synthesizer, such as an Advanced Chemtech Multiple Peptide Synthesizer (MPS396) or an Applied Biosystems Inc. peptide synthesizer (ABI 433a). If the MPS396 was used, up to 96 peptides were simultaneously synthesized. If the ABI 433a synthesizer was used, individual peptides were synthesized sequentially. In both cases the stepwise solid phase peptide synthesis was carried out utilizing the Fmoc/t-butyl protection strategy described herein.

The non-natural non-commercial amino acids present at position-X$_{aa10}$ and at position-X$_{aa11}$ were incorporated into the peptide chain in one of two methods. In the first approach a Boc- or Fmoc-protected non-natural amino acid was prepared in solution using appropriate organic synthetic procedures. The resulting derivative was then used in the step-wise synthesis of the peptide. Alternatively the required non-natural amino acid was built on the resin directly using synthetic organic chemistry procedures. When a non-natural non-commercial amino acid was needed for incorporation at position $X_{aa6}$ or at any other Xaa position, the required Fmoc-protected non-natural amino acid was synthesized in solution. Such a derivative was then used in stepwise solid phase peptide synthesis.

Useful Fmoc amino acids derivatives are shown below.

Examples of Orthogonally Protected Amino Acids Used in Solid Phase Synthesis

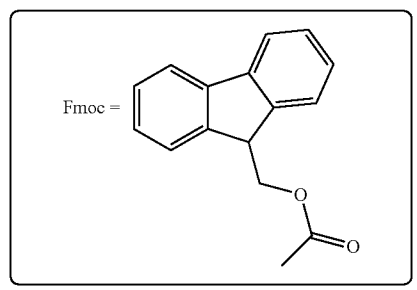

Fmoc-His (Trt)     Fmoc-Asp(Bu$^t$)

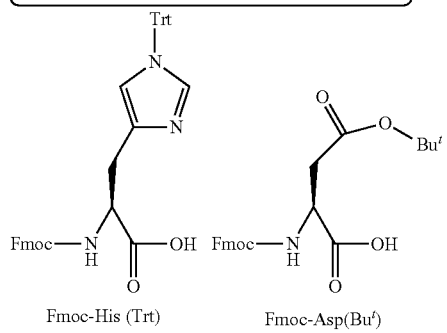

Fmoc-Glu(Bu$^t$)     Fmoc-Ser(Bu$^t$)

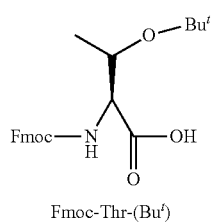

Fmoc-Thr-(Bu$^t$)

Protected Amino Acids Used in Solid Phase Synthesis

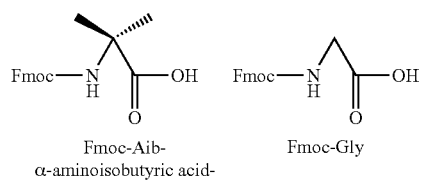

Fmoc-Aib-
α-aminoisobutyric acid-     Fmoc-Gly

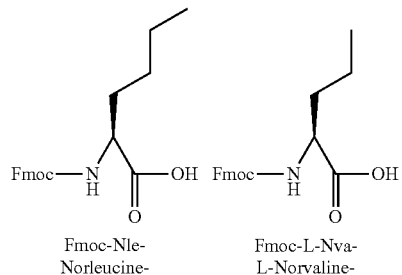

Fmoc-Nle-
Norleucine-     Fmoc-L-Nva-
L-Norvaline-

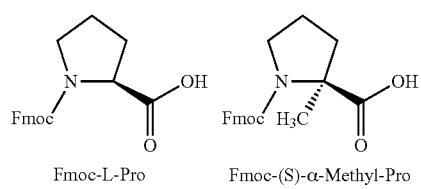

Fmoc-L-Pro     Fmoc-(S)-α-Methyl-Pro

Formula II

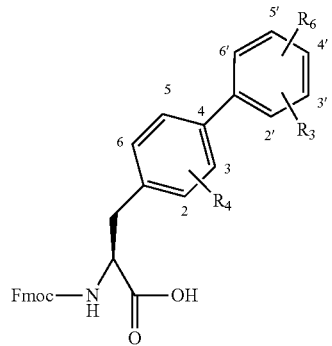

Formula III

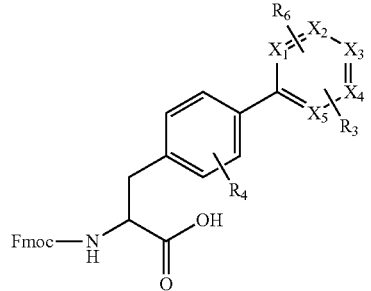

Formula IV

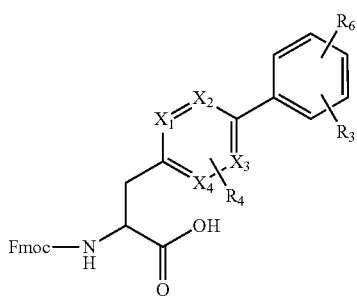

The peptidyl-resin precursors for their respective peptides may be cleaved and deprotected using any standard procedure (see, for example, D. S. King et al. Int. J. Peptide Protein Res. 36, 1990, 255-266). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

The following abbreviations are employed in the Examples and elsewhere herein:
Ph=phenyl
Bn=benzyl
i-Bu=iso-butyl
i-Pr=iso-propyl
Me=methyl
Et=ethyl
Pr=n-propyl
Bu=n-butyl
t-Bu=tert-butyl
Trt=trityl
TMS=trimethylsilyl
TIS=triisopropylsilane
$Et_2O$=diethyl ether
HOAc or AcOH=acetic acid
MeCN or AcCN=acetonitrile
DMF=N,N-dimethylformamide
EtOAc=ethyl acetate
THF=tetrahydrofuran
TFA=trifluoroacetic acid
TFE=α,α,α-trifluoroethanol
$Et_2NH$=diethylamine
NMM=N-methylmorpholine
NMP=N-methylpyrrolidone
DCM=dichloromethane
n-BuLi=n-butyllithium
Pd/C=palladium on carbon
$PtO_2$=platinum oxide
TEA=triethylamine
min.=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
Bip=biphenylalanine
$LiBH_4$=lithium borohydride
Mg=Magnesium
BOP reagent=benzotriazol-1-yloxy-tris-dimethylamino-phosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyluronim hexafluorophosphate
HATU=O-(7-Azabenzotriazol-1-yl)-1,1,3,3-tetramethyluronim hexafluorophosphate
HCTU=2-(6-Chloro-1-H-benzotriazol-1-yl)-1,1,3,3-tetramethyluronium hexafluorophosphate
TFFH=Tetramethyl-fluoroformamidinium hexafluorophosphate
DMAP=4-(dimethylamino)pyridine
DIEA=diisopropylethylamine
EDAC=3-ethyl-3'-(dimethylamino)propyl-carbodiimide hydrochloride (or 1-[(3-(dimethyl)amino)propyl])-3-ethylcarbodiimide hydrochloride)
Fmoc or FMOC=fluorenylmethyloxycarbonyl
Boc or BOC=tert-butyloxycarbonyl
Cbz=carbobenzyloxy or carbobenzoxy or benzyloxycarbonyl
HOBT or HOBT·$H_2O$=1-hydroxybenzotriazole hydrate
Cl-HOBt=6-Chloro-benzotriazole
HOAT=1-hydroxy-7-azabenzotriazole
TLC=thin layer chromatography
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal
GTT=glucose tolerance test One of skill in the art of peptide chemistry is aware that amino acids occur as both D and L isomers, and that the subject matter disclosed and claimed herein (including the subject matter provided in the sequence listing) includes the use of either or a mixture of isomers for amino acids incorporated in the synthesis of the peptides described herein.

General Procedures for the Synthesis of Amino Acids of Formula IVa

Protected amino acids of Formula IVa can be prepared by several methods. For example (Scheme A), iodobromo-heterocycle i (where $X_3$=N) can be coupled via palladium-mediated catalysis with a boronic acid by standard literature methods to provide aryl heterocyclic bromide ii, which by lithiation and reaction with a acylating such as dimethylformamide provides aldehyde iii. The aldehyde is reduced to alcohol iv by sodium borohydride or similar agent and the corresponding bromide v is prepared by extended refluxing of iv in 48% hydrobromic acid. Alkylation of tert-butyl 2-(diphenylmethyl-eneamino)acetate with v using a chiral catalyst after the method of O'Donnell (*Tetrahedron Letters* 39 8775 (1998)) leads to the chiral ester vi, which after deprotection with a strong non-aqueous acid and treatment with Fmoc-Cl provides Fmoc t-butyl ester vii of predominately one chiral form. Recrystallization of vii from common organic solvents provides viii with enantiomeric excess >95%. Removal of the ester using a strong non-aqueous acid provides compounds of Formula IVa.

Alternatively, compounds of Formula IVa can be prepared by radical-induced bromination of methyl heterocycle ix (Scheme B) to give bromomethylheterocycle x. Alkylation of x by the method of O'Donnell as described above and similar recrystallization leads to chiral ester xiii in high enantiomeric excess. Boronic acid coupling as described in Scheme A leads to compounds of Formula IVa.

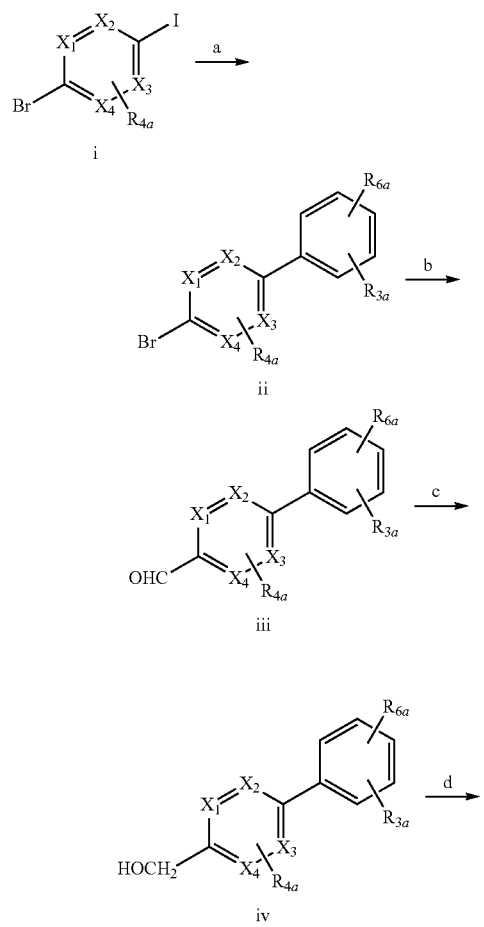

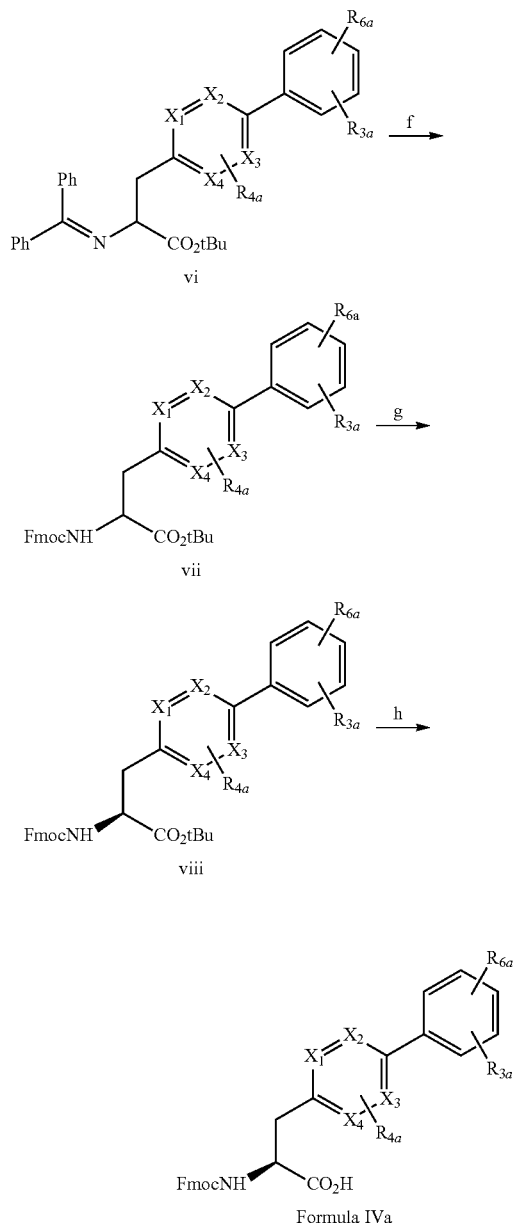

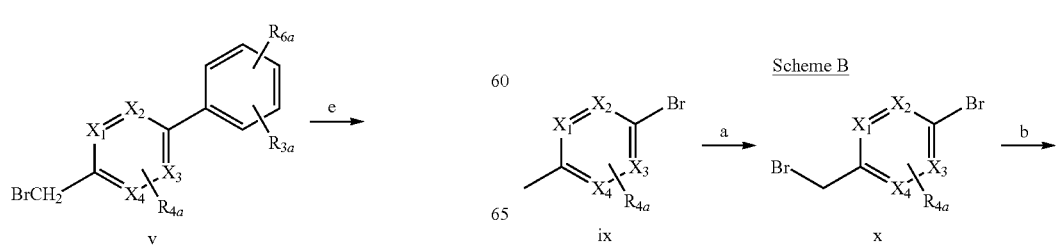

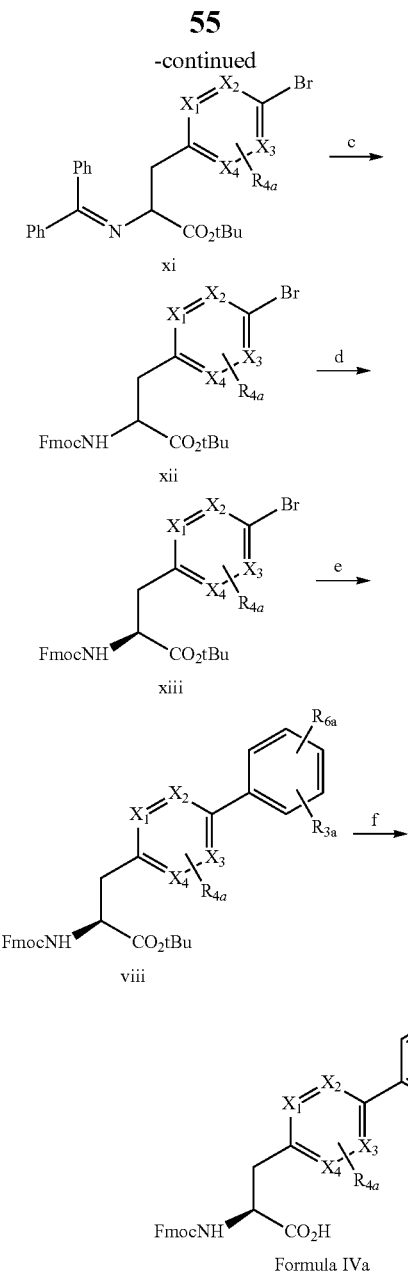

a) NBS, AIBN/CCl₄
b) PhC═NCH₂CO₂tBu, chiral catalyst, 2-tert-Butylimino-2-diethylamino-1,3-dimethyl-perhydro-1,3,2-diazaphos-phorine/THF
c) i. 15% citric acid ii. FmocCl, Na₂CO₃/THF—H₂O
d) recrystallization
e) R$_{3a}$R$_{6a}$C₆H₃B(OH)₂, Pd(Ph₃P)₄/toluene-10% Na₂CO₃
f) TFA Compound ix can be prepared from hydroxyheterocycle xiv by treatment with NBS (Scheme C).

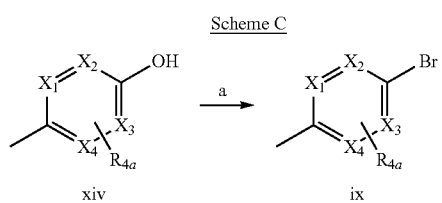

a) NBS, AIBN/CCl₄

An alternative synthesis of intermediate ix uses xv, methyl-3-iodo-alanate, and i by zinc-copper coupling (Scheme D).

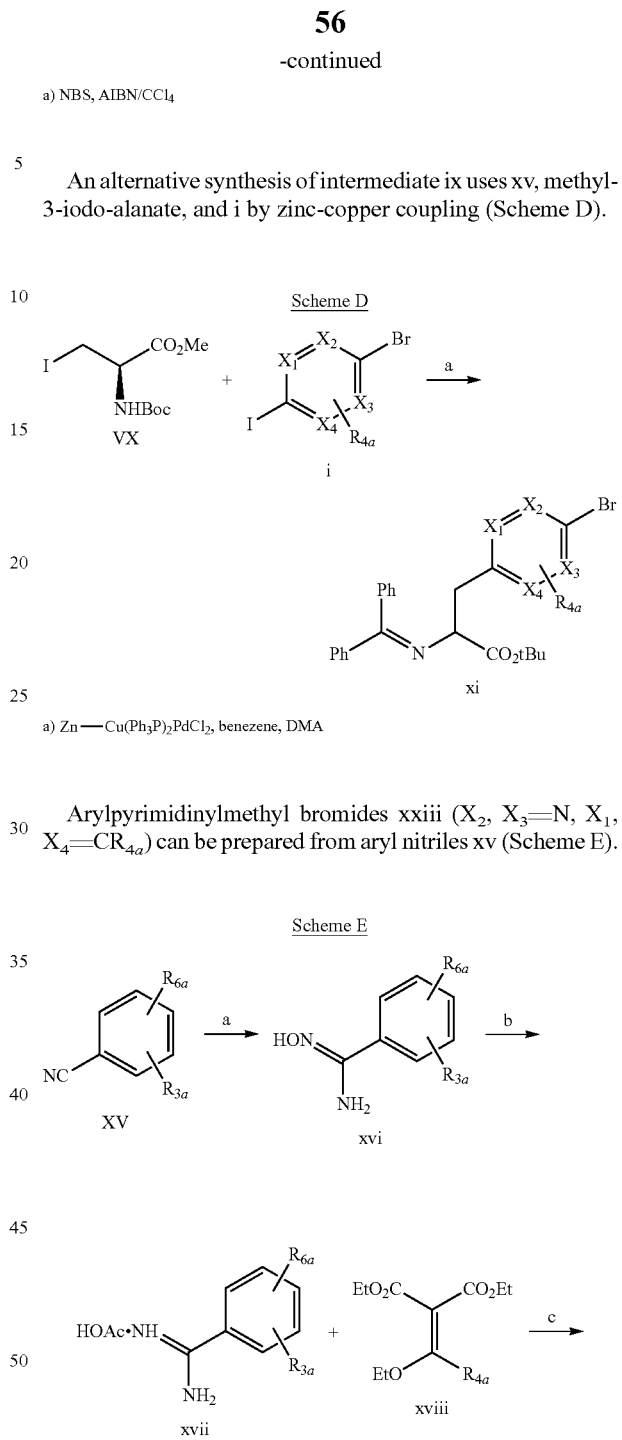

a) Zn—Cu(Ph₃P)₂PdCl₂, benezene, DMA

Arylpyrimidinylmethyl bromides xxiii (X₂, X₃═N, X₁, X₄═CR$_{4a}$) can be prepared from aryl nitriles xv (Scheme E).

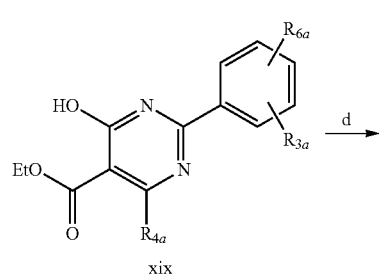

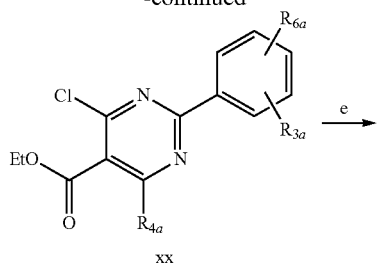
xx

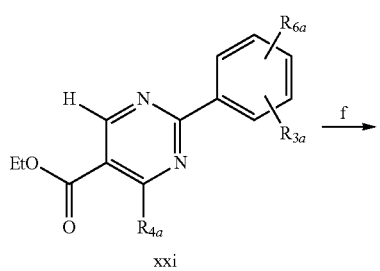
xxi

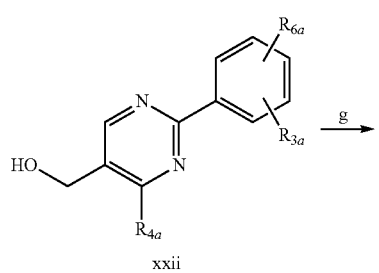
xxii

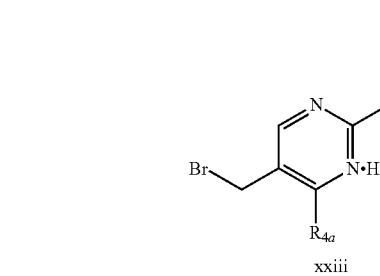
xxiii

Scheme F

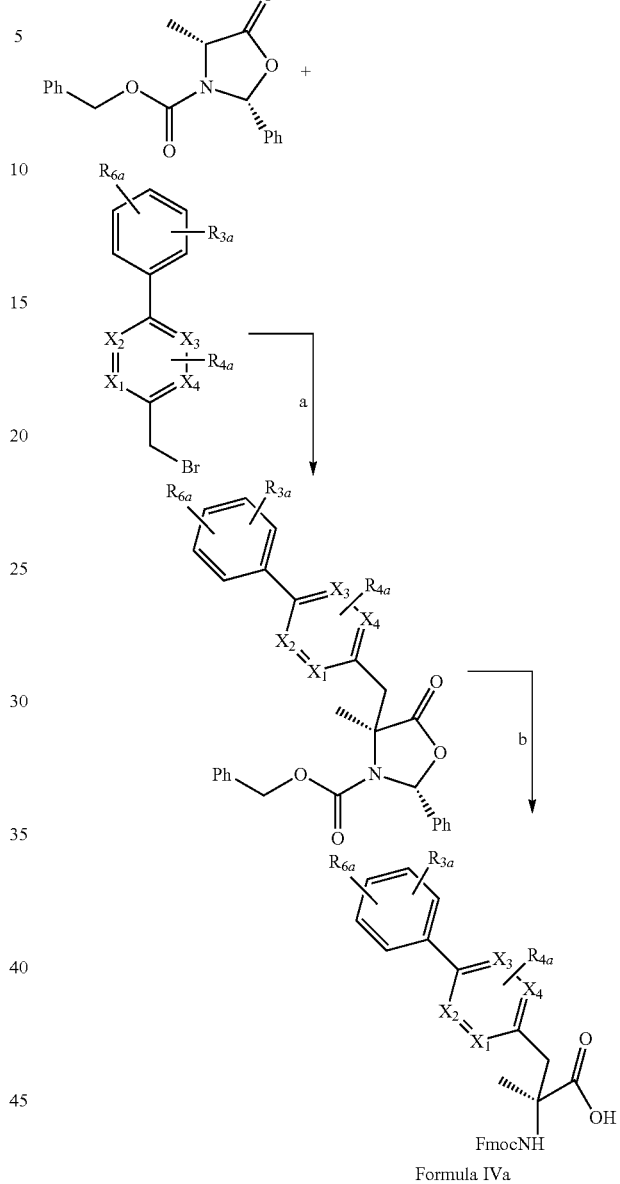
Formula IVa

Hydroxypyrimidine xvi is prepared from xv by treatment of the nitrile with hydroxylamine hydrochloride. The pyrimidine xvii results from hydrogenation of xvi. Condensation of xvii with enolmethylene malonate xviii leads to pyrimidine xix which is chlorinated with phosphorous oxychloride to give xx. Dehalogenation via catalytic hydrogenation leads to xxi and reduction with DiBAl provides alcohol xxii. Treatment of the alcohol with phosphorous oxybromide leads to unstable bromide xxiii, which must be used immediately as in Scheme A to provide protected amino acid vi.

Compounds of Formula IVa ($R_7$=Me) are prepared from oxazolidine xxiv by the method of Kapadia, *J. Org. Chem.* 66 1903 (2001) (Scheme F). Thus alkylation of xxiv with v using potassium hexamethyldisilazide or other strong base provides xxv. Strong acid hydrolysis of xxv followed by protection (with Fmoc-Cl or Fmoc-OSu or the like) of the amine gives compounds of the type of Formula IVa.

The Examples that follow illustrate various methods and specific embodiments of the invention described and claimed herein. One skilled in the art should appreciate that the Examples do not limit the scope of the invention but rather serve to guide those skilled in the art to practice embodiments of the invention. Additional embodiments are contemplated and encompassed by the instant disclosure and claims.

EXAMPLE 1

Simultaneous Solid Phase Peptide Synthesis of Peptides

Dipeptidyl resin, containing, amino acid at positions $X_{aa10}$ and $X_{aa11}$, was prepared using the following manual procedure in a batchwise mode before continuing peptide chain elongation utilizing the automated simultaneous synthesis protocol on an MPS-396 peptide synthesizer. The synthesis of the N-α-Fmoc-protected biphenylalanine or phenyl-heteroaryl-alanine derivatives used in the manual couplings is described in the general experimental above, and in Examples 10-19.

An amount of 9-Fmoc-aminoxanthen-3-yloxy-Merrifield resin (Sieber amide resin; loading: 0.5 to 0.7 mmol/g) sufficient to synthesize several peptide analogs, was swelled by washing with DMF (4×10 mL/g, 5 min.). The Fmoc group was then removed using two treatments, 5 and 15 min. each respectively, with 20% piperidine in DMF (10 mL/g). The resin was washed with DMF (4×10 mL/g) and NMP (4×10 mL/g). A 0.5 M solution of Fmoc-L-4-(2'-Methylphenyl)-3-pyridylalanine-OH(HCl salt) (1.1 eq.), (or of any other amino acid represented by Formula IVa), PyBOP (1.1 eq.) and DIEA (3.3 eq.) in NMP was added to the resin. The resin was then shaken or vortexed for 16-24 hours. Coupling completion was monitored using a qualitative ninhydrin test. The resin was drained, washed with NMP (3×10 mL/g) and DMF (3×10 mL/g), and treated for 90 min. with 10% acetic anhydride in DCM (10 mL/g). After DCM washes (4×10 mL/g), a second manual coupling cycle using a DIC/HOAt mediated was then performed, starting from the removal of the Fmoc group with 20% piperidine in DMF, and using a Fmoc-protected biphenylalanine analog, as represented by Formula II, in the coupling step. This synthesis scheme produced the desired Fmoc-protected dipeptidyl-Sieber amide resin.

Such dipeptidyl-resins required for the synthesis of a set of designed analogs were then used in the automated MPS synthesis of up to 96 peptides per run in the following manner. The dipeptidyl-resins were loaded as suspensions in dichloromethane/DMF (60:40) into the 96-well reactor of an Advanced ChemTech MPS 396 synthesizer in volumes corresponding to 0.01-0.025 mmol (20-50 mg) of resin per reactor well. The reactor was placed on the instrument and drained. The wells were then washed with DMF (0.5-1.0 mL, 3×2 min) and subjected to the number of automated coupling cycles required to assemble the respective peptide sequences as determined by the pre-programmed sequence synthesis table.

The detailed stepwise synthesis protocol used for a typical 0.025 mmol/well simultaneous synthesis of 96 compounds is described below. This protocol was adapted for the simultaneous synthesis of arrays of analogs ranging from 12 to 96 per individual run. The general synthesis protocol is depicted in Scheme 1.

Scheme 1
Automated synthesis of GLP-1 receptor modulator peptide analogs

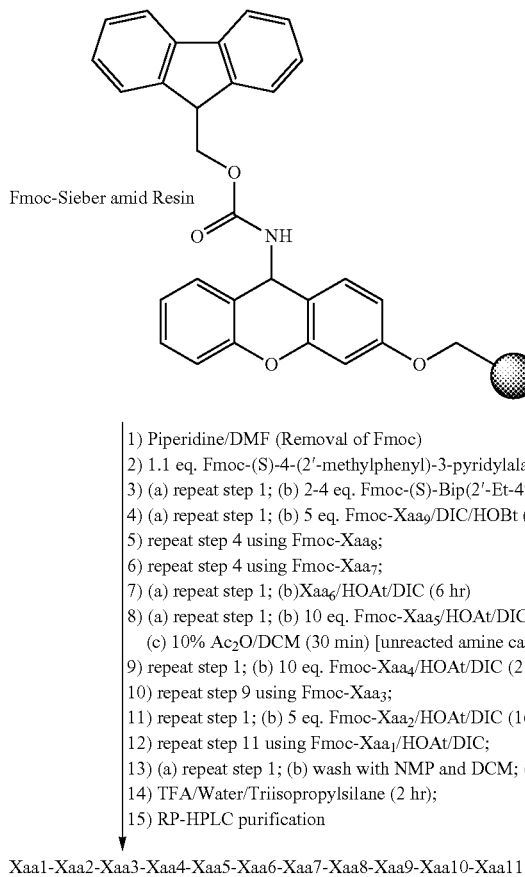

1) Piperidine/DMF (Removal of Fmoc)
2) 1.1 eq. Fmoc-(S)-4-(2'-methylphenyl)-3-pyridylala/PyBOP/DIEA/NMP (16 h);
3) (a) repeat step 1; (b) 2-4 eq. Fmoc-(S)-Bip(2'-Et-4'-OMe)/DIC/HOAt/NMP (16 hr);
4) (a) repeat step 1; (b) 5 eq. Fmoc-Xaa$_9$/DIC/HOBt (2 hr);
5) repeat step 4 using Fmoc-Xaa$_8$;
6) repeat step 4 using Fmoc-Xaa$_7$;
7) (a) repeat step 1; (b)Xaa$_6$/HOAt/DIC (6 hr)
8) (a) repeat step 1; (b) 10 eq. Fmoc-Xaa$_5$/HOAt/DIC (4 hr);
   (c) 10% Ac$_2$O/DCM (30 min) [unreacted amine capping step];
9) repeat step 1; (b) 10 eq. Fmoc-Xaa$_4$/HOAt/DIC (2 hr);
10) repeat step 9 using Fmoc-Xaa$_3$;
11) repeat step 1; (b) 5 eq. Fmoc-Xaa$_2$/HOAt/DIC (16 hr);
12) repeat step 11 using Fmoc-Xaa$_1$/HOAt/DIC;
13) (a) repeat step 1; (b) wash with NMP and DCM; (c) dry in vacuo;
14) TFA/Water/Triisopropylsilane (2 hr);
15) RP-HPLC purification Xaa1-Xaa2-Xaa3-Xaa4-Xaa5-Xaa6-Xaa7-Xaa8-Xaa9-Xaa10-Xaa11

Prior to starting the synthesis, the following reagent solutions were prepared and placed on the instrument as required: 1.5 M (15%) piperidine in DMF; 0.5 M DIEA in NMP; 0.36 M DIC in NMP; 1 M (10%) acetic anhydride in DMF. The required Fmoc-protected amino acids were prepared as 0.36 M solutions in 0.36 M HOAt/NMP and placed into the appropriate positions in the 32-position amino acid rack.

The Fmoc-protected dipeptidyl-resin prepared above was deprotected by treating with 20% piperidine in DMF (1.0 mL; 1×5 min.; 1×15 min.). The resin was then washed with NMP (8×1.0 mL).

Coupling of the next amino acid, typically Fmoc-Asp(OtBu)-OH or another Fmoc-amino acid with appropriate orthogonal protection if required, was carried out by manual addition of a solution of the appropriate Fmoc-amino acid (0.075 mmol, 3.0 eq.), HCTU (0.075 mmol, 3.0 eq.) and DIEA (0.15 mmol, 6.0 eq.) in NMP (1 mL) to all wells. The coupling was allowed to proceed for 3 hrs. After reactor draining by nitrogen pressure (3-5 psi) and washing the wells with NMP (4×1.0 mL).

The next coupling cycle started with the removal of the Fmoc group as described above, and involved the coupling of either Fmoc-Ser(tBu)-OH or of a different Fmoc-amino acid as required by the sequence substitutions desired at this position. The coupling was carried out in a manner identical to that described for Fmoc-Asp(OtBu)-OH. The next coupling step was carried out in the same way to incorporate either Fmoc-Thr(tBu)-OH or any of the other selected Fmoc-amino acids into this sequence position as required.

The next Fmoc-amino acid (for example Fmoc-α-methyl-Phe-OH or an analog thereof) was coupled as follows: after Fmoc deprotection in the usual manner, the Fmoc-amino acid (1-5 eq.), HOAt (1-5 eq.) and DIC (1-5 eq.) were added manually as a solution in NMP (1.0 mL) and the coupling was allowed to proceed for 16-24 hrs. The coupling was not repeated in this case. After the usual post-coupling washes, the peptidyl-resins were capped with acetic anhydride as described herein.

The next coupling step involved either Fmoc-Thr(tBu)-OH or substitution analogs as required by sequence replacements at this position. The coupling was performed as described for the initial MPS coupling of Fmoc-Asp(OtBu)-OH and its analogs, except that 10 eq. of Fmoc-Thr(tBu)-OH or substitution analogs was used and the coupling was allowed to proceed for 16 hrs and the coupling reagents used were DIC/HOAt in NMP. After the usual post-coupling washes, the peptidyl-resins were capped with 10% acetic anhydride in DCM (1×1 mL×60 mins.).

The identical coupling protocol described for the coupling of Fmoc-Asp(OtBu)-OH was used was repeated for the next three amino acid residues. Fmoc-His(Trt)-OH was coupled as the Fmoc-Thr(tBu)-OH residue described in the paragraph above in order to complete the sequence assembly of the desired peptide analogs. For the coupling of commercially and non-commercially available non-natural amino acids needed at a certain sequence position, a single coupling protocol similar to that described above for the novel amino acid at position 6 ($X_{aa6}$) was used.

Finally, the Fmoc group was removed with 20% piperidine in DMF as described above, and the peptidyl-resins were washed with DMF (4×1.0 mL) and DCM (4×1.0 mL). They were then dried on the reactor block by applying a constant pressure of nitrogen gas (5 psi) for 10-15 min.

Cleavage/Deprotection

The desired peptides were cleaved/deprotected from their respective peptidyl-resins by treatment with a TFA cleavage mixture as follows. A solution of TFA/DCM/tri-isopropylsilane (70:28:2) (1.0 mL) was added to each well in the reactor block, which was then vortexed for 10 mins. This was repeated twice more and the TFA solutions from the wells were collected by positive pressure into pre-tared vials located in a matching 96-vial block on the bottom of the reactor. The vials were capped and gently vortexed for an additional 90 min. The vials were uncapped and concentrated in a SpeedVac™ (Savant) to a volume of about 0.2 mL. The crude peptides were then precipitated by the addition of diisopropyl ether (3 mL) and being briefly vortexed. The precipitates were pelleted by centrifugation and the supernatants were decanted. The vials were dried in a SpeedVac™ (Savant) to yield the crude peptides, typically in >100% yields (20-40 mgs). The crude peptides dissolved directly in 2 mL of 0.6% ammonium hydroxide for purification by preparative HPLC as follows.

Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS (20×100 mm) column and eluted using a linear gradient of MeCN in water, both buffered with 0.1% TFA. A typical gradient used was from 20% to 50% 0.1% TFA/MeCN in 0.1% TFA/water over 15 min. at a flow rate of 14 mL/min with effluent UV detection at 220 nm. The desired product eluted well separated from impurities, typically after 10-11 min., and was usually collected in a single 10-15 mL fraction on a fraction collector. The desired peptides were obtained as amorphous white powders by lyophilization of their HPLC fractions.

HPLC Analysis of the Purified Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A autoinjector, a SPD10AV or SPD-M6A UV/VIS detector, or a SPD-M10A diode array detector. A YMC ODS S3 (4.6×50 mm) column was used and elution was performed using one of the following gradients: 10-70% B in A over 8 min, 2.5 mL/min. (method A); 5-80% B in A over 8 min. 2.5 mL/min. (method B); 5-70% B in A over 8 min., 2.5 mL/min. (method C); 25-75% B in A over 8 min, 2.5 mL/min (method D); 20-75% B in A over 8 min, 2.5 mL/min. (method E); 15-70% B in A over 8 min, 2.5 mL/min. (method F); 10-90% B in A over 8 min, 2.5 mL/min. (method G); 20-65% B in A over 8 min, 2.5 mL/min. (method H); 5-90% B in A over 8 min., 2.0 mL/min. (method I); 5-90% B in A over 8 min., 2.5 mL/min. (method J); 20-80% B in A over 8 min., 2.5 mL/min. (method K); 10-100% B in A over 8 min., 2.5 mL/min. (method L); 10-75% B in A over 8 min., 2.5 mL/min. (method M). Mobile phase A: 0.1% TFA/water; mobile phase B: 0.1% TFA/AcCN. The purity was typically >90%.

Characterization by Mass Spectrometry

Each peptide was characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:AcCN with 0.1% ammonium hydroxide. The flow rate for the analyses was 0.42 mL/min. and the injection volume 6 μl. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 μl/min. A linear gradient from 0% to 100% B in A over 4 min. was run, where mobile phase A was 98:2 water:AcCN with 10 mM ammonium acetate and mobile phase B was 10:90 water:AcCN with 10 mM ammonium acetate. The UV response was monitored at 220 nm. The samples were dissolved in 200 μl 50:50 H₂O:MeCN (0.05% TFA). The injection volume was 5 μl.

In all cases, the experimentally measured molecular weight was within 0.5 Daltons of the calculated mono-isotopic molecular weight.

EXAMPLE 2

A. General Procedure for the Synthesis of N-Acylated Peptide Analogs (Scheme 2)

The synthesis of N-acylated peptide analogs was started from the protected peptidyl-resin intermediate (1) (0.015 mmol), prepared as described herein, as shown in Scheme 2. The Fmoc group was removed using the procedure described herein, and the resulting resin intermediate 2 was coupled with the relevant Fmoc-protected amino acid or carboxylic acid using the coupling protocol described in the general method described herein. In cases where the appropriate anhydride was available, the N-acylation was performed using 5 eq. of the anhydride in NMP. The resulting N-acylated peptide analogs (3) were cleaved/deprotected and purified by prep. HPLC by the general method described herein.

and the resulting resin intermediate 2 is allowed to react with the relevant alky/aryl chloroformate in the presence of an appropriate base such as a tertiary amine, or with a di-carbonate or an activated carbonate such as p-nitrophenyl or phenyl or hydroxy-succinimidyl carbonate.

C. General Procedure for the Synthesis of N-Urea Derivatives of Peptide Analogs The synthesis of N-urea derivatives of peptide analogs (e.g., 11-mers) may be started from the protected peptidyl-resin intermediate (1) (0.025 mmol), prepared as described herein. The Fmoc group is removed using the procedure described herein, and the resulting resin intermediate 2 is allowed to react with the relevant isocyanate prepared, for example, as in K. Burgess et al., J. Am. Chem. Soc. 1997, 119, 1556-1564; alternatively, the resin intermediate 2 may be allowed to react with the relevant carbamoyl chloride. Similarly, N-urea derivatives of 10-mer peptide analogs may be prepared starting from a protected 10-mer peptidyl-resin intermediate, Fmoc removal and reaction of the resulting peptidyl-resin intermediate with the relevant isocyanate or carbamyl chloride.

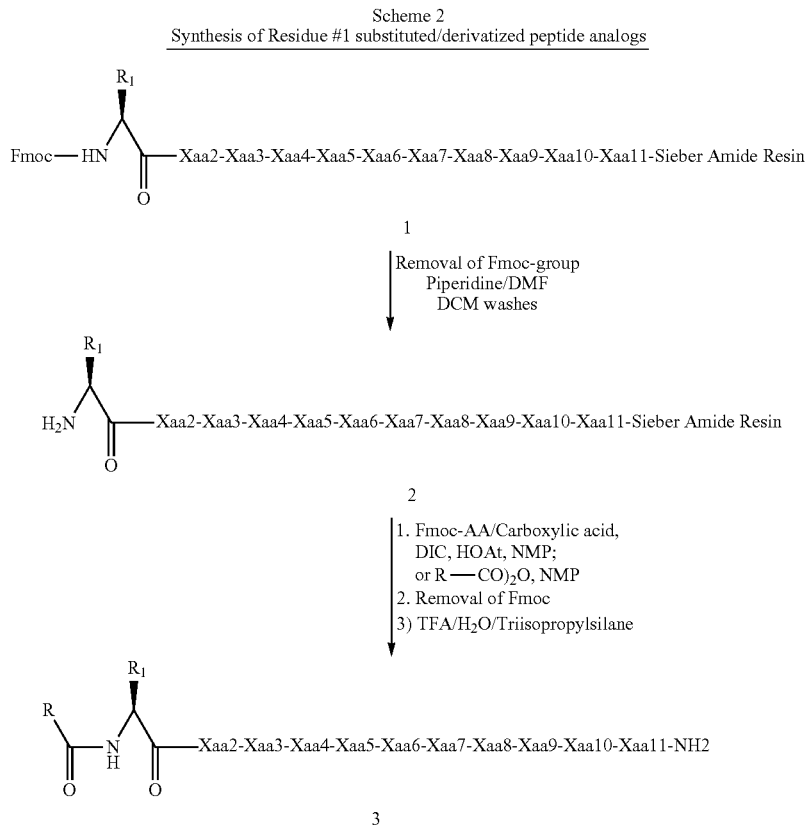

Scheme 2
Synthesis of Residue #1 substituted/derivatized peptide analogs

B. General Procedure for the Synthesis of N-Carbamate Derivatives of Peptide Analogs The synthesis of N-carbamate derivatives of peptide analogs may be started from the protected peptidyl-resin intermediate (1) (0.015 mmol), prepared as described herein. The Fmoc group is removed using the procedure described herein,

D. General Procedure for the Synthesis of N-Sulfonamides of Peptide Analogs

The synthesis of N-sulfonamides of peptide analogs (e.g., 11-mers) may be started from the protected peptidyl-resin intermediate (1) (0.025 mmol), prepared as described herein. The Fmoc group is removed using the procedure described herein, and the resulting resin intermediate 2 is allowed to react with the relevant sulfonyl chloride. Similarly, N-sulfonamides of 10-mer peptide analogs may be prepared starting from a protected 10-mer peptidyl-resin intermediate, Fmoc removal and reaction of the resulting peptidyl-resin intermediate with the relevant sulfonyl chloride.

E. General Procedure for the Synthesis of N-Sulfamide Derivatives of Peptide Analogs The synthesis of N-sulfonylurea derivatives of peptide analogs (e.g., 11-mers) may be started from the peptidyl-resin intermediate (1) (0.025 mmol), prepared as described herein. The Fmoc group is removed using the procedure described herein, and the resulting resin intermediate 2 is allowed to react with the relevant sulfamoyl chloride $R_4R_5N$—$SO_2$—$Cl$ to yield a sulfamide intermediate (see, for example, P. Davern et al. J. Chem. Soc., Perkin Trans. 2, 1994 (2), 381-387). Similarly, N-sulfamide derivatives of 10-mer peptide analogs may be prepared starting from a protected 10-mer peptidyl-resin intermediate, Fmoc removal and reaction of the resulting peptidyl-resin intermediate with the relevant sulfamoyl chloride $R_4R_5N$—$SO_2$—$Cl$.

EXAMPLE 3

Solid Phase Synthesis of Peptide Analogs Using an Applied Biosystems Model 433A Peptide Synthesizer Following is the general description for the solid phase synthesis of typical peptide analogs, using an upgraded Applied Biosystems Model 433A peptide synthesizer. The upgraded hardware and software of the synthesizer enabled conductivity monitoring of the Fmoc deprotection step with feedback control of coupling. The protocols allowed a range of synthesis scale from 0.05 to 1.0 mmol.

The incorporation of the two non-natural C-terminal amino acid was described above in connection with simultaneous synthesis of peptide analogs. Such a Fmoc-protected dipeptidyl resin was used in this ABI synthesis. The Fmoc-protected dipeptidyl-resin (0.1 mmol) was placed into a vessel of appropriate size on the instrument, washed 6 times with NMP and deprotected using two treatments with 22% piperidine/NMP (2 and 8 min. each). One or two additional monitored deprotection steps were performed until the conditions of the monitoring option were satisfied (<10% difference between the last two conductivity-based deprotection peaks). The total deprotection time was 10-12 min. The deprotected dipeptidyl-resin was washed 6 times with NMP and then coupled with the next amino acid. The procedure is illustrated by the example used in the next step.

Thus, Fmoc-Asp(OtBu)-OH was coupled next using the following method: Fmoc-Asp(OtBu)-OH (1 mmol, 10 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP, and subjected to 8 additional deprotection/coupling cycles as described above in order to complete the assembly of the desired sequence. The Fmoc-amino acids sequentially used were: Fmoc-Ser(tBu)-OH, Fmoc-Thr(tBu)-OH, Fmoc-α-methyl-Phe(2-Fluoro)-OH or analog thereof, Fmoc-Thr(tBu)-OH, Fmoc-Gly-OH, Fmoc-Glu(OtBu)-OH, Fmoc-Aib-OH and Fmoc-His(Trt)-OH. Finally, the Fmoc group was removed with 22% piperidine in NMP as described above, and the peptidyl-resin was washed 6 times with NMP and DCM, and dried in vacuo.

Alternatively, a modified coupling protocol was used in which the Fmoc-protected amino acid (0.26 mmol) was activated by subsequent addition of 0.5 M HOAt in DMF (0.52 mL) and DIC (40 μL), transferred to the reaction vessel manually and allowed to couple for 14-18 hrs.

Cleavage/Deprotection

The desired peptide was cleaved/deprotected from its respective peptidyl-resin by treatment with a solution of TFA/water/tri-isopropylsilane (96:2:2) (3.0 mL) for 2 hrs. The resin was filtered off, rinsed with TFA (1.0 mL), and the combined TFA filtrates were added to 35 mL of $Et_2O$. The resulting precipitate was collected by centrifugation and finally dried, to yield 232 mg of crude peptide product as a white solid. This was purified by preparative HPLC as described herein. The gradient used was from 15% to 45% 0.1% TFA/MeCN in 0.1% TFA/water over 40 min. The fractions containing pure product were pooled and lyophilized, to yield 28.4 mg (18% recovery) of pure product.

EXAMPLE 4

Synthesis of Biphenylalanine Analogs at position-$X_{aa10}$ and position-$X_{aa11}$ Represented by Formulas II-IV and IIa-IVa For those analogs wherein position-$X_{aa10}$ and position-$X_{aa11}$ residues were represented by substituted amino acid analogs represented by Formulas II-IV and IIa-IVa, i.e., biphenylalanine analogs (Bip analogs) or hetero-biphenylalanine analogs, their incorporation into the peptide chain was carried out in one of the following two approaches.

Approach A: Solid Phase Suzuki Condensation

In approach A, solid phase Suzuki condensation was practiced to prepare the required modified biphenylalanine or hetero-biphenylalanine residue in a manner suitable for carrying out subsequent solid phase peptide synthesis to obtain the target peptides. When the amino acid at position-$X_{aa11}$ in the target peptide was represented by a modified biphenylalanine or hetero-biphenylalanine residue, it was prepared as shown in Scheme 3. After removal of the Boc α-amine protecting group, chain elongation was continued using multiple peptide synthesis as described in the previous section to obtain the desired peptides or its derivatives thereof. When the modified biphenylalanine or hetero-biphenylalanine analog was in position $X_{aa10}$ of the target peptides, the required amino acid was prepared using a suitable dipeptide on solid support as shown in Scheme 4.

The resulting dipeptidyl segment containing the required modified biphenylalanine or hetero-biphenylalanine derivative was then used to carry out the synthesis of the target peptide or its derivatives thereof. When both position-$X_{aa10}$ and position-$X_{aa11}$ required novel biphenylalanine or hetero-biphenylalanine residues, two sequential solid phase Suzuki reactions were carried out as shown in Scheme 6 (below).

General Procedure for Preparation of SynPhase™ Lanterns Containing Amino Acids Represented by Formulas II-IV and IIa-IVa at Position-$X_{aa11}$ (Suzuki Couplings)

the catalyst used was dichlorobis(triphenylphosphine)palladium(II). For the D-series lantern scale reactions, ca. 10 mol % (0.0035 mol) catalyst was used.

Scheme 3

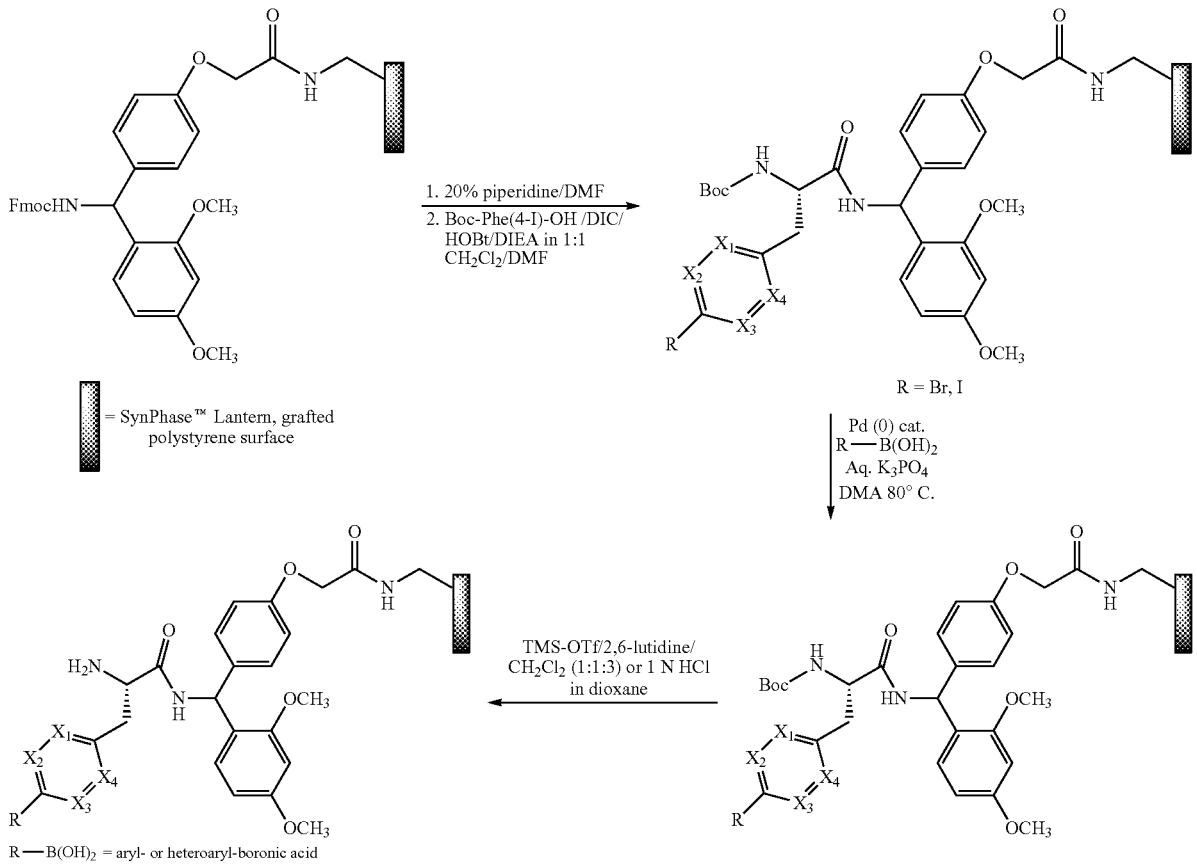

General Procedure A

SynPhase™ Lanterns (A-series (0.075 mmol/lantern)) or D-series ((0.035 mmol/lantern), from Mimotopes) derivatized with an N-α-Boc-4-iodophenylalanine residue either attached directly via a Knorr linkage (Boc-amino acid-resin) or via an amino acid-Knorr linkage (Boc-dipeptide-resin) were placed into 13×100 mm glass culture tubes with screw caps. (The following procedure was used for D-series lanterns. Similar ratios of reactants were used for reactions involving A-series lanterns.) Aryl- or heteroaryl-boronic acids (0.140 mmol, 4 equivalents) were dissolved in 0.30 ml of N,N-dimethylacetamide.

Potassium phosphate (0.280 mmol, 8 equivalents, 0.14 ml of a 2 M aqueous solution) was added to the aryl- or heteroaryl-boronic acid solution, followed by 0.10 ml of an N,N-dimethylacetamide solution containing 4.0 mg of tetrakis (triphenylphosphine)palladium(0) catalyst (ca. 10 mole %, 0.0035 mmol). The resulting mixtures were blanketed with a stream of nitrogen and the reaction vessels tightly capped and maintained at 80° C. for 17-20 hours while placed on an orbital shaker. The lanterns were washed with 3×1 ml of N,N-dimethylacetamide and 3×1 ml of dichloromethane (minimum of 3 min./wash cycle) prior to Boc group cleavage (see General Procedure below).

General Procedure B

The reactions were performed as in General Procedure A except a different catalyst was employed. For this procedure, Procedures for Cleavage of the Boc Group Method A (The following procedure applies to D-series lanterns, 0.035 mmol/lantern. A similar, appropriately scaled procedure was used for A-series lanterns, 0.075 mmol/lantern.) The Boc-protected lanterns prepared as described in General Procedures A or B were treated with 0.5 ml of a reagent solution consisting of trimethylsilyl trifluoromethanesulfonate, 2,6-lutidine and dichloromethane (1:1:3 by volume). After 2 such reagent treatments for 1 hour each with mild agitation, the resins were washed with 4×1.0 ml of dichloromethane, 3×1.0 ml of N,N-dimethylformamide, and 3×1.0 ml dichloromethane. The lanterns were then subjected to the next acylation (coupling reaction) in the peptide synthesis sequence.

Method B

The Boc-protected lanterns prepared as described in General Procedures A or B were treated with 0.5 ml of 1 N HCl in anhydrous 1,4-dioxane for 1 hour at room temperature with mild agitation. The lanterns were washed with 2×1.0 ml of 1,4-dioxane, 2×1.0 ml of 10% N,N-diisopropylethylamine in N,N-dimethylacetamide (vol:vol), 3×1.0 ml of N,N-dimethylacetamide, and 3×1.0 ml of dichloromethane to provide the free amino-lanterns ready for the next acylation (coupling reaction) step.

EXAMPLE 6

General Procedure for Preparation of a Lantern Containing a Modified Biphenylalanine Residue at Position-$X_{aa10}$ The General Procedures described above (A or B) for Suzuki coupling were utilized to obtain the required dipeptidyl lantern containing modified Phe at position-$X_{aa10}$ starting with the amino acid (at position-$X_{aa11}$) bound to SynPhase™ Lantern as shown in Scheme 4.

EXAMPLE 8

General Procedures for Acylation/Elongation of Peptides on Synphase™ Lanterns Procedure for Fmoc-Deprotection A D-series SynPhase™ Lantern (0.035 mmol/lantern loading) was added to 0.5 ml 8:2 N,N-dimethylformamide/piperidine (vol:vol). Mild agitation was applied. After 1 h, the lantern was washed with 3×1.0 ml N,N-dimethylformamide and 3×1.0 ml dichloromethane, allowing lantern to soak at least 3 min/wash.

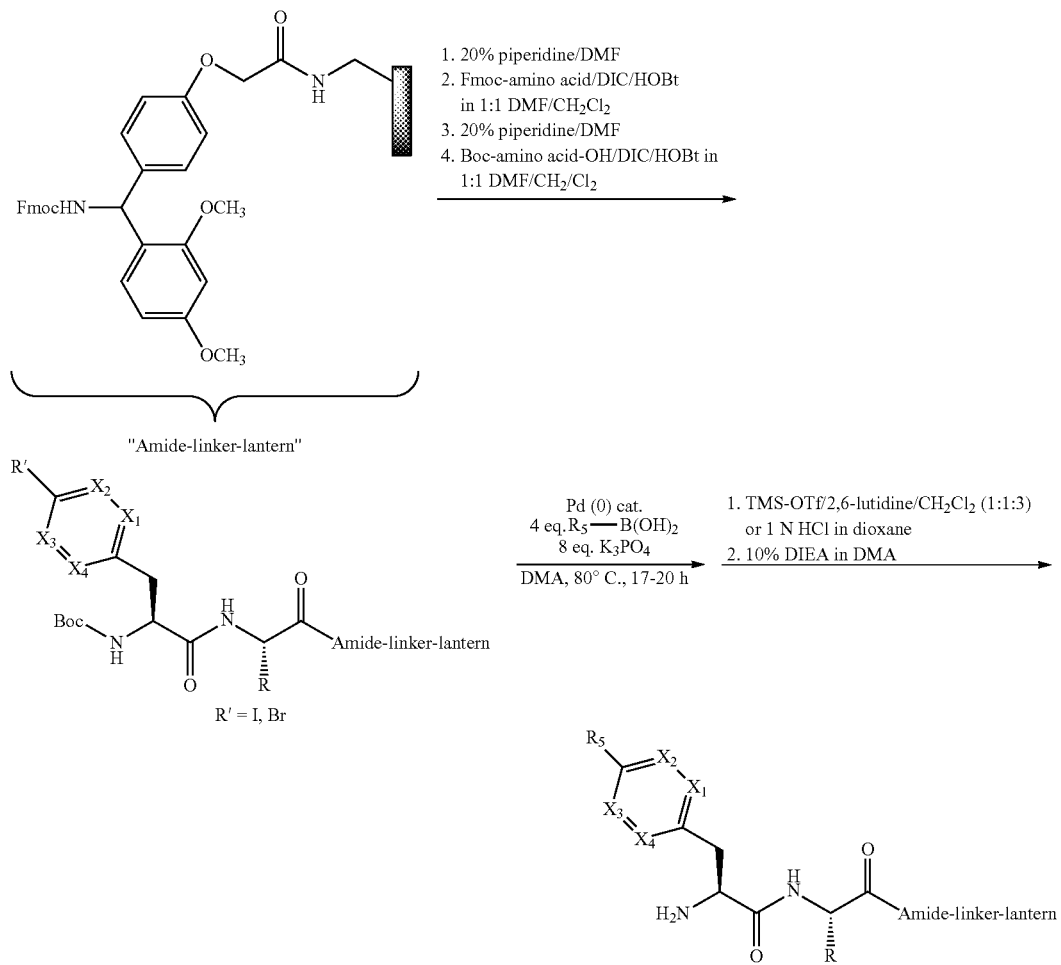

R is represented by the side chains described in Formulas II-V; $R_5$ = aryl or heteroaryl

EXAMPLE 7

General Procedure for Preparation of Lantern Containing Amino Acids Represented by Formulas II-IV and IIa-IVa at both positions-$X_{aa10}$ and -$X_{aa11}$ Utilizing the procedures described above for position-$X_{aa11}$ modified analogs (Scheme 1) and carrying out the Suzuki coupling procedure two successive times produced dipeptidyl lanterns containing modified phenylalanine residues at both positions-$X_{aa10}$ and -$X_{aa11}$ as illustrated in Scheme 6, below.

Procedure for Acylation/Amino Acid Coupling (Scheme 5)

A side chain and α-amine protected amino acid (0.105 mmol) was dissolved in 0.5 ml 1:1 N,N-dimethylformamide/dichloromethane. To this solution was added N-hydroxybenzotriazole (0.105 mmol), N,N-diisopropylethylamine (0.315 mmol), and N,N'-diisopropylcarbodiimide (0.105 mmol). The amino acid solution was allowed to sit for 10 min., after which a D-series lantern containing α-amine deprotected peptide (0.035 mmol/lantern) was added to the solution. The vial was capped and gently agitated for 16-20 h. The lantern was then washed with 3×1.0 ml N,N-dimethylformamide and 3×1.0 ml dichloromethane, letting lantern soak for 3-5 min/wash cycle.

Scheme 5
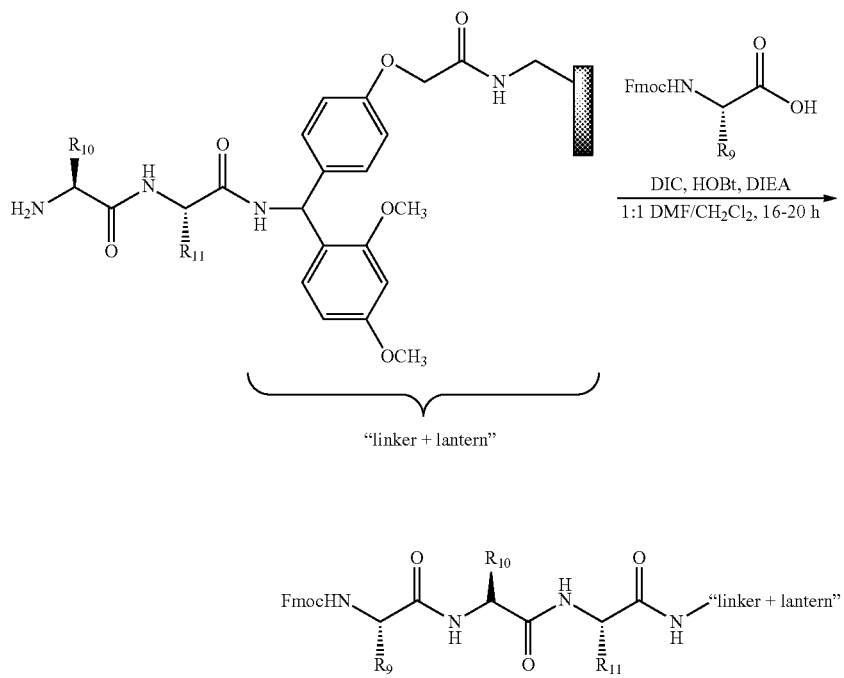
$R_{10}$ and $R_{11}$ are represented by the side chains described in Formulas II-IV and IIa-IVa
Scheme 6
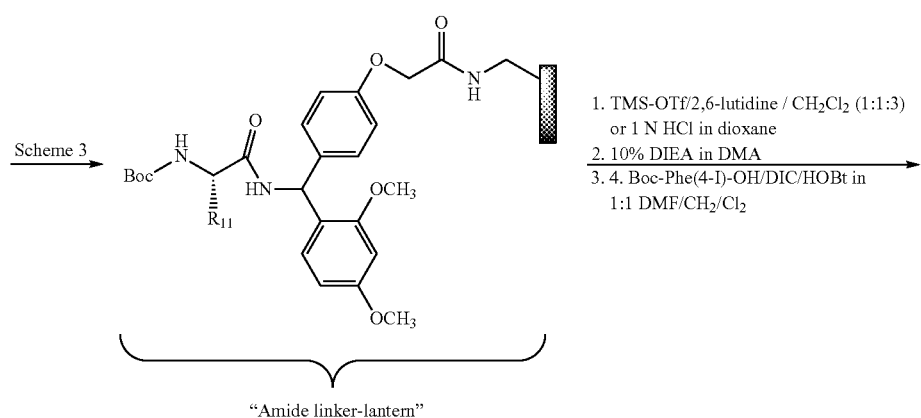
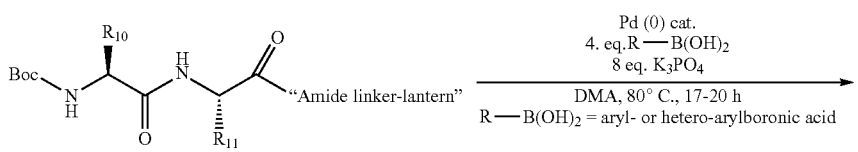

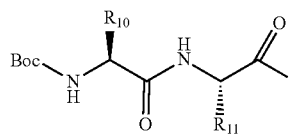

-continued

1. TMS-OTf/2,6-lutidine/CH$_2$Cl$_2$ (1:1:3) or 1 N HCl in dioxane
2. 10% DIEA in DMA

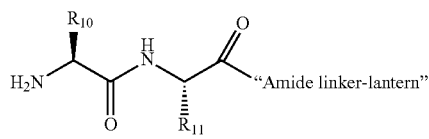

R$_{10}$ and R$_{11}$ are represented by the amino acid side chains described in formulas II-IV and IIa-IVa

EXAMPLE 9

General Procedure for Preparation of Peptides Via Fragment Condensation

In approach A, solid phase Suzuki condensation was practiced to prepare the required amino acids represented by Formulas II-IV and IIa-IVa at positions $X_{aa10}$ and $X_{aa11}$, as described in Example 7. After removal of the Boc α-amine protecting group from the position-$X_{aa10}$ amino acid, the dipeptide was cleaved from support. The dipeptide was then coupled to a fully side chain-protected 9 amino acid peptide (see infra). Subsequent deprotection of side chains and purification resulted in the desired peptide products. In a variation of the above procedure, the dipeptide incorporating the position-$X_{aa10}$ and $X_{aa11}$ amino acids may be coupled to the fully side chain-protected 9 amino acid peptide while on the solid support, as described in Scheme 10B.

Approach A: Solution Phase Fragment Condensation

In Approach A, solid phase Suzuki condensations and acylations were performed (as described in Example 7) to prepare the desired dipeptides bound to SynPhase™ Lanterns, with the N-terminal α-amine either Boc-protected or Fmoc-protected. The dipeptides were cleaved from the Lantern support under acidic conditions. In the case of Boc-protected N-terminal (1-amines, the acidic cleavage afforded simultaneous deprotection of the α-amine as shown in Scheme 7, and these were either purified or carried directly into the fragment coupling sequence.

The dipeptides containing Fmoc-protected N-terminal G-amines were cleaved under acidic conditions and the N-terminal α-amine was deprotected in solution, as shown in Scheme 8. These dipeptides were purified, then carried into the fragment coupling sequence.

Procedures for Cleavage of Dipeptides from Synphase™ Lanterns

Procedure A (Boc-Protected Dipeptides; See Scheme 7)

The D-series SynPhase™ Lantern was placed in a 1 dram glass vial. A solution of 1:1 TFA/dichloromethane (0.5 ml) was added to the vial. The vial was capped, and mildly agitated on an orbital shaker (100 rpm) for 2 h. The cleavage solution was transferred to a fresh vial, and an additional 0.5 ml 1:1 TFA/dichloromethane was added to the lantern. The vial was again capped, and mildly agitated on an orbital shaker (100 rpm) for 2 h. The second cleavage solution was added to the first, and the lantern was rinsed with dichloromethane. The rinse was added to the cleavage solutions, and solvent was evaporated to yield the dipeptide as the TFA salt of the α-amine.

Scheme 7

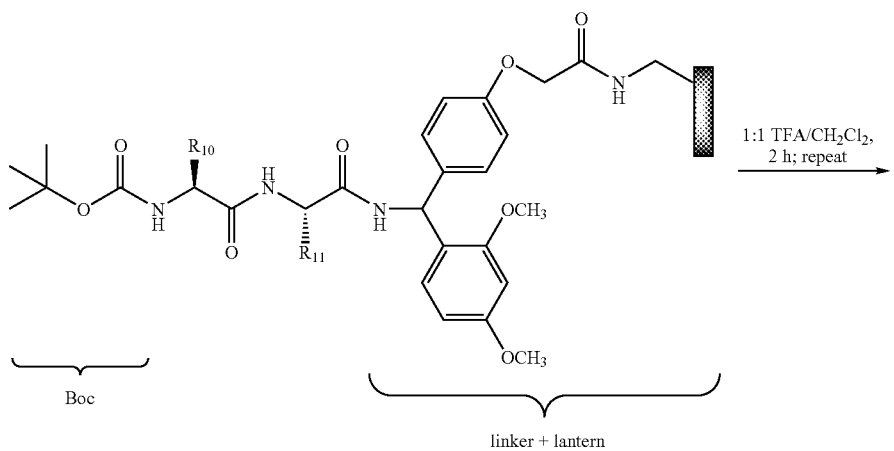

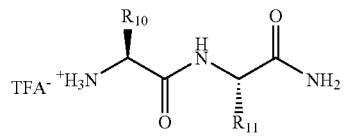

R$_{10}$ and R$_{11}$ are represented by the amino acid side chains described in formulas II-IV and IIa-IV Procedure B (Fmoc-Protected Dipeptides; See Scheme 8)

The Fmoc-protected dipeptides were cleaved from the SynPhase™ Lantern as described above in Procedure A. The lanterns were rinsed with dichloromethane, and solvent was evaporated from the combined rinse/cleavage solutions. To the resulting residue (in a 1 dram vial) was added 0.40 ml 8:2 dimethylformamide/piperidine (vol:vol). The vial was capped and allowed to react for 45 min. The remaining solvent was evaporated off, and the resulting product was purified by HPLC, using a C-18 column and CH$_3$CN/H$_2$O/TFA solvent system to yield (after evaporation of solvent) the dipeptide as the TFA salt of the α-amine.

mmol) for 18 hrs at RT. After several washes with NMP, the Fmoc group was removed by treatment with 1.5 M piperidine/DMF twice (5 min and 10 min). These coupling and deprotection steps were repeated seven times to assemble the desired sequence, except that 1.1 eq. and 1.5 eq. of Fmoc-α-Me-Phe(2-R-6-R")—OH and Boc-(L)-His(Trt)-OH were used, respectively, for their couplings, and that HATU/HOAt and DIEA (4 eq.) were used for coupling Fmoc-Thr(tBu)-OH onto (S)-α-Me-Phe(2-R-6-R")-peptidyl-resin.

Upon assembly completion, the peptidyl-resin was washed with DCM and then the protected 9-mer peptide C-terminal carboxylic acid was released from the resin by treatment with

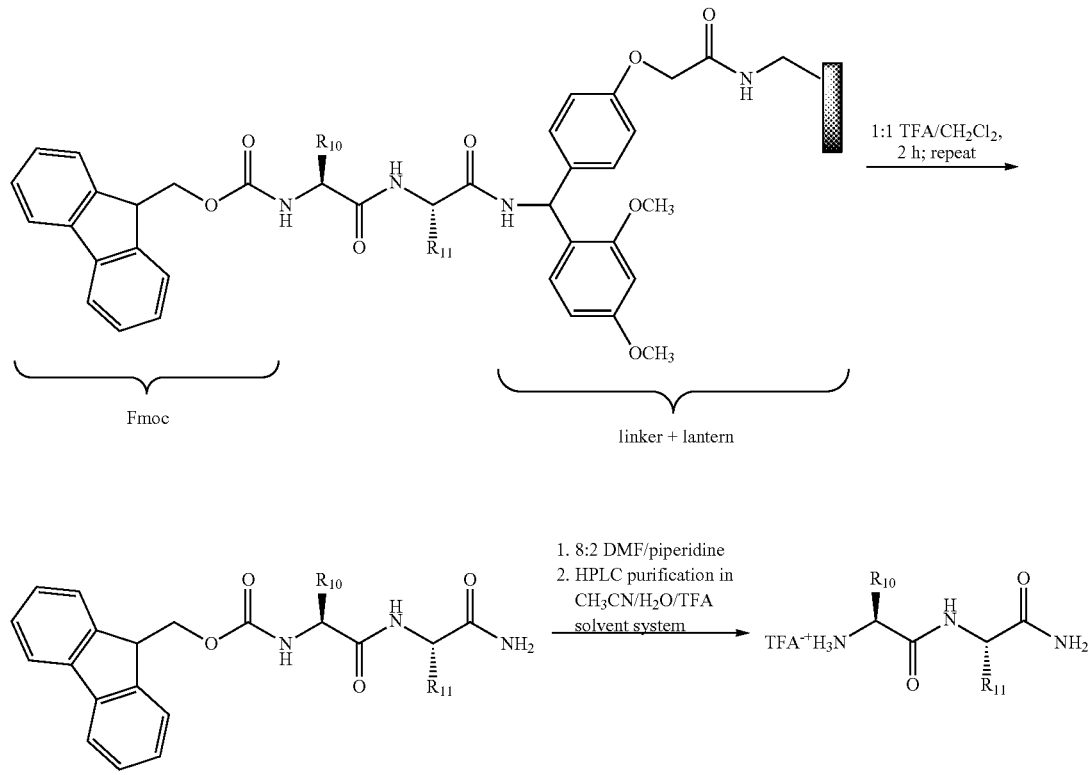

R$_{10}$ and R$_{11}$ are represented by the amino acid side chains described in formulas II-IV and IIa-IVa Procedure for Solid Phase Synthesis of Side Chain Protected 9-mer Peptide C-Terminal Carboxylic Acid (Scheme 9A)

A solution of Fmoc-(L)-Ser(tBu)-OH (5 eq.), 0.5 M HOAt/DMF (5 eq.) and DIC (5 eq.) in NMP (5 mL) was vortexed with(L)-Asp(OtBu)-2-chloro chlorotrityl resin (3.0 g, 2.16

DCM/AcOH/TFE (8:1:1, v:v:v) for 1 hr at RT. The resin was filtered off and the filtrate was evaporated to dryness, redissolved in AcCN/water (2:1) and lyophilized twice, to yield 2.777 g of 81% pure product, which was used in the subsequent fragment coupling step with no further purification.

Scheme 9A

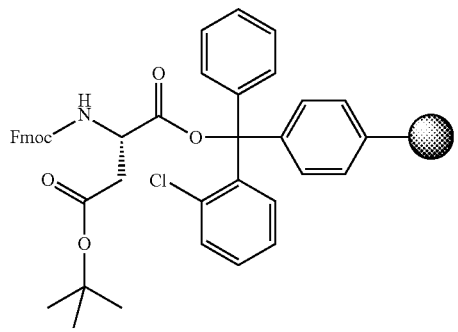

i) Piperidine/DMF (Removal of Fmoc)
ii) Fmoc-AA/DIC/HOAt/NMP/DMF (4-5 eq.)
iii) Repeat the above steps 2 times, changing the Fmoc-AA as required
iv) Piperidine/DMF
v) Fmoc-(S)-a-Me-Phe(2-R-6-R″)-OH, DIC/HOAt/NMP/DMF (1.1 eq.)
vi) Piperidine/DMF
vii) Fmoc-Thr(tBu)-OH/HATU/DIEA/HOAt/NMP/DMF (4 eq.)
viii) Piperidine/DMF
ix) Fmoc-Gly-OH/DIC/HOAt/NMP/DMF (4 eq.)
x) Repeat steps viii-ix 2 times changing the Fmoc-AA as needed
xi) Boc-His(Trt)-OH/DIC/HOAt/NMP/DMF (1.5 eq.)
xii) DCM/HOAc/TFE (8:1:1, v:v:v)
vi) Speed-vac/Lyophilize

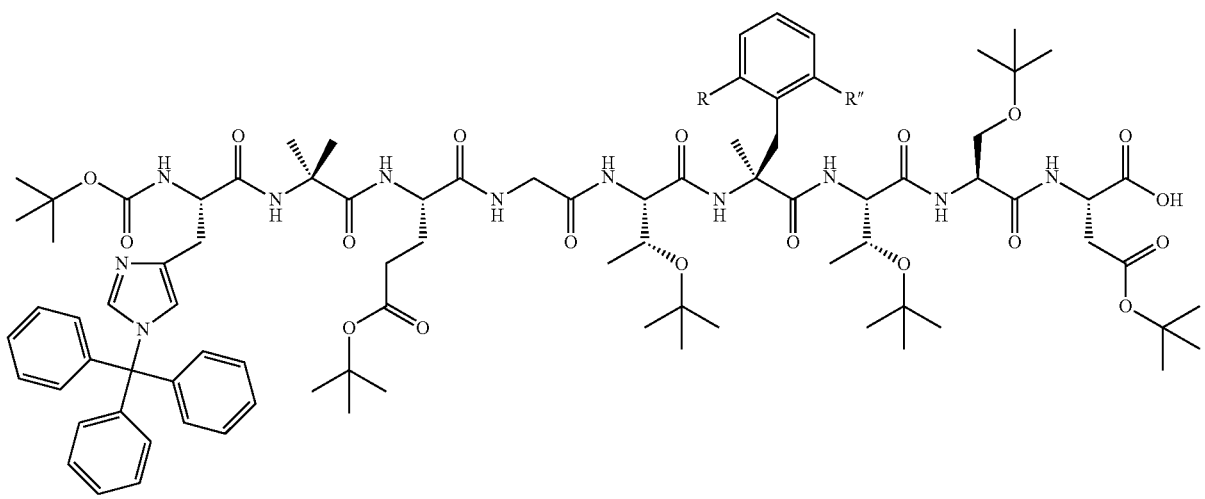

Procedure for Solid Phase Synthesis of Side Chain Protected N-Methoxycarbonyl 9-Mer Peptide C-Terminal Carboxylic Acid (Scheme 9B)

The N-Fmoc side chain protected 8-mer peptidyl-(o-Cl)-Trityl resin (3.5 mmol) was prepared as described above (Scheme 9A). After Fmoc removal and DMF washes, the peptidyl-resin (3.5 mmol) was treated with N-α-Methyloxy-carbonyl-N-im-Trityl-L-Histidine (2.4 g, 5.33 mmol) in 0.546 M HOAt in DMF (9.8 mL, 5.33 mmol), followed by addition of DMF (10 mL) and DIC (0.633 mL, 5.33 mmol). After stirring for 72 hours, the N-derivatized 9-mer peptidyl-resin was washed with DMF (4×50 mL) and DCM (2×50 mL), and the protected 9-mer peptide C-terminal carboxylic acid was released from the resin by treatment with DCM/AcOH/TFE (8:1:1, v:v:v) for 3 hours at RT. The resin was filtered off and the filtrate was evaporated to dryness, redissolved in AcCN/water (1:1.4) and lyophilized twice, to yield 4.05 g of 71% pure product, which was used in the subsequent fragment coupling steps with no further purification.

Scheme 9B

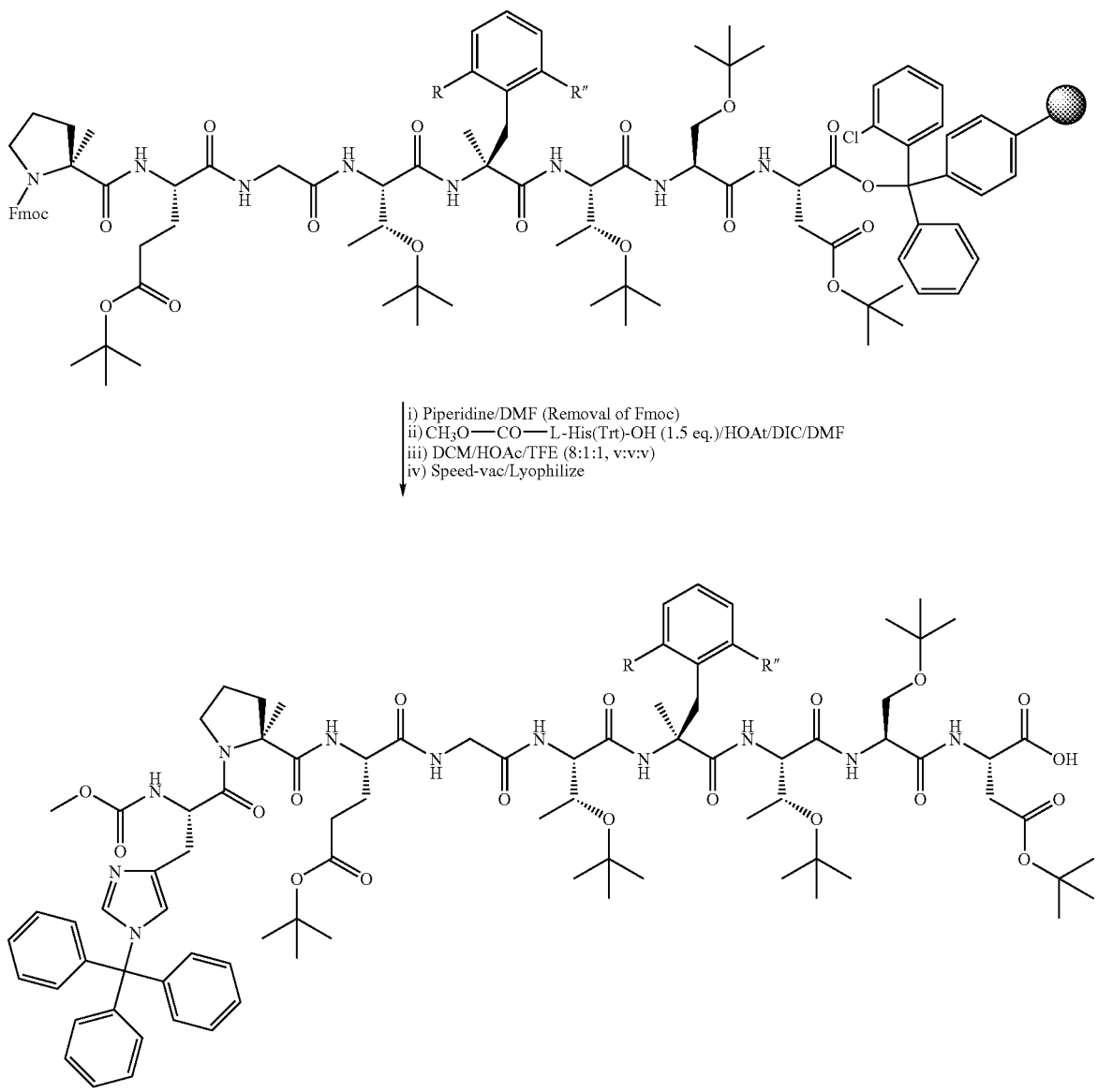

i) Piperidine/DMF (Removal of Fmoc)
ii) CH₃O—CO—L-His(Trt)-OH (1.5 eq.)/HOAt/DIC/DMF
iii) DCM/HOAc/TFE (8:1:1, v:v:v)
iv) Speed-vac/Lyophilize Procedure for Solution Phase Fragment Coupling Reaction These reactions were performed both in a single-compound format in 1 dram vials, and in a parallel array of compounds in a 2 ml 96-well plate. The following description (shown in Scheme 10) applies to the single-compound case, but is entirely analogous to the reactions performed in the 96-well plate.

The TFA-salt of the dipeptide (0.01 mmol) was dissolved in 0.25 ml THF containing 0.5% N,N-diisopropylethylamine in a 1.5 ml glass vial. Macroporous carbonate resin (MP-carbonate, 0.03 mmol, Argonaut Technologies) was added to the vial. The vial was capped and agitated for 2 h at room temperature. The solution was filtered, and excess solvent was removed by evaporation.

A solution of 0.15 ml of 9:1 chloroform/N,N-dimethylformamide containing the side chain protected 9-mer peptide C-terminal carboxylic acid (0.008 mmol) and N-hydroxybenzotriazole (HOBt, 0.008 mmol) was added to the vial containing the dipeptide amine. Diisopropylcarbodiimide (DIC, 0.08 mmol) was added in a solution of 0.05 ml 9:1 chloroform/N,N-dimethylformamide. The vial was capped, and the reaction was stirred on an orbital shaker at room temperature for 16 h. Remaining solvent was evaporated from the vial.

The peptide side chains and N-terminal α-amine were deprotected with 0.40 ml 97.5:2.5 TFA/triisopropylsilane (TFA/TIS) for 1 h. The remaining solvent was evaporated away, and the peptide products were then purified by HPLC, using a CH₃CN/H2O/TFA solvent system, and triggering effluent collection by the detection of desired product mass.

Scheme 10A
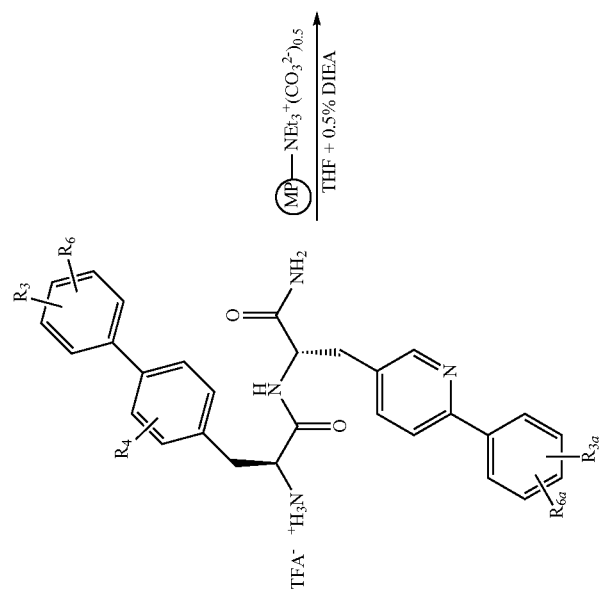

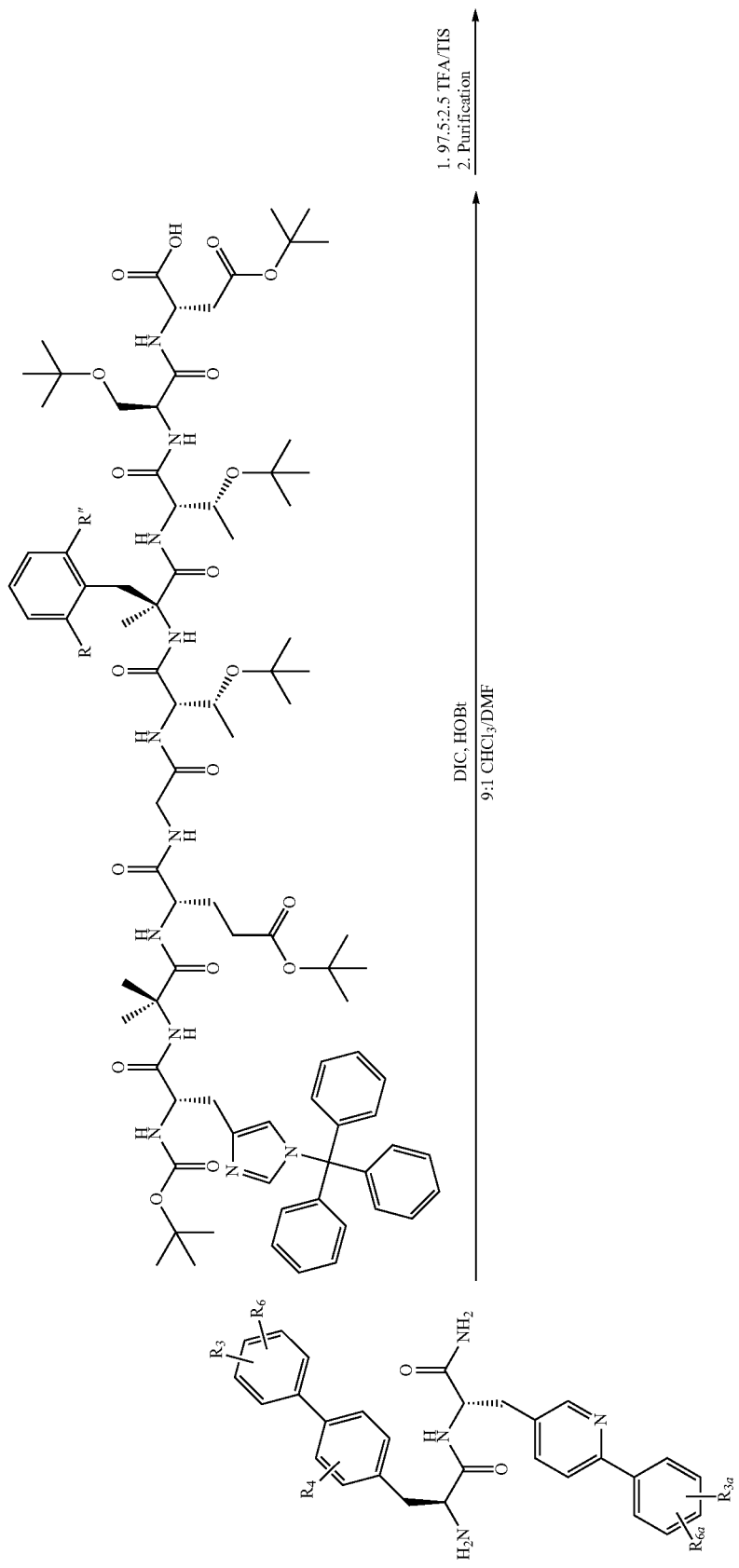

-continued
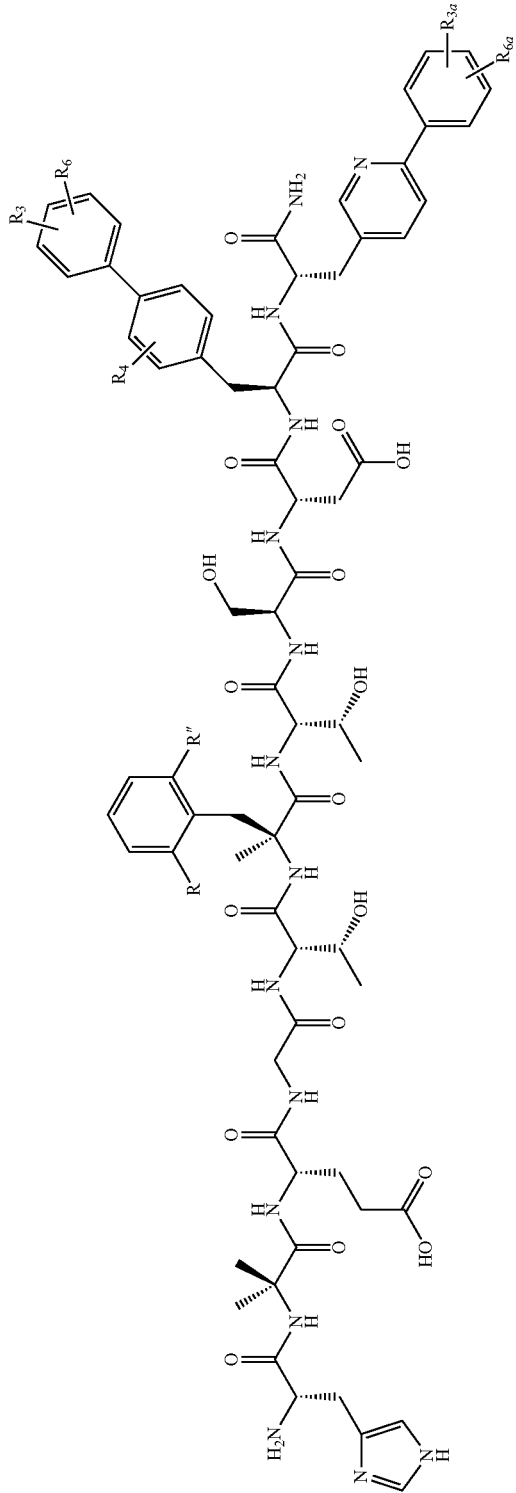
R, R″ = H, or F
$R_3$, $R_4$, $R_6$, $R_{3a}$, and $R_{6a}$ are represented by the side chains described in Formulas II and IVa.

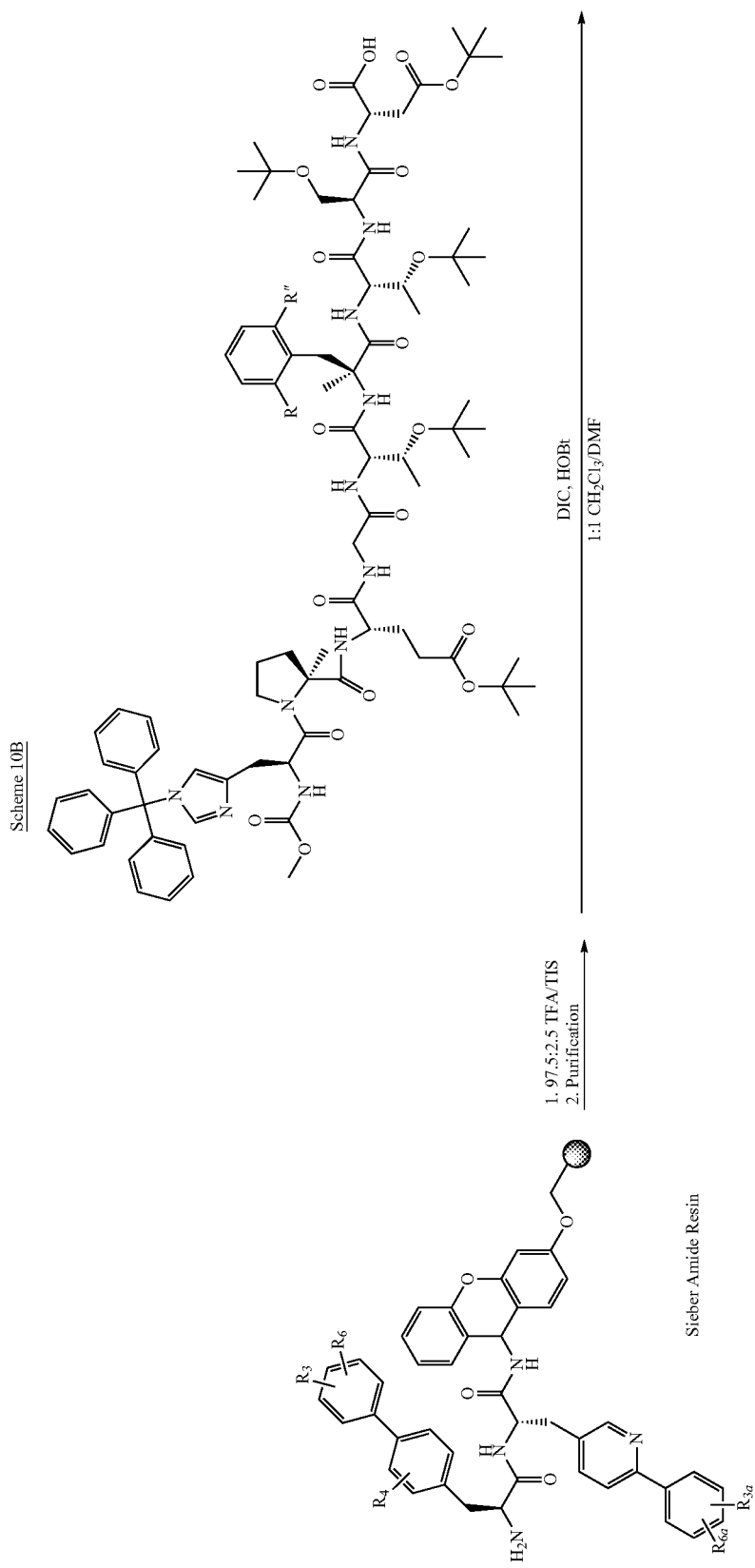
Scheme 10B

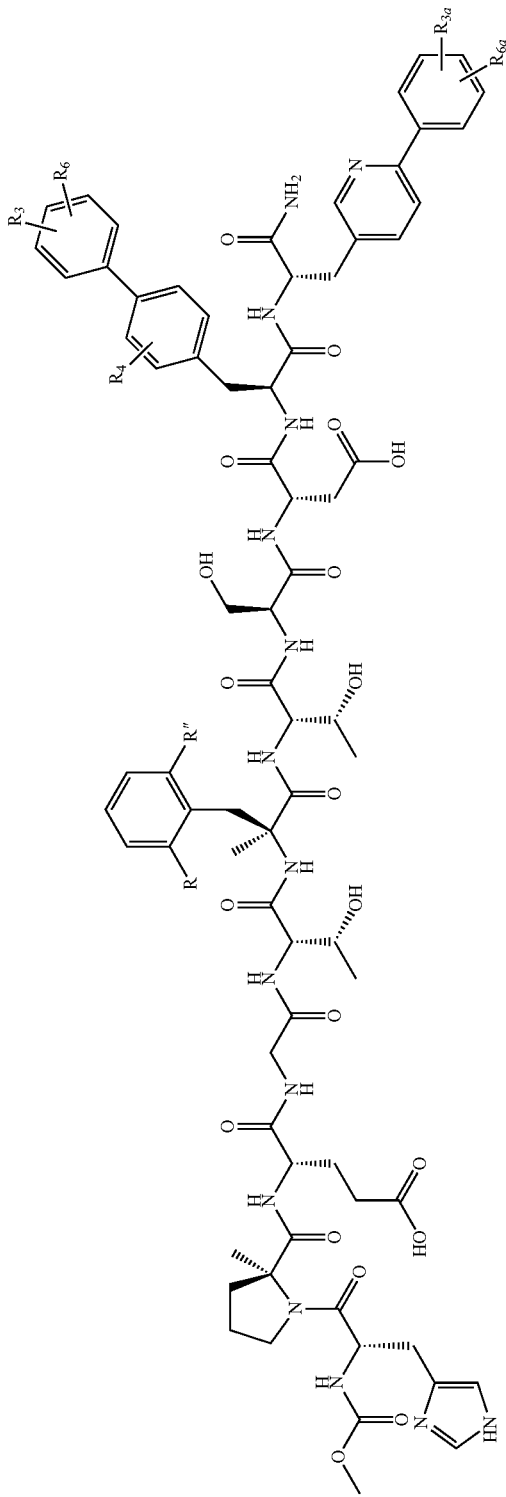
R, R" = H, or F
R3, R4, R6, R3a, R6a are represented by the side chains described in Formulas II and IVa.

Approach B: Synthesis of Fmoc-Amino Acids Analogs Represented by Formulas II-IV and IIa-IVa Using Suzuki Coupling in Solution The examples below illustrate the synthesis of several Fmoc-amino acids analogs represented by Formulas II-IV and IIa-IVa, which were then utilized for the solid phase synthesis of peptides and other peptide analogs as described herein.

EXAMPLE 10

Synthesis of Fmoc-(S)-2'-ethyl-4'-methoxy-biphenylalanine [Fmoc-(S)-Bip(2'-Et-4'-OMe)]

Scheme 11 describes the synthesis of Fmoc-(S)-2'-ethyl-4'-methoxy-biphenylalanine.

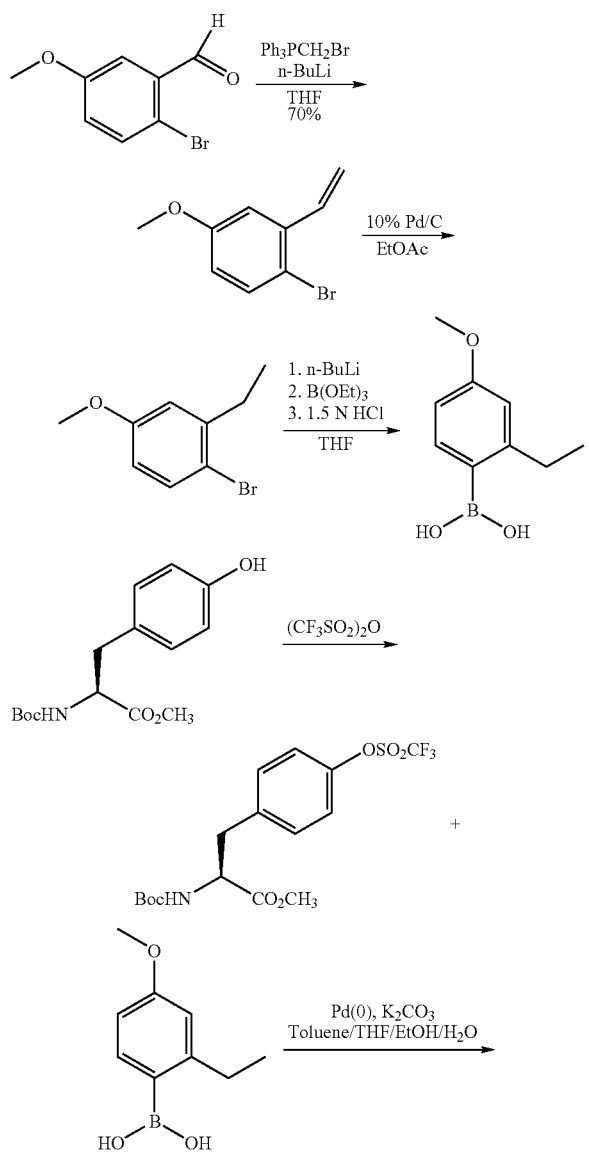

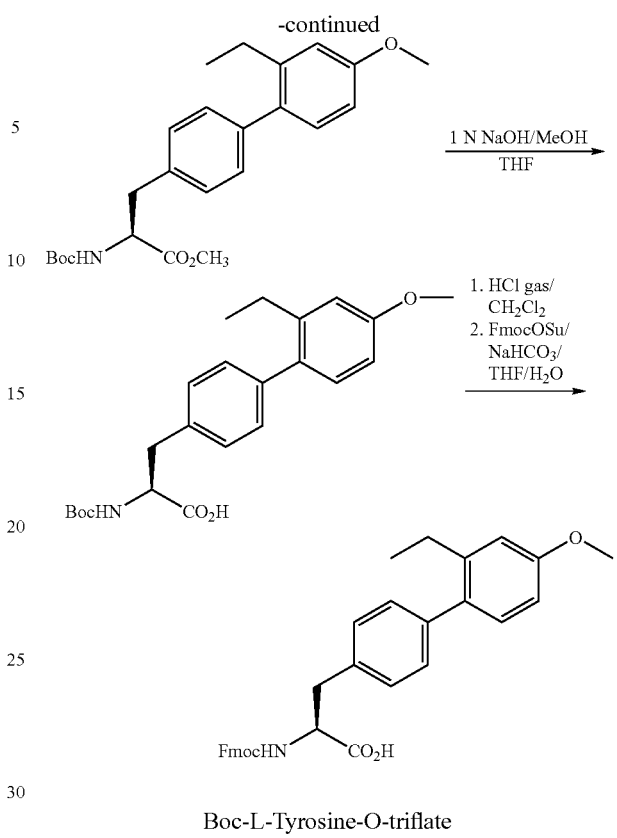

Boc-L-Tyrosine-O-triflate

To a solution of 25 g (85 mmol) of Boc-L-tyrosine methyl ester, and 36.25 g (339 mmol, 4 eq.) of 2,6-lutidine in 200 mL of dry DCM, kept at −40° C. under $N_2$, was added slowly 47.74 mg (169.5 mmol, 2 eq.) of triflic anhydride in DCM (100 ml) over 30 min. The solution was stirred at −40° C. for an additional 2 hours. HPLC analysis indicated that the reaction was complete. The reaction was quenched by addition of 20 mL of water. The layers were separated, and the organic layer was washed with 3×200 ml of 1N HCl, 200 ml of saturated $Na_2CO_3$, 200 ml of water and 200 mL of brine. The organic layer was dried over magnesium sulfate, filtered and dried in vacuo to give the crude product as a red oil. It was subjected to silica gel flash chromatography (300 g silica gel, 0 to 50% EtOAc in hexanes gradient). The product-containing fractions were concentrated in vacuo to give the desired compound (27 g, 75% yield) as a white solid.

2-Ethyl-4-Methoxy-phenylboronic acid

Method A

A suspension of methyl triphenylphosphonium bromide (199.5 g, 0.465 mol) in dry THF (800 ml) was purged for 10 min. and cooled to 10° C. n-Butyl lithium (169 ml, 0.465 mol, 2.75 M solution) was added slowly over 30 min. and stirred for 1 hr. 2-Bromo-5-methoxy benzaldehyde (100 g, 0.465 mol) in dry THF (300 ml) was added slowly over a period of 30 min. After the addition, the reaction mixture was stirred for 1 hr. Petroleum ether (2 L) was added and the reaction mixture was stirred for an additional 30 min. The reaction mixture was filtered over a silica gel pad. The pad was washed with diethyl ether. The combined organic washes were concentrated below 30° C. and the crude product was purified by 60-120 silica gel chromatography using 100% pet ether as eluent. Yield: 92 g, 90%, as pale yellow liquid.

2,2'-Bipyridyl (24.3 g, 0.15 mol) and 2-bromo-5-methoxy-styrene (65 g, 0.31 mol) in ethyl acetate (650 ml) were cooled to 0° C. The solution was purged and 10% palladium on carbon (16.25 g, 25%) was added under a stream of nitrogen. The reaction mixture was stirred under 2 kg pressure in a Parr shaker for 3 days under hydrogen. The reaction progress was monitored by HPLC. The reaction mixture was filtered through Celite and the filtrate was washed with 5% solution of potassium bisulfate, dried over sodium sulfate and concentrated below 30° C. Yield: 60 g, 91%, as pale yellow liquid.

A solution of 4-bromo-3-ethyl anisole (94 g, 0.437 mol) in THF (900 ml) was cooled to −78° C. n-Butyl lithium (249 ml, 0.55 mol) was added dropwise at the same temperature. Stirring was continued for 1 hr at −78° C. Tri-n-butyl borate (177 ml, 0.655 mol) was added slowly at −78° C. The cooling bath was removed, the reaction mixture was allowed to warm to 0° C. and was quenched with 1.5 N hydrochloric acid at 0° C. The organic layer was separated. The aqueous layer was extracted with ethylacetate and the combined organic layers were washed with brine and concentrated. The residue obtained was stirred in petroleum ether for 30 min. The solid obtained was filtered and dried under vacuum. Yield: 65 g, 82%, as a white solid.

Method B (See Scheme 12)

To a mixture of 3-Ethylphenol (50 g, 0.4 mol, 98% pure, Fluka) and $K_2CO_3$ (283 g, 2.05 mol) in dry acetone (500 ml) was added methyliodide (290 g, 2.05 mol). The reaction mixture was transferred to an autoclave and refluxed at 70° C. overnight. The reaction mixture was filtered through a Celite pad. The pad was washed with acetone and the combined filtrate and washes were concentrated. The product was dissolved in DCM, filtered and evaporated to dryness. Yield: 50 g, 90%, as a brown liquid.

3-Ethylanisole (50 g, 0.3676 mol) and N-bromosuccinimide (72 g, 0.4 mol) in AcCN (1 L) were stirred for 8 hr under dark at RT. The reaction mixture was concentrated below 40° C. and the residue obtained was redissolved in $CCl_4$ and filtered. The filtrate was concentrated and the product was purified by fractional distillation. Yield: 35 g, 43%, as pale yellow liquid.

The 4-bromo-3-ethyl anisole was converted to the corresponding boronic acid as described in Method A.

For the purpose of reaction scale up, the conversion of 4-bromo-3-ethyl anisole to 2-ethyl-4-methoxy-boronic acid may be accomplished using a Grignard method. Such method involves formation of the Grignard reagent by reaction of 4-bromo-3-ethyl anisole with Mg (1.1 eq.) in THF, followed by reaction of the resulting Grignard intermediate with tri-n-butyl- or trimethylborate as described in Method A.

Fmoc-(S)-2'-ethyl-4'-methoxy-biphenylalanine

Boc-L-Tyrosine-O-triflate (81 g, 0.19 mol) in dry toluene (600 ml) was purged for 10 min with nitrogen. $K_2CO_3$ (36 g, 0.26 mol) in 200 ml of water was added followed by 2-ethyl-4-methoxy-phenylboronic acid (36 g, 0.2 mol) and the reaction mixture was purged for 10 min using nitrogen. $Pd(PPh_3)_4$ (16.18 g, 0.014 mol), ethanol (200 ml) and THF (400 ml) were added and the reaction mixture was heated to 100° C. with stirring for 4 hr. The reaction mixture was concentrated under vacuum and the residue was dissolved in DCM (1.0 L). The organic layer was washed with 10% sodium hydroxide solution, 15% of citric acid solution, dried over sodium sulfate and concentrated. The crude product was purified by 60-120-mesh silica gel column chromatography with 10% of ethyl acetate in pet-ether. Yield: 50 g, 65%, as a yellow liquid.

To a mixture of the methyl ester of Boc-(S)-2'-ethyl-4'-methoxy-biphenylalanine (60 g, 0.146 mol) in THF (450 ml) and methanol (85 ml) was added sodium hydroxide (24 g, 0.58 mol) in 85 ml of water. The reaction mixture was stirred at RT overnight, concentrated and the residue was dissolved in water (100 ml) and washed with diethyl ether. The aqueous layer was acidified to pH 1 using 20% citric acid and extracted with ethyl acetate. The extract was washed with brine, dried over sodium sulfate and evaporated to dryness. Yield: 55 g, 94%, as colorless liquid.

Boc-(S)-2'-ethyl-4'-methoxy-biphenylalanine (55 g, 0.138 mol) was dissolved in dry DCM (1 lit) and dry HCl gas was purged at RT for 6 hr. The solid product obtained was filtered and dried under vacuum. Yield: 46 g, 100%.

To the free amino acid hydrochloride salt (30 g, 0.089 mol) in THF (700 ml) was added $NaHCO_3$ (29 g, 0.358 mol) in water (240 ml). Fmoc-OSu (30 g, 0.089 mol) was added portionwise over a period of 30 min. The reaction mixture was stirred overnight at RT. The THF was removed under vacuum and water (2.0 L) was added. The clear solution was extracted with ether to remove any impurities. The aqueous solution was acidified to pH 1 and extracted with ethyl acetate. The organic layer was washed with water and brine, and was evaporated to dryness. Yield: 37 g, 80%.

EXAMPLE 11

Synthesis of Fmoc-(S)-2'-ethyl-4'-hydroxy-biphenylalanine [Fmoc-(S)-Bip(2'-Et-4'-OH)]

The following Scheme 13 describes the synthesis of Fmoc-(S)-2'-ethyl-4'-hydroxy-biphenylalanine [Fmoc-(S)-Bip(2'-Et-4'-OH)]:

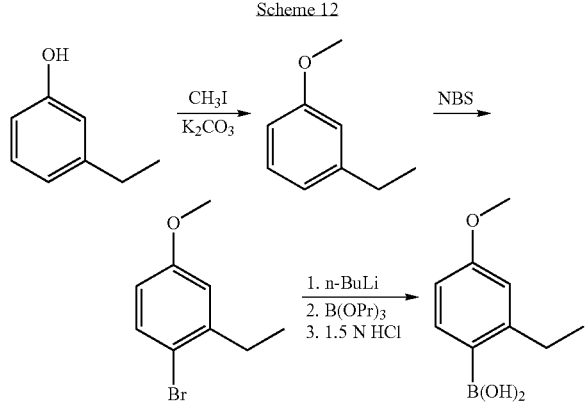

-continued

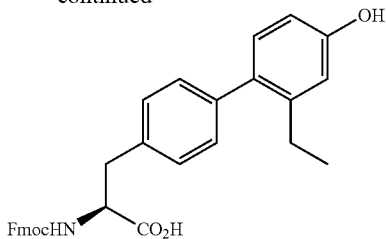

To a stirred solution of 4.46 g (8.55 mmol) of (S)-2-(((9H-fluoren-9-yl)methoxy)carbonylamino)-3-(2'-ethyl-4'-methoxybiphenyl-4-yl)propanoic acid [Fmoc-Bip(2'-Et-4'-OMe)-OH] in dichloromethane (34 mL) at −12° C. under argon was added a solution of 21.4 mL of 1 M borontribromide in dichloromethane (21.2 mmol) over the course of 20 min. The reaction mixture was stirred and allowed to warm to room temperature in situ as a gray slurry formed. After 3 h, the reaction mixture was added slowly to 300 mL of rapidly stirring water at room temperature. After 1 h, the reaction mixture was extracted twice with dichloromethane (100 mL portions). The organic extracts were combined, dried (MgSO₄), filtered and evaporated to provide a tan foam, 4.65 g. The desired product was purified by reverse phase HPLC (Luna 5μ C18 30×100 mm column, 50% to 100% gradient (10 min) (900:100:1 to 100:900:1 water/AcCN/TFA) as elutant; Flow rate at 40 mL/min. UV detection at 220 nm.). Partial evaporation of the pooled fractions provided a gummy material which was decanted from the remaining solution, washed with water, redissolved in dichloromethane, dried (MgSO₄), filtered and evaporated to provide the product as a white amorphous solid, 3.50 g, 81% yield. HPLC/MS: retention time=5.52 min [Zorbax SB C18 (4.6×75 mm) column; 0% to 100% gradient (8 min) (90:10:0.1 to 10:90:0.1 water/AcCN/TFA as elutant). Flow rate at 2.5 mL/min. UV detection at 220 nm.]; [M+H]⁺=508. ¹H NMR (DMSO-d₆): δ 12.77 (br s, 1H), 9.29 (s, 1H), 7.86 (d, J=7.7 Hz, 1H), 7.78 (d, J=8.8 Hz, 1H), 7.65 (t, J=7.1 Hz, 2H), 7.38 (m, 2H), 7.28 (m, 4H), 7.11 (d, J=7.7 Hz, 2H), 6.85 (d, J=8.2 Hz, 1H), 6.65 (d, J=2.2 Hz, 1H), 6.57 (dd, J=2.2, 8.3 Hz, 1H), 4.20 (m, 5H), 3.32 (br s, 1H), 3.10 (dd, J=4.4, 13.8 Hz, 1H), 2.90 (dd, J=10.5, 13.2 Hz, 1H), 2.37 (q, J=7.7 Hz, 2H), 0.91 (t, J=7.7 Hz, 3H).

2.28 g of the above product was further purified by chiral HPLC (CHIRALPAK® AD, 10 μm, 50×500 mm column, isocratic elution (n-heptane/AcCN/methanol/TFA, 839:80:80:1); flow rate at 60 mL/min. UV detection at 217 nm.). Evaporation of the pooled fractions, followed by re-evaporation with chloroform (3×20 mL) provided the product as an off-white amorphous solid, 2.17 g, 95% yield. Reverse phase HPLC: retention time=21.42 mins. [YMC ODS-A C18 3 μm (4.6×150 mm) column; 10% to 100% B gradient (30 min) (Buffer A: 0.1% TFA in water, Buffer B: 0.1% TFA in AcCN). Flow rate at 1 mL/min. UV detection at 217 nm.]. MS analysis: [M+NH₃]⁺=525.3 and [M−H]⁻=506.2. Chiral HPLC analysis: >99% ee, retention time=12.17 mins [CHIRALPAK® AD, 10 μm, 4.6×250 mm column, isocratic elution (n-heptane/AcCN/methanol/TFA, 799:100:100:1); flow rate at 1 mL/min. UV detection at 217 nm.]. [α]²⁵_D=−12.6 (c=1.0 in DMF).

EXAMPLE 12

Synthesis of (2S)-2-(((9H-Fluoren-9-yl)methoxy)carbonylamino)-3-(6-o-tolylpyridin-3-yl)propanoic acid hydrochloride [Fmoc-(S)-4-(2'-methylphenyl)-3-pyridylalanine hydrochloride]

The following Scheme 14 describes the synthesis of (2S)-2-(((9H-fluoren-9-yl)methoxy)carbonylamino)-3-(6-o-tolylpyridin-3-yl)propanoic acid hydrochloride:

Scheme 14

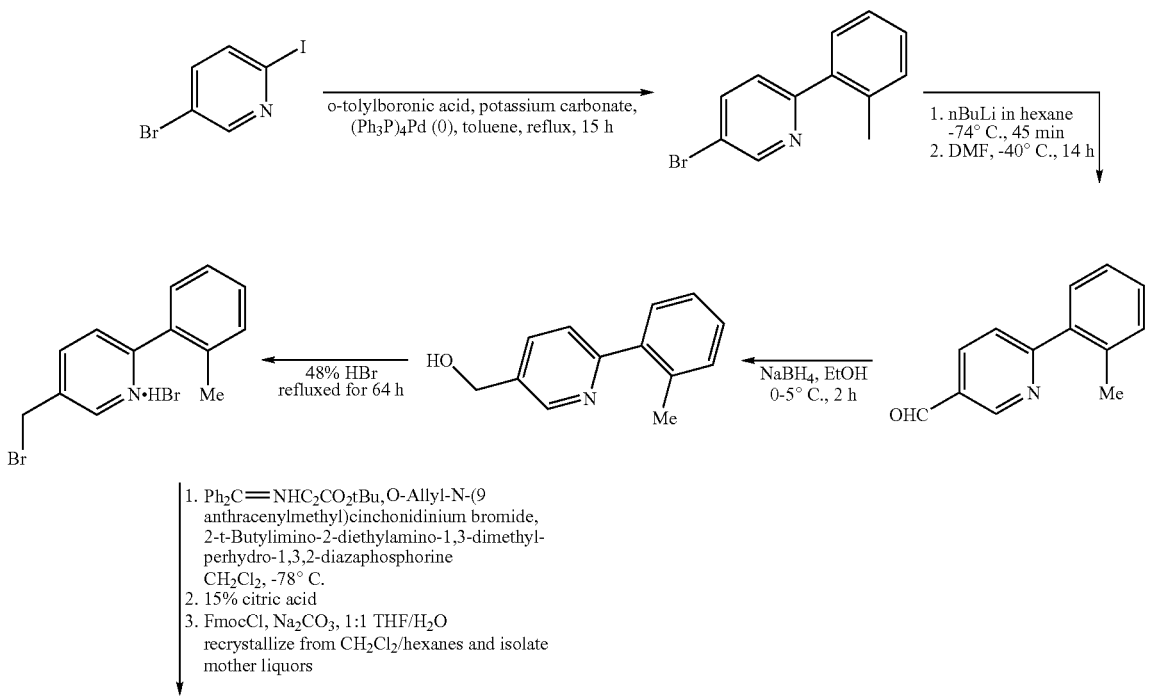

1. Ph₂C=NHC₂CO₂tBu, O-Allyl-N-(9 anthracenylmethyl)cinchonidinium bromide, 2-t-Butylimino-2-diethylamino-1,3-dimethyl-perhydro-1,3,2-diazaphosphorine CH₂Cl₂, -78° C.
2. 15% citric acid
3. FmocCl, Na₂CO₃, 1:1 THF/H₂O recrystallize from CH₂Cl₂/hexanes and isolate mother liquors

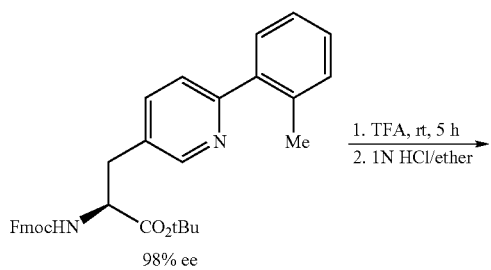
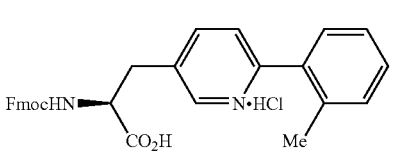

5-Bromo-2-o-tolylpyridine

To an argon-purged and evacuated slurry of 910 mg (3.21 mmol) of 5-bromo-2-iodopyridine and 436 mg (3.21 mmol, 1.0 eq.) of 2-o-tolylboronic acid in 8 mL of toluene and 3.2 mL of 2 M aqueous sodium carbonate, was added 36 mg (0.032 mmol, 0.01 eq) of tetrakis(tri-phenylphosphine)palladium. The reaction mixture was purged and evacuated with argon twice more and then set to reflux under argon for 15 h. The reaction was cooled and partitioned between water and EtOAc. The layers were separated, and the aqueous layer extracted once more with EtOAc. The organic extracts were combined, dried over magnesium sulfate, filtered, concentrated and dried in vacuo to give the crude product as an orange oil. Purification by silica gel chromatography (7:3 $CH_2Cl_2$/hexanes) provided the title compound as a yellow oil, 666 mg, 84% yield.

6-o-Tolylnicotinaldehyde

To a stirred solution of 125 mg of the above compound (0.50 mmol) in THF (2.0 mL) under argon at −74° C. was added 220 μL of nBuLi solution in hexane (2.5 M, 0.55 mmol, 1.1 eq) over 5 min, the temperature not allowed to rise above −71° C. A light green solution formed, which became dark green after 30 min. After 45 min, 49.4 μL (0.61 mmol, 1.2 eq) of DMF was added and the reaction allowed to warm to −40° C. After 14 h, a bright orange solution had formed. The reaction was quenched with 10% citric acid and the mixture stirred rapidly for 20 min at room temperature. The resulting bright yellow solution was extracted twice with EtOAc. The organic extracts were combined, dried over $MgSO_4$, filtered and concentrated to give a yellow oil. The crude mixture thus obtained was purified by silica gel chromatography using ethyl acetate/dichloromethane (1:24) as eluant, (2.5×10 cm column), to give white solid, mp 82-84° C., 90.3 mg, 91% yield.

(6-o-Tolylpyridin-3-yl)methanol

To a solution of 1.070 g (5.43 mmol) of 6-o-tolylnicotinaldehyde in 19 mL of ethanol at 0-5° C., was added 287 mg (7.5 mmol, 1.4 eq.) of sodium borohydride. After 2 h, the reaction mixture was quenched with saturated sodium bicarbonate solution and, after 30 min, partitioned between dichloromethane and brine. The organic extract was dried over magnesium sulfate and concentrated to give the indicated product as a colorless oil, 1.08 g, 100% yield.

5-(Bromomethyl)-2-o-tolylpyridine hydrobromide

A solution of 4.49 g (22.5 mmol) of (6-o-tolylpyridin-3-yl)methanol in 75 mL of 48% hydrobromic acid was heated to reflux for 64 h. The reaction mixture was partially cooled and excess hydrobromic acid was removed by vacuum distillation (110° C.@2 Torr) until a tan solid residue remained in the flask. Distillation was carried out using a large KOH pellet trap placed between the distillation apparatus and the vacuum pump. The solid residue was slurried in diethyl ether, filtered and dried under a nitrogen stream to give 7.38 g of product, 95% yield.

(2S)-tert-butyl 2-(diphenylmethyleneamino)-3-(6-o-tolylpyridin-3-yl)propanoate To a stirred mixture of 800 mg (2.33 mmol) of 5-(bromomethyl)-2-o-tolylpyridine hydrobromide, 689 mg (2.33 mmol, 1.0 equivalent) of tert-butyl 2-(diphenylmethyleneamino)acetate and 141 mg (0.233 mmol, 0.1 equivalent) of O-allyl-N-(9-anthracenylmethyl)cinchonidinium bromide in 14 mL of dichloromethane at −78° C. under argon was added 1.687 mL (5.83 mmol, 2.5 eq) of 2-t-butylimino-2-diethylamino-1,3-dimethyl-perhydro-1,3,2-diazaphosphorine over 5 min. The reaction mixture was stirred at −78° C. for 10 h and then allowed to warm to room temperature in situ. The mixture was directly purified by silica gel chromatography using ethyl acetate/dichloro-methane (1:4) as eluant (5×10 cm column), to give tan oil, 1.10 g, 100% yield.

(2S)-tert-Butyl 2-(((9H-fluoren-9-yl)methoxy)carbonylamino)-3-(6-o-tolylpyridin-3-yl)propanoate To a stirred solution of 1.10 g (2.33 mmol) of (2S)-tert-butyl 2-(diphenylmethyleneamino)-3-(6-o-tolylpyridin-3-yl)propanoate in 9 mL of THF at room temperature under argon was added 2.795 g (14.54 mmol, 6.5 equivalents) of citric acid in 9 mL of water. After 20 h, the reaction mixture was diluted with water (5 mL) and washed twice with ether (10 mL). The aqueous phase was then brought to pH 9 with solid sodium carbonate and extracted twice with dichloromethane.

The dichloromethane extracts were combined, dried with sodium sulfate and concentrated. The resulting oil was dissolved in 10 mL of THF and treated with 7.2 mL of 10% sodium carbonate solution and then 703 mg (2.56 mmol, 1.1 equivalents) of 9-fluorenylmethyloxycarbonylchloride at room temperature. After 14 h, the reaction mixture was extracted twice with dichloromethane, dried with sodium sulfate, filtered, concentrated and purified by chromatography on silica gel using ethyl acetate/dichloromethane (1:19) as eluant (2.5×10 cm column), to give colorless oil, 1.082 g, 91% yield. Recrystallization from 20 mL of 7:1 hexanes:dichloromethane provided a white solid, 287 mg. The mother liquors were concentrated to provide an amorphous white solid, the title compound, 779 mg, 63% yield. Chiral HPLC analysis (4.6×250 mm AD column, 38:1:1 heptane:methanol:ethanol as eluant 1 mL/min flow rate) indicated 98% ee.

(2S)-2-(((9H-Fluoren-9-yl)methoxy)carbonylamino)-3-(6-o-tolylpyridin-3-yl)propanoic acid hydrochloride A solution of 1.75 g (3.19 mmol) of (2S)-tert-butyl 2-(((9H-fluoren-9-yl)methoxy)carbonylamino)-3-(6-o-tolylpyridin-3-yl)propanoate in TFA (5.0 mL), protected from the atmosphere by a calcium chloride-filled drying tube was stirred at room temperature for two hours. The reaction mixture was concentrated in vacuo at less than 40° C. and the resulting orange oil was dissolved in 10 mL of ether to which a solution of 5 mL of 1 M HCl/ether was added. The resulting white solid was filtered and washed with ether to give the desired compound as a white powder, 1.65 g, 100% yield.

EXAMPLE 13

Synthesis of (2S)-2-(((9H-Fluoren-9-yl)methoxy)carbonylamino)-4-(6-bromopyridin-3-yl)propanoic acid hydrochloride The following Scheme 15 describes the synthesis of 3-(((9H-fluoren-9-yl)methoxy)carbonylamino)-3-(6-bromopyridin-3-yl)propanoic acid hydrochloride:

(S)-tert-Butyl 2-(((9H-fluoren-9-yl)methoxy)carbonylamino)-3-(6-bromopyridin-3-yl)propanoate To a stirred mixture of 2-bromo-5-(bromomethyl)pyridine (nominally 26.4 mmol), 7.798 g (26.4 mmol, 1.0 equivalents) of tert-butyl 2-(diphenyl methyleneamino)acetate and 1.60 g (2.64 mmol, 0.1 equivalent) of O-allyl-N-(9-anthracenylmethyl)cinchonidinium bromide in 100 mL of dichloromethane at −78° C. under argon was added 11.46 mL (39.6 mmol, 1.5 eq) of 2-t-butylimino-2-diethylamino-1,3-dimethyl-perhydro-1,3,2-diazaphosphorine over 5 min. The reaction mixture was stirred at −78° C. for 7 h and then allowed to warm to room temperature in situ. The reaction mixture was then concentrated, redissolved in 75 mL of THF and treated with citric acid (22 g) in 75 mL of water. After stirring vigorously for 7 h, the mixture was extracted twice with ether (75 mL). The organic extracts were combined and washed once with water (25 mL). The aqueous extracts were combined and brought to pH 8 with solid sodium carbonate. The aqueous solution was used without further treatment for the next reaction.

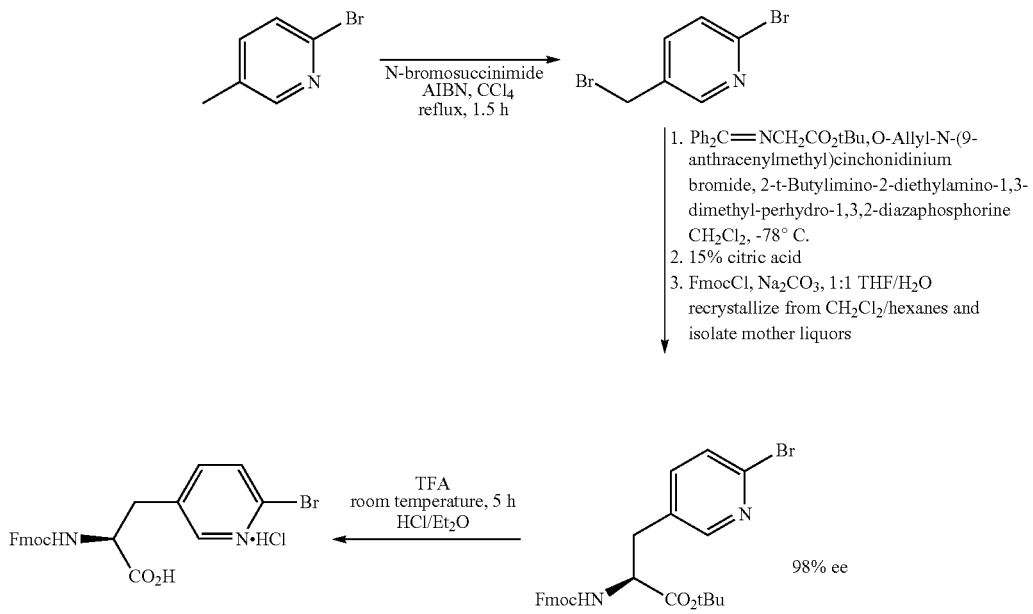

Scheme 15

2-Bromo-5-(bromomethyl)pyridine

To a stirred slurry of 10.320 g (60.0 mmol) of 5-methyl-2-bromopyridine and 5.339 g (30.0 mmol, 0.5 eq) of recrystallized N-bromosuccinimide in 150 mL of carbon tetrachloride was added 200 mg of AIBN. The reaction mixture was purged twice with argon and evacuated and set to reflux under argon. After 90 min, the reaction mixture was cooled to room temperature, filtered and the filtrate concentrated to give a yellow oil. Proton NMR indicated that the mixture contains 53% (mol) unreacted 5-methyl-2-bromopyridine, 43% of the title product and 4% of 2-bromo-5-(dibromomethyl)pyridine. The mixture was used immediately without further purification for the following procedure.

(S)-tert-Butyl 2-(((9H-fluoren-9-yl)methoxy)carbonylamino)-3-(6-bromopyridin-3-yl)propanoate The aqueous solution from above was added to a solution of 7.545 g (27.5 mmol, 1.04 equivalents) of 9-fluorenylmethyloxycarbonylchloride in 75 mL of THF at room temperature. After 14 h, the reaction mixture was extracted twice with ethyl acetate, dried with magnesium sulfate, filtered, concentrated and purified by chromatography on silica gel using ethyl acetate/dichloro-methane (1:24) as eluant (12×25 cm column), to give colorless oil, 7.25 g, 91% yield. Recrystallization from 120 mL of 5:1 hexanes/dichloromethane gave a small amount of a white solid, which was filtered off. The mother liquors were concentrated to provide an amorphous white solid, the title compound, 4.96 g, 62% yield. Chiral HPLC analysis (4.6×250 mm AD column, 38:1:1 heptane: methanol:ethanol as eluant 1 mL/min flow rate) indicated 97.2% ee.

2-(((9H-Fluoren-9-yl)methoxy)carbonylamino)-3-(6-bromopyridin-3-yl)propanoic acid hydrochloride A solution of 1.02 g (1.95 mmol) of (2S)-tert-butyl 2-(((9H-fluoren-9-yl)methoxy)carbonylamino)-3-(6-bromopyridin-3-yl)propanoate in TFA (3.0 mL), protected from the atmosphere by a calcium chloride-filled drying tube was stirred at room temperature for two hours. The reaction mixture was concentrated in vacuo at less than 35° C. and the resulting orange oil was dissolved in 3 mL of dichloromethane to which a solution of 6 mL of 1 M HCl/ether was added. The resulting white solid was filtered and washed with ether to give the title compound as a white powder, 845 mg, 86% yield.

EXAMPLE 14

Synthesis of (2S) 2-(((9H-Fluoren-9-yl)methoxy)carbonylamino)-3-(6-(2-ethylphenyl)pyridin-3-yl)propanoic acid hydrochloride [Fmoc-(S)-4-(2'-ethylphenyl)-3-pyridylalanine]

The following Scheme 16 describes the synthesis of (2S)-2-(((9H-fluoren-9-yl)methoxy)carbonylamino)-3-(6-(2-ethylphenyl)pyridine-3-yl)propanoic acid hydrochloride:

under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.25 g, 77% yield.

(2S) 2-(((9H-Fluoren-9-yl)methoxy)carbonylamino)-3-(6-(2-ethylphenyl)pyridine-3-yl)propanoic acid hydrochloride A solution of 1.53 g (2.79 mmol) of (2S)-tert-butyl 2-(((9H-fluoren-9-yl)methoxy)carbonylamino)-4-(6-(2-ethylphenyl)pyridine-3-yl)propanoate in TFA (5.0 mL), protected from the atmosphere by a calcium chloride-filled drying tube was stirred at room temperature for two hours. The reaction mixture was concentrated in vacuo at less than 35° C. and the resulting orange oil was dissolved in ether to which a solution of 6 mL of 1 M HCl/ether was added. The resulting white solid was filtered and washed with ether to give the desired product as a white powder, 1.38 g, 93% yield.

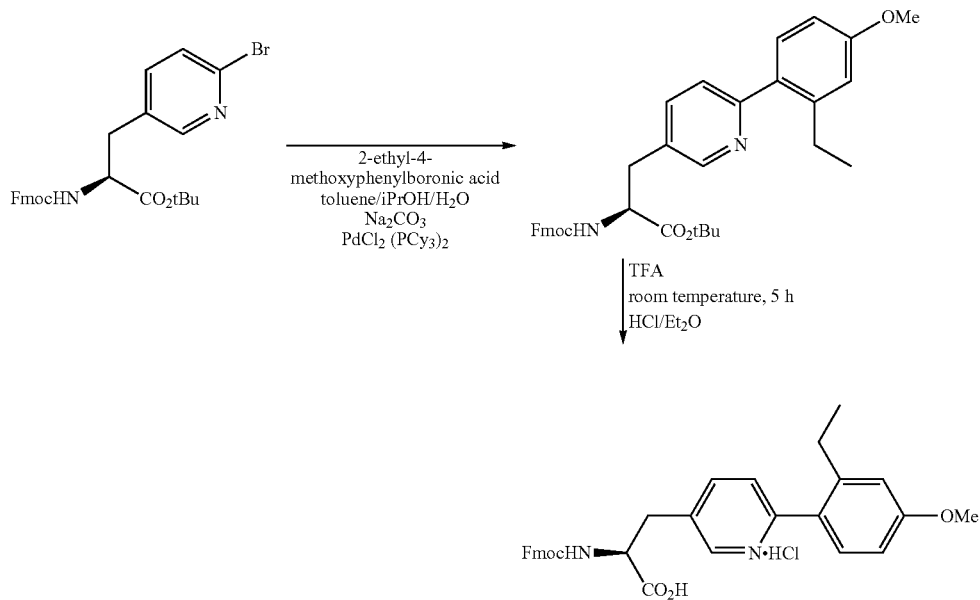

Scheme 16

((S)-tert-Butyl 2-(((9H-fluoren-9-yl)methoxy)carbonylamino)-3-(6-(2-ethylphenyl)pyridine-3-yl)propanoate To a stirred slurry of 1.75 g (3.35 mmol) of (S)-tert-butyl 2-(((9H-fluoren-9-yl)methoxy)carbonylamino)-3-(6-bromopyridin-3-yl)propanoate and 1.005 g (6.70 mmol, 2 eq.) of 2-ethylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium(II)chloride was added and the mixture was again purged with argon and evacuated. The rapidly stirred mixture was heated at 80° C.

EXAMPLE 15

Synthesis of (2S) 2-(((9H-Fluoren-9-yl)methoxy)carbonylamino)-3-(6-(2-ethyl-4-methoxy)phenyl)pyridin-3-yl)propanoic acid hydrochloride [Fmoc-(S)-4-[(2'-ethyl-4'-methoxy)phenyl]-3-pyridylalanine]

The following Scheme 17 describes the synthesis of (2S)-2-(((9H-fluoren-9-yl)methoxy)carbonylamino)-3-(6-(2-ethyl-4-methoxy)phenyl)pyridine-3-yl)propanoic acid hydrochloride:

Scheme 17

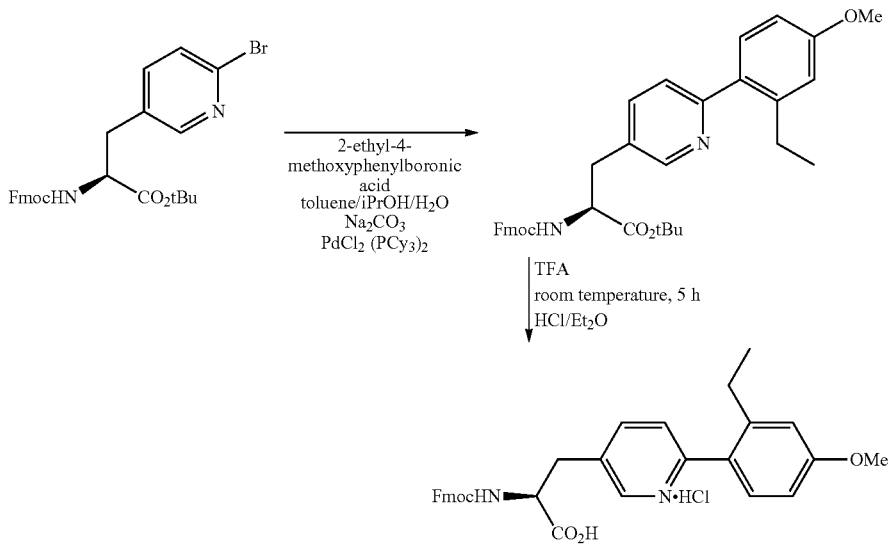

(S)-tert-Butyl 2-(((9H-fluoren-9-yl)methoxy)carbonylamino)-3-(6-(2-ethyl-4-methoxyphenyl)pyridine-3-yl)propanoate To a stirred slurry of 613 mg (1.17 mmol) of (S)-tert-butyl 2-(((9H-fluoren-9-yl)methoxy)carbonylamino)-3-(6-bromopyridin-3-yl)propanoate and 422 mg (2.34 mmol, 2 eq.) of 2-ethylphenylboronic acid in 20 mL of 1:1 isopropanol/toluene was added 10.0 mL of 2 M aqueous sodium carbonate solution. The reaction mixture was purged twice with argon and evacuated and then 43.2 mg (0.059 mmol, 0.05 equivalents) of bis(tricyclohexylphosphine)palladium(II)chloride was added and the mixture was again purged with argon and evacuated. The rapidly stirred mixture was heated at 80° C. under argon. After 9 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (3:17) as eluant (5×15 cm column), gave the expected compound as a colorless oil, 401 mg, 59% yield.

(2S)-2-(((9H-Fluoren-9-yl)methoxy)carbonylamino)-3-(6-(2-ethyl-4-methoxyphenyl)pyridine-3-yl)propanoic acid hydrochloride A solution of 401 mg (0.69 mmol) of (2S)-tert-butyl 2-(((9H-fluoren-9-yl)methoxy)carbonylamino)-3-(6-(2-ethyl-4-methoxyphenyl)pyridine-3-yl)propanoate in TFA (2.0 mL), protected from the atmosphere by a calcium chloride-filled drying tube was stirred at room temperature for two hours. The reaction mixture was concentrated in vacuo at less than 30° C. and the resulting orange oil was dissolved in ether to which a solution of 2 mL of 1 M HCl/ether was added. The resulting white solid was filtered and washed with ether to give the desired product as a white powder, 336 mg, 84% yield.

EXAMPLE 16

Alternative synthesis of (S)-tert-Butyl 2-(((9H-fluoren-9-yl)methoxy)carbonylamino)-3-(6-(2-methylphenyl)pyridin-3-yl)propanoate The following Scheme 18 describes the alternate synthesis of (S)-tert-Butyl 2-(((9H-fluoren-9-yl)methoxy)carbonylamino)-3-(6-(2-methylphenyl)pyridin-3-yl)propanoate:

Scheme 18

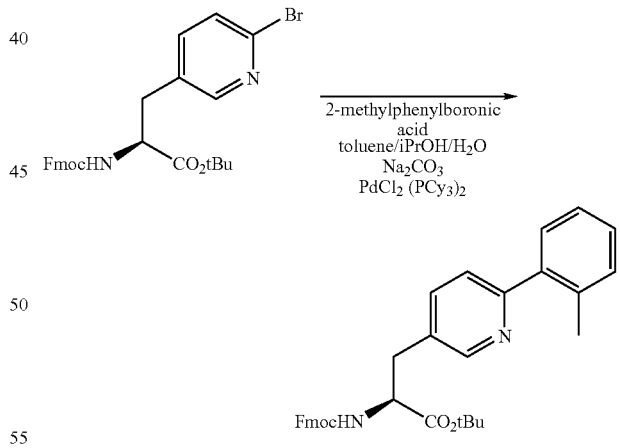

(S)-tert-Butyl 2-(((9H-fluoren-9-yl)methoxy)carbonylamino)-3-(6-(2-methylphenyl)pyridin-3-yl)propanoate To a stirred slurry of 1.75 g (3.35 mmol) of (S)-tert-butyl 2-(((9H-fluoren-9-yl)methoxy)carbonylamino)-3-(6-bromopyridin-3-yl)propanoate and 913 mg (6.70 mmol, 2 eq.) of 2-methylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium(II)chloride was added and the mixture again purged with argon and evacuated.

The rapidly stirred mixture was set to heating at 80° C. under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.81 g, 90% yield.

EXAMPLE 17

Synthesis of (2S)-tert-butyl 2-(((9H-fluoren-9-yl)methoxy)carbonylamino)-3-(6-(2-ethylphenyl)pyridazin-3-yl)propanoate [Fmoc-(S)-4-(2'-ethylphenyl)-2,3-pyridazylalanine]

The following Scheme 19 describes the synthesis of (2S)-tert-butyl 2-(((9H-fluoren-9-yl)methoxy)carbonylamino)-3-(6-(2-ethylphenyl)pyridazin-3-yl)propanoate:

(5×15 cm column), provided the title compound as a light yellow solid, 1.37 g, 39% yield.

3-Bromo-6-(bromomethyl)pyridazine

A solution of 1.00 g (5.78 mmol) of 3-bromo-6-methylpyridazine and 1.03 g (5.79 mmol, 1.0 eq) of recrystallized N-bromosuccinimide in 20 mL of carbon tetrachloride was added 95 mg of AIBN. The reaction mixture was purged twice with argon and evacuated and set to reflux under argon. After 3 h, the reaction mixture was cooled to room temperature, filtered and the filtrate was concentrated to give a yellow oil. The mixture was directly purified by silica gel chromatography using hexanes/dichloromethane (1:9) as eluant (5×12 cm column), to give a colorless oil, 444 mg, 30% yield.

(S)-tert-Butyl 2-(((9H-fluoren-9-yl)methoxy)carbonylamino)-3-(6-bromopyridazin-3-yl)propanoate To a stirred mixture of 374 mg (1.48 mmol) of 3-bromo-6-(bromomethyl)pyridazine, 439 mg (1.48 mmol, 1.0 equivalent) of tert-butyl 2-(diphenylmethyleneamino)acetate and 112 mg (0.186 mmol, 0.12 equivalent) of O-allyl-N-(9-anthracenylmethyl)cinchonidinium bromide in 4 mL of dichloromethane at −78° C. under argon was added 0.645 mL (2.23 mmol, 1.5 eq) of 2-t-butylimino-2-diethylamino-1,3-dim-

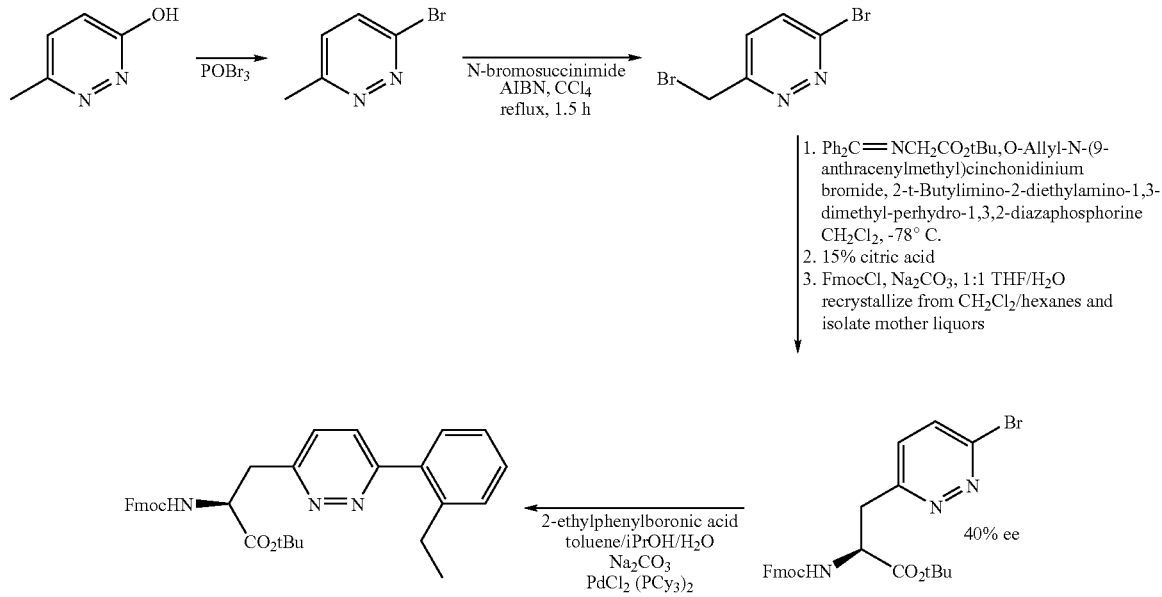

Scheme 19

3-Bromo-6-methylpyridazine

A mixture of 2.20 g of 3-methyl-6-pyrazinol (20.0 mmol) and 13.06 g of phosphorous oxybromide (45.6 mmol, 2.3 equivalents) was stirred and heated to 130 deg C. (pre-heated oil bath) for 50 min. The solid reaction mixture was cooled in an ice bath and ~20 g of chipped ice was added. The resulting solution was chilled in an ice bath and 50% KOH was added to neutralize. The resulting solid was collected, washed with water and air-dried for 15 h. Purification by silica gel chromatography using ether/dichloromethane (3:17) as eluant ethyl-perhydro-1,3,2-diazaphosphorine over 5 min. The reaction mixture was stirred at −78° C. for 1 h and then allowed to warm to −40° C. in situ. After 16 h, the mixture was directly purified by silica gel chromatography using ethyl acetate/dichloro-methane (1:9) as eluant (5×10 cm column), to give a yellow oil, 540 mg, 78% yield.

To a stirred solution of the above product in 10 mL of THF at room temperature under argon was added 10 mL of 15% aqueous citric acid. After 16 h, the reaction mixture was diluted with water (5 mL) and washed twice with ether (10 mL).

The aqueous phase was then brought to pH 9 with solid sodium carbonate and extracted twice with dichloromethane. The dichloromethane extracts were combined, dried with sodium sulfate and concentrated. The resulting oil was dissolved in 5 mL of THF and treated with 5 mL of 10% sodium carbonate solution and then 480 mg (1.86 mmol, 1.3 eq.) of 9-fluorenylmethyloxycarbonylchloride at room temperature. After 6 h, the reaction mixture was extracted twice with dichloromethane, dried with sodium sulfate, filtered, concentrated and purified by chromatography on silica gel using ethyl acetate/dichloromethane (1:5) as eluant (5×15 cm column), to give a colorless oil, 507 mg, 65% yield. Chiral HPLC analysis (4.6×250 mm AD column, 38:1:1 heptane:methanol:ethanol as eluant, 1 mL/min flow rate) indicated 40% ee.

(2S)-tert-Butyl 2-(((9H-fluoren-9-yl)methoxy)carbonylamino)-3-(6-(2-ethylphenyl)pyridazin-3-yl)propanoate To a stirred slurry of 507 mg (0.967 mmol) of (S)-tert-butyl 2-(((9H-fluoren-9-yl)methoxy)carbonylamino)-3-(6-bromopyridazin-3-yl)propanoate and 290 mg (1.93 mmol, 2 eq.) of 2-ethylphenylboronic acid in 16 mL of 1:1 isopropanol/toluene was added 8.0 mL of 2 M aqueous sodium carbonate solution. The reaction mixture was purged twice with argon and evacuated and then 35.7 mg (0.048 mmol, 0.05 equivalents) of bis(tricyclohexylphosphine)palladium(II)chloride was added and the mixture was again purged with argon and evacuated. The rapidly stirred mixture was heated at 90° C. under argon.

After 8 h, the reaction mixture was cooled to room temperature and partially concentrated to remove isopropanol. The residue was partitioned between ethyl acetate and water and the aqueous phase was extracted once more with ethyl acetate. The organic extracts were combined, concentrated and the residue was redissolved in 2 mL of THF. To this solution was added 300 mg (1.17 mmol) of 9-fluorenylmethylchloroformate and 100 µL of triethylamine. After 21 h, the reaction mixture was diluted with ethyl acetate and washed once with brine. The organic phase was dried over magnesium sulfate, filtered and concentrated. Purification by chromatography on silica gel using ethyl acetate/dichloromethane (1:2) as eluant (2.5×15 cm column), gave the desired compound as a colorless oil, 428 mg, 81% yield.

EXAMPLE 18

Synthesis of (2S)-2-(tert-Butoxycarbonylamino)-3-(5-o-tolylpyridin-2-yl)propanoic acid [Boc-(S)-4-(2'-methylphenyl)-2-pyridylalanine)]

The following Scheme 20 describes the synthesis of (2S)-2-(tert-butoxycarbonylamino)-3-(5-o-tolylpyridin-2-yl)propanoic acid:

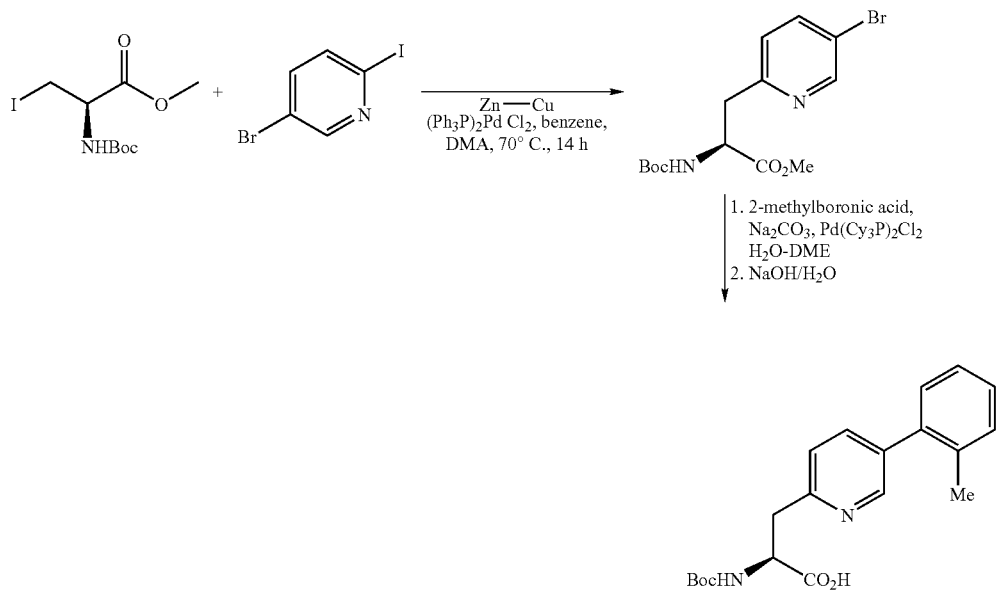

(S)-Methyl 2-(tert-butoxycarbonylamino)-3-(5-bromopyridin-2-yl)propanoate

An argon-purged and evacuated slurry of 210 mg of zinc-copper couple (prepared as in Organic Synthesis Collective Volume 5, page 855) and 580 mg (1.76 mmol) of 3-iodoalanine were dissolved in 7 mL of benzene to which was added 0.5 mL of N,N-dimethylacetamide. The slurry was sonicated in a sealed flask for 40 min, and then 500 mg (1.76 mmol, 1.0 eq.) of 5-bromo-2-iodopyridine and 82 mg (0.11 mmol, 0.06 eq.) of bis(tri-phenylphosphine)palladium dichloride were added.

The reaction mixture was purged and evacuated with argon twice more and then heated at 70° C. under argon for 15 h. The reaction was cooled and partitioned between water and EtOAc. The layers were separated, and the aqueous layer was extracted once more with EtOAc. The organic extracts were combined, dried over magnesium sulfate, filtered, concentrated and dried in vacuo to give the crude product as a yellow oil. Purification by silica gel chromatography $CH_2Cl_2$/hexanes (3:1) as eluant (2.5×15 cm column), provided the expected compound as a yellow oil, 288 mg, 46% yield.

(2S)-2-(tert-Butoxycarbonylamino)-3-(5-o-tolylpyridin-2-yl)propanoic acid

To a stirred slurry of 285 mg (0.79 mmol) of (S)-methyl 2-(tert-butoxycarbonylamino)-3-(5-bromopyridin-2-yl)propanoate and 162 mg (1.19 mmol, 1.5 eq.) of 2-methylphenylboronic acid in 7 mL of 1,2-dimethoxyethane was added 168 mg (1.59 mmol, 2.0 eq.) of sodium carbonate and 0.5 mL of water. The reaction mixture was purged twice with argon and evacuated and then 29 mg (0.040 mmol, 0.05 eq.) of bis (tricyclohexylphosphine)palladium(II)chloride was added and the mixture again purged with argon and evacuated. The rapidly stirred mixture was heated at 80° C. under argon.

After 14 h, the reaction mixture was cooled to room temperature and 4 mL of 1 N sodium hydroxide solution was added. The reaction mixture was heated to 70° C. for 1 h. After cooling to room temperature the mixture was extracted once with ether. The aqueous phase was acidified to pH 3 with 10% sodium bisulfate solution and then extracted twice with DCM. The DCM extracts were combined, dried over magnesium sulfate, filtered and concentrated to give a yellow semi-solid. Purification by preparative reverse-phase HPLC (YMC ODS S5 30×100 mm column, 10% to 90% AcCN/water gradient [10 min], 0.1% TFA) gave (after concentration) the desired product as a white amorphous solid, 46.5 mg, 17% yield.

EXAMPLE 19

The following Scheme 21 describes the general synthesis of analogs of (2S)-2-(((9H-fluoren-9-yl)methoxy)carbonylamino)-3-(6-phenyl)pyridin-3-yl)propanoate.

(2S)-tert-Butyl 2-(((9H-fluoren-9-yl)methoxy)carbonylamino)-3-(6-[(3-chloro-4-fluoro)phenyl)pyridin-3-yl)propanoate To a round bottom flask was added 300 mg Fmoc-L-bromo-3-pyridylalanine (0.573 mmol), 200 mg 3-chloro-4-fluorophenylboronic acid (1.145 mmol, 2 eq.), 1.145 mL 2M sodium carbonate solution (2.29 mmol, 4 eq.), 5 mL toluene, 5 mL isopropylnol and 42 mg $PdCl_2(PCy)_3)_2$ (0.0573 mmol, 0.1 eq.). The reaction solution was purged with argon before it was brought to 80° C. for 5 hrs. The reaction was cooled to room temperature and diluted with 50 mL EtOAc. The solution was washed with water (30 mL) and brine (20 mL), dried over magnesium sulfate, filtered and concentrated. The crude oil was subjected to silica gel chromatography (12 gm silica gel, 0-40% EtOAc/Hexanes gradient) to give 245 mg of the desired compound (75% yield) as an oil.

(2S)-2-(((9H-fluoren-9-yl)methoxy)carbonylamino)-3-(6-[(3-chloro-4-fluoro)phenyl)pyridin-3-yl)propanoic acid To a solution of (2S)-tert-butyl 2-(((9H-fluoren-9-yl)methoxy)carbonylamino)-3-(6-[(3-chloro-4-fluoro)phenyl)pyridin-3-yl)propanoate (240 mg, 0.429 mmol) and 3 mL dichloromethane was added TFA (3 mL). The reaction was stirred at room temperature for 5 hrs. The solvent was evaporated to dryness and the residue was subjected to prep-HPLC (methanol-water gradient, 0.1% TFA). Concentration of the fractions containing the product yielded 200 mg (93% yield) of the desired compound as the TFA salt.

EXAMPLE 20

General Synthesis of Peptides Starting from Dipeptidyl Resin Containing Non-Natural Non-Commercial Amino Acid at Positions 10 and 11

Dipeptidyl resin, containing non-natural non-commercial amino acid at positions 10 and 11, was prepared using the following procedure on a Advanced Chemtech ACT 90 syn-

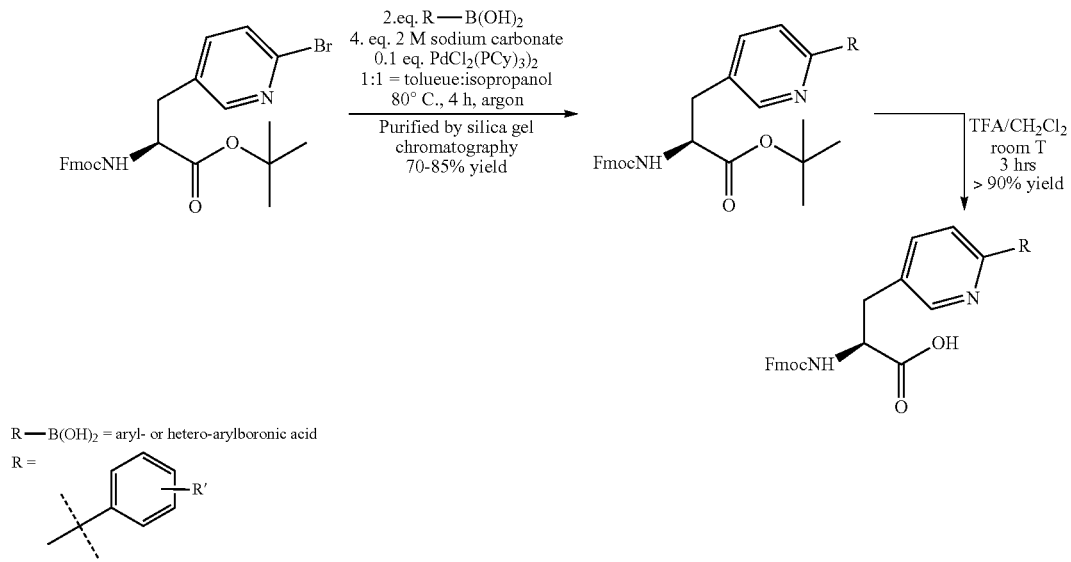

Scheme 21

R—B(OH)$_2$ = aryl- or hetero-arylboronic acid thesizer in a batch-wise mode before continuing peptide chain elongation utilizing the automated simultaneous synthesis protocol on a MPS-396 peptide synthesizer.

An amount of 9-Fmoc-aminoxanthen-3-yloxy-Merrifield resin(Sieber Amide resin; loading: 0.5 mmol/g; Novabiochem) sufficient to synthesize several peptide analogs, was swelled by washing with DMF (2×$_1$0 mL/g, 1 min.). The Fmoc group was then removed using two treatments, 5 and 15 min. each respectively, with 20% piperidine in DMF (10 mL/g). The resin was washed with DMF (2×10 mL/g) and NMP (4×10 mL/g). A solution of Fmoc-(S)-4-(2'-Methylphenyl)-3-pyridylalanine-OH(HCl salt) (1.2 eq.), or analog thereof, PyBOP (1.07 eq.), HOBt (1.07 eq.), and DIEA (3.6 eq.) in NMP were added to the resin. The resin was then shaken or vortexed for 18 hours. Coupling completion was monitored using a qualitative ninhydrin test. The resin was drained, washed with NMP (3×10 mL/g) and DCM (3×10 mL/g), and any unreacted amines were capped with 2.6% acetic anhydride, 2.4% DIEA in DCM (v/v) for 30 min. After DMF washes (3×10 mL/g), the capping protocol was repeated with 10% acetic anhydride, 2% DIEA in DCM (v/v) for 30 min. A quantitative Fmoc determination assay indicated a 0.39 mmol/gram substitution.

A second manual coupling cycle was then performed as described above, starting from the removal of the Fmoc group with 20% piperidine in DMF, and, after several DMF washes, by adding to the deprotected resin a solution of Fmoc-L-(2'-Ethyl-4'-Methoxy)biphenylalanine-OH (1.27 eq.), or analog thereof, and HOBt (1.29 eq.) in NMP (4 mL), which was vortexed for 5 min. DIC (1.27 eq.) was then added to the resin slurry and the resin was shaken or vortexed for 15 hours. The resin was drained, washed with NMP (3×10 mL/g) and DCM (3×10 mL/g), and then capped with 5.0% acetic anhydride, 1.0% DIEA in DCM (10 mL) for 30 min. The resin was finally washed with DCM (3×10 mL/g). This synthesis scheme produced the desired Fmoc-protected dipeptidyl-Sieber Amide resin.

The Fmoc group was removed as described previously. A solution of Fmoc-L-Asp(OtBu)-OH (3 eq.) and HOBt (3 eq.) in NMP (2 mL) was vortexed for 5 min., and DIC (3 eq.) was then added. The resulting solution was added to the resin. The resin was then shaken or vortexed for 2 hours. The resin was drained, and washed with NMP (3×10 mL/g) and DCM (3×10 mL/g). Coupling completion was monitored using a qualitative ninhydrin test.

This resin was subjected to 2 additional deprotection/coupling cycles as described above in order to assemble the desired sequence from $X_{aa7}$ to $X_{aa11}$ onto the resin. The Fmoc-amino acids sequentially used were: Fmoc-L-Ser (tBu)-OH and Fmoc-L-Thr(tBu)-OH. Fmoc-[(S)-2-fluoro-α-Me-Phe]-OH was coupled using the following protocol. A solution of Fmoc-[(S)-2-fluoro-α-Me-Phe]-OH (1.5 eq.), PyBOP (1.5 eq.), HOBt (1.5 eq.), and DIEA (3.0 eq.) in NMP (2 mL) were added to the resin. The resin was then shaken or vortexed for 2 hours. The resin was drained, and washed with NMP (3×10 mL/g) and DCM (3×10 mL/g).

In order to couple residue $X_{aa5}$, the Fmoc group was removed as described previously. A solution of Fmoc-The (tBu)-OH (5 eq.) and 2-Cl-HOBt (5 eq.) and DIC (5 eq.) in NMP (4 mL) was vortexed briefly, then added to the resin. The resin was then shaken or vortexed for 18 hours. The resin was drained, and washed with NMP (3×10 mL/g) and DCM (3×10 mL/g). The resin was capped with 10.0% acetic anhydride in DCM (10 mL/g) for 30 min. After DCM washes (3×10 mL/g), the Fmoc group was removed as described previously and Fmoc-Gly-OH, residue $X_{aa4}$, was coupled/deprotection as described for Fmoc-L-Asp(OtBu)-OH. The resulting $X_{aa4}$-$X_{aa11}$ peptidyl-resin used was used to synthesize different peptide analogs as follows.

Synthesis of the Compound of SEQ ID NO: 118

A sample of the $X_{aa4}$-$X_{aa11}$ peptidyl-resin (0.067 mmol) described above was vortexed with a solution of Fmoc-L-Glu (OtBu)-OH (5 eq.), residue $X_{aa3}$, and 0.5M HOAt (5 eq.) in DMF, pre-vortexed for 5 min., and DIC (5 eq.) for 18 hours. The resin was drained, washed with DMF (4×3 mL). The resin bound peptide (0.034 mmol) was deprotected and coupled with Fmoc-[(S)-α-Me-Pro]-OH (5 eq.) as described previously for residue $X_{aa3}$ to afford the resin bound Fmoc-[$X_{aa2}$-$X_{aa11}$]-peptide.

The resin (0.017 mmol) was deprotected and coupled with Boc-L-His(Trt)-OH (5 eq.) as described for residue $X_{aa2}$. The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated to yield 39 mg of crude peptide product as a oily solid. This was purified by preparative HPLC using a gradient of 0.1% TFA/AcCN in 0.1% TFA/water, from 5% to 65% over 20 min. The fractions containing pure product were pooled and lyophilized, to yield 5.4 mg (18.9% recovery) of the compound of SEQ ID NO: 118.

Synthesis of the Compound of SEQ ID NO: 119

A sample of the Fmoc-[$X_{aa3}$-$X_{aa11}$]-peptidyl-Sieber resin (0.015 mmol), described in the previous synthesis, was vortexed with a solution of Fmoc-[N-methyl-(D)-Ala]-OH (5 eq.) and 0.5M HOAt (5 eq.) in DMF, pre-vortexed for 5 min., and DIC (5 eq.) for 4 hours. The resin was drained and washed with DMF (4×3 mL). The Fmoc group was removed by treating with 20% piperidine in DMF (3 mL) for 5 and 15 min. The resin was washed with DMF (8×3 mL) and then coupled with Boc-L-His(Trt)-OH (5 eq.) as described in the previous synthesis. The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid was dissolved in (1:1) AcCN/water (2 mL) and purified by preparative HPLC using a gradient used of 0.1% TFA/MeCN in 0.1% TFA/water, from 5% to 65% over 20 min. The fractions containing pure product were pooled and lyophilized, to yield 5.2 mg (18.5% recovery) of the compound of SEQ ID NO: 119.

Synthesis of the Compound of SEQ ID NO: 133

A sample of the Fmoc-deprotected [$X_{aa2}$-$X_{aa11}$]-peptidyl-Sieber resin (0.017 mmol), described in the previous synthesis, was vortexed with a solution of des-amino-His(Trt)-OH (5 eq) and HATU (5 eq.) in 0.5 HOAt in DMF (5 eq.), and a solution of 2M DIEA in NMP (5 eq.) for 18 hours. The resin was drained and washed with DMF (6×$_2$ mL) and DCM (3×2 mL). The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid (32 mg) was dissolved in (1:1) AcCN/water (2 mL) and purified by preparative HPLC using a gradient of 0.1% TFA/MeCN in 0.1% TFA/water, from 5% to 65% over 20 min. The fractions containing pure product were pooled and lyophilized, to yield 7.4 mg (24.6% recovery) of the compound of SEQ ID NO: 133.

Synthesis of the Compound of SEQ ID NO: 120

A sample of Fmoc-deprotected [$X_{aa10}$-$X_{aa11}$]-dipeptidyl-Sieber resin (0.05 mmol), prepared as described previously, was subjected to 9 additional coupling cycles using the Fast-Moc™ protocol of an Applied Biosystems 433a Peptide Synthesizer as described in Example 3.

The Fmoc-protected dipeptidyl-resin (0.05 mmol) was placed into a vessel of appropriate size on the instrument, washed 6 times with NMP and deprotected using two treatments with 20% piperidine/NMP (2 and 8 min. each). One additional monitored deprotection step was performed until the conditions of the monitoring option were satisfied. The total deprotection time was 10-12 min. The deprotected dipeptidyl-resin was washed 6 times with NMP and then coupled with the next amino acid. The procedure is illustrated by the example used in the next step.

Fmoc-L-Asp(OtBu)-OH was coupled next using the following method: Fmoc-L-Asp(OtBu)-OH (1 mmol, 20 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP and the coupling protocol was repeated. This was subjected to 5 additional deprotection/coupling cycles as described above in order to complete the assembly of the desired $X_{aa4}$-$X_{a11}$ sequence. The Fmoc-amino acids sequentially coupled were: Fmoc-(L)-His(Trt)-OH, Fmoc-(L)-Thr(tBu)-OH, Fmoc-(S)-2-fluoro-α-Me-Phe-OH, Fmoc-(L)-Thr(tBu)-OH and Fmoc-Gly-OH. Finally, the peptidyl-resin was washed 6 times with NMP and DCM. The Fmoc-protected dipeptidyl-resin (0.025 mmol) was added to a ACT 396 multiple peptide synthesizer in a slurry of N,N-dimethylformamide/dichloromethane (55:45). The resin was washed 2 times with DMF and deprotected using two treatments with 1.5 M piperidine/DMF as described in Example 1. Fmoc-L-Glu(OtBu)-OH (4.0 eq.) was activated by subsequent addition of 0.5 M HOAt in DMF (4.0 eq.) and DIC (4.0 eq.), transferred to the reaction vessel manually and allowed to couple for 2 hrs. The resin was rinsed with NMP (4×0.5 mL) with vortexing for 1 min. After deprotection of the Fmoc group as described for the previous coupling, Fmoc-[(S)-α-Me-Pro]-OH was coupled as follows: Fmoc-[(S)-α-Me-Pro]-OH (2.4 eq.) was activated by subsequent addition of 0.5 M HOAt in DMF (2.4 eq.), diluted with NMP (0.12 mL), and of DIC (2.4 eq.). The solution was transferred to the reaction vessel manually and allowed to couple for 18 hrs. The resin was rinsed with NMP. After deprotection of the Fmoc group, Fmoc-(L)-His(Trt)-OH was coupled by adding manually a solution of the amino acid (4 eq.) in 0.5 M HOAt in DMF (4 eq.), diluted with NMP (0.2 mL), and DIC (4 eq.) to the reaction vessel. The coupling reaction was allowed to couple for 18 hrs. The resin was rinsed with NMP. The Fmoc group was removed as described for the previous coupling. The TFA cleavage/deprotection of the peptide was performed as described in Example 1. This was purified by preparative HPLC using a gradient of 0.1% TFA/MeCN in 0.1% TFA/water, from 10% to 60% over 20 min. The fractions containing a pure product were pooled and lyophilized, to yield 21.7 mg (42% recovery) of the compound of SEQ ID NO: 120.

EXAMPLE 21

Synthesis of the Compound of SEQ ID NO: 151

The synthesis was initiated on an Advanced ChemTech Model 90 Synthesizer in a 50 ml reactor starting with 2.67 g (0.56 mmol/g, 1.5 mmol) of Sieber Amide resin. The general deprotection/coupling repetitive cycle used for the stepwise assembly was as follows:
1. DMF wash 1×20 ml×1 min.
2. 20% piperidine in DMF 1×20 ml×5 min.
3. 20% piperidine in DMF 1×20 ml×15 min.
4. DMF washes 3×20 ml×1 min.
5. NMP washes 4×20 ml×1 min.
6. Coupling step (see below).
7. DMF washes 4×15 ml×1 min.
8. Kaiser Ninhydrin test or cleavage/deprotection with HPLC and mass spectral analyses.

The Fmoc group was removed from the Sieber Amide resin using steps 1 to 5 above. N-α-Fmoc-4-(2'-Methylphenyl)-3-pyridylalanine (0.73 g, 1.50 mmol), PyBOP (0.78 g, 1.50 mmol) and HOBt (0.39 g, 1.50 mmol) were dissolved in NMP (5 ml) and the solution was then added to the resin followed by the addition of DIEA (0.39 g, 3.05 mmol). The coupling mixture was vortexed for 16 hours. The resin was treated with 10% acetic anhydride in DCM (1×50 mL×60 mins.), washed with DCM (4×50 ml×1 min.) and dried in vacuo for overnight. An Fmoc determination test gave a substitution of 0.456 mmol/gram. The synthesis was continued with 3.11 g (1.42 mmol) of resin. Following resin deprotection, a solution of N-α-Fmoc-(L)-Bip(2'-Et-4'-OMe)-OH (0.98 g, 1.9 mmol), HCTU (0.78 g, 1.9 mmol) in NMP (5 ml) was added to the resin, followed by the addition of DIEA (0.48 g, 3.80 mmol), and the mixture was vortexed for 16 hrs. After washing with NMP, a Kaiser ninhydrin test was negative. Following deprotection of the resin, N-α-Fmoc-L-Aspartic acid β-t-butyl ester (0.6487 g, 1.24 mmol) was coupled for 48 hrs using HCTU (1.03 g, 2.49 mmol) and DIEA (0.65 g, 5.03 mmol) in NMP (10 ml). Following deprotection of the resin, N-α-Fmoc-N-im-trityl-L-Histidine (3.85 g, 6.25 mmol) was coupled for 16 hours using 0.546 M HOAt in DMF (11.5 mL, 6.3 mmol) and DIC (0.96 mL, 6.3 mmol). The protocol was repeated to couple N-α-Fmoc-O-t-butyl-L-Threonine (2.5 g, 6.30 mmol) to the resin. After resin deprotection, N-α-Fmoc-α-methyl-2-fluoro-L-Phenylalanine (0.78 g, 1.86 mmol) in 0.546M HOAt in DMF (3.4 mL, 1.87 mmol) was added to the resin followed by DIC (0.24 g, 1.87 mmol) in DMF (3.5 ml), and coupling was allowed to proceed for 4 hours. After resin deprotection, N-α-Fmoc-O-t-butyl-L-Threonine (4.97 g, 12.50 mmol) was coupled for 16 hours using a solution of 0.546 M HOAt in DMF (25 mL, 12.50 mmol) and DIC (1.58 g, 12.52 mmol). The resin was capped with 10% acetic anhydride in DMF (20 mL) for 1 hour and washed with DMF (4×20 mL). The Fmoc group was removed, and N-Fmoc-Glycine (1.11 g, 3.75 mmol) was coupled for 90 min. as described for the previous N-α-Fmoc-L-Aspartic acid β-t-butyl ester coupling step, followed by N-α-Fmoc-L-glutamic acid γ-t-butyl ester (1.60 g, 3.75 mmol) in the same manner. A portion of the peptidyl-resin (0.030 mmol) was deprotected and N-α-Fmoc-α-methyl-L-proline (21.2 mg, 0.06 mmol) was coupled for 16 hours using 0.546 M HOAt in DMF (0.110 ml, 0.83 mmol) and DIC (7.6 mg, 0.06 mmol) in DMF (0.1 ml). Finally, L-β-(N-1-Trityl)imidazolelactic acid (39.8 mg, 0.10 mmol) and HATU (38 mg, 0.10 mmol) in NMP (0.9 mL) was added to a portion of peptidyl-resin (0.01 mmol) followed by addition of DIEA (17.4 mL, 0.10 mmol). After vortexing for one hour and washing with NMP, the coupling was repeated as described above and allowed to proceed for 48 hours. The resin-bound peptide was treated with TFA/TIS/water (94:3:3) (2 mL) for 2.5 hours, followed by two rinses of TFA/TIS/water (94:3:3) (2×1 mL each). The combined filtrates were concentration in vacuo to yield 18.1 mg (92%) of crude peptide. This was dissolved in 2 mL of (1:1) AcCN/ water and the solution was loaded onto a Luna [C18(2), 5 μm] Phenomenex column, 250×21.2 mm I.D. The column was eluted with a gradient of 15% to 55% solvent B in solvent A over 50 min. at a flow rate of 15 ml/min. Solvent A: 0.1% TFA in water. Solvent B: 0.1% TFA in AcCN. The fractions containing a pure product were pooled and lyophilized to give 4.2 mg of Compound of SEQ ID NO:151.

EXAMPLE 22

Synthesis of (S)-3-(N-1-Trityl-imidazol-4-yl)-2-hydroxypropanoic acid (L-β-(N-1-Trityl)imidazolelactic acid)

The following Scheme 22 describes the synthesis of (S)-3-(N-1-Trityl-imidazol-4-yl)-2-hydroxypropanoic acid:

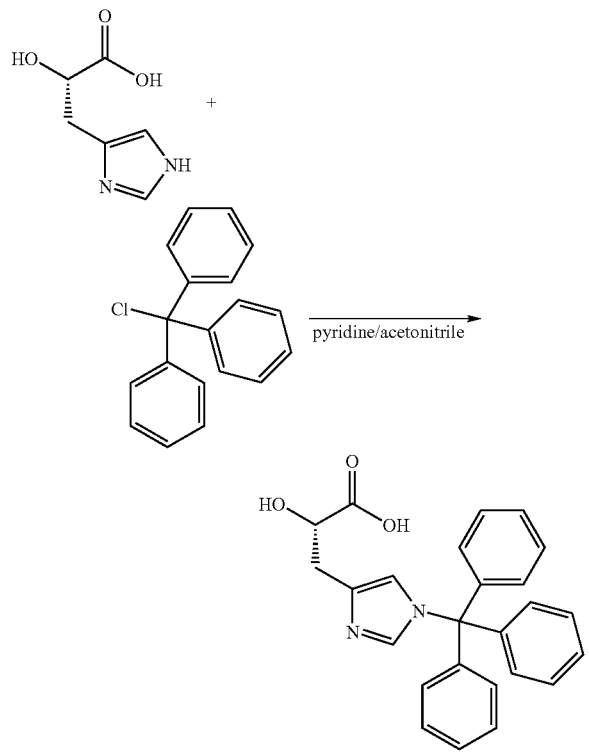

(S)-3-(1H-imidazol-4-yl)-2-hydroxypropanoic acid (0.5265 g, 3.0 mmol) and trityl chloride (1.2991 g, 4.7 mmol) were charged to a 100 mL flask. Pyridine/AcCN 1:1 (20 mL) was added under stirring. The flask was heated in an oil bath at 50° to 55° C. for 4 hours. The solvents were removed to near dryness on a rotovap. To the residue was added equal volumes of water and ethyl acetate (30 mL each). The mixture was stirred for about 20 min. The resultant solid was collected by filtration, washed with water (2×10 mL), then with ethyl acetate (2×10 mL) and dried in vacuo. Yield: 0.6953 g (58%).

EXAMPLE 23

Synthesis of (S)-3-(N-1-(2,4-dinitrophenyl)imidazol-4-yl)-2-hydroxypropanoic acid (L-β-(N-1-(2,4-dinitrophenyl)imidazolelactic acid)

The following Scheme 23 describes the synthesis of (S)-3-(N-1-(2,4-dinitrophenyl)imidazol-4-yl)-2-hydroxypropanoic acid:

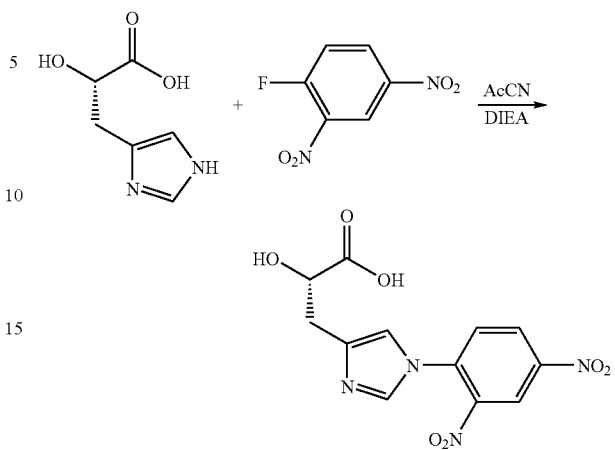

(S)-3-(1H-imidazol-4-yl)-2-hydroxypropanoic acid monohydrate (0.8971 g, 5.2 mmol), AcCN (60 mL), DIEA (1.3438 g, 10.4 mmol) and 1-fluoro-2,4-dinitrobenzene (0.9564 g, 5.1 mmol) were charged to a round bottom flask, covered with aluminum foil and stirred overnight. The reaction mixture was filtered and the solvent was removed under reduced pressure. The oily residue was triturated with diisopropyl ether (2×20 mL) and was then dissolved in chloroform (20 mL) and re-evaporated from chloroform and AcCN. Addition of DCM (60 mL) produced a precipitate, which was stirred at RT after adding more DCM (30 mL). The solid product was collected, washed with DCM (2×10 mL) and dried in vacuo overnight. Yield: 1.37 g (83%).

EXAMPLE 24

Synthesis of the Compound of SEQ ID NO: 158

Method A. Fragment Coupling (Schemes 10A and 10B)

The synthesis was performed manually in an 8 ml reactor starting with 0.1896 g (0.56 mmol/g, 0.11 mmol) of Sieber Amide resin. The following cycles were used to remove the Fmoc group from the resin:
1. DMF wash 1×2 ml×5 mins.
2. 20% piperidine in DMF 1×2 ml×5 mins.
3. 20% piperidine in DMF 1×2 ml×15 mins.
4. DMF washes 8×2 ml×1 min.

N-α-Fmoc-4-(2'-Methylphenyl)-3-pyridylalanine HCl salt (0.0549 g, 0.11 mmol) and PyBOP (0.0667 g, 0.13 mmol) were dissolved in DMF (1 ml). This solution was added to the deprotected resin, followed by DIEA (0.0423 g, 0.33 mmol) in DMF (1 mL). The resin was vortexed for 3.5 hours, washed with DMF and DCM (4×2 mL×1 min). The resin was treated with 10% acetic anhydride in DCM (2 mL) overnight, washed with DCM (6×2 ml×1 min.) and dried in vacuo for 1 hour. Yield: 0.2508 g. An Fmoc determination test gave a substitution of 0.35 mmol/gram. 0.083 g (0.029 mmol) of the resin was used in the next step.

Following deprotection of the resin using the above cycles 1 to 4, a solution of N-α-Fmoc-(L)-Bip(2'-Et-4'-OH)—OH (0.0251 g, 0.049 mmol), HOBt (0.0084 g, 0.055 mmol) and DIC (0.0067 g, 0.053 mmol) in DMF (1 ml) was added to the resin. After vortexing for 16 hours, the peptidyl-resin was washed with DMF then DCM (4×1 mL×1 min.). The Fmoc group was removed as using steps 1 to 3 above followed by DMF then DCM washes (4×1 mL×1 min.).

The peptide-resin was treated with TFA/triisopropylsilane/water 96:2:2 (2×1 mL×10 mins.). The filtrates were collected and concentrated in vacuo to a residue which was triturated with diisopropyl ether and centrifuged to yield a solid product. This was washed with diisopropyl ether and dried in vacuo to give 0.0244 g of dipeptide. The dipeptide was dissolved in 0.2% DIEA in THF (1 mL) and treated for 2 hours with macroporous triethylammonium methylpolystyrene carbonate resin (0.0682 g, 0.211 mmol, Argonaut Technologies). The resin beads were removed and washed with 0.2% DIEA in THF (2×1 mL). The combined filtrate and wash solution was dried in vacuo. To the resulting residue was added a solution of the side-chain protected N-methyloxycarbonyl Xaa1-Xaa9 9-mer peptide (55.8 mg, 0.035 mmol), HOBt (5.47 mg, 0.036 mmol) and DIC (6 µL, 0.035 mmol) in CHCl$_3$/DMF 9:1 (1 mL). The resultant solution was vortexed overnight. After solvent removal in vacuo, the resulting residue was treated with 2% triisopropylsilane in TFA (1 mL) for 90 min. after which diisopropyl ether (20 mL) was added. The precipitated solid was dried and dissolved in 2 mL of 1.5% ammonium hydroxide. The pH was adjusted to ~9.5 with acetic acid. This solution was loaded onto a Luna [C18(2), 5 µm] Phenomenex column, 250×21.2 mm I.D. The column was eluted with a gradient of 20% to 50% solvent B over 60 min. at a flow rate of 15 ml/min. Solvent A: 0.1% TFA in water. Solvent B: 0.1% TFA in AcCN. The fractions containing a pure product were pooled and lyophilized to give 5.5 mg of the Compound of SEQ ID NO:158.

A different fragment coupling procedure for the synthesis of the Compound of SEQ ID NO:158 followed the method described in Scheme 10B. The synthesis was performed manually in an 8 ml reactor starting with 0.1182 g (0.47 mmol/g, 0.056 mmol) of N-α-Fmoc-4-(2'-Methylphenyl)-3-pyridylalanyl-Sieber Amide resin prepared as described earlier in this Example. The cycles used to remove the Fmoc group from the resin were the same as those described above. N-α-Fmoc-(L)-Bip(2'-Et-4'-OH)—OH (0.0419 g, 0.083 mmol) was coupled to the resin as described above. Following resin treatment with 10% acetic anhydride in DCM (2 mL) for 30 min., DCM washes (6×2 ml×1 min.) and removal of the Fmoc group, a solution of the side-chain protected N-methyloxycarbonyl Xaa1-Xaa9 9-mer peptide (0.1347 g, 0.084 mmol), HOBt (0.0130 g, 0.085 mmol) and DIC (0.0118 g, 0.94 mmol) in DCM (0.1 mL) and DMF (0.45 mL) was added to the deprotected dipeptidyl-resin and the mixture was vortexed for 4.5 hours. The resin was washed with DMF and DCM (4×2 mL×1 min.), and then treated with 2% triisopropylsilane, 2% water in TFA (5×1 mL×3 mins.); the filtrates were collected and allowed to stand for 75 min. The solvents were removed in vacuo and the resultant residue triturated with diisopropyl ether (20 mL) to yield the crude peptide as a solid (0.0818 g). This was purified as described above, except that the gradient used was 25% to 35% solvent B in solvent A over 120 min. at a flow rate of 15 ml/min. Solvent A: 0.1% TFA in water; solvent B: 0.1% TFA in AcCN. The fractions containing a pure product were pooled and lyophilized to give 19 mg of the Compound of SEQ ID NO:158.

Method B. Stepwise Elongation (Scheme 1)

The synthesis was performed on an Advanced ChemTech Model 90 Synthesizer in a 50 ml reactor starting with 1.46 g (0.72 mmol/g, 1.05 mmol) of Sieber Amide resin. The general deprotection/coupling repetitive cycle used for the stepwise assembly was as follows:

1. DMF wash 1×15 ml×1 min.
2. 20% piperidine in DMF 1×15 ml×5 min.
3. 20% piperidine in DMF 1×15 ml×15 min.
4. DMF washes 4×15 ml×1 min.
5. NMP washes 4×15 ml×1 min.
6. Coupling step (see below).
7. DMF washes 4×15 ml×1 min.
8. DCM washes 4×15 ml×1 min.
9. Kaiser Ninhydrin test or cleavage/deprotection with HPLC and mass spectral analyses.

The Fmoc group was removed from the Sieber Amide resin using steps 1 to 5 above. N-α-Fmoc-4-(2-Methylphenyl)-3-pyridylalanine HCl salt (1.0977 g, 2.13 mmol), PyBOP (1.0972 g, 2.11 mmol) and HOBt monohydrate (0.3228 g, 2.11 mmol) were dissolved in DMF (8 ml). DIEA (0.8052 g, 6.23 mmol) was added to the solution, which was then added to the resin. The coupling mixture was vortexed for 16 hours. The resin was treated with 10% acetic anhydride in DCM (1×15 mL×60 mins.), washed with DCM (6×15 ml×1 min.) and dried in vacuo for 6 hours. Yield: 1.6816 g. An Fmoc determination test gave a substitution of 0.48 mmol/gram. The synthesis was continued with 0.8602 g (0.41 mmol) of resin. Following resin deprotection, a solution of N-α-Fmoc-(L)-Bip(2'-Et-4'-OH)—OH (0.2660 g, 0.524 mmol), HOBt (0.0796 g, 0.520 mmol) and DIC (0.0647 g, 0.513 mmol) in DMF (8 ml) was added to the resin and the mixture was vortexed for 16 hrs. After washing with DMF and DCM, a Kaiser ninhydrin test was negative. Following deprotection of the resin, N-α-Fmoc-L-Aspartic acid β-t-butyl ester (0.6487 g, 1.24 mmol) was coupled for 45 min. using HOBt (0.1893 g, 1.24 mmol) and DIC (0.1566 g, 1.24 mmol) in DMF/DCM (1:1) (6 ml). The same coupling cycle was repeated with N-α-Fmoc-O-t-butyl-L-Serine (0.4750 g, 1.24 mmol) and N-α-Fmoc-O-t-butyl-L-Threonine (0.4924 g, 1.24 mmol). After resin deprotection, N-α-Fmoc-α-methyl-2-fluoro-L-Phenylalanine (0.3497 g, 0.834 mmol) was coupled for 1 hour using HOBt (0.1271 g, 0.830 mmol) and DIC (0.1044 g, 0.827 mmol) in DMF/DCM (1:1) (6 ml). After resin deprotection, N-α-Fmoc-O-t-butyl-L-Threonine (1.6413 g, 4.14 mmol) was coupled for 16 hours using a solution of 0.5 M HOAt in DMF (8.3 mL, 4.15 mmol) and DIC (0.5240 g, 4.15 mmol). After DMF and DCM washes, 3 mg of wet resin was treated with 1 ml of TFA/TIS/water (96:2:2) for 1.5 hours. The resin was filtered off and the solvents were removed in a speed-vac. The residue was dissolved in 2 ml of water/AcCN (1:1). HPLC and MS analyses showed no uncoupled peptide. The Fmoc group was removed, and N-Fmoc-Glycine (0.3691 g, 1.24 mmol) was coupled for 1 hr as described for the previous N-α-Fmoc-L-Aspartic acid β-t-butyl ester coupling step, followed by N-α-Fmoc-L-glutamic acid γ-t-butyl ester (0.5297 g, 1.24 mmol) in the same manner. N-α-Fmoc-α-methyl-L-proline (0.2902 g, 0.83 mmol) was then coupled for 3.5 hours using HOBt (0.1271 g, 0.83 mmol) and DIC (0.1042 g, 0.83 mmol) in DMF/DCM 1:1 (6 ml). Finally, N-α-Fmoc-N-im-trityl-L-Histidine (2.5564 g, 4.13 mmol) was coupled for 12 hours as described for the N-α-Fmoc-O-t-butyl-L-Threonine coupling to the N-α-Fmoc-α-methyl-2-fluoro-L-Phenylalanine. A deprotected peptide sample released from the peptidyl-resin as described above showed some uncoupled peptide by MS. The Fmoc group was manually removed and, after DMF and DCM washes, a solution of N-(methyloxycarbonyloxy)succinimide (0.2163 g, 1.25 mmol) in DCM (6 mL) was added and the mixture was vortexed for 16 hours. The peptide-resin was washed with DCM (4×10 ml×1 min.). A Kaiser ninhyrin test was negative. The N-methyloxycarbonyl-derivatized peptidyl-resin was treated with TFA/TIS/water (96:2:2) (10 mL) for 10 min., followed by two additional treatments with 5 mL each. The combined filtrates were left to stand for an additional 2 hours at RT. Following concentration in vacuo to about 4 mL, the solution was added dropwise to diethyl ether (50 ml) with stirring. The resulting solid was collected by filtration, washed with diethyl ether (2×5 ml) and dried in vacuo to yield 0.691 g (92%) of crude peptide. This was purified by preparative HPLC using the procedures described in Method A of this Example.

EXAMPLE 25

Synthesis of N-(methyloxycarbonyloxy)succinimide [2,5-(dioxopyrrolidin-1-yl)methyl carbonate]

The following Scheme 24 describes the synthesis of N-(methyloxycarbonyloxy)succinimide [2,5-(dioxopyrrolidin-1-yl)methyl carbonate]:

Scheme 24

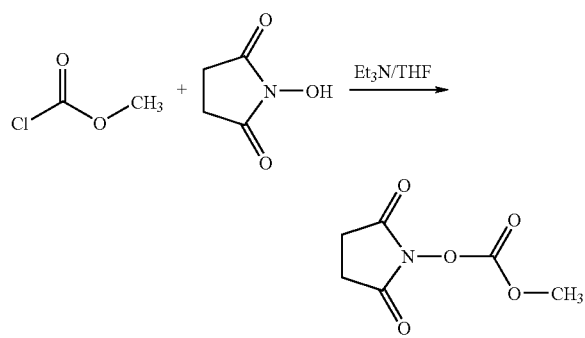

To a stirred solution of 64.61 g (0.561 mol) of N-hydroxysuccinimide and 58.95 g (0.624 mol) of methyl chloroformate in THF (900 mL) at −5° C. under argon was added 82.6 mL (0.593 mol) of triethylamine at a rate such that the temperature remained below +3° C. The reaction mixture was stirred and allowed to warm to RT. After 15 h, the resulting slurry was filtered and the solids were washed with THF (100 mL). The filtrate was evaporated under reduced pressure to give a white solid. Recrystallization from EtOAc/hexanes (2:1, 150 mL) provided the desired product as white crystals, mp 84-86° C., 79.4 g, 82% yield.

EXAMPLE 26

Synthesis of (R,S)-3-(1-(2,4-dinitrophenyl)-imidazol-4-yl)-2-methylpropionic acid [α-Methyl-β-[1-(2,4-dinitrophenyl)-imidazol-4-yl]propionic acid, Imp (DNP)]

1-Tosyl-4(5)-hydroxymethylimidazole

The following procedure was adapted from Agr. Biol. Chem., 38 (5), 1097-1099, 1974. To a solution of $Na_2CO_3$ (8.4 g., 0.08 mole) in water (40 mL) was added 4-(hydroxymethyl)imidazole hydrochloride (2.7 g, 0.02 mole). Upon complete dissolution, a solution of p-toluenesulfonyl chloride (4.58 g, 0.024 mole) in ethyl acetate (30 mL) was added dropwise over a 5 minute period. The reaction mixture was allowed to stir for 5 hours. The layers were separated and more ethyl acetate was added (20 mLs). The organic phase was washed with 0.1 M $Na_2CO_3$ (2×20 mL), water (1×20 mL) and then saturated NaCl (1×20 mL). The ethyl acetate was treated with 2 g of $MgSO_4$ and 1 g of activated charcoal for 10 min. The solids were removed by filtration through a celite pad and the solvent removed on a rotavap. The residue began to crystallize. Fresh ethyl acetate was added (10 mL) and the solution was warmed with a heat gun to redissolve the solids. The product crystallized overnight at room temperature. The crystalline material was collected, washed with ethyl acetate (5 mL) and then ethyl ether (10 mL), and dried in vacuo to a constant weight of 3.59 g.

1-Tosyl-4(5)-acetoxymethylimidazole

1-Tosyl-4(5)-hydroxymethylimidazole (2.52 g, 10 mmol) was dissolved in chloroform (10 ml). To this was added triethylamine (2.02 g, 20 mmol) dropwise at room temperature, followed by dropwise addition of acetic anhydride (1.33 g, 13 mmol) over 15 min. The mixture was stirred at room temperature and monitored by LC/MS for four days. The chloroform was removed by reduced pressure and the residue was dissolved in ethyl acetate (60 ml). The organic layer was washed successively with 0.1 M sodium bicarbonate, water and then saturated sodium chloride, all 1×40 ml each. The organic layer was treated with activated charcoal and magnesium sulfate simultaneously and then filtered through a celite pad. The solvent was removed by reduced pressure and the resultant residue was dissolved in warm ethyl acetate (10 ml). To this solution was slowly added 20 ml of diethyl ether. The solution was left to crystallize overnight at room temperature. The crystals were collected, washed with diethyl ether (2×10 ml) and dried in vacuo overnight to yield 1.55 g.

Methyl-α-carbomethoxy-α-methyl-O-4-(1-tosylimidazole)-propionate

The following procedure was adapted from Synthetic Communications, 19 (7&8), 1157-1165, 1989. A solution of 1-Tosyl-4(5)-acetoxymethylimidazole (0.3516 g, 1.2 mmol) and dimethyl methylmalonate (0.1485 g, 1.0 mmol) in AcCN (2 ml) was added to a stirred suspension of powdered KOH (0.1694 g, 3.0 mmol) and tetrabutylammonium bromide (0.0496 g, 0.15 mmol) in AcCN (1 ml). The reaction was complete after 40 mins, as determined by HPLC analysis. The reaction mixture was poured into ethyl ether (100 ml), filtered through a celite pad and the solvents were removed by evaporation under reduced pressure. The residual oil was dissolved in 30 ml of ethyl acetate and washed with 0.1 M $NaHCO_3$ (1×15 ml), saturated NaCl (1×15 ml) and dried over $MgSO_4$. The solvent was removed under reduced pressure and the resultant oil was left in a desiccator in vacuum for 3 days to yield 0.207 g.

α-Methyl-β-4-imidazole propionic acid

Methyl-α-carbomethoxy-α-methyl-O-4-(1-tosylimidazole)-propionate (0.186 g, 0.5 mmol) was dissolved in 2 ml of methanol. To this was added 1.5 ml of 1.0 N NaOH and the reaction was allowed to stir overnight. After purification by preparative HPLC, the product obtained by lyophilization (0.1366 g) was dissolved with 5 ml of 1.0 N NaOH and heated at 100° C. for 2 hours in a 16×100 mm screw-cap tube sealed with a PTFE lined cap, followed by addition of 2 ml of concentrated HCl and heating at 145° C. for 6 hours. The desired decarboxylated product was formed. The entire solution was filtered and loaded onto a YMC G-340-10P ODS 50×20 mm preparative HPLC column. The product was eluted with a gradient of 0% to 60% 0.1% TFA/MeCN in 0.1% TFA/water over 60 min. The fractions corresponding to 11 to 13 min. in the gradient were pooled, frozen and lyophilized to give 32 mg of product.

α-Methyl-β-[1-(2,4-dinitrophenyl)-imidazol-4-yl] propionic acid

To a solution of α-Methyl-O-4-imidazole propionic acid (0.0305 g, 0.114 mmols) and sodium bicarbonate (0.0617 g, 0.734 mmol) in water (1 mL) (pH 8.04) was added a solution of 2,4-dinitrofluorobenzene (0.0323 g, 0.174 mmol) in MeCN (1.0 mL). The reaction mixture was vortexed overnight. The MeCN was removed under reduced pressure and the residue was re-dissolved in 2 mL of water, filtered and loaded onto a Phenomenex Luna C18(2) 5 μm 100×21.2 mm preparative HPLC column in two aliquots of 1.5 and 0.5 mL each. The product was eluted with a gradient of 0% to 80% 0.1% TFA/MeCN in 0.1% TFA/water over 40 min. The fractions corresponding to 12.5 to 14.5 min. in the gradient were pooled and dried in a Savant SpeedVac™ overnight. Additional product was recovered by dissolving the water-insoluble crude product in DMSO, followed by preparative HPLC as described above. The combined fractions produced 31 mg of pure product after lyophilization.

EXAMPLE 27

Synthesis of the Compounds of SEQ ID NOs: 137 and 138

(R,S)-3-(1-(2,4-dinitrophenyl)-imidazol-4-yl)-2-methyl-propionic acid was coupled to the relevant $X_{aa2}$-$X_{aa11}$-peptidyl-Sieber resin as described below.

To a solution of (R,S)-3-(1-(2,4-dinitrophenyl)-imidazol-4-yl)-2-methylpropionic acid (0.0267 g, 0.083 mmols), 6-Cl-HOBt (0.0151 g, 0.089 mmols) and HCTU (0.0360 g, 0.087 mmols) in 1 mL of NMP/DCM (3:1) was added DIEA (0.0315 g, 0.244 mmol); the solution was briefly vortexed and then added to the relevant Fmoc deprotected $X_{aa2}$-$X_{aa11}$-peptidyl-Sieber resin prepared as described in Example 19. The coupling was allowed to proceed for 16 hours. The peptidyl-resin was washed with NMP then DCM (3×1.5 mL×1 min) and then treated with 10% acetic anhydride in DCM, 1×2 mL×90 min., followed by DCM then DMF washes (3×1.5 mL×1 min). The peptidyl-resin was treated with 10% thiophenol in DMF (1.5 mL) for 1 hr and washed with DMF and DCM (4×1.5 mL×1 min). The peptidyl-resin was then treated with TFA/DCM/TIS (3:1.9:0.1) (1 mL) for 10 min and filtered. The filtrates were collected and gently vortexed for another hr. The TFA mixture was concentrated in a speed-vac to about 0.5 mL and added to 4 mL of MTBE. After 1 hr the precipitated product was collected by centrifugation, washed and then dried to give 0.0841 g of crude product. This was purified by preparative HPLC as follows: the crude peptide was dissolved and injected into a Phenomenex Luna C18(2) (5 μm, 250×30 mm) column and eluted using a linear gradient from 20% to 50% 0.1% TFA/MeCN in 0.1% TFA/water over 40 min at a flow rate of 15 mL/min with effluent UV detection at 217 nm. The fractions containing the desired product pooled and lyophilized to give 26.7 mg of 97.5% pure peptide.

Preparative Chiral HPLC Purification of the Peptide

The diastereomeric peptide mixture (10 mg) was dissolved in MeCN/MeOH. The solution was loaded onto a Chirobiotic V 2.2×50 cm, 5 μm column and eluted with MeCN/MeOH/N(CH$_2$CH$_3$)$_3$/CH$_3$COOH: 65/35/0.5/0.5 at 20 mL/min. Isomer A was collected between 29 and 35 min. Isomer B was collected between 36 and 44 min. A second run was made as described above. The fractions containing Isomer A were combined, concentrated to about 5 mL, diluted with water/MeCN (4:1) and the solution was lyophilized. Isomer B was processed in the same manner. The resultant residues were converted to TFA salts by preparative HPLC. Each peptide was injected into a Phenomenex Luna C18(2) 5 μm 100×21.2 mm column and eluted using a linear gradient from 20% to 50% 0.1% TFA/MeCN in 0.1% TFA/water over 40 min. at a flow rate of 10 mL/min with effluent UV detection at 217 nm. The fractions containing the desired product were pooled, frozen and lyophilized to give 6.0 mg of purified peptide Isomer A and 4.9 mg of purified peptide Isomer B.

EXAMPLE 28

Synthesis of (+)- and (−)-3-(1-trityl-1H-imidazol-4-yl)-2-methylpropionic acid [α-Methyl-β-(1-trityl-1H-imidazol-4-yl)propionic acid, Imp(Trt)] (1-trityl-1H-imidazol-4-yl)methanol Scheme 25

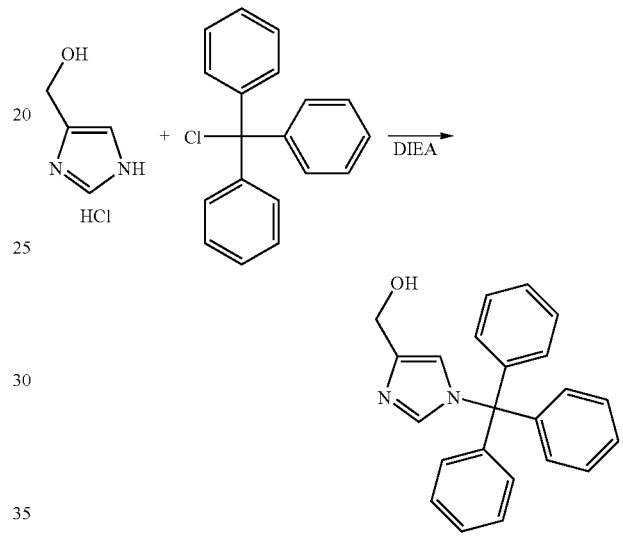

4-hydroxymethylimidazole (4.53 g, 34 mmol) and triphenylmethylchloride (10.54 g, 38 mmol) were dissolved in DMF (50 mL). To this was added with stirring DIEA (13.46 g, 104 mmol) and the reaction mixture was stirred for 14 hrs. The reaction mixture was poured into water (750 mL) and stirred for about 30 min. The resulting solid was collected, washed with water (3×25 mL) and diisopropyl ether (3×25 mL), and dried in vacuo to yield 11.55 g (99%) of (1-trityl-1H-imidazol-4-yl)methanol. Purity (HPLC): 93%; retention time, 6.37 min.; column: Phenomenex Luna C18(2) (5 μm, 50×4.6 mm); gradient: 10% to 100% B in A over 10 min. at 1.25 mL/min. Solvent A: 0.1% TFA in water, Solvent B: 0.1% TFA in AcCN. ES-MS: (M+H)$^+$=341.1.

4-(chloromethyl)-1-trityl-1H-imidazole

Scheme 26

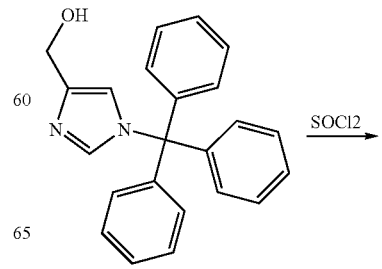

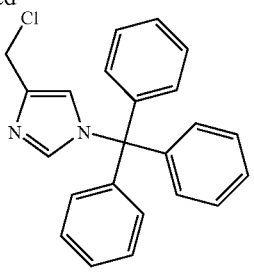

To a suspension of 4-hydroxymethyl-1-tritylimidazole (6.13 g, 18 mmol) in dichloromethane (75 mL), cooled using an ice/water, was added dropwise thionyl chloride (5.0 g, 42 mmol) over 6 min. The ice/water bath was removed and the reaction was stirred for an additional 30 min. The DCM and SOCl$_2$ were removed under reduced pressure. The resulting solid was triturated with diisopropyl ether (200 mL), collected by filtration and dried in vacuo to give 7.37 g (>100%) of 83% pure 4-(chloromethyl)-1-trityl-1H-imidazole; retention time, 7.33 min.; column: YMC ODS-A (3 μm, 50×4.6 mm); gradient: 10% to 100% B in A over 10 min. at 1.25 mL/min. Solvent A: 0.1% TFA in water, Solvent B: 0.1% TFA in AcCN. LC/MS: ESI (M+H)$^+$=359.2.

Dimethyl 2-methyl-2-((1-trityl-1H-imidazol-4-yl)methyl)malonate

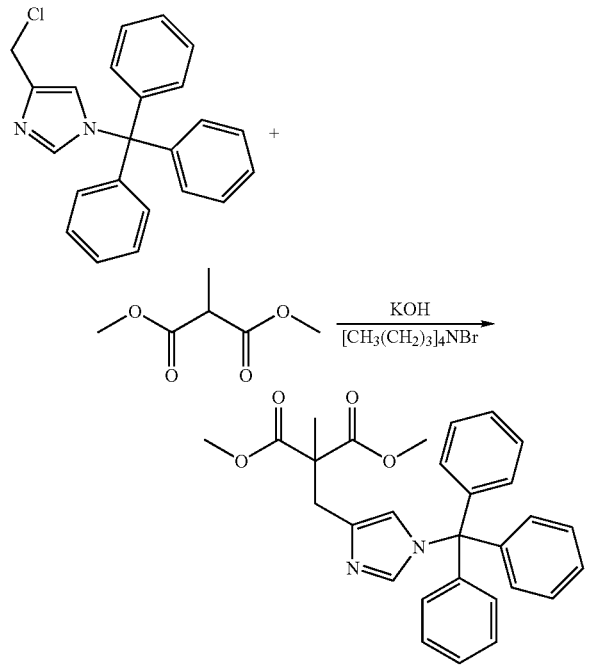

4-(chloromethyl)-1-trityl-1H-imidazole (2.73 g, 7.6 mmol) and dimethyl 2-methylmalonate (2.22 g, 15.2 mmol) were dissolved in AcCN (30 ml). This solution was added over 6 min. to freshly pulverized KOH (0.89 g, 15.9 mmol) and tetrabutylammonium bromide (0.25 g, 0.8 mmol) stirred in AcCN (2 mL). After stirring for 3 hours, more pulverized KOH (0.89 g, 15.9 mmol) was added and the mixture stirred overnight.

The solids were removed by filtration and the solvent removed under reduced pressure. The residue was dissolved in EtOAc (40 mL) and washed with water (2×20 mL) and then saturated NaCl (1×20 mL). The EtOAc was removed under reduced pressure to yield 3.46 g of an oily residue. This was purified by flash chromatography on silica gel 60 (250 g, 0.040 to 0.063 mm particle size) column (5.0×30 cm) using CHCl$_3$/EtOAc (9:1) as the eluent. Fractions of 25 mL were collected and pure product was found in fractions 53 to 72. These were pooled and the solvent was removed under reduced pressure. The resulting residue was re-evaporated twice from CHCl$_3$ (~15 mL), and then dried to yield 1.72 g of 98% pure dimethyl 2-methyl-2-((1-trityl-1H-imidazol-4-yl)methyl)malonate; retention time, 13.02 min.; column: YMC ODS-A (3 μm, 50×4.6 mm); gradient: 10% to 100% B in A over 20 min. at 1.25 mL/min. Solvent A: 0.1% TFA in water, Solvent B: 0.1% TFA in AcCN. LC/MS: ESI (M+H)$^+$=469.3. $^1$H-NMR (CDCl$_3$, 400 MHz): δ 1.42 (s, 3H), 3.15 (s, 2H), 3.63 (s, 6H), 6.48 (s, 1H), 7.05-7.15 (m, 6H), 7.26 (s, 1H) 7.28-7.37 (m, 9H).

Methyl 2-methyl-3-(1-trityl-1H-imidazol-4-yl)propanoate

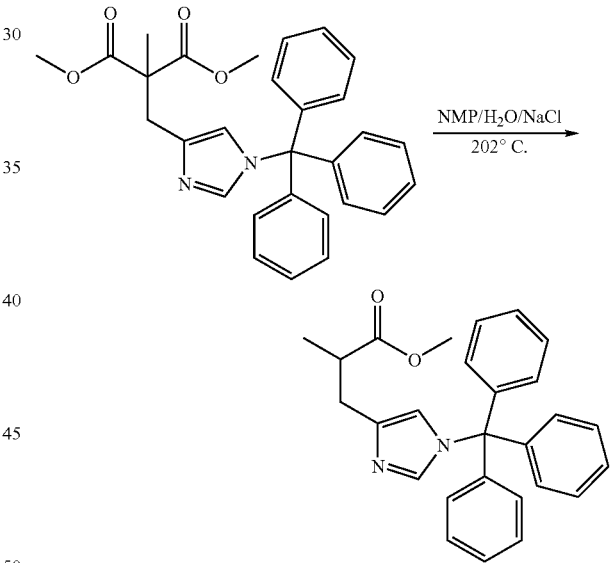

To dimethyl 2-methyl-2-((1-trityl-1H-imidazol-4-yl)methyl)malonate (0.7344 g, 1.57 mmol) in NMP (5 mL) were added NaCl (0.212 g) and water (0.3 mL) and the mixture was heated to reflux (202° C.) for 4.5 hrs. The reaction mixture was partitioned between water (20 mL) and EtOAc (20 mL) in a separatory funnel. The aqueous phase was extracted with EtOAc (2×20 mL) and the combined organic layers were washed with water (2×20 mL), saturated NaCl (1×20 mL) and dried over MgSO$_4$. The EtOAc was removed under reduced pressure to give 0.8 g of an oily residue. This was purified by elution through a silica gel pad (13.5 g of silica gel 60, 0.040 to 0.063 mm particle size) using CHCl$_3$ (5×20 mL), followed by 20% EtOAc in CHCl$_3$ (8×20 mL). The fractions containing the product were dried to yield 0.45 g of 79% pure methyl 2-methyl-3-(1-trityl-1H-imidazol-4-yl)propanoate; retention time, 7.35 min.; column: YMC ODS-A (3 μm, 50×4.6 mm);

gradient: 10% to 100% B in A over 10 min. at 1.25 mL/min. Solvent A: 0.1% TFA in water, solvent B: 0.1% TFA in AcCN. LC/MS: ESI (M+H)⁺=411.3.

Chiral Separation of the Enantiomers of methyl 2-methyl-3-(1-trityl-1H-imidazol-4-yl)propanoate A solution of racemic methyl 2-methyl-3-(1-trityl-1H-imidazol-4-yl)propanoate (0.45 g) in isopropanol (2 mL) and N-heptane (16 mL) was loaded, 1-2.5 mL at a time, onto a Chiralcel OD column (20 mm I.D.×500 mm, Chiral Technologies Inc.) and eluted with 3% isopropanol in heptane at 10 mL/min. The faster eluting enantiomer was collected in fractions from 58 to 70 min.; the later eluting enantiomer in fractions from 75 to 100 min. Each enantiomer was obtained by removing the solvent under reduced pressure and drying in vacuo. This yielded 0.205 g of the faster eluting enantiomer as a 98% pure product; retention time, 9.28 min.; column: Phenomenex Luna C18(2) (5 μm, 50×4.6 mm); gradient: 10% to 100% B in A over 15 min. at 1.25 mL/min. Solvent A: 0.1% TFA in water, Solvent B: 0.1% TFA in AcCN. LC/MS: ESI (M+H)⁺=411.3; optical rotation, $[\alpha]_D$=+12.9° (c=1.05 in CHCl₃).

The yield of the later eluting enantiomer was 0.203 g (98% pure); RT, 9.27 min. The same column and gradient were used as described for the faster eluting isomer. LC/MS: ESI (M+H)⁺=411.3; optical rotation, $[\alpha]_D$=−13.5° (c=1.16 in CHCl₃).

(+)- and (−)-2-Methyl-3-(1-trityl-1H-imidazol-4-yl)propanoic acid

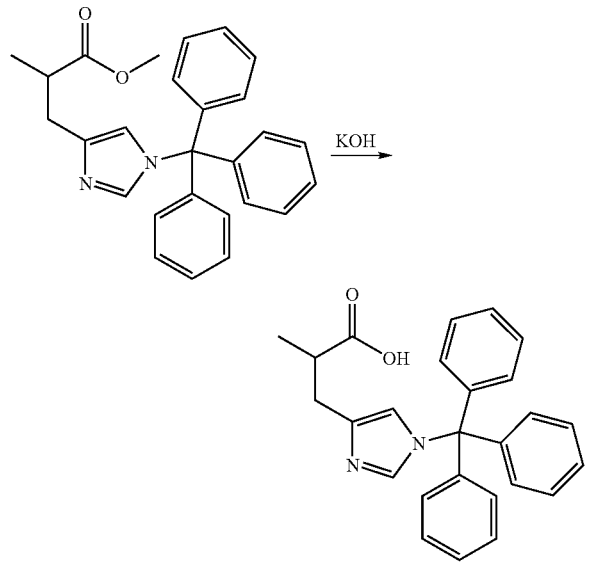

Scheme 29

The faster eluting enantiomer of methyl 2-methyl-3-(1-trityl-1H-imidazol-4-yl)propanoate (0.186 g, 0.453 mmol) was saponified by stirring in THF (2 mL) and 1 N LiOH (0.45 mL) for 2 hours. HPLC analysis shows 50% conversion to product. Nearly complete conversion (97.5%) required two additional additions of 1 N LiOH (0.1 mL each) and stirring for a total of 36 hrs. After concentrating under reduced pressure and addition of water (20 mL), the aqueous phase was extracted with DCM (3×20 mL) and the combined DCM extracts were washed with water, saturated sodium chloride (each 1×20 mL) and dried over MgSO₄. The DCM was removed and the resulting solid was dried in vacuo to yield 0.1728 g of 97% pure (+)-2-methyl-3-(1-trityl-1H-imidazol-4-yl)propanoic acid; retention time, 9.36 min.; column: YMC ODS-A (3 μm, 50×4.6 mm); gradient: 10% to 100% B in A over 15 min. at 1.25 mL/min. Solvent A: 0.1% TFA in water, solvent B: 0.1% TFA in AcCN. LC/MS: ESI (M+H)⁺=397.30, (M−H)−=395.30. Optical rotation, $[\alpha]_D$=+12.8° (c=1.03 in CHCl₃). ¹H-NMR (CD₃OD, 500 MHz): δ 1.13 (d, 3H), 2.57-2.65 (m, 1H), 2.67-2.80 (m, 1H), 2.82-2.92 (m, 1H), 6.75 (s, 1H), 7.10-7.17 (m, 6H), 7.34-7.41 (m, 9H), 7.58 (s, 1H).

The later eluting enantiomer of methyl 2-methyl-3-(1-trityl-1H-imidazol-4-yl)propanoate (0.181 g, 0.442 mmol) was saponified as described above for the faster eluting enantiomer, to yield 0.163 g of 97% pure (−)-2-methyl-3-(1-trityl-1H-imidazol-4-yl)propanoic acid; retention time, 9.32 min. (same column and gradient as described for the (+)-isomer). LC/MS: ESI (M+H)⁺=397.24, (M−H)−=395.26. Optical rotation, $[\alpha]_D$=−12.2° (c=1.03 in CHCl₃)-1H-NMR (CD₃OD, 500 MHz): δ 1.12 (d, 3H), 2.56-2.64 (m, 1H), 2.68-2.78 (m, 1H), 2.82-2.90 (m, 1H), 6.69 (s, 1H), 7.10-7.16 (m, 6H), 7.34-7.39 (m, 9H), 7.45 (s, 1H).

EXAMPLE 29

Synthesis of Compounds of SEQ ID NOs:167, 168, 169 and 170

The protected $X_{aa2}$-$X_{aa11}$ peptide sequence of SEQ ID Nos:167, 168, 169 and 170 was assembled on an Advanced ChemTech Model 90 Synthesizer starting from Sieber Amide resin (9.56 g, 0.72 mmol/gram, 6.88 mmol) using the following wash and deprotection protocol:
 1. DMF wash 1×85 ml×1 min.
 2. 20% piperidine in DMF 1×85 ml×5 mins.
 3. 20% piperidine in DMF 1×85 ml×15 mins.
 4. DMF washes 3×85 ml×1 min.
 5. NMP washes 3×85 ml×1 min.

A solution of (S)-2-(((9H-fluoren-9-yl)methoxy)carbonylamino)-3-(6-o-tolylpyridin-3-yl)propanoic acid HCl salt (6.70 g, 13.0 mmol), PyBOP (7.29 g, 14.0 mmol) and HOBt monohydrate (2.14 g, 14.0 mmol) in NMP (70 ml) was added to the deprotected resin, followed by DIEA (7.28 g, 56.3 mmol) and the mixture was vortexed until a Kaiser ninhydrin test on a resin sample was negative (4.5 hrs). The resin was washed with DMF (3×85 ml×1 min.), then DCM (7×85 ml×1 min.) and dried in vacuo to yield 11.344 g. Fmoc determination gave a substitution of 0.53 mmol/gram. Following deprotection of the resin with steps 1 to 4 above and 6 DMF washes, a solution of (S)-2-(((9H-fluoren-9-yl)methoxy)carbonylamino)-3-((2'-ethyl-4'-hydroxy)biphen-4-yl)propanoic acid [Fmoc-(S)-(2'-ethyl-4'hydroxy)-Bip-OH] (3.79 g, 7.47 mmol) and HOBt monohydrate (1.14 g, 7.44 mmol) in DMF (50 ml) and DIC (0.94 g, 7.45 mmol) was added to the resin and the mixture was vortexed for 20 hrs. After a resin sample gave a slightly positive Kaiser ninhydrin test, the peptidyl-resin was washed with DMF and DCM (both 4×85 mL×1 min.), and was then treated with 10% acetic anhydride in DCM (1×100 mL×30 mins.). The peptidyl-resin was washed with DCM (4×85 mL×1 min.) and about 1 mmol was removed and dried in vacuo.

The dipeptidyl-resin (2.50 g, 1.0 mmol) was loaded into a 50 mL reactor on an Advanced ChemTech Model 90 Synthesizer. The Fmoc group was removed using the following cycle:

1. DMF wash 1×25 ml×1 min.
2. 20% piperidine in DMF 1×25 ml×5 mins.
3. 20% piperidine in DMF 1×25 ml×15 mins.
4. DMF washes 8×25 ml×1 min.

A solution of N-α-Fmoc-L-aspartic acid β-t-butyl ester (1.2345 g, 3.00 mmol) and HOBt monohydrate (0.4599 g, 3.00 mmol) in DMF (5 ml) and DIC (0.3829 g, 3.03 mmol) was added to the deprotected peptidyl-resin and the mixture was vortexed for 2 hours to yield a negative Kaiser ninhydrin test. The peptide-resin was washed with DMF then DCM (both 4×25 mL×1 min.) and divided equally into 2 reactors on a Model 90 Synthesizer. The synthesis was then continued as described below. The Fmoc group was removed using the following cycle:

1. DMF wash 1×12 ml×1 min.
2. 20% piperidine in DMF 1×12 ml×5 mins.
3. 20% piperidine in DMF 1×12 ml×15 mins.
4. DMF washes 8×12 ml×1 min.

A solution of N-α-Fmoc-N-im-trityl-L-histidine or N-α-Fmoc-O-t-butyl-L-serine (0.9282 g, 1.50 mmol) and HOBt monohydrate (0.2296 g, 1.50 mmol) in DMF/DCM (1:1) (10 ml) and DIC (0.1995 g, 1.58 mmol) was added to the deprotected resin. After 90 min., the peptide-resin was washed with DMF and DCM (both 4×12 mL×1 min.) and gave a negative Kaiser ninhydrin test. After removal of the Fmoc group as described, N-α-Fmoc-O-t-butyl-L-threonine (0.6006 g, 1.51 mmol) was coupled as described in the previous step, followed by removal of the Fmoc group. Coupling of N-α-Fmoc-α-methyl-2-fluoro-L-phenylalanine (0.4167 g, 0.993 mmol) was performed by mixing a solution of the amino acid and HOBt monohydrate (0.1529 g, 0.998 mmol) in DMF/DCM 1:1 (10 ml) and DIC (0.1260 g, 0.998 mmol) with the deprotected peptidyl-resin for 4 hours. After DMF and DCM (both 4×12 mL×1 min.) washes, a sample of the peptide-resin gave a negative Kaiser ninhydrin test. Performed steps 1 to 4 above to remove the Fmoc group.

After removal of the Fmoc group, N-α-Fmoc-O-t-butyl-L-threonine (1.9880 g, 5.00 mmol) was coupled by mixing a solution of the amino acid in 0.5 M HOAt in DMF (10.0 mL, 5.00 mmol) and DIC (0.6360 g, 5.04 mmol) with the deprotected peptidyl-resin for 16 hours. After DMF and DCM washes (both 4×12 mL×1 min.), a sample of wet peptidyl-resin was cleaved using 1 ml of TFA/triisopropylsilane/water (96:2:2) for 1.5 hours and showed, upon HPLC and MS analysis, only a very small amount of uncoupled peptide. The peptide-resin was treated with 10% acetic anhydride in DCM (1×12 mL×1 hr.) and then washed with DCM (6×12 mL×1 min.). After removal of the Fmoc group, N-Fmoc-glycine (0.8941 g, 3.01 mmol) and N-α-Fmoc-L-glutamic acid γ-t-butyl ester (1.2765 g, 3.00 mmol) were successively coupled for 2 hrs as solutions with HOBt monohydrate (0.4604 g, 3.01 mmol) and DIC (0.3885 g, 3.08 mmol) in DMF/DCM (1:1) (20 ml). Negative Kaiser ninhydrin tests were obtained after each coupling step. The two peptidyl-resins thus obtained were each transferred to separate 35 mL syringes fitted with frits and dried in vacuo. The synthesis was then continued with 0.28 mmol of each peptidyl-resin. After Fmoc removal, a solution of N-α-Fmoc-α-methyl-L-proline (0.3943 g, 1.12 mmol) in 0.5 M HOAt in DMF (2.24 mL, 1.12 mmol) and DIC (0.1413 g, 1.12 mmol), diluted with an additional 8 mL of DMF, was divided into two equal volumes, which were added to each of the deprotected peptide-resins. After vortexing for 12 hrs and washing with DMF and DCM (both 3×8 mL×1 min.), 0.02 mmol aliquots of the peptidyl-resins were placed into 3-4 reaction wells on an Advanced ChemTech Ω396 Synthesizer. The Fmoc group was removed as follows:

1. 20% piperidine in DMF 1×1 ml×5 mins.
2. 20% piperidine in DMF 1×1 ml×15 mins.
3. NMP washes 8×1 ml×1 min.

A solution of (+)-2-methyl-3-(1-trityl-1H-imidazol-4-yl)propanoic acid (79.9 mg, 0.202 mmol), TFFH (0.0538 g, 0.204 mmol) and DIEA (0.0532 g, 0.412 mmol) in DMF (2 mL), divided into 2 equal volumes, was added to the relevant deprotected peptide-resins, which, after mixing for 12 hrs, were washed with NMP (2×1 mL×1 min.) and then DCM (3×1 mL×1 min.). Cleavage of a small resin sample using TFA/TIS/water (96:2:2), followed by HPLC and MS analysis of the products, showed nearly complete coupling. The peptide-resins were treated with 10% acetic anhydride in DCM (1×1 mL×1 hour) and then washed with DCM (6×1.5 mL×1 min.).

The peptide-resins were treated with TFA/TIS/water 96:2:2 (3×1 mL×30 mins.) and the filtrates were collected and concentrated in a speed-vac to near dryness. The crude peptides were precipitated by addition of diisopropyl ether (5 mL), washed with diisopropyl ether and dried. The crude peptides were purified by preparative HPLC as described herein using a YMC ODS-A (10 μm, 250×20 mm) column. The gradient used was from 25% to 55% B in A over 60 min. Solvent A: 0.1% TFA in water; Solvent B: 0.1% TFA in AcCN; flow rate, 15 mL/min. The fractions containing a pure product were pooled and lyophilized. Compound of SEQ ID NO:169 (or 170) was obtained as a 95% pure product; retention time, 22.0 min. (column:YMC ODS-AQ 3 μm (4.6×150 mm); gradient: 15-45% B in A over 60 min., 1 mL/min.). ES-MS analysis: $(M+H)^+=1590.0$, $(M+2H)^+/2=795.9$.

Compound of SEQ ID NO:167 (or 168) was obtained as a 96% pure product (7.2 mg, 9% recovery); retention time, 22.7 min. (column: YMC ODS-AQ 3 μm (4.6×150 mm); gradient: 15-45% B in A over 60 min., 1 mL/min.). ES-MS analysis: $(M+H)^+=1539.8$, $(M+2H)^+/2=770.9$.

EXAMPLE 30

Synthesis of Compound of SEQ ID NO:157

A solution of Fmoc-His(Trt)-OH (0.1278 g, 0.206 mmol), TFFH (0.0542 g, 0.205 mmol) and DIEA (0.0533 g, 0.412 mmol) in DMF (1 mL) was added to the relevant deprotected peptide-resin prepared as described in Example 29. The coupling was repeated using a solution of Fmoc-His(Trt)-OH (0.1257 g, 0.20 mmol) and DIC (0.0262 g, 0.21 mmol) in 0.5 M HOAt in DMF (0.40 mL) and DMF (0.40 mL). The peptide-resin was deprotected as follows:

1. 20% piperidine in DMF 1×1 ml×5 mins.
2. 20% piperidine in DMF 1×1 ml×15 mins.
3. DMF washes 8×1 ml×1 min.
4. DCM washes 3×1 mL×1 min.

2,5-dioxopyrrolidin-1-yl methyl carbonate (0.0241 g, 0.14 mmol) was dissolved in DCM (0.5 mL), added to the deprotected resin, and the mixture vortexed for 14 hrs. After washing with DCM (4×1 ml×1 min.), a resin sample gave a negative Kaiser ninhydrin test. The crude product was cleaved from the resin and precipitated as described in Example 29, yielding 40 mg of product. This was purified by preparative HPLC as described in Example 29, except that the gradient used was from 20% to 55% B in A over 60 min. The fractions containing a pure product were pooled and lyophilized to yield 12.0 mg (30% recovery) of 97% pure product; retention time, 33.3 min. (column, YMC ODS-AQ 3 μm (4.6×150 mm); gradient: 15-55% B in A over 60 min., 1 mL/min.). ES-MS analysis: $(M+H)^+=1648.8$, $(M+2H)^+/2=824.9$.

EXAMPLE 31

Synthesis of Compounds of SEQ ID Nos:175 and 176

A solution of 2-methoxy-3-(1-trityl-1H-imidazol-4-yl)propanoic acid (0.0417 g, 0.101 mmol), HATU (0.0390 g, 0.103 mmol) and DIEA (0.0284 g, 0.220 mmol) in 0.5 M HOAt in DMF (0.202 mL, 0.101 mmol) and DMF (0.2 mL) was added to Fmoc-deprotected $Xaa_2$-$Xaa_{11}$ peptidyl-resin (0.010 mmol), where $Xaa_8$=His, prepared as described in Example 29. After vortexing for 14 hrs, the peptide-resin was washed with DMF and DCM (both 3×1 mL×1 min.), and then treated with 10% acetic anhydride in DCM (1×1 mL×30 mins.), followed by DCM washes (6×1 mL×1 min.). The peptide product was released and deprotected from the resin using TFA/TIS/water (96:2:2) as described in Example 29.

The crude peptide was purified by preparative HPLC as described herein using a gradient from 30% to 40% B in A over 60 min. Solvent A: 10 mM sodium phosphate pH 7 in water/AcCN (95:5); Solvent B: 1 mM sodium phosphate pH 7 in water/AcCN (20:80); column: Phenomenex Luna C18 (2), 5 μm (250×21.2 mm); flow rate: 15 mL/min. The fractions containing the early eluting diastereomer (isomer A) were pooled and concentrated to about 5 mL. This solution was desalted by elution into a Phenomenex Luna C18(2) column (5 μm, 100×21.2 mm) using a gradient 0% to 100% B in A over 20 min. Solvent A: 0.1% TFA in water; Solvent B: 0.1% TFA in AcCN; flow rate, 15 mL/min. The fractions containing the product were pooled and lyophilized to yield 1.2 mg of 93% pure Compound of SEQ ID No:175 (or 176); retention time, 40.4 min.; column: YMC ODS-AQ 3 μm (4.6×150 mm); gradient: 15-45% B in A over 60 min., 1 mL/min. ES-MS analysis: $(M+H)^+$=1605.6, $(M+2H)^+/2$=803.5.

Compound of SEQ ID No:176 (or 175) was obtained as described above from the fractions containing the later-eluting diastereomer from the first preparative HPLC step. Yield: 3.0 mg of 96% pure product; retention time, 40.7 min. under the same analytical HPLC conditions as above. ES-MS analysis: $(M+H)^+$=1605.7, $(M+2H)^+/2$=803.7.

EXAMPLE 32

Synthesis of 2-Methoxy-3-(1-trityl-1H-imidazol-4-yl)propanoic acid Dimethyl 2-methoxy-2-((1-trityl-1H-imidazol-4-yl)methyl)malonate Scheme 30

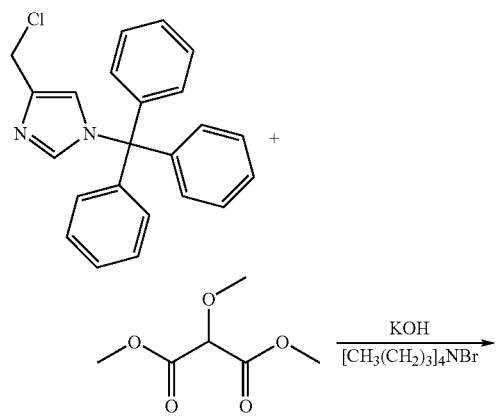

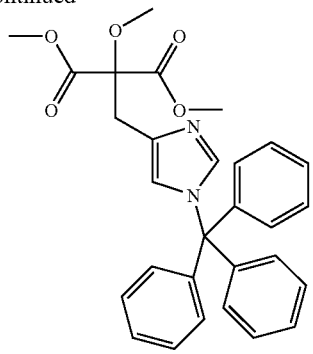

A solution of 4-(chloromethyl)-1-trityl-1H-imidazole (0.3655 g, 1.02 mmol) and dimethyl 2-methoxymalonate (0.1822 g, 1.25 mmol) in AcCN (10 mL) was rapidly added to a stirred slurry of freshly pulverized potassium hydroxide (0.1760 g, 3.14 mmol) and tetrabutylammonium bromide (0.0521 g, 0.16 mmol) in AcCN (2 mL). After 16 hrs, the reaction was diluted with ethyl acetate (20 mL) and filtered through celite pad, which was washed with EtOAc (2×5 mL). The combined organic layers were washed with water (2×10 mL), saturated NaCl (1×10 mL) and dried over $MgSO_4$. The oily residue (0.41 g) obtained upon solvent removal was purified by chromatography on a silica gel 60 (42 g, 0.040 to 0.063 mm particle size) 2.5×30 cm column using $CHCl_3$/EtOAc (9:1) as the eluent and collecting 72×25 mL fractions. Fractions 28 to 72 were pooled and dried, to yield 0.1628 g (33%) of 89.5% pure dimethyl 2-methoxy-2-((1-trityl-1H-imidazol-4-yl)methyl)malonate; retention time, 7.52 min.; column: YMC ODS-A (3 μm, 50×4.6 mm); gradient: 10% to 100% B in A over 10 min. at 1.25 mL/min. Solvent A: 0.1% TFA in water, Solvent B: 0.1% TFA in AcCN. LC/MS: ESI $(M+H)^+$=485.3. $^1$H-NMR ($CDCl_3$, 500 MHz): δ 3.39 (s, 3H), 3.49 (s, 2H), 3.69 (s, 6H), 6.70 (s, 1H), 6.99-7.03 (m, 6H), 7.30-7.35 (m, 9H), 7.92 (s, 1H).

Methyl 2-methoxy-3-(1-trityl-1H-imidazol-4-yl)propanoate

Scheme 31

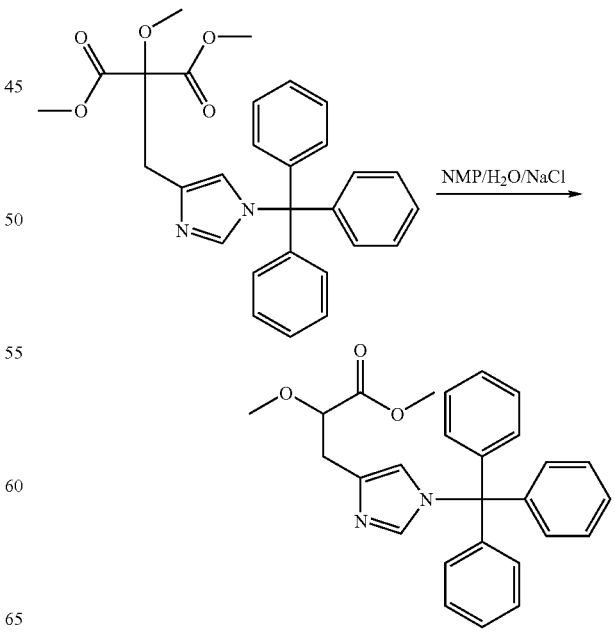

A solution of dimethyl 2-methoxy-2-((1-trityl-1H-imidazol-4-yl)methyl)malonate (0.1520 g, 0.31 mmol) and sodium chloride (0.0398 g, 0.68 mmol) in NMP (2 mL) and water (0.3 mL) was heated to 201° C. for 1 hr. After cooling to room temperature, ethyl acetate (15 mL) was added and the organic layer was washed with water (2×10 mL), saturated sodium chloride (1×10 mL) and then dried over $NaSO_4$. Solvent removal yielded 0.1030 g of crude product. This was purified by chromatography on a silica gel 60 (11 g, 0.040 to 0.063 mm particle size) column (2.5×10 cm) using $CHCl_3$/MeOH (98:2) as the eluent and collecting 12 mL fractions. Fractions 2 to 10 were pooled and dried, and the residue was re-purified as above, except that 5 g of silica gel was used and the eluent was $CHCl_3$/MeOH (99:1). Fractions 10 to 16 were pooled and afforded, after drying, 0.0592 g (45%) of 94.5% pure methyl 2-methoxy-3-(1-trityl-1H-imidazol-4-yl)propanoate; retention time, 7.29 min.; column: YMC ODS-A (3 μm, 50×4.6 mm); gradient: 10% to 100% B in A over 10 min. at 1.25 mL/min. Solvent A: 0.1% TFA in water, Solvent B: 0.1% TFA in AcCN. LC/MS: ESI $(M+H)^+$=427.1.

2-Methoxy-3-(1-trityl-1H-imidazol-4-yl)propanoic acid

Scheme 32

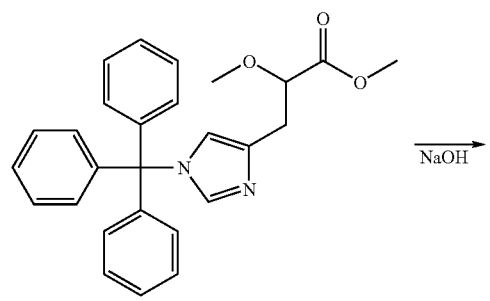

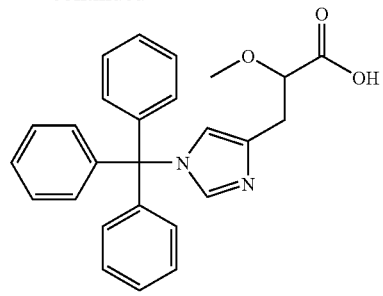

To a solution of methyl 2-methoxy-3-(1-trityl-1H-imidazol-4-yl)propanoate (0.0592 g, 0.139 mmol) in tetrahydrofuran (1 mL), methanol (1 mL) and water (0.5 mL) was added 2N NaOH (0.278 mL) and the reaction mixture was stirred for 1.75 hrs. The organic solvents were removed and 1 N $KHSO_4$ (5 mL) and ethyl acetate (10 mL) were added. The organic phase was washed with water (2×5 mL), then saturated sodium chloride (1×5 mL) and dried over $MgSO_4$. The combined aqueous layers were re-extracted with DCM (2×10 mL), and dried over $MgSO_4$—Solvent removal and drying in vacuo yielded 0.0552 g (96%) of 92.6% pure 2-methoxy-3-(1-trityl-1H-imidazol-4-yl)propanoic acid; retention time, 6.80 min.; column: Phenomenex Luna C18(2) (5 μm, 50×4.6 mm); gradient: 10% to 100% B in A over 10 min. at 1.25 mL/min. Solvent A: 0.1% TFA in water, Solvent B: 0.1% TFA in AcCN. LC/MS: ESI $(M+H)^+$=413.1. $^1$H-NMR ($CDCl_3$, 500 MHz): δ 3.10-3.18 (m, 1H), 3.31-3.38 (m, 1H), 3.45 (s, 3H), 4.26-4.31 (m (1H), 6.86 (s, 1H), 7.04-7.11 (m, 6H), 7.37-7.47 (m, 9H), 8.16 (s, 1H).

EXAMPLE 33

Synthesis of the Compound of SEQ ID NO:164

Scheme 33

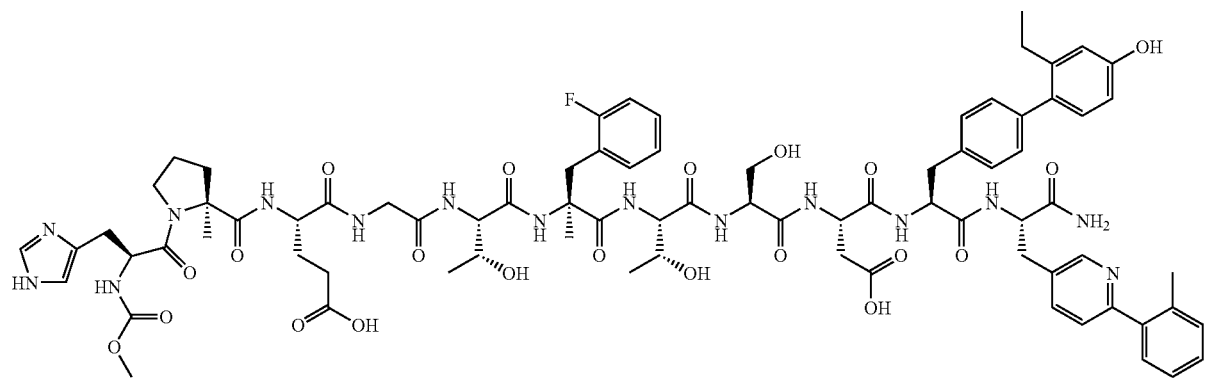

Compound of SEQ ID NO: 158

Chloramine T
NaI

-continued

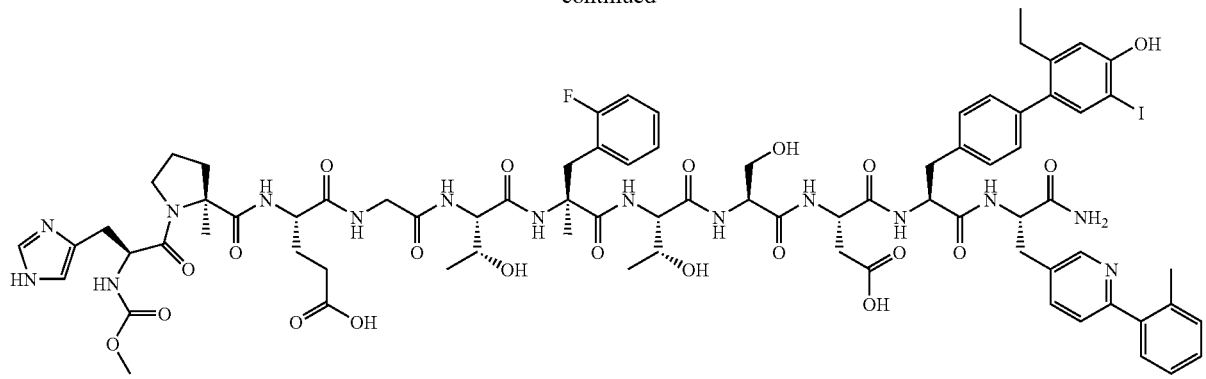

To a solution of Compound of SEQ ID NO:158 (0.0211 g, 0.0132 mmole) in AcCN (0.610 mL) and aqueous sodium iodide (3.93 mg/mL, 0.610 mL, 0.016 mmol) was added a solution of chloramine T (10.05 mg/mL, 0.540 mL, 0.016 mmole) in water/AcCN (1:1). The resulting solution was vortexed for 35 min. and filtered, and the product was purified by preparative HPLC as described herein. Column: Phenomenex Luna C18(2) (5 μm, 250×21.2 mm); gradient: 15% to 75% B in A over 60 min. Solvent A: 0.1% TFA in water; Solvent B: 0.1% TFA in AcCN; flow rate, 15 mL/min. The fractions containing a pure product were pooled and lyophilized, yielding 11.6 mg of 99% pure iodinated peptide; retention time, 30.41 min.; column: YMC ODS-AQ (3 μm, 4.6×150 mm); gradient: 15-75% B in A over 60 min., 1 mL/min. Solvent A: 10 mM sodium phosphate, pH 7.5, in water/AcCN (95:5); Solvent B: 1 mM sodium phosphate, pH 7.5, in water/AcCN (20:80). ES-MS analysis: $(M+H)^+=$ 1725.0, $(M+2H)^+/2=863.0$.

EXAMPLE 34

Exemplary peptides are set forth in Table 3C.

TABLE 3C

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-$NH_2$ |
|---|---|---|---|---|---|---|---|---|---|---|---|
| 1. | H | Aib | E | G | T | L-α-Me-Phe(2-Fluoro) | T | S | D | Bip(2'-Me) | 4-(2'-pyridyl)Phenylalanine-$NH_2$ |
| 2. | H | Aib | E | G | T | L-α-Me-Phe(2-Fluoro) | T | S | D | Bip(3',5'-di-Me) | 4-(2'-pyridyl)Phenylalanine-$NH_2$ |
| 3. | H | Aib | E | G | T | L-α-Me-Phe(2-Fluoro) | T | S | D | Bip(2'-OBu) | 4-(2'-pyridyl)Phenylalanine-$NH_2$ |
| 4. | H | Aib | E | G | T | L-α-Me-Phe(2-Fluoro) | T | S | D | Bip(2'-Me) | 4-(4'-pyridyl)Phenylalanine-$NH_2$ |
| 5. | H | Aib | E | G | T | L-α-Me-Phe(2-Fluoro) | T | S | D | Bip(2'-Cl) | 4-(4'-pyridyl)Phenylalanine-$NH_2$ |
| 6. | H | Aib | E | G | T | L-α-Me-Phe(2-Fluoro) | T | S | D | Bip(2'-methoxy-5'-iso-propyl) | 4-(4'-pyridyl)Phenylalanine-$NH_2$ |
| 7. | H | Aib | E | G | T | L-α-Me-Phe(2-Fluoro) | T | S | D | 4-(2'-Ethylphenyl)-3-pyridylalanine | Bip(2'-Me)—$NH_2$ |
| 8. | H | Aib | E | G | T | L-α-Me-Phe(2-Fluoro) | T | S | D | 4-[(2'-Ethyl-4'-methoxy)phenyl]-3-pyridylalanine | Bip(2'-Me)—$NH_2$ |
| 9. | H | Aib | E | G | T | L-α-Me-Phe(2-Fluoro) | T | S | D | Bip(2'-Et-4'-OMe) | 4-(2'-Methylphenyl)-3-pyridylalanine-$NH_2$ |
| 10. | H | Aib | E | G | T | L-α-Me-Phe(2,6-di-Fluoro) | T | S | D | Bip(2'-Et-4'-OMe) | 4-(2'-Methylphenyl)-3-pyridylalanine-$NH_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 11. | Des-NH$_2$-His | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 12. | Des-NH$_2$-His | Aib | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 13. | H | Aib | E | G | T | L-α-Me-Phe(2-Fluoro) | T | S | D | 4-(2'-ethylphenyl)-3-pyridylalanine | 4-(2'-Methylphenyl)-3-pyridylalanine-NH$_2$ |
| 14. | H | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-NH$_2$ |
| 15. | H | Aib | E | G | T | L-α-Me-Phe(2-Fluoro) | T | S | D | Bip(2'-Et-4'-OMe) | 4-[3-(4-Methyl)pyridyl]phenylalanine-NH$_2$ |
| 16. | H | Aib | E | G | T | L-α-Me-Phe(2,6-di-Fluoro) | T | S | D | Bip(2'-Et-4'-OMe) | 4-[3-(4-Methyl)pyridyl]phenylalanine-NH$_2$ |
| 17. | H | Aib | E | G | T | L-α-Me-Phe(2-Fluoro) | T | S | D | Bip(2'-Et-4'-OMe) | 4-(3-Pyridazyl)phenylalanine-NH$_2$ |
| 18. | H | Aib | E | G | T | L-α-Me-Phe(2,6-di-Fluoro) | T | S | D | Bip(2'-Et-4'-OMe) | 4-(3-Pyridazyl)phenylalanine-NH$_2$ |
| 19. | H | Aib | E | G | T | L-α-Me-Phe(2-Fluoro) | T | S | D | Bip(2'-Et-4'-OMe) | 4-[3-(4-Me,6-OMe)pyridyl]phenylalanine-NH$_2$ |
| 20. | H | Aib | E | G | T | L-α-Me-Phe(2,6-di-Fluoro) | T | S | D | 4-[3-(4'-Methyl)pyridyl]phenylalanine | Bip(2'-Me)—NH$_2$ |
| 21. | H | Aib | E | G | T | L-α-Me-Phe(2-Fluoro) | T | S | D | 4-[(4'-Me-6'-OMe)-3-pyridyl]phenylalanine | Bip(2'-Me)—NH$_2$ |
| 22. | H | Aib | E | G | T | L-α-Me-Phe(2,6-di-Fluoro) | T | S | D | 4-[(4'-Me-6'-OMe)-3-pyridyl]phenylalanine | Bip(2'-Me)—NH$_2$ |
| 23. | H | Aib | E | G | T | L-α-Me-Phe(2,6-di-Fluoro) | T | S | D | Bip(2'-Et-4'-OMe) | 4-[2(1H)Pyridonyl]phenylalanine-NH$_2$ |
| 24. | H | Aib | E | G | T | L-α-Me-Phe(2-Fluoro) | T | S | D | Bip(2'-Et-4'-OMe) | Bip(8-Quinoline)-NH$_2$ |
| 25. | H | Aib | E | G | T | L-α-Me-Phe(2-Fluoro) | T | S | D | Bip(2'-Et-4'-OMe) | Bip(3-Quinoline)-NH$_2$ |
| 26. | H | Aib | E | G | T | L-α-Me-Phe(2-Fluoro) | T | S | D | Bip(2'-Et-4'-OMe) | Bip(6-Quinoline)-NH$_2$ |
| 27. | H | Aib | E | G | T | L-α-Me-Phe(2-Fluoro) | T | S | D | Bip(2'-Et-4'-OMe) | Bip(5-Quinoline)-NH$_2$ |
| 28. | H | Aib | E | G | T | L-α-Me-Phe(2-Fluoro) | T | S | D | Bip(2'-Et-4'-OMe) | 4-(3-(6-OMe)pyridyl)phenylalanine-NH$_2$ |
| 29. | H | Aib | E | G | T | L-α-Me-Phe(2-Fluoro) | T | S | D | Bip(2'-Et-4'-OMe) | 4-(3-(2-Methoxy)pyridyl)phenylalanine-NH$_2$ |
| 30. | H | Aib | E | G | T | L-α-Me-Phe(2-Fluoro) | T | S | D | Bip(2'-Et-4'-OMe) | 4-(3'-pyridyl)phenylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-$NH_2$ |
|---|---|---|---|---|---|---|---|---|---|---|---|
| 31. | Des-NH$_2$-His | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-NH$_2$ |
| 32. | H | Aib | E | G | T | L-α-Me-Phe(2-Fluoro) | T | S | D | 4-(5-Quinoline)phenylalanine | Bip(2'-Me)—NH$_2$ |
| 33. | H | Aib | E | G | T | L-α-Me-Phe(2-Fluoro) | T | S | D | 4-[3-(2'-OMe)pyridyl]phenylalanine | Bip(2'-Me)—NH$_2$ |
| 34. | H | Aib | E | G | T | L-α-Me-Phe(2-Fluoro) | T | S | D | 4-(6-Quinoline)phenylalanine | Bip(2'-Me)—NH$_2$ |
| 35. | H | Aib | E | G | T | L-α-Me-Phe(2-Fluoro) | T | S | D | 4-(4'-pyridyl)phenylalanine | Bip(2'-Me)—NH$_2$ |
| 36. | H | Aib | E | G | T | L-α-Me-Phe(2-Fluoro) | T | S | D | 4-[4'-(3',5'-dimethylisoxazole)]phenylalanine | Bip(2'-Me)—NH$_2$ |
| 37. | H | Aib | E | G | T | L-α-Me-Phe(2-Fluoro) | T | S | D | Bip(2'-Et-4'-OMe) | 4-(2-trifluoromethylphenyl)-3-pyridylalanine-NH$_2$ |
| 38. | H | Aib | E | G | T | L-α-Me-Phe(2-Fluoro) | T | S | D | Bip(2'-Et-4'-OMe) | 4-(2-methyl-5-fluorophenyl)-3-pyridylalanine-NH$_2$ |
| 39. | H | Aib | E | G | T | L-α-Me-Phe(2-Fluoro) | T | S | D | Bip(2'-Et-4'-OMe) | 4-(4-methanesulfonylphenyl)-3-pyridylalanine-NH$_2$ |
| 40. | H | Aib | E | G | T | L-α-Me-Phe | T | S | D | Bip(2'-Et-4'-OMe) | 4-(2'-Methylphenyl)-3-pyridylalanine-NH$_2$ |
| 41. | H | Aib | E | G | T | L-α-Me-Phe(2-Fluoro) | T | S | D | Bip(2'-Et) | 4-(2'-Methylphenyl)-3-pyridylalanine-NH$_2$ |
| 42. | H | Aib | E | G | Nle | L-α-Me-Phe(2-Fluoro) | T | S | D | Bip(2'-Et-4'-OMe) | 4-(2'-Methylphenyl)-3-pyridylalanine-NH$_2$ |
| 43. | H | Aib | E | G | T | L-α-Me-Phe(2-Fluoro) | T | S | D | Bip(2'-Et-4'-OMe) | 4-[(2'-Cl, 4'-CF3)-3'-pyridyl]phenylalanine-NH$_2$ |
| 44. | H | Aib | E | G | T | L-α-Me-Phe(2,6-di-Fluoro) | T | S | D | Bip(2'-Et-4'-OMe) | 4-[3'-(2'-CN-6'-Me)pyridyl]phenylalanine-NH$_2$ |
| 45. | H | Aib | E | G | T | L-α-Me-Phe(2,6-di-Fluoro) | T | S | D | Bip(2'-Cl) | 4-(2'-Methylphenyl)-3-pyridylalanine-NH$_2$ |
| 46. | H | Aib | E | G | T | L-α-Me-Phe(2,6-di-Fluoro) | T | S | D | Bip(2',4'-di-OMe) | 4-(2'-Methylphenyl)-3-pyridylalanine-NH$_2$ |
| 47. | H | Aib | E | G | T | L-α-Me-Phe(2,6-di-Fluoro) | T | S | D | 4-(3'-pyridyl)phenylalanine | 4-(2'-Methylphenyl)-3-pyridylalanine-NH$_2$ |

TABLE 3C-continued

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH$_2$ |
|---|---|---|---|---|---|---|---|---|---|---|---|
| 48. | H | Aib | E | G | T | L-α-Me-Phe(2,6-di-Fluoro) | T | S | D | 4-(4'-pyridyl)phenylalanine | 4-(2'-Methylphenyl)-3-pyridylalanine-NH$_2$ |
| 49. | H | Aib | E | G | T | L-α-Me-Phe(2,6-di-Fluoro) | T | S | D | Bip(2'-Me-3'-F) | 4-(2'-Methylphenyl)-3-pyridylalanine-NH$_2$ |
| 50. | H | Aib | E | G | T | L-α-Me-Phe(2-Fluoro) | T | S | D | Bip(2'-F) | 4-(2'-Methylphenyl)-3-pyridylalanine-NH$_2$ |
| 51. | H | Aib | E | G | T | L-α-Me-Phe(2,6-di-Fluoro) | T | S | D | 4-[3'-(2'-Cl-6'-CF3)pyridyl]phenylalanine | 4-(2'-Methylphenyl)-3-pyridylalanine-NH$_2$ |
| 52. | H | Aib | E | G | T | L-α-Me-Phe(2,6-di-Fluoro) | T | S | D | 4-(2'-ethylphenyl)-3-pyridylalanine | Bip(2'-Cl)—NH$_2$ |
| 53. | H | Aib | E | G | T | L-α-Me-Phe(2,6-di-Fluoro) | T | S | D | 4-(2'-ethylphenyl)-3-pyridylalanine | Bip(3'-Cl-4'-F)—NH$_2$ |
| 54. | H | Aib | E | G | Nva | L-α-Me-Phe(2-Fluoro) | T | S | D | Bip(2'-Et-4'-OMe) | 4-(2'-Methylphenyl)-3-pyridylalanine-NH$_2$ |
| 55. | H | Aib | E | G | T | L-α-Me-Phe(2,6-di-Fluoro) | T | S | D | 4-(2'-ethylphenyl)-3-pyridylalanine | Bip(3',5'-di-Me)—NH$_2$ |
| 56. | H | Aib | E | G | T | L-α-Me-Phe(2,6-di-Fluoro) | T | S | D | 4-(2'-ethylphenyl)-3-pyridylalanine | 4-(2',3'-pyridazyl)phenylalanine-NH$_2$ |
| 57. | H | Aib | E | G | T | L-α-Me-Phe(2-Fluoro) | T | S | D | Bip(2'-Et-4'-OMe) | 4-(2'-ethylphenyl)-3-pyridylalanine-NH$_2$ |
| 58. | H | Aib | E | G | T | L-α-Me-Phe(2,6-di-Fluoro) | T | S | D | 4-(2'-ethylphenyl)-3-pyridylalanine | 4-[3'-(2'-Cl-6'-CF3)pyridyl]phenylalanine-NH$_2$ |
| 59. | H | Aib | E | G | T | L-α-Me-Phe(2,6-di-Fluoro) | T | S | D | 4-(2'-ethylphenyl)-3-pyridylalanine | 4-[3'-(2'-CN-6'-Me)pyridyl]phenylalanine-NH$_2$ |
| 60. | H | Aib | E | G | T | L-α-Me-Phe(2,6-di-Fluoro) | T | S | D | 4-[3'-(4'-Me)pyridyl]phenylalanine | Bip(2'-Cl)—NH$_2$ |
| 61. | H | Aib | E | G | T | L-α-Me-Phe(2,6-di-Fluoro) | T | S | D | 4-[3'-(4'-Me)pyridyl]phenylalanine | Bip(3'-Cl-4'-F)—NH$_2$ |
| 62. | H | Aib | E | G | T | L-α-Me-Phe(2,6-di-Fluoro) | T | S | D | 4-[3'-(4'-Me)pyridyl]phenylalanine | Bip(3',5'-di-Me)—NH$_2$ |
| 63. | H | Aib | E | G | T | L-α-Me-Phe(2,6-di-Fluoro) | T | S | D | 4-[3'-(4'-Me)pyridyl]phenylalanine | Bip(2'-Me-4'-OMe)—NH$_2$ |
| 64. | H | Aib | E | G | T | L-α-Me-Phe(2,6-di-Fluoro) | T | S | D | 4-[3'-(4'-Me)pyridyl]phenylalanine | Bip(2'-Me-3'-F)—NH$_2$ |
| 65. | H | Aib | E | G | T | L-α-Me-Phe(2,6-di-Fluoro) | T | S | D | 4-[3'-(4'-Me)pyridyl]phenylalanine | Bip(2'-F)—NH$_2$ |
| 66. | H | Aib | E | G | T | L-α-Me-Phe(2,6-di-Fluoro) | T | S | D | 4-[(4'-Me-6'-OMe)-3-pyridyl]phenylalanine | Bip(2'-Cl)—NH$_2$ |
| 67. | H | Aib | E | G | T | L-α-Me-Phe(2,6-di-Fluoro) | T | S | D | 4-[(4'-Me-6'-OMe)-3-pyridyl]phenylalanine | Bip(3',4'-di-OMe)—NH$_2$ |
| 68. | H | Aib | E | G | T | L-α-Me-Phe(2,6-di-Fluoro) | T | S | D | 4-[(4'-Me-6'-OMe)-3-pyridyl]phenylalanine | 4-(2'-pyridyl)phenylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 69. | H | Aib | E | G | T | L-α-Me-Phe(2,6-di-Fluoro) | T | S | D | 4-[(4'-Me-6'-OMe)-3-pyridyl]phenylalanine | Bip(2'-Me-4'-OMe)—NH$_2$ |
| 70. | H | Aib | E | G | T | L-α-Me-Phe(2,6-di-Fluoro) | T | S | D | 4-[(4'-Me-6'-OMe)-3-pyridyl]phenylalanine | 4-(2'-Methylphenyl)-3-pyridylalanine-NH$_2$ |
| 71. | H | Aib | E | G | T | L-α-Me-Phe(2,6-di-Fluoro) | T | S | D | Bip(2'-Et) | 4-(2'-ethylphenyl)-3-pyridylalanine-NH$_2$ |
| 72. | H | Aib | E | G | T | L-α-Me-Phe(2,6-di-Fluoro) | T | S | D | 4-[3'-(4'-Methyl)pyridyl]phenylalanine | 4-(2'-Methylphenyl)-3-pyridylalanine-NH$_2$ |
| 73. | H | Aib | E | G | T | L-α-Me-Phe(2,6-di-Fluoro) | T | S | D | Bip(2'-Et-4'-OMe) | 4-(4'-pyridyl)-phenylalanine-NH$_2$ |
| 74. | H | Aib | E | G | T | L-α-Me-Phe(2-Fluoro) | T | S | D | Bip(2'-Et-4'-OMe) | 4-(3'-quinoline)phenylalanine-NH$_2$ |
| 75. | H | Aib | E | G | T | L-α-Me-Phe(2-Fluoro) | T | S | D | Bip(2'-Et-4'-OMe) | 4-(3'-(2'-Methoxy)pyridyl]phenylalanine-NH$_2$ |
| 76. | H | Aib | E | G | T | L-α-Me-Phe(2-Fluoro) | T | S | D | Bip(2'-Et-4'-OMe) | 4-phenyl-3-pyridylalanine-NH$_2$ |
| 77. | H | Aib | E | G | T | L-α-Me-Phe(2-Fluoro) | T | S | D | Bip(2'-Et-4'-OMe) | 4-(3',5'-dimethylphenyl)-3-pyridylalanine-NH$_2$ |
| 78. | H | Aib | E | G | T | L-α-Me-Phe(2-Fluoro) | T | S | D | Bip(2'-Et-4'-OMe) | 4-[(3'-chloro-4'-fluoro)phenyl]-3-pyridylalanine-NH$_2$ |
| 79. | H | Aib | E | G | T | L-α-Me-Phe(2-Fluoro) | T | S | D | Bip(2'-Et-4'-OMe) | 4-[(3',4'-dimethoxy)phenyl]-3-pyridylalanine-NH$_2$ |
| 80. | H | Aib | E | G | T | L-α-Me-Phe(2-Fluoro) | T | S | D | Bip(2'-Et-4'-OMe) | 4-[(2'-ethyl-4'-methoxy)phenyl)]-3-pyridylalanine-NH$_2$ |
| 81. | L-β-Imidazole-lactyl | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 82. | H | Aib | E | G | T | L-α-Me-Phe(2-Fluoro) | T | S | D | Bip(2'-Et-4'-OMe) | 2-(5-o-Tolyl)thienylalanine-NH$_2$ |
| 83. | H | Aib | E | G | T | L-α-Me-Phe(2-Fluoro) | T | S | D | Bip(2'-Et-4'-OMe) | 2-[(5-(3'-Methoxy)phenyl]thienylalanine-NH$_2$ |
| 84. | H | Aib | E | G | T | L-α-Me-Phe(2-Fluoro) | T | S | D | Bip(2'-Et-4'-OMe) | 2-[(5-(3',5'-di-Methyl)phenyl]thienylalanine-NH$_2$ |
| 85. | H | Aib | E | G | T | L-α-Me-Phe(2-Fluoro) | T | S | D | Bip(2'-Et-4'-OMe) | 2-[(5-(3'-Cl,5'-F)phenyl]thienylalanine-NH$_2$ |
| 86. | H | Aib | E | G | T | L-α-Me-Phe(2-Fluoro) | T | S | D | Bip(2'-Et-4'-OMe) | 4-(3'-Isopropoxyphenyl)-3-pyridylalanine-NH$_2$ |

TABLE 3C-continued

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH$_2$ |
|---|---|---|---|---|---|---|---|---|---|---|---|
| 87. | H | Aib | E | G | T | L-α-Me-Phe(2-Fluoro) | T | S | D | Bip(2'-Et-4'-OMe) | 4-(2'-Methyl, 5'-Fluoro)phenyl)-3-pyridylalanine-NH$_2$ |
| 88. | H | Aib | E | G | T | L-α-Me-Phe(2-Fluoro) | T | S | D | Bip(2'-Et-4'-OMe) | 4-(2'-Isopropoxyphenyl)-3-pyridylalanine-NH$_2$ |
| 89. | H | Aib | E | G | T | L-α-Me-Phe(2-Fluoro) | T | S | D | Bip(2'-Et-4'-OMe) | 3-(4-Br)pyridylalanine-NH$_2$ |
| 90. | H | Aib | E | G | T | L-α-Me-Phe(2-Fluoro) | T | S | D | Bip(2'-Et-4'-OMe) | 4-(4'-Methoxyphenyl)-3-pyridylalanine-NH$_2$ |
| 91. | H | Aib | E | G | T | L-α-Me-Phe(2-Fluoro) | T | S | D | Bip(2'-Et-4'-OMe) | 4-(2'-Methyl, 4'-Fluoro)phenyl)-3-pyridylalanine-NH$_2$ |
| 92. | H | Aib | E | G | T | L-α-Me-Phe(2-Fluoro) | T | S | D | Bip(2'-Et) | 4-(2'-Methylphenyl)-3-pyridylalanine-NH$_2$ |
| 93. | H | Aib | E | G | T | L-α-Me-Phe(2-Fluoro) | T | S | D | Bip(2'-Et-4'-OMe) | 4-(2'-Trifluoromethoxyphenyl)-3-pyridylalanine-NH$_2$ |
| 94. | H | Aib | E | G | T | L-α-Me-Phe(2-Fluoro) | T | S | D | Bip(2'-Et-4'-OMe) | 4-(4'-Trifluoromethoxyphenyl)-3-pyridylalanine-NH$_2$ |
| 95. | H | Aib | E | G | T | L-α-Me-Phe(2-Fluoro) | T | S | D | Bip(2'-Et-4'-OMe) | 3-pyridylalanine-NH$_2$ |
| 96. | H | Aib | E | G | T | L-α-Me-Phe(2-Fluoro) | T | S | D | Bip(2'-Et-4'-OMe) | 4-(2'-Methyl, 4'-Chloro)phenyl)-3-pyridylalanine-NH$_2$ |
| 97. | H | Aib | E | G | T | L-α-Me-Phe(2-Fluoro) | T | S | D | Bip(2'-Me-4'-OMe) | 4-(2'-Methylphenyl)-3-pyridylalanine-NH$_2$ |
| 98. | H | Aib | E | G | T | L-α-Me-Phe(2-Fluoro) | T | S | D | Bip(2'-Et-4'-OMe) | 4-(3'-Trifluoromethylphenyl)-3-pyridylalanine-NH$_2$ |
| 99. | H | Aib | E | G | T | L-α-Me-Phe(2-Fluoro) | T | S | D | Bip(2'-Et-4'-OMe) | 4-(4'-Fluorophenyl)-3-pyridylalanine-NH$_2$ |
| 100. | H | Aib | E | G | T | L-α-Me-Phe(2-Fluoro) | T | S | D | Bip(2'-Et-4'-OMe) | 4-(2'-Trifluoromethylphenyl)-3-pyridylalanine-NH$_2$ |
| 101. | H | Aib | E | G | T | L-α-Me-Phe(2-Fluoro) | T | S | D | Bip(2'-Et-4'-OMe) | 4-(2'-Chlorophenyl)-3-pyridylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 102. | H | Aib | E | G | T | L-α-Me-Phe(2-Fluoro) | T | S | D | Bip(2'-Et-4'-OMe) | 4-(3'-Chlorophenyl)-3-pyridylalanine-NH$_2$ |
| 103. | H | Aib | E | G | T | L-α-Me-Phe(2-Fluoro) | T | S | D | Bip(2'-Et-4'-OMe) | 4-(4'-Isopropylphenyl)-3-pyridylalanine-NH$_2$ |
| 104. | H | Aib | E | G | T | L-α-Me-Phe(2-Fluoro) | T | S | D | Bip(2'-Et-4'-OMe) | 4-(3',5'-dimethylisoxazol-4'-yl)-3-pyridylalanine-NH$_2$ |
| 105. | H | Aib | E | G | T | L-α-Me-Phe(2-Fluoro) | T | S | D | Bip(2'-Et-4'-OMe) | 4-[(2'-Methyl-4'-methoxy)phenyl]-3-pyridylalanine-NH$_2$ |
| 106. | H | Aib | E | G | T | L-α-Me-Phe(2-Fluoro) | T | S | D | Bip(2'-Et-4'-OMe) | 4-(4'-Trifluoromethylphenyl)-3-pyridylalanine-NH$_2$ |
| 107. | H | Aib | E | G | T | L-α-Me-Phe(2-Fluoro) | T | S | D | Bip(2'-Et-4'-OMe) | 4-(4'-Chlorophenyl)-3-pyridylalanine-NH$_2$ |
| 108. | H | Aib | E | G | T | L-α-Me-Phe(2-Fluoro) | T | S | D | Bip(2'-Et-4'-OMe) | 4-(4'-Pyridyl)-3-pyridylalanine-NH$_2$ |
| 109. | H | Aib | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 110. | H | Aib | E | G | T | L-α-Me-Phe(2-Fluoro) | T | S | D | Bip(2'-Et-4'-OMe) | 4-(6'-Methoxypyridin-3'-yl)-3-pyridylalanine-NH$_2$ |
| 111. | H | Aib | E | G | T | L-α-Me-Phe(2-Fluoro) | T | S | D | Bip(2'-Et-4'-OMe) | 4-(2'-Isopropylphenyl)-3-pyridylalanine-NH$_2$ |
| 112. | H | Aib | E | G | T | L-α-Me-Phe(2-Fluoro) | T | S | D | Bip(2'-Et-4'-OMe) | 4-(2'-Methoxyphenyl)-3-pyridylalanine-NH$_2$ |
| 113. | H | Aib | E | G | T | L-α-Me-Phe(2-Fluoro) | T | S | D | Bip(2'-Et-4'-OMe) | 4-[(3',5'-di-Fluoro-2'-methoxy)phenyl]-3-pyridylalanine-NH$_2$ |
| 114. | H | Aib | E | G | T | L-α-Me-Phe(2-Fluoro) | T | S | D | Bip(2'-Et-4'-OMe) | 4-(3'-methylphenyl)-3-pyridylalanine-NH$_2$ |
| 115. | H | Aib | E | G | T | L-α-Me-Phe(2-Fluoro) | T | S | D | Bip(2'-Et-4'-OMe) | 4-(2'-fluorophenyl)-3-pyridylalanine-NH$_2$ |
| 116. | H | Aib | E | G | T | L-α-Me-Phe(2,6-di-Fluoro) | T | S | D | Bip(2'-Et-4'-OMe) | 4-(2'-fluorophenyl)-3-pyridylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 117. | H | Aib | E | G | T | L-α-Me-Phe(2,6-di-Fluoro) | T | S | D | Bip(2'-Et-4'-OMe) | 4-(3'-Methoxyphenyl)-3-pyridylalanine-NH$_2$ |
| 118. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 119. | H | N-Me-(D)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 120. | H | (S)-α-Me-Pro | E | G | T | L-α-Me-Phe(2-Fluoro) | T | H | D | Bip(2'-Et-4'-OMe) | 4-(2'-Methylphenyl)-3-pyridylalanine-NH$_2$ |
| 121. | H | (S)-α-Me-Pro | E | G | T | L-α-Me-Phe(2-Fluoro) | T | S | D | Bip(2'-Et-4'-OMe) | (S)-4-(2'-Methylphenyl)-α-Me-3-pyridylalanine-NH$_2$ |
| 122. | H | Aib | E | G | T | L-α-Me-Phe(2-Fluoro) | T | S | D | Bip(2'-Et-4'-OMe) | (S)-4-(2'-Methylphenyl)-α-Me-3-pyridylalanine-NH$_2$ |
| 123. | H | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 124. | H | (S)-α-Me-Pro | E | G | T | L-α-Me-Phe(2,6-di-Fluoro) | T | H | D | Bip(2'-Et-4'-OMe) | 4-(2'-Methylphenyl)-3-pyridylalanine-NH$_2$ |
| 125. | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 126. | H | (S)-α-Me-Pro | E | G | T | L-α-Me-Phe(2,6-di-Fluoro) | T | S | D | Bip(2'-Et-4'-OMe) | 4-(3'-Methoxyphenyl)-3-pyridylalanine-NH$_2$ |
| 127. | H | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH$_2$ |
| 128. | H | (S)-α-Me-Pro | E | G | T | L-α-Me-Phe(2,6-di-Fluoro) | T | S | D | Bip(2'-Et-4'-OMe) | 4-(2'-Fluorophenyl)-3-pyridylalanine-NH$_2$ |
| 129. | H | N-Me-(L)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 130. | H | Aib | E | G | T | L-α-Me-Phe(2-Fluoro) | T | S | D | Bip(2'-Et-4'-OMe) | 4-(2'-Methylphenyl)-3,5-pyrimidylalanine-NH$_2$ |
| 131. | H | (S)-α-Me-Pro | D | G | T | L-α-Me-Phe(2-Fluoro) | T | S | D | Bip(2'-Et-4'-OMe) | 4-(2'-Methylphenyl)-3-pyridylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 132. | H | (S)-α-Me-Pro | E | G | T | L-α-Me-Phe(2-Fluoro) | T | S | D | Bip(2'-Et) | 4-(2'-Ethylphenyl)-3-pyridylalanine-NH$_2$ |
| 133. | Des-NH$_2$-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 134. | Des-NH$_2$-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 135. | Des-NH$_2$-His | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH$_2$ |
| 136. | Des-NH$_2$-His | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 137. | (R)-Imp | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 138. | (S)-Imp | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 139. | CH3O—CO-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 140. | CH3O—CO-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 141. | CH3O—CO-His | N-Me-(D)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 142. | CH3O—CO-His | N-Me-(D)-Ala | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 143. | CH3SO2-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 144. | CH3SO2-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 145. | L-Lactyl-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 146. | L-Lactyl-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |

TABLE 3C-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH$_2$ |
|---|---|---|---|---|---|---|---|---|---|---|---|
| 147. | H | Aib | E | G | T | L-α-Me-Phe(2-Fluoro) | T | S | D | Bip(2'-Et-4'-OMe) | 4-(3',5'-di-Me)phenyl-3-pyridylalanine-NH$_2$ |
| 148. | H | Aib | E | G | T | L-α-Me-Phe(2-Fluoro) | T | H | D | Bip(2'-Et-4'-OMe) | 4-(2'-Methylphenyl)-3-pyridylalanine-NH$_2$ |
| 149. | H | D-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 150. | H | Aib | H | G | T | L-α-Me-Phe(2-Fluoro) | T | S | D | Bip(2'-Et-4'-OMe) | 4-(2'-Methylphenyl)-3-pyridylalanine-NH$_2$ |
| 151. | L-β-Imidazole-lactyl | (S)-α-Me-Pro | E | G | T | L-α-Me-Phe (2-Fluoro) | T | H | D | Bip(2'-Et-4'-O-Me) | 4-(2'-Methylphenyl)-3-pyridylalanine-NH$_2$ |
| 152. | L-β-Imidazole-lactyl | (S)-α-Me-Pro | E | G | T | L-α-Me-Phe (2-Fluoro) | T | S | D | Bip(2'-Et-4'-O-Me) | 4-(2'-Methylphenyl)-3-pyridylalanine-NH$_2$ |
| 153. | L-β-Imidazole-lactyl | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 154. | L-β-Imidazole-lactyl | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 155. | L-β-Imidazole-lactyl | N-Me-D-Ala | E | G | T | L-α-Me-Phe (2-Fluoro) | T | H | D | Bip(2'-Et-4'-O-Me) | 4-(2'-Methylphenyl)-3-pyridylalanine-NH$_2$ |
| 156. | L-β-Imidazole-lactyl | N-Me-D-Ala | E | G | T | L-α-Me-Phe (2-Fluoro) | T | S | D | Bip(2'-Et-4'-O-Me) | 4-(2'-Methylphenyl)-3-pyridylalanine-NH$_2$ |
| 157. | CH$_3$O—CO-His | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH$_2$ |
| 158. | CH$_3$O—CO-His | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH$_2$ |
| 159. | CH$_3$O—CO-His | N-Me-D-Ala | E | G | T | L-α-Me-Phe (2-Fluoro) | T | H | D | Bip(2'-Et-4'-OH) | 4-(2'-Methylphenyl)-3-pyridylalanine-NH$_2$ |
| 160. | CH$_3$O—CO-His | N-Me-D-Ala | E | G | T | L-α-Me-Phe (2-Fluoro) | T | S | D | Bip(2'-Et-4'-OH) | 4-(2'-Methylphenyl)-3-pyridylalanine-NH$_2$ |
| 161. | CH$_3$O—CO-His | Aib | E | G | T | L-α-Me-Phe (2-Fluoro) | T | H | D | Bip(2'-Et-4'-OH) | 4-(2'-Methylphenyl)-3-pyridylalanine-NH$_2$ |
| 162. | CH$_3$O—CO-His | Aib | E | G | T | L-α-Me-Phe (2-Fluoro) | T | S | D | Bip(2'-Et-4'-OH) | 4-(2'-Methylphenyl)-3-pyridylalanine-NH$_2$ |
| 163. | L-β-Imidazole-lactyl | N-Me-D-Ala | E | G | T | L-α-Me-Phe (2-Fluoro) | T | H | D | Bip(2'-Et-4'-OH) | 4-(2'-Methylphenyl)-3-pyridylalanine-NH$_2$ |
| 164. | CH$_3$O—CO-His | (S)-α-Me-Pro | E | G | T | L-α-Me-Phe (2-Fluoro) | T | S | D | Bip(2'-Et-4'-OH-5'-I) | 4-(2'-Methylphenyl)-3-pyridylalanine-NH$_2$ |

TABLE 3C-continued

| SEQ ID No. | X_{aa1} | X_{aa2} | X_{aa3} | X_{aa4} | X_{aa5} | X_{aa6} | X_{aa7} | X_{aa8} | X_{aa9} | X_{aa10} | X_{aa11}-NH_2 |
|---|---|---|---|---|---|---|---|---|---|---|---|
| 165. | Des-NH_2-His | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH_2 |
| 166. | Des-NH_2-His | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH_2 |
| 167. | (R)-Imp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH_2 |
| 168. | (S)-Imp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH_2 |
| 169. | (R)-Imp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH_2 |
| 170. | (S)-Imp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH_2 |
| 171. | (R)-IMeOp | (S)-α-Me-Pro | E | G | T | L-α-Me-Phe (2-Fluoro) | T | H | D | Bip(2'-Et-4'-OMe) | 4-(2'-Methylphenyl)-3-pyridylalanine-NH_2 |
| 172. | (S)-IMeOp | (S)-α-Me-Pro | E | G | T | L-α-Me-Phe (2-Fluoro) | T | H | D | Bip(2'-Et-4'-OMe) | 4-(2'-Methylphenyl)-3-pyridylalanine-NH_2 |
| 173. | (R)-IMeOp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH_2 |
| 174. | (S)-IMeOp | (S)-α-Me-Pro | E | G | T | L-α-Me-Phe (2-Fluoro) | T | S | D | Bip(2'-Et-4'-OH) | 4-(2'-Methylphenyl)-3-pyridylalanine-NH_2 |
| 175. | (R)-IMeOp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH_2 |
| 176. | (S)-IMeOp | (S)-α-Me-Pro | E | G | T | L-α-Me-Phe (2-Fluoro) | T | H | D | Bip(2'-Et-4'-OH) | 4-(2'-Methylphenyl)-3-pyridylalanine-NH_2 |
| 177. | | | | | | | T | S | D | Bip(2'-Et-4-OH) | 4-(2'-Methylphenyl)-3-pyridylalanine-NH_2 |
| 178. | | (S)-α-Me-Pro | | | | | T | S | D | Bip(2'-Et-4-OH) | 4-(2'-Methylphenyl)-3-pyridylalanine-NH_2 |
| 179. | | | | | | | T | H | D | Bip(2'-Et-4-OH) | 4-(2'-Methylphenyl)-3-pyridylalanine-NH_2 |

Amino Acid Abbreviations and Structures
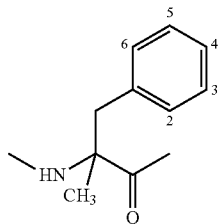
Numbering of the a-methyl-
phenylalanine
(a-Me-Phe) ring carbons
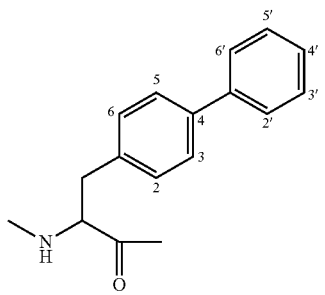
Numbering of the
biphenylalanine
ring carbons
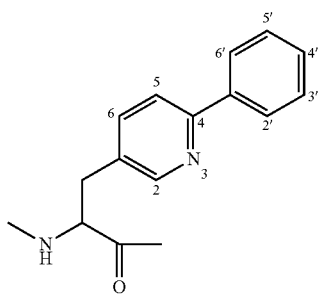
Numbering of the hetero-
biphenylalanine
ring carbons
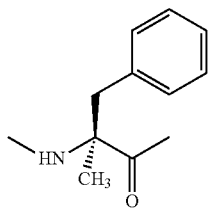
(L)-a-Me-Phe
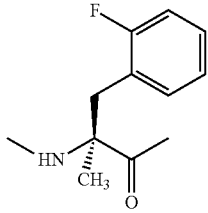
(L)-a-Me-Phe(2-Fluoro)
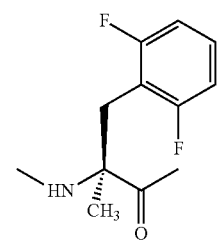
(L)-a-Me-Phe(2,6-di-Fluoro)
-continued
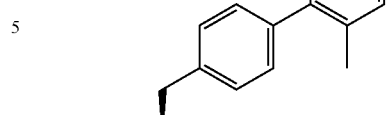
Bip(2'-Me)
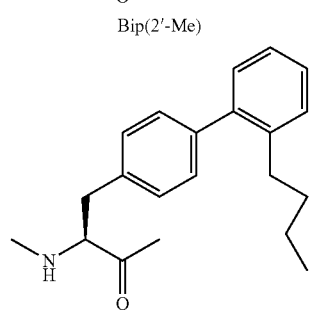
Bip(2'-OBu)
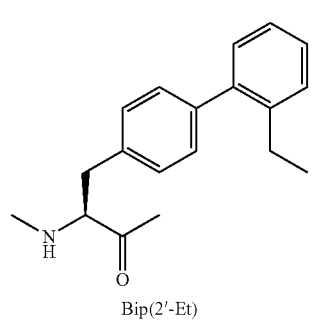
Bip(2'-Et)
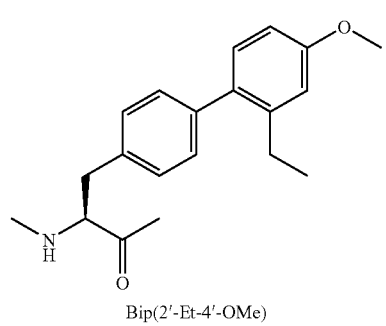
Bip(2'-Et-4'-OMe)
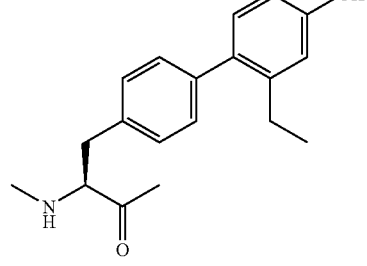
Bip(2'-Et-4'-OH)

-continued
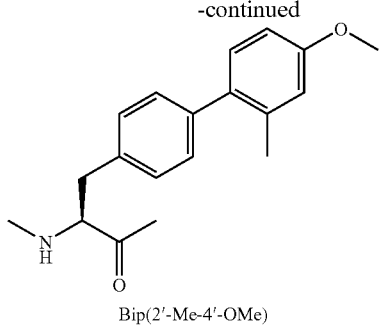
Bip(2'-Me-4'-OMe)
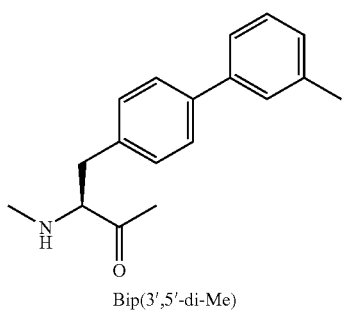
Bip(3',5'-di-Me)
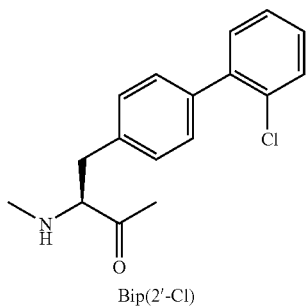
Bip(2'-Cl)
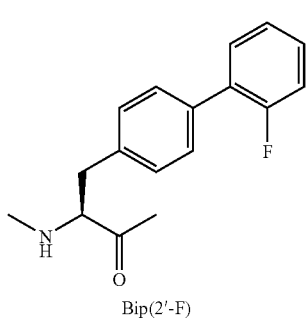
Bip(2'-F)
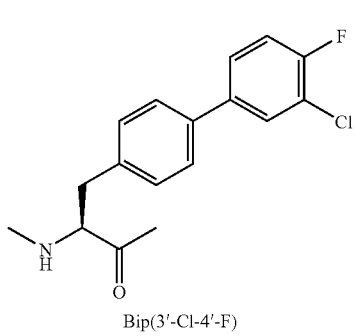
Bip(3'-Cl-4'-F)
-continued
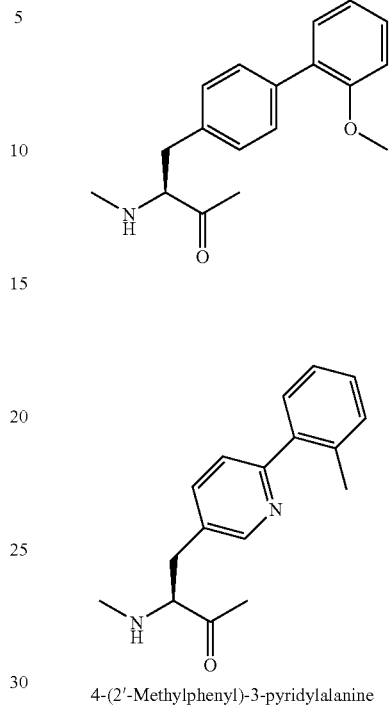
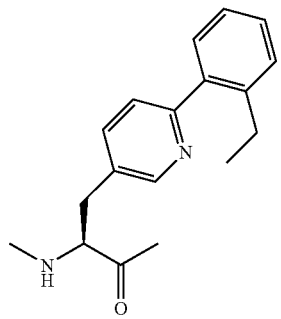
4-(2'-Methylphenyl)-3-pyridylalanine
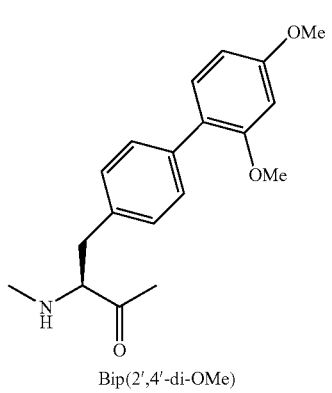
4-(2'-Ethylphenyl)-3-pyridylalanine
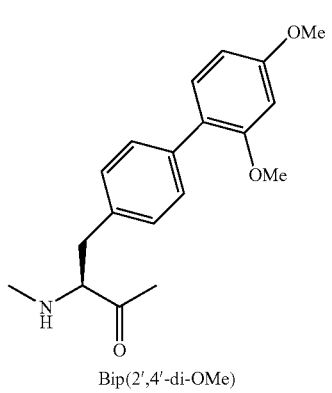
Bip(2',4'-di-OMe)

-continued
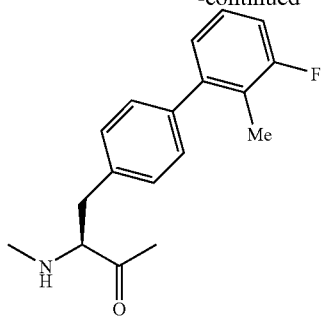
Bip(2'-Me-3'-F)
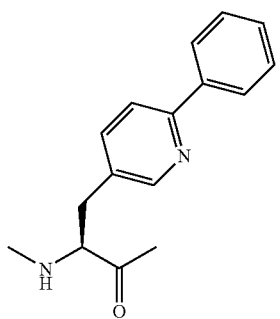
4-phenyl-3-pyridylalanine
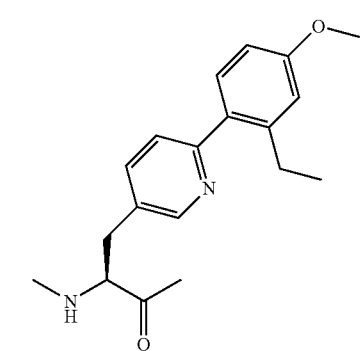
4-[(2'-Ethyl-4'-Methoxy)phenyl]-3-pyridylalanine
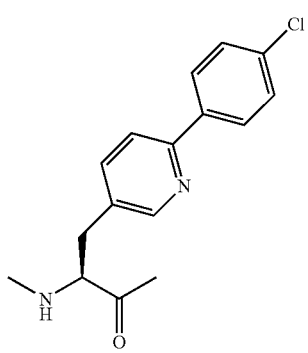
4-(4'-Chlorophenyl)-3-pyridylalanine
-continued
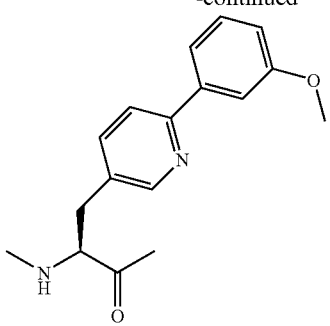
4-(3'-Methoxyphenyl)-3-pyridylalanine
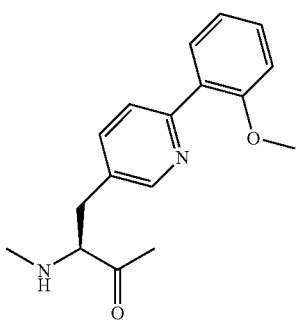
4-(2'-Methoxyphenyl)-3-pyridylalanine
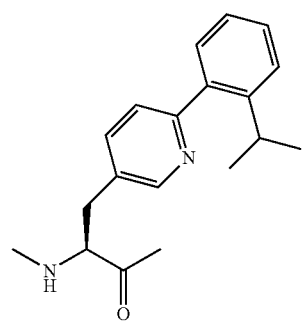
4-(2'-Isopropylphenyl)-3-pyridylalanine
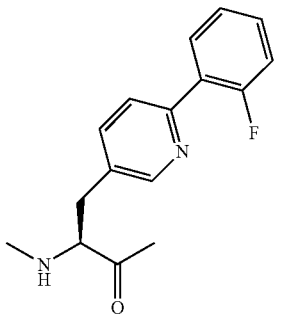
4-(2'-fluorophenyl)-3-pyridylalanine -continued
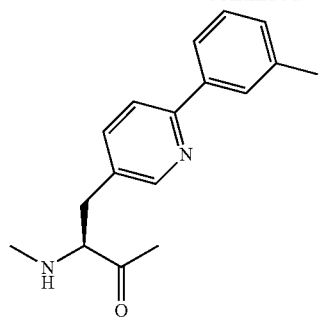
4-(3'-methylphenyl)-3-pyridylalanine
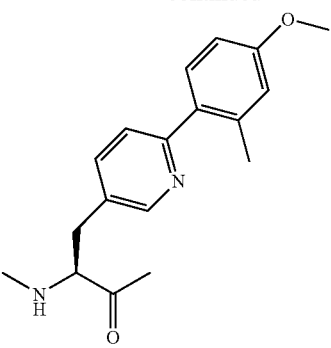
4-[(2'-Methyl, 4'-methoxy)phenyl)-3-pyridylalanine
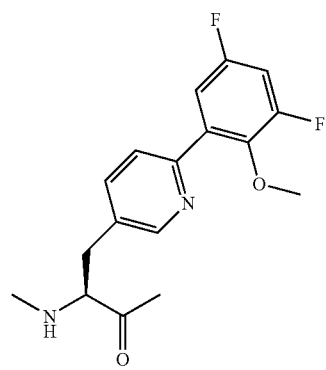
4-[(3',5'-di-Fluoro-2'-methoxy)phenyl]-3-pyridylalanine
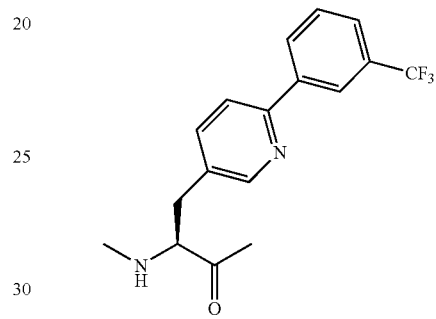
4-(3'-Trifluoromethylphenyl)-3-pyridylalanine
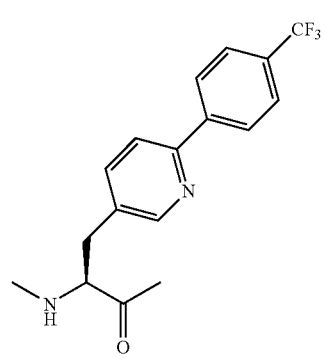
4-(4'-Trifluoromethylphenyl)-3-pyridylalanine
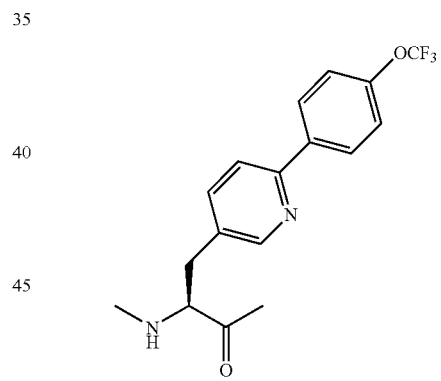
4-(4'-Trifluoromethoxyphenyl)-3-pyridylalanine
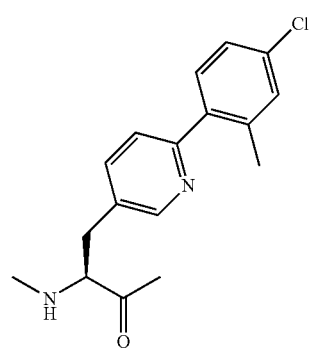
4-(2'-Methyl, 4'-Chloro)phenyl)-3-pyridylalanine
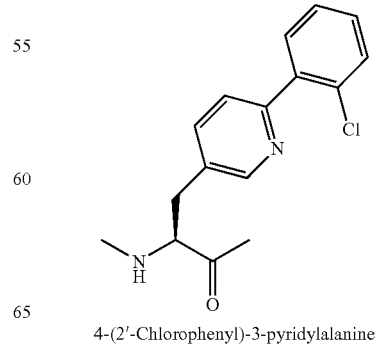
4-(2'-Chlorophenyl)-3-pyridylalanine

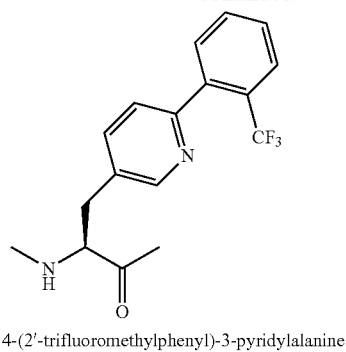
4-(2'-trifluoromethylphenyl)-3-pyridylalanine
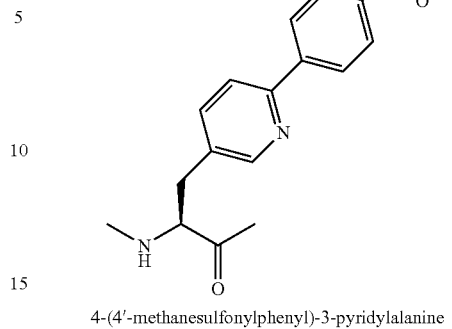
4-(4'-methanesulfonylphenyl)-3-pyridylalanine
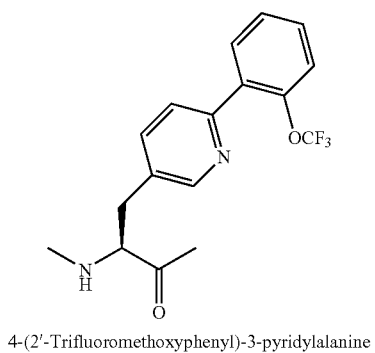
4-(2'-Trifluoromethoxyphenyl)-3-pyridylalanine
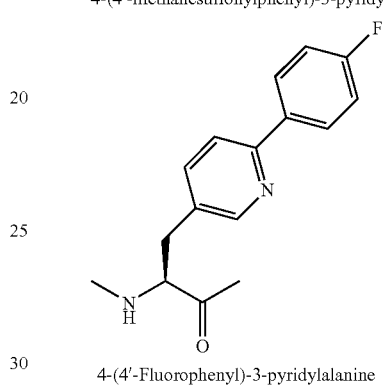
4-(4'-Fluorophenyl)-3-pyridylalanine
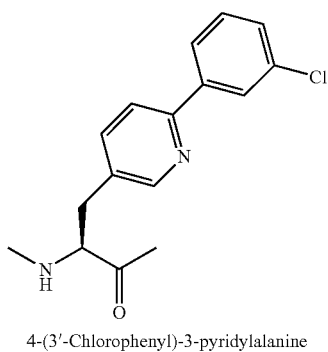
4-(3'-Chlorophenyl)-3-pyridylalanine
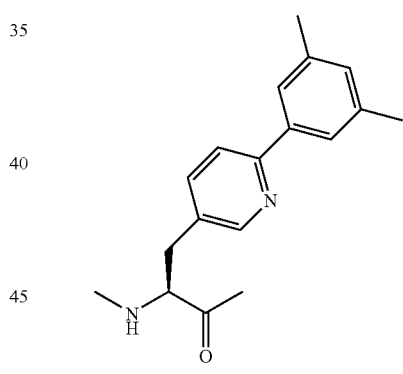
4-(3',5'-dimethylphenyl)-3-pyridylalanine
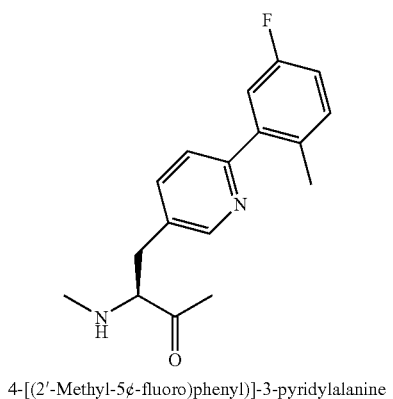
4-[(2'-Methyl-5¢-fluoro)phenyl)]-3-pyridylalanine
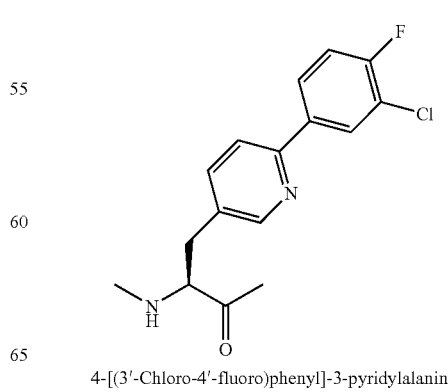
4-[(3'-Chloro-4'-fluoro)phenyl]-3-pyridylalanine -continued
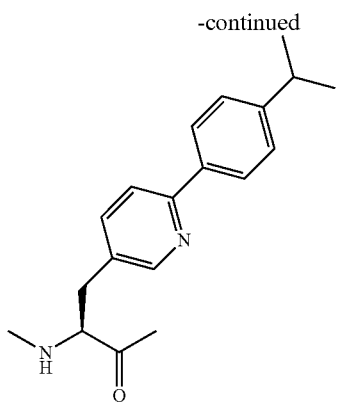
4-(4'-Isopropylphenyl)-3-pyridylalanine
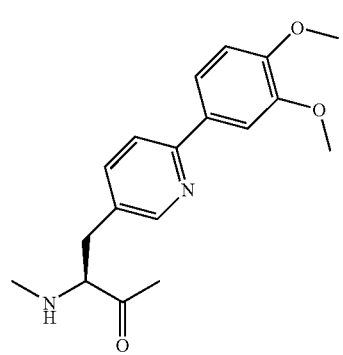
4-(3',4'-dimethoxy)phenyl]-3-pyridylalanine
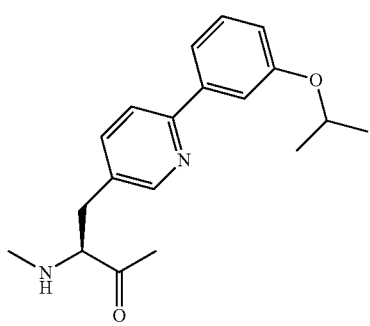
4-(3'-Isopropoxyphenyl)-3-pyridylalanine
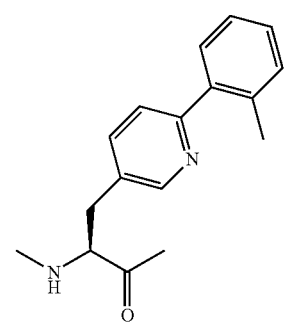
4-(2'-Methylphenyl)-3-pyridylalanine
-continued
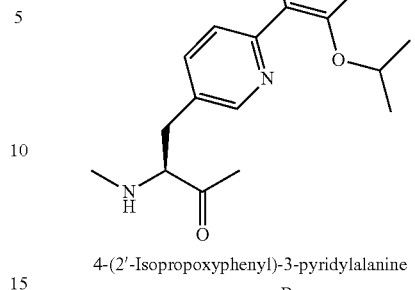
4-(2'-Isopropoxyphenyl)-3-pyridylalanine
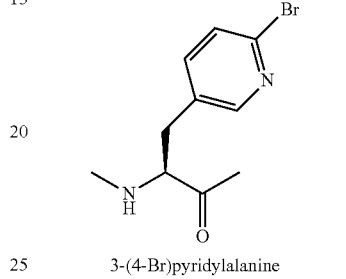
3-(4-Br)pyridylalanine
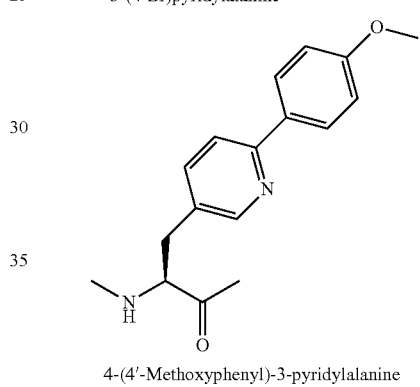
4-(4'-Methoxyphenyl)-3-pyridylalanine
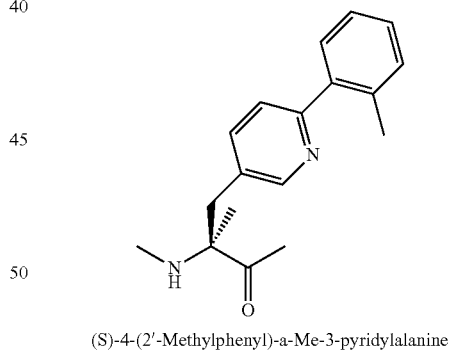
(S)-4-(2'-Methylphenyl)-a-Me-3-pyridylalanine
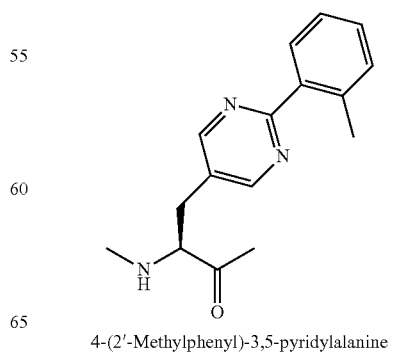
4-(2'-Methylphenyl)-3,5-pyridylalanine -continued

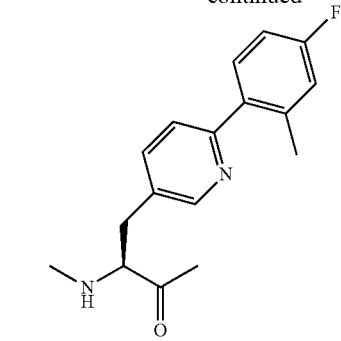
4-(2'-Methyl-4'–Fluoro)phenyl)-3-pyridylalanine

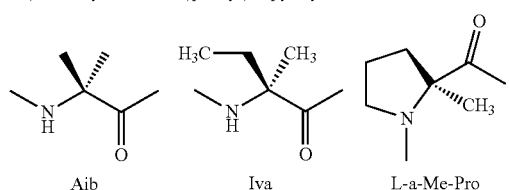
Aib        Iva        L-a-Me-Pro

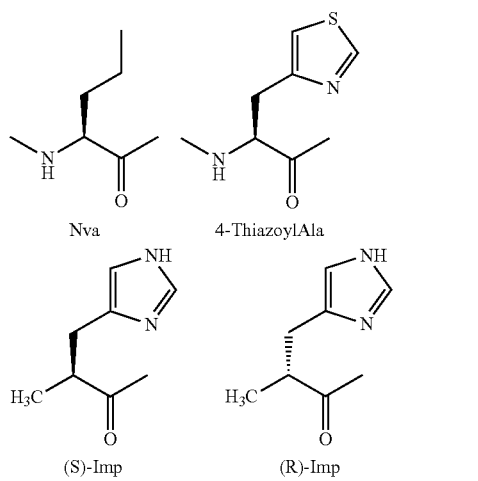
Nva        4-ThiazoylAla (S)-Imp        (R)-Imp

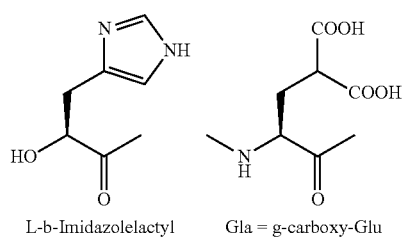
L-b-Imidazolelactyl        Gla = g-carboxy-Glu

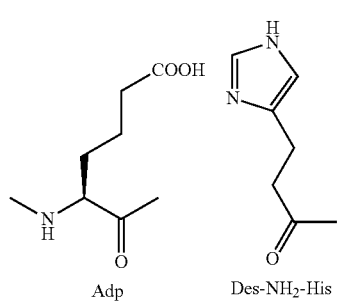
Adp        Des-NH$_2$-His

-continued

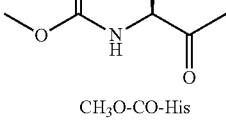
CH$_3$O-CO-His

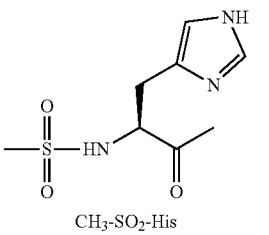
CH$_3$-SO$_2$-His        hSer

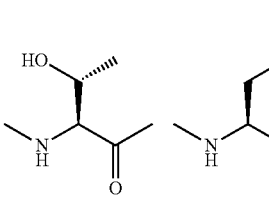
Allo-Thr        Aoc

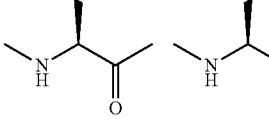
(S)-IOMep        (R)-IOMep

A = L-Ala; ala = D-Ala
Aib = a-aminoisobutyric acid
Bip = L-4,4'-biphenylalanine;
D = L-Asp
E = L-Glu
G = Gly
H = L-His
Nle = L-norleucine
Nva = L-norvaline
F = L-Phe
S = L-Ser;
T = L-Thr.

Those skilled in the art of amino acid and peptide chemistry are aware that a phenylalanine amino acid bearing a phenyl substituent at the 4 or para position may otherwise be defined as a 4-(phenyl)phenylalanine or 4,4'-biphenylalanine and thus may be abbreviated as "Bip". For the purpose of the abbreviations shown in the "Amino Acid Abbreviations and Structures" section and in the Tables herein, a biphenylalanine amino acid may be abbreviated, for example, as "Bip(2'-Me)", which is intended to represent a phenylalanine substituted at its 4 position with a 2'-methylphenyl group in which the 2'-methyl group is ortho relative to the attachment point of the phenyl ring.

EXAMPLE 35

Cyclic AMP Determination

The GLP-1 receptor is a G-protein coupled receptor. GLP-1 (7-36)-amide, the biologically active form, binds to the GLP-1 receptor and through signal transduction causes activation of adenylyl cyclase and increases intracellular cAMP concentrations. To monitor agonism of peptides in stimulating the GLP-1 receptor, adenylyl cyclase activity was monitored by assaying for intracellular cAMP content. Full-length human glucagon-like peptide 1 receptor was stably expressed in CHO-K1 cells and clonal lines were established. The clones were screened for the greatest increase in cAMP content in response to a saturating dose of GLP-1 and clone CHO-GLP1R-19 was selected.

Cells were cultured in Ham's F12 nutritional media (Gibco # 11765-054), 10% FBS, 1×L-Glutamine, 1× Pen/Strep, and 0.4 mg/ml G418. CHO-GLP-1R-19 cells (20,000 in 100 µl of media) were plated into each well of a 96-well tissue culture microtiter plate and incubated overnight in a 5% CO2 atmosphere at 37° C. On the day of the assay, cells were washed once with 100 µl of phosphate-buffered saline (PBS). A Biomek 2000 was used to serially dilute all peptides prior to beginning the assay. Serial dilutions were carried out in 100% DMSO. Peptide plates were created prior to the initiation of the assay using a Platemate Plus; 1.5 uL of Compound was transferred to a V bottom plate and 150 uL of assay buffer supplemented with 100 µM 3-isobutyl-1-methylxanthine (a nonselective phosphodiesterase inhibitor) was added to the plate to give a 1:100 dilution and a 1% final concentration of DMSO.

In order to create a cAMP standard curve, a serial dilution of cAMP in the range 0.2-25.6 µmol/well was made up in lysis reagent 1 (Amersham cAMP SPA kit). 50 µl of each cAMP standard was added by hand and 70 µl of mix reagent (Amersham cAMP SPA kit) was added using the multidrop. The plates were then sealed and counted on a Trilux counter after 15 hours. This standard curve was used to convert CPM to pmol of cAMP.

cAMP Assay Protocol on the Platemate Plus

Cell plates and peptide plates were loaded onto the Platemate. The media was aspirated from the wells and discarded. 100 uL per well of the peptide/buffer mixture were then added from the peptide plates to initiate the assay. After 30 min. of incubation the peptide/buffer was removed and 50 uL of the lysis reagent 1 solution was added per well. The plate was kept for one hour at RT or overnight if refrigerated and sealed. 70 uL of the cAMP detection reagent (premixed $^{125}$I-cAMP analog, anti-cAMP antibody and anti-rabbit antibody conjugated to SPA beads—all from the Amersham cAMP SPA kit) was added using the multidrop and the plates were sealed. After 15 hours the plates were counted on the Trilux counter.

Dose dependence for Compounds was determined at half-log concentrations in duplicate. In each 96-well plate, GLP-1 (control), and five Compounds (in duplicate) were run at seven half-log doses. Ten nM GLP-1 was plated into ten additional wells to serve as a reference standard for determination of maximal activity. A standard curve was determined using known amounts of cyclic AMP. The amounts of cAMP synthesized by the treated cells were determined from the cyclic AMP standard curve, and the percent of the maximal GLP-1 stimulated activity was calculated and plotted against log compound concentration. The data were analyzed by nonlinear regression curve fitting (4 parameter sigmoidal dose-response curve) to determine the EC50 of the compounds. By way of example, the peptides described herein have EC50 values in the range of 0.0005 nM to 10 nM, more preferably in the range of 0.0005 nM to 0.200 nM.

Alternatively, CHO cells expressing the GLP-1 receptor were plated at 10,000 cells per well in a 384 well plate and cultured overnight at 37° C. in 5% $CO_2$ as described above. Following treatment with peptidyl GLP-1 receptor agonists, the intracellular level of cAMP was measured with the Hithunter™ XS cAMP kit (DiscoveRx®) following the manufacturer's protocol.

EXAMPLE 36

In Vivo Studies

Peptides were dissolved in an appropriate vehicle at a concentration in nmol/ml equivalent to the dose that was to be administered in nmol/kg so that each mouse would receive the same volume/weight of dosing solution. Male C57BL/6-ob/ob mice (10 weeks old) were randomized into groups of 6 mice per group based on fed plasma glucose and body weight. After an overnight fast, mice were weighed and placed in the experimental lab. After 30 min in the environment, the mice were bled via tail tip at −30 min and immediately injected subcutaneously (sc) with vehicle or the peptide dissolved in vehicle (0.1 ml solution/100 g body weight). At time 0 the mice were bled and then injected intraperitoneally with 50% glucose (2 g/kg) to initiate the intraperitoneal glucose tolerance test (ipGTT). The mice were bled 30, 60, 120 and 180 min after the glucose injection. Blood samples were drawn into potassium EDTA, placed on ice during the study and subsequently centrifuged for 10 min at 3000 rpm at 4° C. Plasma samples were diluted 11-fold for glucose analysis in the Cobas System. Another 5 µl plasma sample was diluted 5-fold with 20 µl of Sample Diluent (Insulin ELISA assay kit, Crystal Chem. Inc.) and stored at −20° C. for subsequent analysis using the Ultra Sensitive Mouse Insulin ELISA kit (Crystal Chem Inc.).

Figure 2:
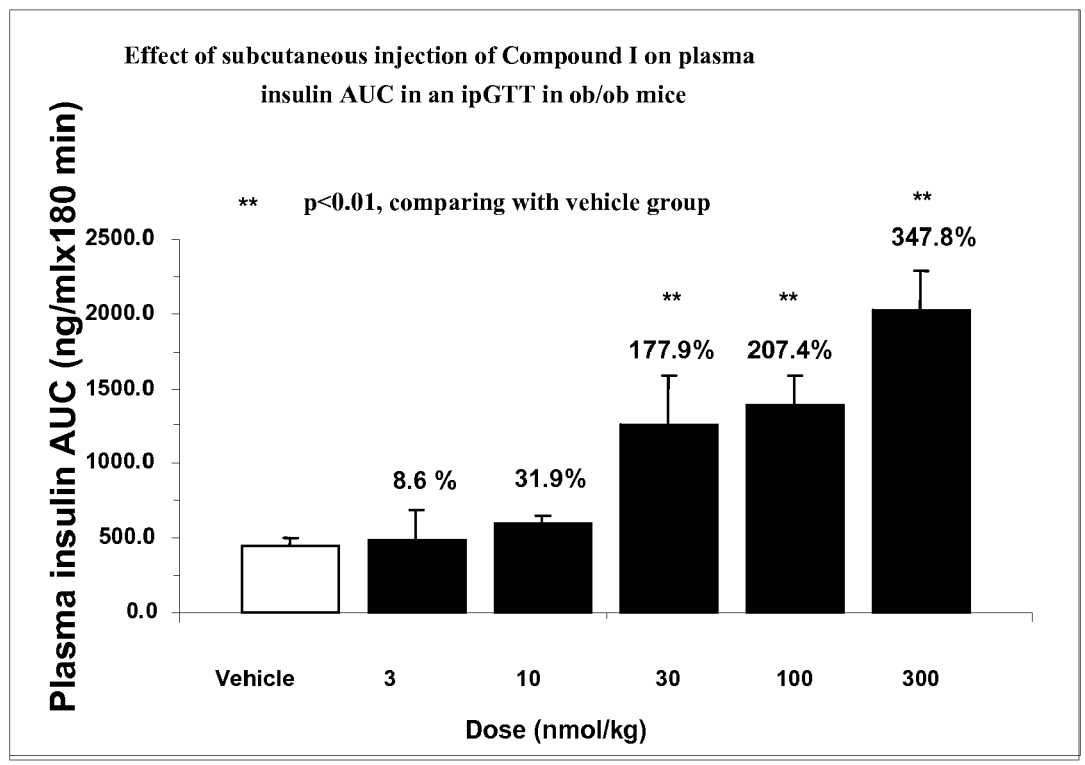
FIG. 2 illustrates the effects of subcutaneous injection of Compound I on plasma insulin in an ipGTT in ob/ob mice.

The in vivo glucose lowering properties for Compound I, and for the compounds of SEQ ID NOs: 9, 118, 151 and 158 in ob/ob mice (a mouse model of insulin resistance) are described below. Subcutaneous administration of Compound I attenuated the postprandial glucose excursion curve in an intraperitoneal glucose tolerance test (ipGTT), with the plasma glucose area under the curve (AUC) decreasing in a dose-dependent manner between 0 and 180 min. (FIG. 1). The ED50 of Compound I was determined to be 50 nmoles/kg. There was a concomitant and statistically significant dose-dependent increase in postprandial plasma insulin levels in these animals (FIG. 2). The correlation between changes in plasma glucose and insulin in animals treated with Compound I (FIG. 1 and FIG. 2) suggests that the glucose lowering effect is mediated by stimulation of insulin release by said compound.

Figure 3:
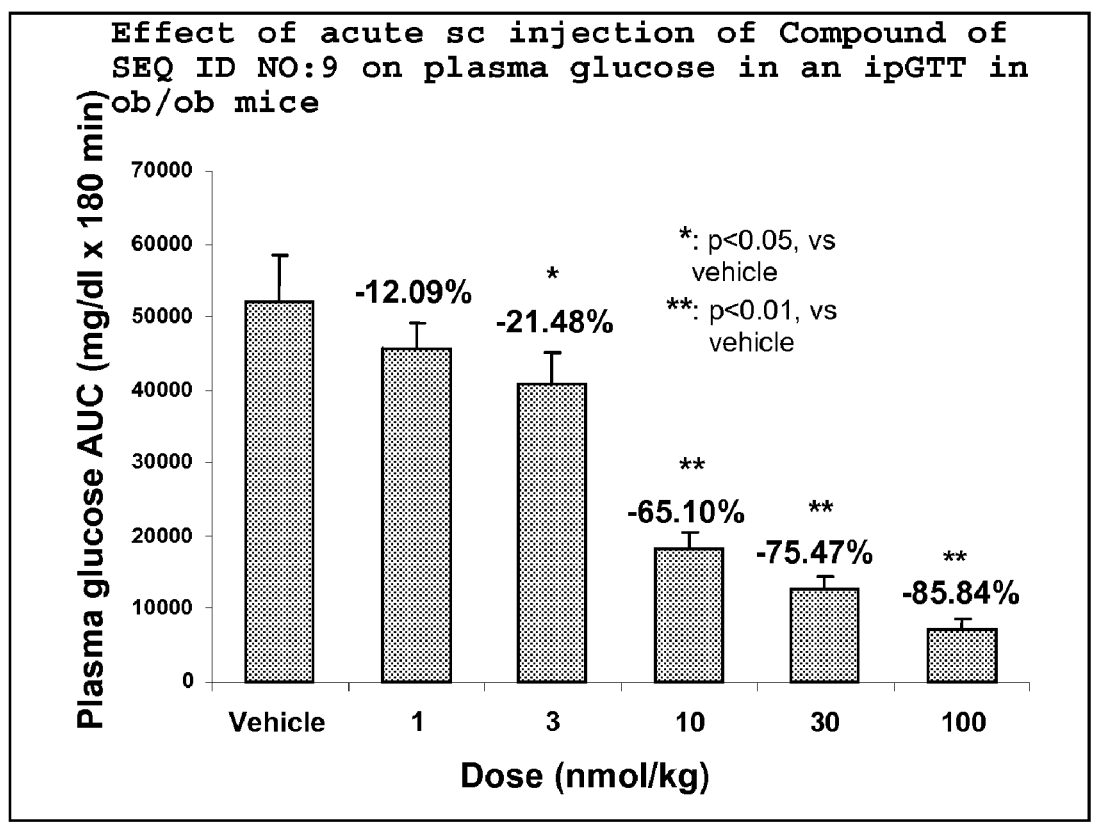
FIG. 3 illustrates the effects of subcutaneous injection of a compound of SEQ ID NO: 9 on plasma glucose in an ipGTT in ob/ob mice.
Figure 4:
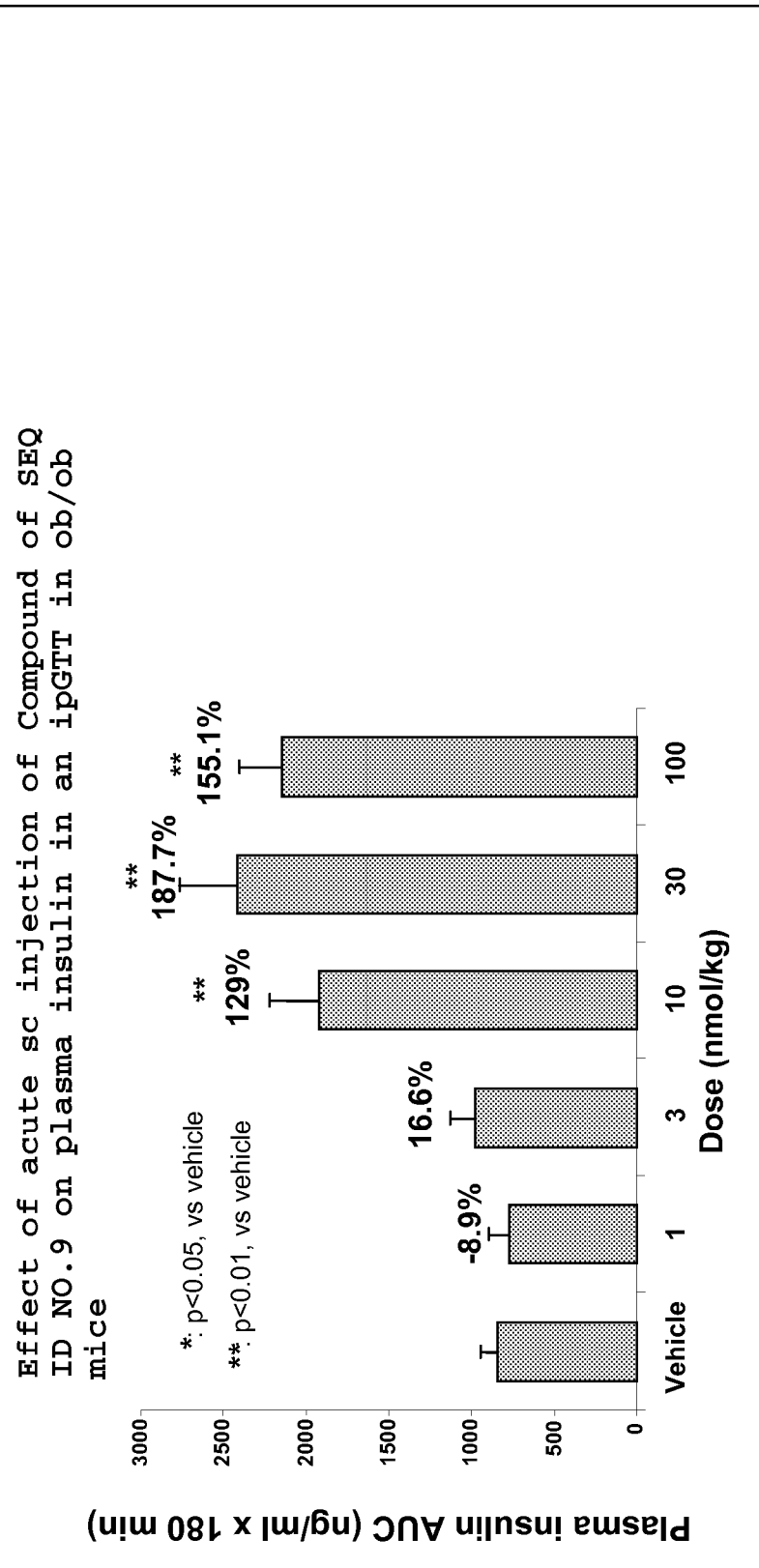
FIG. 4 illustrates the effects of subcutaneous injection of a compound of SEQ ID NO: 9 on plasma insulin in an ipGTT in ob/ob mice.

More significantly and unexpectedly, the compounds of SEQ ID NOs: 9, 118, 151 and 158 produced a time-dependent (between 0 and 180 or 210 min.) statistically significant decrease in postprandial plasma glucose following subcutaneous administration in ob/ob mice (FIGS. 3, 5, 6 and 7). The effect of the compound of SEQ ID NO: 9 on postprandial glucose was dose-dependent between 1-100 nmol/kg and plasma glucose AUC decreased 85.8% at 100 nmol/kg dose (FIG. 3). The ED50 for the compound of SEQ ID NO: 9 was determined to be 5 nmoles/kg. The effect of the compound of SEQ ID NO: 9 on plasma glucose is also accompanied by a significant increase in postprandial insulin in these animals (FIG. 4). The effect on insulin appears to be dose-dependent with a maximum increase of 187.7% in AUC at 30 nmol/kg dose (FIG. 4).

Figure 5:
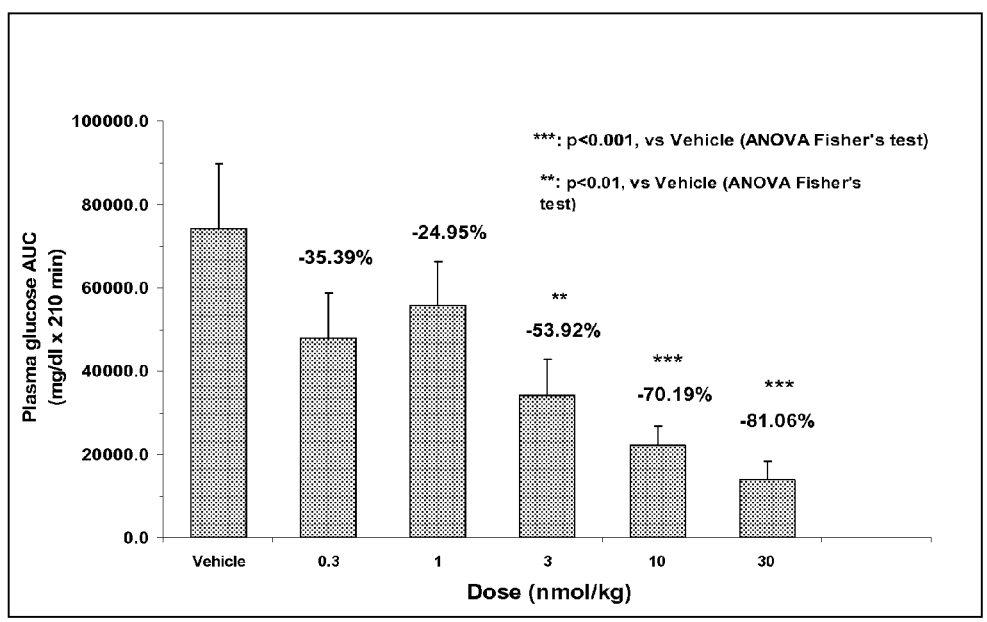
FIG. 5 illustrates the effects of subcutaneous injection of a compound of SEQ ID NO: 118 on plasma glucose in an ipGTT in ob/ob mice.

The effect of the compound of SEQ ID NO: 118 on postprandial glucose was dose-dependent between 1-30 nmol/kg and plasma glucose AUC decreased 81% at 30 nmol/kg dose (FIG. 5). The ED50 for the compound of SEQ ID NO: 118 was determined to be 2.5 nmoles/kg.

Figure 6:
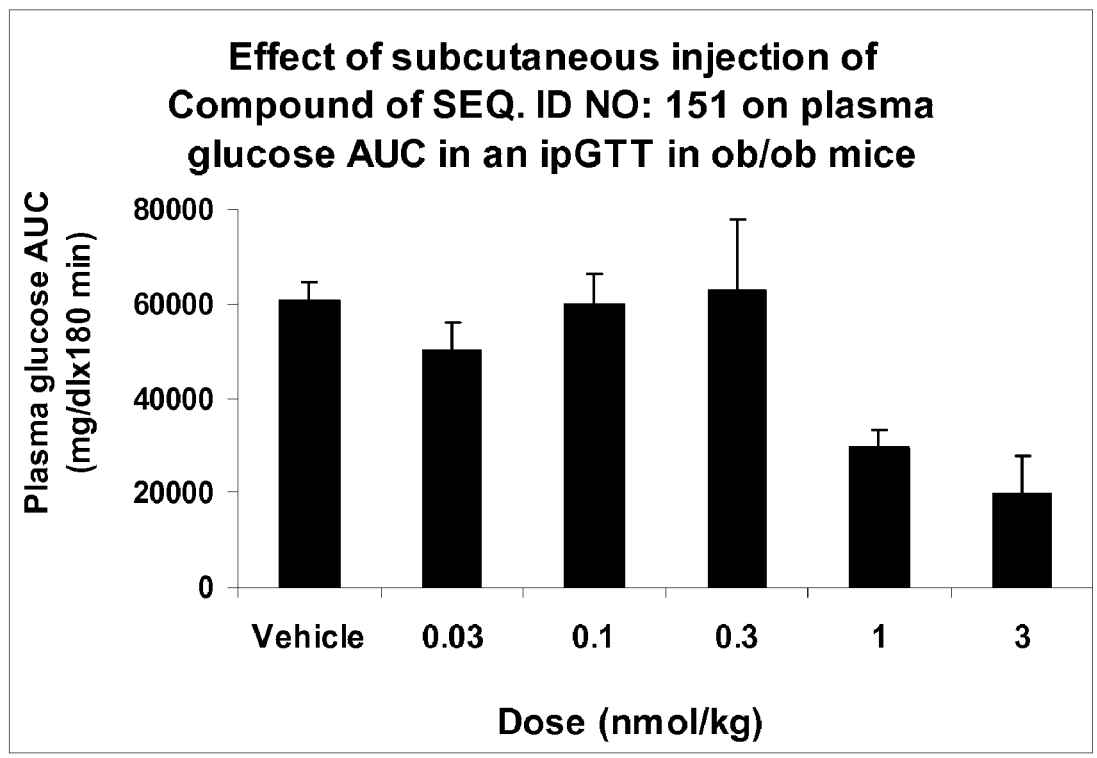
FIG. 6 illustrates the effects of subcutaneous injection of a compound of SEQ ID NO: 151 on plasma glucose in an ipGTT in ob/ob mice.

The effect of the compound of SEQ ID NO: 151 on postprandial glucose was dose-dependent between 0.03 and 3 nmol/kg and plasma glucose AUC decreased 67% at 3 nmol/kg dose (FIG. 6). The ED50 for the compound of SEQ ID NO: 151 was determined to be 1 nmoles/kg.

Figure 7:
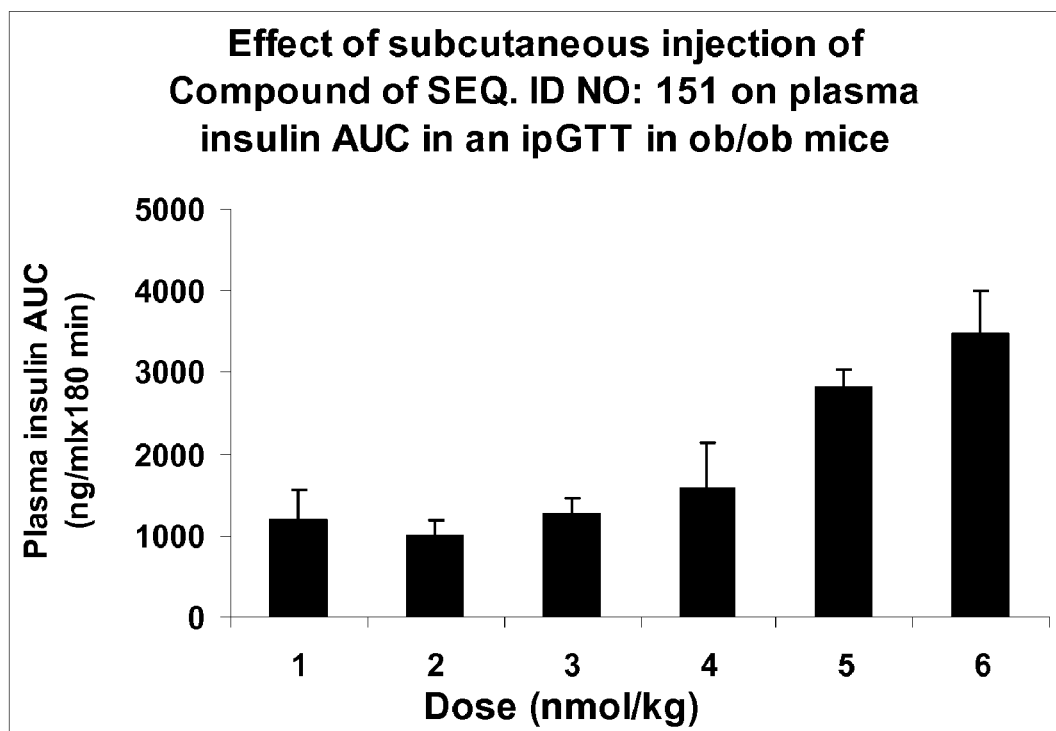
FIG. 7 illustrates the effects of subcutaneous injection of a compound of SEQ ID NO: 151 on plasma insulin in an ipGTT in ob/ob mice.
Figure 8:
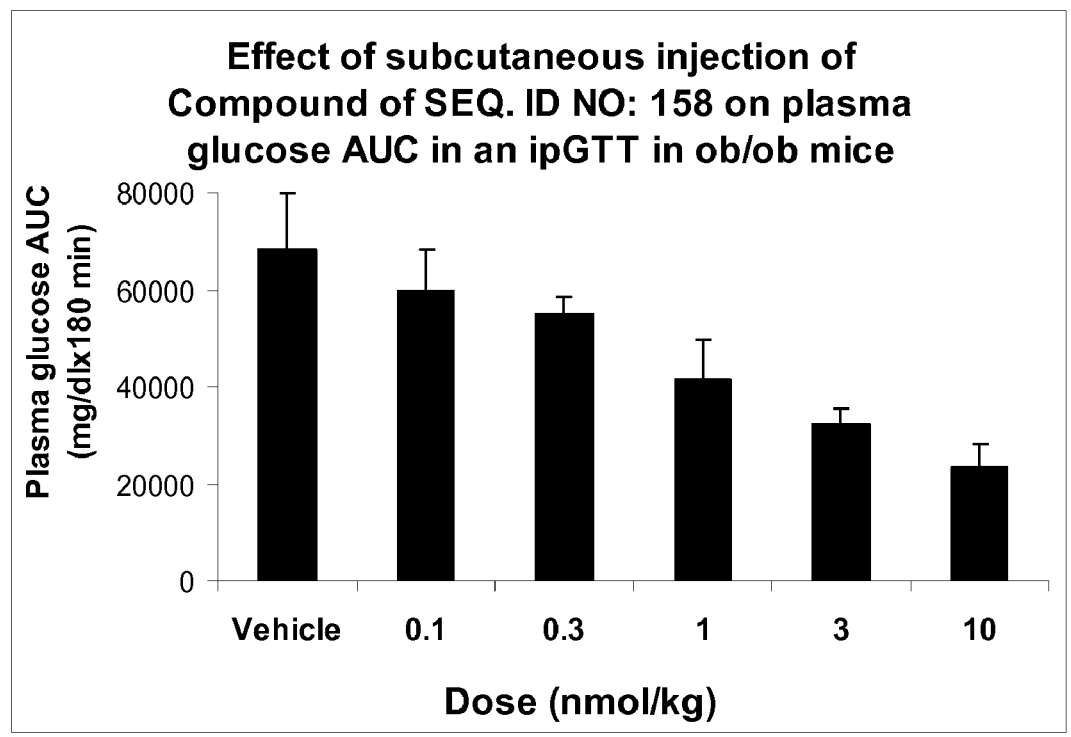
FIG. 8 illustrates the effects of subcutaneous injection of a compound of SEQ ID NO: 158 on plasma glucose in an ipGTT in ob/ob mice.
Figure 9:
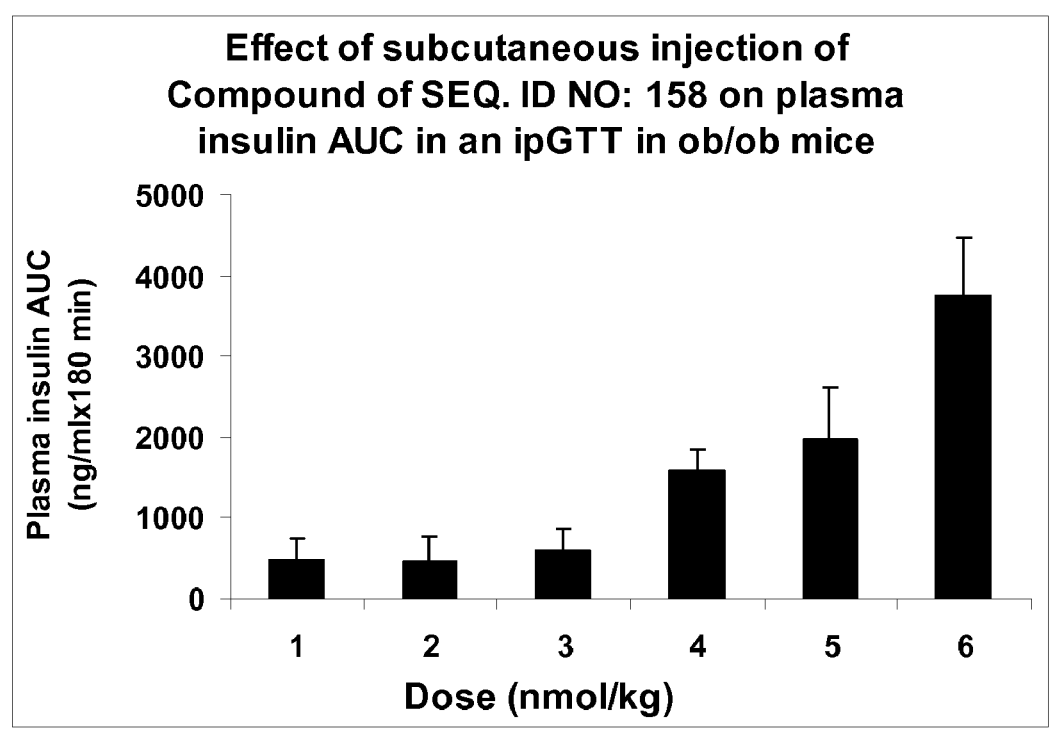
FIG. 9 illustrates the effects of subcutaneous injection of a compound of SEQ ID NO: 158 on plasma insulin in an ipGTT in ob/ob mice.

The effect of the compound of SEQ ID NO: 158 on postprandial glucose was dose-dependent between 0.1 and 10 nmol/kg and plasma glucose AUC decreased 66% at 10 nmol/kg dose (FIG. 7). The ED50 for the compound of SEQ ID NO: 151 was determined to be 2 nmoles/kg.

EXAMPLE 37

Dog Pharmacokinetic Study

The pharmacokinetic parameters of the Compounds of SEQ ID NO: 9, 118, 151 and 158 were determined in male beagle dogs (n=3-4, 14±1 kg). Following an overnight fast, each animal received the Compounds of SEQ ID NO: 9, 118, 151 and 158 either as an intravenous bolus via femoral vein (67 µg/kg) or by subcutaneous injection given at near the shoulder blades (67 µg/kg). Each animal received both intravenous and subcutaneous doses with a one-week washout between doses following a crossover design. The dosing vehicle for both routes of administration was propylene glycol:pH 7.4 phosphate buffer (50:50) or 0.2 M Tris (pH 8.0). Serial blood samples were collected in EDTA-containing microcentrifuge tubes at predose, 0.083, 0.25, 0.5, 0.75, 1, 2, 4, 6, 8, 24, and 30 hours post-dose after intravenous administration; at predose, 0.25, 0.5, 0.75, 1, 2, 4, 6, 8, 24, and 30 hours post-dose after subcutaneous administration. Approximately 0.3 mL of blood was collected at each time point. Blood samples were immediately centrifuged at 4° C. The obtained plasma was frozen with dry ice and stored at –20° C. Plasma drug levels were determined using the LC-MS/MS assay described below.

Quantitation of the Compound of SEQ ID NO: 158 by LC-MS/MS

Plasma samples from the in vivo dog study were prepared for analysis by precipitating plasma proteins with two volumes of AcCN containing an internal standard. The samples were vortex mixed and the precipitated proteins were removed by centrifugation. The resulting supernatants were transferred to a 96-well plate and 10 µL were injected for TFC-LC/MS/MS analysis.

The TFC-HPLC system (Cohesive TX-1 Flux, Aria 2300 System) consisted of a loading pump, an eluting pump, and a CTC PAL autosampler (Cohesive Technologies, Franklin, Mass.). The columns used were Phenomenex Synergi Fusion-RP (C18, 2.0×50 mm, 4µ) (Phenomenex, Torrance, Calif.) as the analytical column and Turbo-Flow (TF) HTLC Cyclone column (0.5×50 mm) (Cohesive Technologies, Franklin, Mass.) as the extraction column for on-line sample processing. The mobile phase A consisted of 10 mM ammonium formate and 0.1% formic acid in water and mobile phase B consisted of 0.1% formic acid in AcCN. Turbo-Flow Chromatography was used to obtain a cleaner sample. A rapid gradient elution was used for analyte separation. The samples were injected onto the Turbo-Flow HTLC Cyclone column and analytes were separated from biological fluid components with using 100% $H_2O$ at 1.5 mL/min. The TF column was back flushed and analytes were back eluted from the TF to HPLC analytical column using a ramp to 60% B over 2 min and held there for 30 seconds at 0.3 mL/min to separate and to elute the analytes from the HPLC column into the mass spectrometer. Both columns were washed for an additional minute and then both columns were re-equilibrated at initial conditions.

The HPLC was interfaced to a Sciex API 4000 mass spectrometer (Applied Biosystems, Foster City, Calif.) and was equipped with a TurboIonspray ionization source. Ultra high purity nitrogen was used as the nebulizing and turbo-gas. The temperature of turbo-gas was set at 300° C. and the interface heater was set at 60° C. Selected Reaction Monitoring (SRM) was used for data acquisition. Multiple charged ion species, i.e. $(M+2H)^{2+}$ for Compound of SEQ ID NO: 158 were selected in Q1 and were collisionally dissociated with high purity nitrogen at a pressure of $3.5 \times 10^{-3}$ torr in Q2 to form specific product ions which were subsequently monitored in Q3. The ion transitions and voltages are summarized below (Table 4).

TABLE 4

| Transitions Monitored and Mass Spectrometer Settings for LC-MS/MS Sample Analysis | |
|---|---|
| SRM transition (mz) | 800.0→152.0 |
| Declustering Potential (V) | 100 |
| Collision Energy (V) | 91 |

The standard curve concentrations, ranging from 1 to 1000 nM, were analyzed in duplicate. The curves were fitted with a linear regression weighted by reciprocal concentration ($1/x^2$). Quality control (QC) samples, prepared in blank matrix at the same concentrations as the standards were also analyzed in each analytical set. For the analysis of Compound of SEQ ID NO: 158 more than 80% of the calculated QC concentrations were within 20% of nominal concentrations, indicating the assay performance is acceptable.

Data Analysis

The compound of SEQ ID NO: 158 plasma concentration vs. time data were analyzed by noncompartmental methods using the KINETICA™ software program. The Cmax and Tmax values were recorded directly from experimental observations. The AUC0-n and AUCtot values were calculated using a combination of linear and log trapezoidal summations. The total plasma clearance (CLP), terminal half life (t½), mean residence time (MRT), and the steady state volume of distribution (Vss) were calculated after intravenous administration. The total blood clearance (CLB) was calculated using the total plasma clearance and the blood to plasma concentration ratio. CLB and Vss values were compared to standard liver blood flow and total body water values, respectively, reported in the literature. The absolute subcutaneous bioavailability (expressed as %) was estimated by taking the ratio of dose-normalized AUC values after a subcutaneous dose of the compound of SEQ ID NO: 158 to that after an intravenous dose.

Dog Pharmacokinetics Results

The pharmacokinetic parameters of the compounds of SEQ ID NO: 9, 151 and 158 in male beagle dogs, following intravenous (IV) and subcutaneous (SC) administration are summarized in Tables 5A, 5B, and 5C, respectively.

The compound of SEQ ID NO: 158 exhibited low systemic clearance (0.51±0.08 mL/min/kg). The steady-state volume of distribution (Vss) was 0.15±0.02 L/kg, indicating limited extravascular distribution. The estimated elimination half-life was 4.4±0.4 h and the mean residence time was 4.9±0.7 h. The time to reach peak concentrations (Tmax) after a subcutaneous dose of 67 µg/kg occurred at 1.4±0.7 h. The maximum plasma concentration (Cmax) after subcutaneous administration was 279±82 nM. The subcutaneous bioavailability of Compound of SEQ ID NO: 158 in dogs was 110±49%.

TABLE 5A

Pharmacokinetic Parameters of Compound of SEQ ID NO: 9 in the Dog (dosing vehicle: 0.2 M Tris, pH 8.0)

| Parameter | Intravenous (n = 3) | Subcutaneous (n = 3, Mean ± SD) |
|---|---|---|
| Dose (μg/kg) | 67 | 67 |
| Cmax (nM) | — | 116 ± 34 |
| Tmax (h) | — | 1.1 ± 0.6 |
| AUCtot (nM × h) | 529 ± 125 | 452 ± 153 |
| CLp (mL/min/kg) | 1.4 ± 0.4 | — |
| Vss (L/kg) | 0.21 ± 0.07 | — |
| t½ (h) | 7.1 ± 2.1 | 2.6 ± 1.2 |
| MRT (h) | 2.4 ± 0.5 | 3.6 ± 1.0 |
| Bioavailability (%) | — | 93 ± 22 |

TABLE 5B

Pharmacokinetic Parameters of Compound of SEQ ID NO: 151 in the Dog

| Parameter | Intravenous (n = 3, Mean ± SD) | Subcutaneous (n = 3, Mean ± SD) |
|---|---|---|
| Dose (μg/kg) | 67 | 67 |
| Cmax (nM) | — | 252 ± 15 |
| Tmax (h) | — | 1.8 ± 0.5 |
| AUCtot (nM × h) | 1519 ± 424 | 1566 ± 235 |
| CLp (mL/min/kg) | 0.49 ± 0.16 | — |
| Vss (L/kg) | 0.13 ± 0.05 | — |
| t½ (h) | 4.0 ± 0.2 | 4.4 ± 1.4 |
| MRT (h) | 4.4 ± 0.1 | 5.8 ± 1.0 |
| Bioavailability (%) | — | 110 ± 41 |

TABLE 5C

Pharmacokinetic Parameters of Compound of SEQ ID NO: 158 in the Dog

| Parameter | Intravenous (n = 3, Mean ± SD) | Subcutaneous (n = 3, Mean ± SD) |
|---|---|---|
| Dose (μg/kg) | 67 | 67 |
| Cmax (nM) | — | 279 ± 82 |
| Tmax (h) | — | 1.4 ± 0.7 |
| AUCtot (nM × h) | 1385 ± 227 | 1467 ± 563 |
| CLp (mL/min/kg) | 0.51 ± 0.08 | — |
| Vss (L/kg) | 0.15 ± 0.018 | — |
| t½ (h) | 4.4 ± 0.4 | 3.9 ± 1.3 |
| MRT (h) | 4.9 ± 0.7 | 5.2 ± 1.5 |
| Bioavailability (%) | — | 110 ± 49 |

EXAMPLE 38

Parenteral Routes of Administration

A liquid formulation for pulmonary/inhalation or nasal delivery, having the following composition is prepared as described below.

| Ingredient | Amount |
|---|---|
| peptide drug | 10 mg |
| HCl or NaOH | To adjust pH between 5-8 |
| SBE-cyclodextrin (Captisol) | 50 mg |
| Purified water | q.s. to 1 ml |

Weighed amounts of peptide are dissolved in a portion of water at an optimum pH. Captisol is added to the drug solution and stirred for about 5 min. NaOH and HCl are added to adjust pH to desired value (between 5-8). Purified water is added to bring final volume to 1 ml. Other inactive ingredients such as preservatives, antioxidants, buffer salts, and cosolvents may be added as needed, prior to pH adjustment. Water is added to the desired target volume.

The above solution formulation can be administered to the lung as a fine spray with a syringe microsprayer, or an air-jet or ultrasound nebulizer. The above solution can be delivered to the nasal cavity with a metered nasal spray pump or syringe microsprayer.

A dry powder formulation for pulmonary/inhalation or nasal delivery, having the following composition is prepared as described below.

| Ingredient | Amount |
|---|---|
| peptide drug | 10 mg |
| Lactose | 90 mg |

Weighed amounts of peptides, preferably with a mass median aerodynamic diameter (MMAD) of less than 5 micron, are blended with inhalation grade lactose 30-100 μm (Respitose, DMV International) in a Turbula® mixer for 5 min. The above dry powder blend can be delivered to the lung by a powder insufflator, or dry powder inhaler.

A suspension formulation for pulmonary/inhalation or nasal delivery, having the following composition is prepared as described below.

| Ingredient | Amount |
|---|---|
| peptide drug | 10 mg |
| Lecithin | 0.1% |
| Propellant gas | 1 ml |

Micronized peptides are homogeneously suspended in a mixture of lecithin and propellant gas such as hydrofluorocarbons (HFA's). The suspension is transferred to a pressurized metered dose inhaler.

Peptide Absorption from a Solution Formulation in Rats

| Pharmacokinetic Parameters | Intra-trachea | Intra-nasal |
|---|---|---|
| Dose (mg/kg) | 1 | 0.6 |
| AUC (nM · h) | 918.9 ± 103 | 177 ± 77 |
| Cmax (nM) | 359 ± 50.9 | 236 ± 125 |
| Tmax (h) | 0.03 | 0.17 |

A peptide was administered as a solution (described above) to male Sprague-Dawley rats anesthetized with intraperitoneal injection of pentobarbital. Drug was introduced into the trachea with a syringe microsprayer to assess pulmonary delivery or instilled with a pipettor into each nostril for intranasal delivery. Blood samples were collected from the cannulated carotid artery into heparinized vaccutainers over a 4 hr period. The blood samples were centrifuged, the isolated plasma stored at −80° C. till analysis by LC/MS. From the plasma-time concentration curves the pharmacokinetic parameters were calculated and reported in the table. Three rats were used for each route of administration. Data is provided as a mean ±standard deviation. Tmax is reported as a median value.

Utilities and Combinations

A. Utilities

The subject matter described herein provides novel peptides which have superior properties and act as GLP-1 receptor modulators, for example such that the peptides have agonist activity for the GLP-1 receptor. Further, the peptides described herein exhibit increased stability to proteolytic cleavage as compared to GLP-1 native sequences.

Accordingly, compounds described herein can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis, hypertension, AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, dysmetabolic syndrome, as well as inflammatory bowel disease (such as Crohn's disease and ulcerative colitis). The compounds described herein may also be utilized to increase the blood levels of high density lipoprotein (HDL).

In addition, the conditions, diseases, and maladies collectively referenced to as "Syndrome X" or Metabolic Syndrome as detailed in Johannsson J. Clin. Endocrinol. Metab., 82, 727-34 (1997), may be treated employing the compounds described herein.

B. Combinations

The subject matter described and claimed herein includes pharmaceutical compositions comprising, as an active ingredient, a therapeutically effective amount of at least one of the compounds of Formula I, alone or in combination with a pharmaceutical carrier or diluent. Optionally, the compounds described herein can be used alone, in combination with other compounds described herein, or in combination with one or more other therapeutic agent(s), e.g., an antidiabetic agent or other pharmaceutically active material.

The compounds described herein may be employed in combination with other GLP-1 receptor modulators (e.g., agonists or partial agonists, such as a peptide agonist) or other suitable therapeutic agents useful in the treatment of the aforementioned disorders including: anti-diabetic agents; anti-hyperglycemic agents; hypolipidemic/lipid lowering agents; anti-obesity agents (including appetite suppressants/modulators) and anti-hypertensive agents. In addition, the compounds described herein may be combined with one or more of the following therapeutic agents; infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Examples of suitable anti-diabetic agents for use in combination with the compounds described herein include biguanides (e.g. metformin or phenformin), glucosidase inhibitors (e.g., acarbose or miglitol), insulins (including insulin secretagogues or insulin sensitizers), meglitinides (e.g., repaglinide), sulfonylureas (e.g. glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), DPP-IV inhibitors, GPR119 modulators, and SGLT2 inhibitors.

Other suitable thiazolidinediones include Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include muraglitazar (Bristol-Myers Squibb), AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/644,598, filed Sep. 18, 2000, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors that may be used in combination with the compounds described herein include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, LAF237, saxagliptin, MK0431, TSL-225 (tryptophyl-1,2,3,4-tetrahydroisoquinoline-3-carboxylic acid (disclosed by Yamada et al, Bioorg. & Med. Chem. Lett. 8 (1998) 1537-1540, 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996) employing dosages as set out in the above references.

Suitable meglitinides include nateglinide (Novartis) or KAD1229 (PF/Kissei).

Examples of other suitable glucagon-like peptide-1 (GLP-1,) compounds that may be used in combination with the GLP-1 receptor modulators (e.g., agonists or partial agonists) described herein include GLP-1 (1-36) amide, GLP-1 (7-36)

amide, GLP-1 (7-37) (as disclosed in U.S. Pat. No. 5,614,492 to Habener), as well as AC2993 (Amylin), LY-315902 (Lilly) and NN2211 (Novo Nordisk).

Examples of suitable hypolipidemic/lipid lowering agents for use in combination with the compounds described herein include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440, all of which are incorporated by reference herein.

The HMG CoA reductase inhibitors which may be employed in combination with one or more compounds of Formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Desired hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds described herein.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with one or more compounds of Formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of Formula I include those disclosed in Drugs of the Future 24, 9-15 (1999), (Avasimibe); "The ACAT inhibitor, CI-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds described herein include SCH48461 (Schering-Plough), as well as those disclosed in Atherosclerosis 115, 45-63 (1995) and J. Med. Chem. 41, 973 (1998).

Examples of suitable ileal Na+/bile acid cotransporter inhibitors for use in combination with the compounds described herein include compounds as disclosed in Drugs of the Future, 24, 425-430 (1999).

The lipoxygenase inhibitors which may be employed in combination with one or more compounds of Formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compounds described herein include beta adrenergic blockers, calcium channel blockers (L-type and T-type; e.g. diltiazem, verapamil, nifedipine, amlodipine and mybefradil), diuretics (e.g. chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds described herein include a NPY receptor antagonist, a NPY-Y2 or NPY-Y4 receptor agonist, Oxyntomodulin, a MCH antagonist, a GHSR antagonist, a CRH antagonist, a beta 3 adrenergic agonist, a lipase inhibitor, a serotonin (and dopamine) reuptake inhibitor, a thyroid receptor beta drug, a CB-1 antagonist and/or an anorectic agent.

The beta 3 adrenergic agonists which may be optionally employed in combination with compounds described herein include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds described herein include orlistat or ATL-962 (Alizyme), with orlistat being preferred.

The serotonin (and dopamine) reuptake inhibitor which may be optionally employed in combination with a compound of Formula I may be sibutramine, topiramate (Johnson & Johnson) or axokine (Regeneron), with sibutramine and topiramate being preferred.

Examples of thyroid receptor beta compounds which may be optionally employed in combination with compounds described herein include thyroid receptor ligands, such as those disclosed in WO97/21993 (U. Cal SF), WO99/00353 (KaroBio) and WO 00/039077 (KaroBio), with compounds of the KaroBio applications being preferred.

Examples of CB-1 antagonists which may be optionally employed in combination with compounds described herein include CB-1 antagonists and rimonabant (SR141716A).

Examples of NPY-Y2 and NPY-Y4 receptor agonists include PYY(3-36) and Pancreatic Polypeptide (PP), respectively.

The anorectic agent which may be optionally employed in combination with compounds described herein include dexamphetamine, phentermine, phenylpropanolamine or mazindol, with dexamphetamine being preferred.

Examples of suitable anti-psychotic agents include clozapine, haloperidol, olanzapine (Zyprexa®), Prozac and aripiprazole (Abilify®).

The aforementioned patents and patent applications are incorporated herein by reference.

The above other therapeutic agents, when employed in combination with the compounds described herein may be used, for example, in those amounts indicated in the Physician's Desk Reference, as in the patents set out above or as otherwise determined by one of ordinary skill in the art.

Dosage and Formulation

A suitable peptide of Formula I, or more specifically a peptide comprising any one of SEQ ID NOs: 1-179, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in "The Pharmacological Basis of Therapeutics", Ch. 1, p. 1, 1975; "Remington's Pharmaceutical Sciences", 18th ed., Mack Publishing Co, Easton, Pa., 1990).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington: "The Science and Practice of Pharmacy", Nineteenth Edition, Mack Publishing Company, 1995, a standard reference text in this field Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Numerous modifications and variations of the subject matter described and claimed herein are possible in light of the above teachings. It is therefore understood that within the scope of the appended claims, the subject matter recited in the claims may be practiced otherwise than as specifically described herein.

The subject matter recited in the claims is not to be limited in scope by the specific embodiments described that are intended as single embodiments of the claimed subject matter. Functionally equivalent methods and components in addition to those shown and described herein will become apparent to those skilled in the art from the foregoing description and accompanying drawings. Such modifications are intended to fall within the scope of the appended claims. All references cited herein are hereby incorporated by reference in their entirety.

---

What is claimed is:

1. A polypeptide comprising the sequence Thr-Ser-Asp-Bip (2-Et-4'-OH)-pyridylalanine (SEQ ID NO: 177), wherein said polypeptide binds and activates a GLP-1 receptor.

2. The polypeptide of claim 1 wherein said polypeptide further comprises a proline.

3. The polypeptide of claim 2 wherein said proline is the second residue from the amino terminal residue and is alpha methyl proline.

4. The polypeptide of claim 1 wherein said pyridylalanine is 4-(2'methyl phenyl) 3-pyridyl alanine.

5. The polypeptide of claim 1 wherein said polypeptide further comprises an amino terminal carbamate.

6. The polypeptide of claim 1 wherein said Thr-Ser-Asp-Bip(2-Et-4-OH)-pyridylalanine residues are at the seventh, eighth, ninth, and tenth, positions respectively, of said polypeptide and wherein position two comprises alpha methyl proline.

7. The polypeptide of claim 1 wherein said polypeptide is a peptide comprising SEQ ID NO: 158.

8. A polypeptide comprising SEQ ID NO: 158.

9. A pharmaceutical composition, comprising an isolated polypeptide of SEQ ID NO: 158, and a pharmaceutically acceptable carrier thereof.

10. A pharmaceutical combination comprising an isolated polypeptide of SEQ ID NO: 158, and at least one therapeutic agent selected from the group consisting of an antidiabetic agent, an anti-obesity agent, an anti-hypertensive agent, an anti-atherosclerotic agent and a lipid-lowering agent.

11. The combination of claim 10 wherein the antidiabetic agent is at least one agent selected from the group consisting of a biguanide, a sulfonyl urea, a glucosidase inhibitor, a PPAR γ agonist, a PPAR α/γ dual agonist, an aP2inhibitor, a DPP4 inhibitor, an insulin sensitizer, a glucagon-like peptide-1 (GLP-1), insulin, a SGLT-2 inhibitor, a GPR119 modulator and a meglitinide.

12. The combination of claim 11 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, farglitizar, isaglitazone, reglitizar, balaglitazone, CAS RN:335149-08-1, (Z)-1,4-bis{4-[(3,5-Dioxo-1,2,4-oxadiazolidin-2-yl) methyl]phenoxy}but-2-ene, rivoglitazone, rafaegron, repaglinide, nateglinide, (S)-2-benzyl-4-oxo-4-(cis-perhydroisoindol-2-yl)butyric acid calcium salt, tesaglitizar, L-phenylalanine, N-[(1Z)-1-methyl-3-oxo-3-phenyl-1-propenyl]-4[3-(5-methyl-2-phenyl-4-oxazoly)propyl] benzamide, 5-[(2,4-dioxo-5-thiazolidinyl) methyl]-2-methoxy-N-[[4-(trifluoromethyl) phenyl]methyl] benzamide, exenatide, 8-37-glucagon-like peptide I (human), N-[3-(1H -imidazol-4-yl)-1-oxopropyl[-26-L-arginine-34-[N6-(1-oxooctyl)-L-lysine], 8-36-glucagon-related peptide 1(octodon degas), N-[3-(1H-imidazol-4-yl)-1- oxopropyl]-26-L-arginine-34-[N6-(1-oxooctyl)-L-lysine]-36a, and vildagliptin.

13. The combination of claim 10 wherein the anti-obesity agent is at least one agent selected from the group consisting of a CB-1antagonist or inverse agonist, a Y2receptor agonist, a Y4receptor agonist, a beta 3adrenergic agonist, a lipase inhibitor, a serotonin reuptake inhibitor, a dopamine reuptake inhibitor, a serotonin and dopamine reuptake inhibitor, a thyroid receptor beta compound, and an anorectic agent.

14. The combination of claim 13 wherein the anti-obesity agent is at least one agent selected from the group consisting of rimonabant, MK-0364, SLV-319,orlistat, cetilistat, rafabregon, benzenesulfonamide, N-[4-[2-[[(2S)-3-[(6-amino-3-pyridinyl)oxy]-2-hydroxypropyl]amino]ethyl]phenyl]-4-(1-methylethyl) benzenesulfonamide, N-[4-[2[[3-[(6-amino-3-pyridinyl)oxy]-2-hydroxypropyl] amino]ethyl]phenyl]-4-(1-methylethyl)-(S) benzenesulfonamide CAS RN:335149-25-2, sibutramine, topiramate, axokine, dexamphetamine, phentermine, phenylpropanolamine and mazindol.

15. The combination of claim 10 wherein the lipid lowering agent is at least one agent selected from the group consisting of an MTP inhibitor, cholesterol ester transfer protein, an HMG CoA reductase inhibitor, a squalene synthetase inhibitor, a fibric acid derivative, an upregulator of LDL receptor activity, a lipoxygenase inhibitor, or an ACAT inhibitor.

16. The combination of claim 15 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, acetamide, N-[2,6-bis(1-methylethyl)phenyl]-2-(tetradecylthio)-benzamide, 3-(13-hydroxy-10-oxotetradecyl)-5,7-dimethoxy-1-(3H) isobenzofuranone, torcetrapib, and (3alpha, 4alpha, 5alpha)-4-(2-propenylcholestan-3-ol).

17. A polypeptide comprising SEQ ID NO: 160.

18. A polypeptide comprising SEQ ID NO: 162.

* * * * *

```
                        SEQUENCE LISTING

<160> NUMBER OF SEQ ID NOS: 179

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is Biphenylalanine(2'-Me)
<220> FEATURE:
<221> NAME/KEY: MISC_FEATURE
<222> LOCATION: (11)..(11)
<223> OTHER INFORMATION: X is 4-(2'-pyridyl)Phenylalanine-NH2

<400> SEQUENCE: 1

His Xaa Glu Gly Thr Phe Thr Ser Asp Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
```

```
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(3',5'-di-Me)
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 2

His Xaa Glu Gly Thr Phe Thr Ser Asp Xaa Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-OBu)
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 3

His Xaa Glu Gly Thr Phe Thr Ser Asp Xaa Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Me)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 4

His Xaa Glu Gly Thr Phe Thr Ser Asp Xaa Xaa
1               5                   10

<210> SEQ ID NO 5
<211> LENGTH: 11
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Cl)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 5

His Xaa Glu Gly Thr Phe Thr Ser Asp Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-methoxy-5'-iso-propyl)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 6

His Xaa Glu Gly Thr Phe Thr Ser Asp Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(2'-Ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 7
```

```
His Xaa Glu Gly Thr Phe Thr Ser Asp Xaa Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[(2'-Ethyl-4'-methoxy)phenyl]-3-
      pyridylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 8

His Xaa Glu Gly Thr Phe Thr Ser Asp Xaa Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 9

His Xaa Glu Gly Thr Phe Thr Ser Asp Xaa Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
```

<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 10

His Xaa Glu Gly Thr Phe Thr Ser Asp Xaa Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 11

His Xaa Glu Gly Thr Phe Thr Ser Asp Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 12

His Xaa Glu Gly Thr Phe Thr Ser Asp Xaa Xaa
1               5                   10

<210> SEQ ID NO 13
<211> LENGTH: 11

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 13

His Xaa Glu Gly Thr Phe Thr Ser Asp Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 14

His Xaa Glu Gly Thr Phe Thr Ser Asp Xaa Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Methyl)pyridyl)phenylalanine-NH2

<400> SEQUENCE: 15
```

```
His Xaa Glu Gly Thr Phe Thr Ser Asp Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Methyl)pyridyl)]phenylalanine-NH2

<400> SEQUENCE: 16

His Xaa Glu Gly Thr Phe Thr Ser Asp Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-Pyridazyl)phenylalanine-NH2

<400> SEQUENCE: 17

His Xaa Glu Gly Thr Phe Thr Ser Asp Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
```

```
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-Pyridazyl)phenylalanine-NH2

<400> SEQUENCE: 18

His Xaa Glu Gly Thr Phe Thr Ser Asp Xaa Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Me,6-OMe)pyridyl)]phenylalanine-
      NH2

<400> SEQUENCE: 19

His Xaa Glu Gly Thr Phe Thr Ser Asp Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-[3-(4'-Methyl)pyridyl)]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 20

His Xaa Glu Gly Thr Phe Thr Ser Asp Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
```

```
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 21

His Xaa Glu Gly Thr Phe Thr Ser Asp Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 22

His Xaa Glu Gly Thr Phe Thr Ser Asp Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[2(1H)Pyridonyl]phenylalanine-NH2

<400> SEQUENCE: 23

His Xaa Glu Gly Thr Phe Thr Ser Asp Xaa Xaa
1               5                   10

<210> SEQ ID NO 24
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(8-Quinoline)-NH2

<400> SEQUENCE: 24

His Xaa Glu Gly Thr Phe Thr Ser Asp Xaa Xaa
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(3-Quinoline)-NH2

<400> SEQUENCE: 25

His Xaa Glu Gly Thr Phe Thr Ser Asp Xaa Xaa
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(6-Quinoline)-NH2

<400> SEQUENCE: 26
```

```
His Xaa Glu Gly Thr Phe Thr Ser Asp Xaa Xaa
1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(5-Quinoline)-NH2

<400> SEQUENCE: 27

```
His Xaa Glu Gly Thr Phe Thr Ser Asp Xaa Xaa
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-(6-OMe)pyridyl)phenylalanine-NH2

<400> SEQUENCE: 28

```
His Xaa Glu Gly Thr Phe Thr Ser Asp Xaa Xaa
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)

```
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-(2-Methoxy)pyridyl)phenylalanine-NH2

<400> SEQUENCE: 29

His Xaa Glu Gly Thr Phe Thr Ser Asp Xaa Xaa
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-pyridyl)phenylalanine-NH2

<400> SEQUENCE: 30

His Xaa Glu Gly Thr Phe Thr Ser Asp Xaa Xaa
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6,di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 31

His Xaa Glu Gly Thr Phe Thr Ser Asp Xaa Xaa
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(5-Quinoline)phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 32

His Xaa Glu Gly Thr Phe Thr Ser Asp Xaa Xaa
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[3-(2'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 33

His Xaa Glu Gly Thr Phe Thr Ser Asp Xaa Xaa
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(6-Quinoline)phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 34

His Xaa Glu Gly Thr Phe Thr Ser Asp Xaa Xaa
1               5                   10
```

```
<210> SEQ ID NO 35
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(4'-pyridyl)phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 35

His Xaa Glu Gly Thr Phe Thr Ser Asp Xaa Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: 4-[4'-(3',5'-dimethylisoxazole)]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 36

His Xaa Glu Gly Thr Phe Thr Ser Asp Xaa Xaa
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
```

```
<223> OTHER INFORMATION: X is 4-(2-trifluoromethylphenyl)-3-
      pyridylalanine-NH2

<400> SEQUENCE: 37

His Xaa Glu Gly Thr Phe Thr Ser Asp Xaa Xaa
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2-methyl-5-fluorophenyl)-3-
      pyridylalanine-NH2

<400> SEQUENCE: 38

His Xaa Glu Gly Thr Phe Thr Ser Asp Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4-methanesulfonylphenyl)-3-
      pyridylalanine-NH2

<400> SEQUENCE: 39

His Xaa Glu Gly Thr Phe Thr Ser Asp Xaa Xaa
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
```

```
<221> NAME/KEY: MISC_FEATURE
<222> LOCATION: (6)..(6)
<223> OTHER INFORMATION: Phe is L-alpha-Me-phe
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: 4-(2'-Methylphenyl)-3-pyridylalanine-NH2

<400> SEQUENCE: 40

His Xaa Glu Gly Thr Phe Thr Ser Asp Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 41

His Xaa Glu Gly Thr Phe Thr Ser Asp Xaa Xaa
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 42

His Xaa Glu Gly Leu Phe Thr Ser Asp Xaa Xaa
1               5                   10
```

```
<210> SEQ ID NO 43
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[2'-Cl, 4'-CF3)-3'-
      pyridyl]phenylalanine-NH2

<400> SEQUENCE: 43

His Xaa Glu Gly Thr Phe Thr Ser Asp Xaa Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is Biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3'-(2'-CN-6'-Me)pyridyl]phenylalanine-
      NH2

<400> SEQUENCE: 44

His Xaa Glu Gly Thr Phe Thr Ser Asp Xaa Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Cl)
<220> FEATURE:
<221> NAME/KEY: MISC_FEATURE
```

```
<222> LOCATION: (11)..(11)
<223> OTHER INFORMATION: X is 4-(2'-Methylphenyl)-3-pyridylalanine-NH2

<400> SEQUENCE: 45

His Xaa Glu Gly Thr Phe Thr Ser Asp Xaa Xaa
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2',4'-di-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 46

His Xaa Glu Gly Thr Phe Thr Ser Asp Xaa Xaa
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(3'-pyridyl)phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 47

His Xaa Glu Gly Thr Phe Thr Ser Asp Xaa Xaa
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
```

```
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(4'-pyridyl)phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 48

His Xaa Glu Gly Thr Phe Thr Ser Asp Xaa Xaa
 1               5                  10

<210> SEQ ID NO 49
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Me-3'-F)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 49

His Xaa Glu Gly Thr Phe Thr Ser Asp Xaa Xaa
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-F)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 50

His Xaa Glu Gly Thr Phe Thr Ser Asp Xaa Xaa
 1               5                  10

<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(2'-Cl-6'-CF3)pyridyl]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 51

His Xaa Glu Gly Thr Phe Thr Ser Asp Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 52

His Xaa Glu Gly Thr Phe Thr Ser Asp Xaa Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(3'-Cl-4'-F)-NH2

<400> SEQUENCE: 53

His Xaa Glu Gly Thr Phe Thr Ser Asp Xaa Xaa
1               5                   10
```

```
<210> SEQ ID NO 54
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nva
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 54

His Xaa Glu Gly Val Phe Thr Ser Asp Xaa Xaa
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(3',5'-di-Me)-NH2

<400> SEQUENCE: 55

His Xaa Glu Gly Thr Phe Thr Ser Asp Xaa Xaa
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
```

<223> OTHER INFORMATION: X is 4-(2'-ethylphenyl)-3-pyridylalanine-NH2
<220> FEATURE:
<221> NAME/KEY: MISC_FEATURE
<222> LOCATION: (11)..(11)
<223> OTHER INFORMATION: X is 4-(2',3'-pyridazyl)phenylalanine-NH2

<400> SEQUENCE: 56

His Xaa Glu Gly Thr Phe Thr Ser Asp Xaa Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 57

His Xaa Glu Gly Thr Phe Thr Ser Asp Xaa Xaa
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine-NH2
<220> FEATURE:
<221> NAME/KEY: MISC_FEATURE
<222> LOCATION: (11)..(11)
<223> OTHER INFORMATION: X is 4-[3'-(2'-Cl-6'-CF3)pyridyl]phenylalanine-NH2

<400> SEQUENCE: 58

His Xaa Glu Gly Thr Phe Thr Ser Asp Xaa Xaa
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)

```
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-[3'-(2'-CN-6'-Me)pyridyl]phenylalanine-
      NH2

<400> SEQUENCE: 59

His Xaa Glu Gly Thr Phe Thr Ser Asp Xaa Xaa
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 60

His Xaa Glu Gly Thr Phe Thr Ser Asp Xaa Xaa
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(3'-Cl-4'-F)-NH2

<400> SEQUENCE: 61

His Xaa Glu Gly Thr Phe Thr Ser Asp Xaa Xaa
1               5                   10

<210> SEQ ID NO 62
```

```
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(3',5'-di-Me)-NH2

<400> SEQUENCE: 62

His Xaa Glu Gly Thr Phe Thr Ser Asp Xaa Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-4'-OMe)-NH2

<400> SEQUENCE: 63

His Xaa Glu Gly Thr Phe Thr Ser Asp Xaa Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-3'-F)-NH2
```

```
<400> SEQUENCE: 64

His Xaa Glu Gly Thr Phe Thr Ser Asp Xaa Xaa
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-F)-NH2

<400> SEQUENCE: 65

His Xaa Glu Gly Thr Phe Thr Ser Asp Xaa Xaa
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 66

His Xaa Glu Gly Thr Phe Thr Ser Asp Xaa Xaa
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
```

```
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(3',4'-di-OMe)-NH2

<400> SEQUENCE: 67

His Xaa Glu Gly Thr Phe Thr Ser Asp Xaa Xaa
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 68

His Xaa Glu Gly Thr Phe Thr Ser Asp Xaa Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-4'-OMe)-NH2

<400> SEQUENCE: 69

His Xaa Glu Gly Thr Phe Thr Ser Asp Xaa Xaa
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
```

```
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 70

His Xaa Glu Gly Thr Phe Thr Ser Asp Xaa Xaa
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 71

His Xaa Glu Gly Thr Phe Thr Ser Asp Xaa Xaa
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Methyl)pyridyl)]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 72

His Xaa Glu Gly Thr Phe Thr Ser Asp Xaa Xaa
1               5                   10

<210> SEQ ID NO 73
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 73

His Xaa Glu Gly Thr Phe Thr Ser Asp Xaa Xaa
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-quinoline)phenylalanine-NH2

<400> SEQUENCE: 74

His Xaa Glu Gly Thr Phe Thr Ser Asp Xaa Xaa
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-(2'-Methoxy)pyridyl)phenylalanine-
      NH2
```

```
<400> SEQUENCE: 75

His Xaa Glu Gly Thr Phe Thr Ser Asp Xaa Xaa
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-phenyl-3-pyridylalanine-NH2

<400> SEQUENCE: 76

His Xaa Glu Gly Thr Phe Thr Ser Asp Xaa Xaa
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-dimethylphenyl)-3-pyridylalanine-
      NH2

<400> SEQUENCE: 77

His Xaa Glu Gly Thr Phe Thr Ser Asp Xaa Xaa
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
```

```
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3'-chloro-4'-fluoro)phenyl]-3-
      pyridylalanine-NH2

<400> SEQUENCE: 78

His Xaa Glu Gly Thr Phe Thr Ser Asp Xaa Xaa
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',4'-dimethoxy)phenyl]-3-
      pyridylalanine-NH2

<400> SEQUENCE: 79

His Xaa Glu Gly Thr Phe Thr Ser Asp Xaa Xaa
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-ethyl-4'-methoxy)phenyl]-3-
      pyridylalanine-NH2

<400> SEQUENCE: 80

His Xaa Glu Gly Thr Phe Thr Ser Asp Xaa Xaa
1               5                   10

<210> SEQ ID NO 81
<211> LENGTH: 11
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-imidazole-lactyl
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 81

Xaa Xaa Glu Gly Thr Phe Thr Ser Asp Xaa Xaa
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-(5-o-Tolyl)thienylalanine-NH2

<400> SEQUENCE: 82

His Xaa Glu Gly Thr Phe Thr Ser Asp Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-[(5-(3'-Methoxy)phenyl]thienylalanine-
      NH2
```

<400> SEQUENCE: 83

His Xaa Glu Gly Thr Phe Thr Ser Asp Xaa Xaa
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-[(5-(3',5'-di-
      Methyl)phenyl]thienylalanine-NH2

<400> SEQUENCE: 84

His Xaa Glu Gly Thr Phe Thr Ser Asp Xaa Xaa
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-[(5-(3'-Cl,5'-F)phenyl]thienylalanine-
      NH2

<400> SEQUENCE: 85

His Xaa Glu Gly Thr Phe Thr Ser Asp Xaa Xaa
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)

```
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Isopropoxyphenyl)-3-pyridylalanine-
      NH2

<400> SEQUENCE: 86

His Xaa Glu Gly Thr Phe Thr Ser Asp Xaa Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl, 5'-Fluoro)phenyl)-3-
      pyridylalanine-NH2

<400> SEQUENCE: 87

His Xaa Glu Gly Thr Phe Thr Ser Asp Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropoxyphenyl)-3-pyridylalanine-
      NH2

<400> SEQUENCE: 88

His Xaa Glu Gly Thr Phe Thr Ser Asp Xaa Xaa
1               5                   10

<210> SEQ ID NO 89
<211> LENGTH: 11
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 3-(4-Br)pyridylalanine-NH2

<400> SEQUENCE: 89

His Xaa Glu Gly Thr Phe Thr Ser Asp Xaa Xaa
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Methoxyphenyl)-3-pyridylalanine-NH2

<400> SEQUENCE: 90

His Xaa Glu Gly Thr Phe Thr Ser Asp Xaa Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl, 4'-Fluoro)phenyl)-3-
      pyridylalanine-NH2

<400> SEQUENCE: 91
```

His Xaa Glu Gly Thr Phe Thr Ser Asp Xaa Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 92

His Xaa Glu Gly Thr Phe Thr Ser Asp Xaa Xaa
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethoxyphenyl)-3-
      pyridylalanine-NH2

<400> SEQUENCE: 93

His Xaa Glu Gly Thr Phe Thr Ser Asp Xaa Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE

```
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethoxyphenyl)-3-
      pyridylalanine-NH2

<400> SEQUENCE: 94

His Xaa Glu Gly Thr Phe Thr Ser Asp Xaa Xaa
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 3-pyridylalanine-NH2

<400> SEQUENCE: 95

His Xaa Glu Gly Thr Phe Thr Ser Asp Xaa Xaa
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl,4'-Chloro)phenyl)-3-
      pyridylalanine-NH2

<400> SEQUENCE: 96

His Xaa Glu Gly Thr Phe Thr Ser Asp Xaa Xaa
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Me-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 97

His Xaa Glu Gly Thr Phe Thr Ser Asp Xaa Xaa
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Trifluoromethylphenyl)-3-
      pyridylalanine-NH2

<400> SEQUENCE: 98

His Xaa Glu Gly Thr Phe Thr Ser Asp Xaa Xaa
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Fluorophenyl)-3-pyridylalanine-NH2

<400> SEQUENCE: 99

His Xaa Glu Gly Thr Phe Thr Ser Asp Xaa Xaa
1               5                   10
```

```
<210> SEQ ID NO 100
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethylphenyl)-3-
      pyridylalanine-NH2

<400> SEQUENCE: 100

His Xaa Glu Gly Thr Phe Thr Ser Asp Xaa Xaa
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Chlorophenyl)-3-pyridylalanine-NH2

<400> SEQUENCE: 101

His Xaa Glu Gly Thr Phe Thr Ser Asp Xaa Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
```

```
<222> LOCATION: (11)..(11)
<223> OTHER INFORMATION: X is 4-(3'-Chlorophenyl)-3-pyridylalanine-NH2

<400> SEQUENCE: 102

His Xaa Glu Gly Thr Phe Thr Ser Asp Xaa Xaa
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Isopropylphenyl)-3-pyridylalanine-
      NH2

<400> SEQUENCE: 103

His Xaa Glu Gly Thr Phe Thr Ser Asp Xaa Xaa
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-dimethylisoxazol-4'-yl)-3-
      pyridylalanine-NH2

<400> SEQUENCE: 104

His Xaa Glu Gly Thr Phe Thr Ser Asp Xaa Xaa
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
```

```
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-Methyl-4'-methoxy)phenyl]-3-
      pyridylalanine-NH2

<400> SEQUENCE: 105

His Xaa Glu Gly Thr Phe Thr Ser Asp Xaa Xaa
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethylphenyl)-3-
      pyridylalanine-NH2

<400> SEQUENCE: 106

His Xaa Glu Gly Thr Phe Thr Ser Asp Xaa Xaa
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Chlorophenyl)-3-pyridylalanine-NH2

<400> SEQUENCE: 107

His Xaa Glu Gly Thr Phe Thr Ser Asp Xaa Xaa
1               5                   10

<210> SEQ ID NO 108
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Pyridyl)-3-pyridylalanine-NH2

<400> SEQUENCE: 108

His Xaa Glu Gly Thr Phe Thr Ser Asp Xaa Xaa
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 109

His Xaa Glu Gly Thr Phe Thr Ser Asp Xaa Xaa
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(6'-Methoxypyridin-3'-yl)-3-
      pyridylalanine-NH2
```

```
<400> SEQUENCE: 110

His Xaa Glu Gly Thr Phe Thr Ser Asp Xaa Xaa
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropylphenyl)-3-pyridylalanine-
      NH2

<400> SEQUENCE: 111

His Xaa Glu Gly Thr Phe Thr Ser Asp Xaa Xaa
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methoxyphenyl)-3-pyridylalanine-NH2

<400> SEQUENCE: 112

His Xaa Glu Gly Thr Phe Thr Ser Asp Xaa Xaa
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
```

```
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',5'-di-Fluoro-2'-methoxy)phenyl]-3-
      pyridylalanine-NH2

<400> SEQUENCE: 113

His Xaa Glu Gly Thr Phe Thr Ser Asp Xaa Xaa
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-methylphenyl)-3-pyridylalanine-NH2

<400> SEQUENCE: 114

His Xaa Glu Gly Thr Phe Thr Ser Asp Xaa Xaa
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-fluorophenyl)-3-pyridylalanine-NH2

<400> SEQUENCE: 115

His Xaa Glu Gly Thr Phe Thr Ser Asp Xaa Xaa
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-fluorophenyl)-3-pyridylalanine-NH2

<400> SEQUENCE: 116

His Xaa Glu Gly Thr Phe Thr Ser Asp Xaa Xaa
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 117

His Xaa Glu Gly Thr Phe Thr Ser Asp Xaa Xaa
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 118

His Pro Glu Gly Thr Phe Thr Ser Asp Xaa Xaa
1               5                   10
```

```
<210> SEQ ID NO 119
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 119

His Ala Glu Gly Thr Phe Thr Ser Asp Xaa Xaa
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 120

His Pro Glu Gly Thr Phe Thr His Asp Xaa Xaa
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
``` pyridylalanine-NH2

<400> SEQUENCE: 121

His Pro Glu Gly Thr Phe Thr Ser Asp Xaa Xaa
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
      pyridylalanine-NH2

<400> SEQUENCE: 122

His Xaa Glu Gly Thr Phe Thr Ser Asp Xaa Xaa
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 123

His Pro Glu Gly Thr Phe Thr Ser Asp Xaa Xaa
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)

```
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 124

His Pro Glu Gly Thr Phe Thr His Asp Xaa Xaa
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 125

His Pro Glu Gly Thr Phe Thr Ser Asp Xaa Xaa
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 126

His Pro Glu Gly Thr Phe Thr Ser Asp Xaa Xaa
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 127

His Pro Glu Gly Thr Phe Thr Ser Asp Xaa Xaa
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 128

His Pro Glu Gly Thr Phe Thr Ser Asp Xaa Xaa
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is N-Me-(L)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 129

His Ala Glu Gly Thr Phe Thr Ser Asp Xaa Xaa
1               5                   10
```

```
<210> SEQ ID NO 130
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3,5-pyrimidylalanine-
      NH2

<400> SEQUENCE: 130

His Xaa Glu Gly Thr Phe Thr Ser Asp Xaa Xaa
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 131

His Pro Asp Gly Thr Phe Thr Ser Asp Xaa Xaa
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
```

```
<222> LOCATION: (11)..(11)
<223> OTHER INFORMATION: X is 4-(2'-Ethylphenyl)-3-pyridylalanine-NH2

<400> SEQUENCE: 132

His Pro Glu Gly Thr Phe Thr Ser Asp Xaa Xaa
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 133

His Pro Glu Gly Thr Phe Thr Ser Asp Xaa Xaa
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 134

His Pro Glu Gly Thr Phe Thr Ser Asp Xaa Xaa
1               5                   10

<210> SEQ ID NO 135
<211> LENGTH: 11
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 135

His Pro Glu Gly Thr Phe Thr Ser Asp Xaa Xaa
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 136

His Pro Glu Gly Thr Phe Thr Ser Asp Xaa Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
```

```
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 137

Xaa Xaa Glu Gly Thr Phe Thr Ser Asp Xaa Xaa
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 138

Xaa Xaa Glu Gly Thr Phe Thr Ser Asp Xaa Xaa
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 139

His Pro Glu Gly Thr Phe Thr Ser Asp Xaa Xaa
1               5                   10
```

```
<210> SEQ ID NO 140
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 140

His Pro Glu Gly Thr Phe Thr Ser Asp Xaa Xaa
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 141

His Ala Glu Gly Thr Phe Thr Ser Asp Xaa Xaa
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
```

```
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 142

His Ala Glu Gly Thr Phe Thr Ser Asp Xaa Xaa
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 143

His Pro Glu Gly Thr Phe Thr Ser Asp Xaa Xaa
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

<400> SEQUENCE: 144

His Pro Glu Gly Thr Phe Thr Ser Asp Xaa Xaa
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 145

His Pro Glu Gly Thr Phe Thr Ser Asp Xaa Xaa
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 146

His Pro Glu Gly Thr Phe Thr Ser Asp Xaa Xaa
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-di-Me)phenyl)-3-pyridylalanine-
      NH2

<400> SEQUENCE: 147

His Xaa Glu Gly Thr Phe Thr Ser Asp Xaa Xaa
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 148

His Xaa Glu Gly Thr Phe Thr His Asp Xaa Xaa
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 149

His Ala Glu Gly Thr Phe Thr Ser Asp Xaa Xaa
1               5                   10
```

```
<210> SEQ ID NO 150
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 150

His Xaa His Gly Thr Phe Thr Ser Asp Xaa Xaa
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 151

Xaa Pro Glu Gly Thr Phe Thr His Asp Xaa Xaa
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
```

```
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 152

Xaa Pro Glu Gly Thr Phe Thr Ser Asp Xaa Xaa
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 153

Xaa Pro Glu Gly Thr Phe Thr His Asp Xaa Xaa
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 154

Xaa Pro Glu Gly Thr Phe Thr Ser Asp Xaa Xaa
1               5                   10
```

```
<210> SEQ ID NO 155
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 155

Xaa Ala Glu Gly Thr Phe Thr His Asp Xaa Xaa
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 156

Xaa Ala Glu Gly Thr Phe Thr Ser Asp Xaa Xaa
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
```

```
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 157

His Pro Glu Gly Thr Phe Thr His Asp Xaa Xaa
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 158

His Pro Glu Gly Thr Phe Thr Ser Asp Xaa Xaa
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 159

His Ala Glu Gly Thr Phe Thr His Asp Xaa Xaa
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 160

His Ala Glu Gly Thr Phe Thr Ser Asp Xaa Xaa
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 161

His Xaa Glu Gly Thr Phe Thr His Asp Xaa Xaa
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 162

His Xaa Glu Gly Thr Phe Thr Ser Asp Xaa Xaa
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-imidazole-lactyl
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 163

Xaa Ala Glu Gly Thr Phe Thr His Asp Xaa Xaa
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
```

```
<223> OTHER INFORMATION: X is biphenylalanine(2'-Et-4'-OH-5'-Iodine)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 164

His Pro Glu Gly Thr Phe Thr Ser Asp Xaa Xaa
 1               5                  10

<210> SEQ ID NO 165
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 165

His Pro Glu Gly Thr Phe Thr Ser Asp Xaa Xaa
 1               5                  10

<210> SEQ ID NO 166
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 166

His Pro Glu Gly Thr Phe Thr His Asp Xaa Xaa
 1               5                  10

<210> SEQ ID NO 167
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 167

Xaa Pro Glu Gly Thr Phe Thr Ser Asp Xaa Xaa
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 168

Xaa Pro Glu Gly Thr Phe Thr Ser Asp Xaa Xaa
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
```

<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 169

Xaa Pro Glu Gly Thr Phe Thr His Asp Xaa Xaa
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 170

Xaa Pro Glu Gly Thr Phe Thr His Asp Xaa Xaa
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)3-(1H-imidazol-4-yl)-2-methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OMe)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 171

Xaa Pro Glu Gly Thr Phe Thr His Asp Xaa Xaa
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)3-(1H-imidazol-4-yl)-2-methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OMe)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 172

Xaa Pro Glu Gly Thr Phe Thr His Asp Xaa Xaa
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)3-(1H-imidazol-4-yl)-2-methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 173

Xaa Pro Glu Gly Thr Phe Thr Ser Asp Xaa Xaa
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MISC_FEATURE
<222> LOCATION: (1)..(1)
<223> OTHER INFORMATION: X is (S)3-(1H-imidazol-4-yl)-2-methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 174

Xaa Pro Glu Gly Thr Phe Thr Ser Asp Xaa Xaa
 1               5                  10

<210> SEQ ID NO 175
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1H-imidazol-4-yl)-2-
      methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 175

Xaa Pro Glu Gly Thr Phe Thr His Asp Xaa Xaa
 1               5                  10

<210> SEQ ID NO 176
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)3-(1H-imidazol-4-yl)-2-methoxypropanoyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe (2-Fluoro)
<220> FEATURE:
<221> NAME/KEY: MISC_FEATURE
```

-continued

```
<222> LOCATION: (10)..(10)
<223> OTHER INFORMATION: X is biphenylalanine (2'-Et-4'-OH)
<220> FEATURE:
<221> NAME/KEY: MISC_FEATURE
<222> LOCATION: (11)..(11)
<223> OTHER INFORMATION: X is 4-(2'-methylphenyl)-3-pyridylalanine-NH2

<400> SEQUENCE: 176

Xaa Pro Glu Gly Thr Phe Thr His Asp Xaa Xaa
1               5                   10

<210> SEQ ID NO 177
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is biphenylalanine (2'-Et-4'-OH)
<220> FEATURE:
<221> NAME/KEY: MISC_FEATURE
<222> LOCATION: (5)..(5)
<223> OTHER INFORMATION: X is 4-(2'-methylphenyl)-3-pyridylalanine-NH2

<400> SEQUENCE: 177

Thr Ser Asp Xaa Xaa
1               5

<210> SEQ ID NO 178
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Pro is (S)-alpha-Me-Pro
<220> FEATURE:
<221> NAME/KEY: MISC_FEATURE
<222> LOCATION: (5)..(5)
<223> OTHER INFORMATION: X is biphenylalanine (2'-Et-4'-OH)
<220> FEATURE:
<221> NAME/KEY: MISC_FEATURE
<222> LOCATION: (6)..(6)
<223> OTHER INFORMATION: X is 4-(2'-methylphenyl)-3-pyridylalanine-NH2

<400> SEQUENCE: 178

Pro Thr Ser Asp Xaa Xaa
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is biphenylalanine (2'-Et-4'-OH)
<220> FEATURE:
<221> NAME/KEY: MISC_FEATURE
<222> LOCATION: (5)..(5)
<223> OTHER INFORMATION: X is 4-(2'-methylphenyl)-3-pyridylalanine-NH2

<400> SEQUENCE: 179

Thr His Asp Xaa Xaa
1               5
```